United States Patent
Arndt et al.

(10) Patent No.: US 8,791,148 B2
(45) Date of Patent: Jul. 29, 2014

(54) SUBSTITUTED BENZIMIDAZOLONE DERIVATIVES, MEDICAMENTS COMPRISING THEM AND THEIR USE

(75) Inventors: Torsten Arndt, Bensheim (DE); Thorsten Oost, Biberach an der Riss (DE); Wilfried Lubisch, Heidelberg (DE); Wilfried Homberger, Ludwigshafen (DE); Liliane Unger, Ludwigshafen (DE); Juliana Ruiz Caro, Rainbach im Muehlkreis (AT); Wolfgang Wernet, Ludwigshafen (DE); Alfred Hahn, legal representative, Mannheim (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 365 days.

(21) Appl. No.: 13/302,194

(22) Filed: Nov. 22, 2011

(65) Prior Publication Data

US 2012/0172335 A1 Jul. 5, 2012

Related U.S. Application Data

(62) Division of application No. 12/438,712, filed as application No. PCT/EP2007/058840 on Aug. 24, 2007, now Pat. No. 8,119,676.

(30) Foreign Application Priority Data

Aug. 26, 2006 (DE) .......................... 10 2006 040 914

(51) Int. Cl.
*A61K 31/4184* (2006.01)
*C07D 235/26* (2006.01)

(52) U.S. Cl.
CPC .......... *A61K 31/4184* (2013.01); *C07D 235/26* (2013.01)
USPC ....................................... 514/395; 548/304.4

(58) Field of Classification Search
CPC ................ A61K 31/4184; C07D 235/26
USPC ........................................ 514/395; 548/304.4
See application file for complete search history.

(56) References Cited

U.S. PATENT DOCUMENTS 5,585,394 A * 12/1996 Di Malta et al. ......... 514/217.09

OTHER PUBLICATIONS

Bundgaard, Design of Prodrugs, 1985, Elsevier, Chapter 1, p. 1-4.*
DECAUX, Non-peptide arginine-vasopressin antagonists: the vaptans, 2008, Lancet, vol. 37, No. 1, p. 1624-1632.*
Han, Targeted Prodrug Design to Optimize Drug Delivery, 2000, AAPS Pharmsci, vol. 2(1), p. 1-11.*
Serradeil-Le Gal, An Overview of SSR149415, S Selective Nonpeptide Vasopressin V1b Receptor Antagonist for the Treatment of Stress-Related Disorders, 2005, CNS Drug Reviews, vol. 11, No. 1, p. 53-68.*
Lemmens-Gruber, 2006, Cell. Mol. Life Sci., vol. 63, p. 1766-1779.*
Oshikawa et al., Mol. Pharmacol. 65:623-629, 2004.
Japundžić-Žigon et al., J. Pharmacol. Sci. 95, 47-55, 2004.
Scheurer et al., J. Thorac. Cardiovasc. Surg. 2005; 129:464-6.
Lee et al., Am. Heart J. 2003; 146:9-18.
Ring, R.H., Current Pharmaceutical Design, 2005, 11, 205-225.
Kocsis et al., Invest. Radiol. 1987; 22:973-977.
Maturi et al., Circulation 1991, 83:2111-2121.
Yatagai et al., Eur. J. Endocrinol. 2003, 148:221-226.
Jonat et al., Arch. Dis. Child 1999, 81:57-59.
Thibonnier et al., Current Opinion in Pharmacology 2003, 3:683-687.
Kocsis et al., Br. J. exp. Path. (1987) 68, 35-43.
Pávó et al., J. Physiol. (Paris) 94 (2000) 63-66.
Cheung et al., J. Clin. Pharmacol. 1994; 34:664-670.
Grant et al., Clinical Science (1985) 69, 471-476.
Emsley et al., Alcohol & Alcoholism, vol. 30, No. 2, pp. 223-229, 1995.
Thibonnier, M., "Development and therapeutic indications of orally-active non-peptide vasopressin receptor antagonists," Expert Opinion on Investigational Drugs, (1998), 7(5): pp. 729-740.

* cited by examiner

*Primary Examiner* — Rebecca Anderson
*Assistant Examiner* — Karen Cheng
(74) *Attorney, Agent, or Firm* — Lisa V. Mueller; Michael Best & Friedrich LLP

(57) ABSTRACT

The present invention relates to novel benzimidazolone derivatives of the general formula (I) in which the substituents $R^1$, $R^2$, $R^3$, $A^1$, $A^2$, and B are as defined in claim 1, medicaments comprising these, and the use thereof for the prophylaxis and/or treatment of vasopressin-dependent diseases.

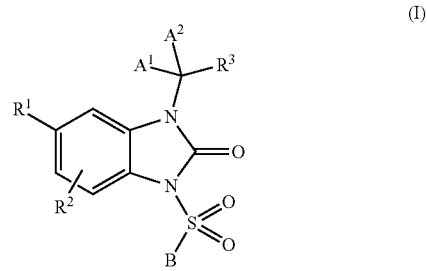

(I)

15 Claims, No Drawings

SUBSTITUTED BENZIMIDAZOLONE DERIVATIVES, MEDICAMENTS COMPRISING THEM AND THEIR USE

CROSS-REFERENCE TO RELATED APPLICATIONS

This is a divisional of U.S. patent application Ser. No. 12/438,712, filed on Mar. 1, 2010, which is the U.S. national stage entry of International Patent Application No. PCT/EP2007/058840, filed on Aug. 24, 2007, which claims the benefit of German Patent Application No. 10 2006 040 914.0, filed on Aug. 26, 2006, the contents of all of which are hereby incorporated by reference.

The present invention relates to novel substituted benzimidazolone derivatives, to medicaments comprising them and to their use for the treatment of diseases.

Vasopressin (AVP) is an endogenous hormone which exerts various effects on organs and tissues. Vasopressin is related to oxytocin (OT), so that the two peptides are combined to form a vasopressin/oxytocin family. It is suspected that the vasopressin/oxytocin system is involved in various pathological states. At present, three vasopressin receptors (V1a, V1b or V3 and V2 receptors) and one oxytocin receptor (OT receptor) are known, via which vasopressin and oxytocin mediate their effects. Antagonists of these receptors, especially including antagonists which bind specifically to only one of the above receptors, represent novel therapeutic approaches to the treatment of diseases (M. Thibonnier, Exp. Opin. Invest. Drugs 1998, 7(5), 729-740). It has been found, for example, that a selective antagonist of the vasopressin V1b receptor exerts anxiolytic and anti-depressant effects in animal models (Griebel et al., PNAS 2002, 99, 6370; Serradeil-Le Gal et al., J. Pharm. Exp. Ther. 2002, 300, 1122). Since the described models have a certain predictive value for the clinical effects to be expected, antagonists of the V1b receptor are of particular interest for the treatment of emotional disturbances or disorders such as, for example, stress, anxiety states and/or depression.

The present application describes novel substituted benzimidazol-2-ones which have an arylsulfonyl group in position 1.

1-Phenylsulfonyl-1,3-dihydro-2H-indol-2-ones have previously been described as ligands of vasopressin receptors. WO 93/15051, WO 95/18105, WO 98/25901, WO 01/55130, WO 01/55134, WO 01/064668, WO 01/98295, WO 05/021534 and WO 05/030755 describe derivatives derived from the oxindole structure and having arylsulfonyl groups in position 1. These compounds differ essentially in the substitution in position 3.

In particular, WO 93/15051 and WO 98/25901 describe 1-phenylsulfonyl-1,3-dihydro-2H-indol-2-one as ligands of vasopressin receptors in which the oxindole structure is substituted in position 3 by two alkyl radicals which may likewise be a cycloalkyl radical (spiro linkage). As alternative, the spiro ring may comprise heteroatoms such as oxygen and nitrogen (optionally with substituents).

WO 95/18105 describes 1-phenylsulfonyl-1,3-dihydro-2H-indol-2-one as ligands of vasopressin receptors which have a nitrogen atom in position 3. In addition, radicals which may be alkyl, cycloalkyl, phenyl or benzyl radicals (in each case optionally with substituents) are bonded in position 3.

Other publications, for example WO 01/55130, describe compounds which have nitrogen-containing rings (e.g. proline, homoproline, morpholine, tetrahydroisoquinoline, dihydroindole; in each case optionally with substituents) which are linked via their nitrogen atom to position 3 of the oxindole structure but which are substituted by phenylsulfonyl or phenyl groups (optionally with substituents) both in position 1 and in position 3 on the oxindole ring.

WO 03/008407 describes 1-phenylsulfonyloxindoles in which pyridylpiperazines are linked via an oxycarbonyl group to the oxindole in position 3.

WO 02/055514 describes substituted benzimidazol-2-ones which are substituted by a 4-piperidinyl group in position 1 and have a hydrogen atom, alkyl substituents or amine linked via an alkyl linker, in position 3. Said compounds are effective as vasopressin receptor antagonists and modulators of neuropeptide Y.

WO 05/009996 describes 1-arylsulfonylbenzimidazol-2-ones as active ingredients for the therapy of disorders of the central nervous system connected to the 5-HT6 receptor. The compounds have either an amine linked via an alkyl linker, or a monocyclic, nitrogen-containing heteroalicyclic ring with optional substituents, in position 3. WO 05/010003 claims corresponding compounds which represent aza derivatives of the basic benzimidazol-2-one structure.

WO 05/080334 describes heterocyclic compounds for the treatment of anxiety states and depression. Examples are amides of N-(2-acetyl)substituted benzimidazol-2-ones. The second nitrogen atom of the benzimidazol-2-one may moreover be replaced by oxygen, sulfur, or an alkyl-substituted nitrogen atom.

U.S. Pat. No. 5,585,394 describes 1-arylsulfonylbenzimidazol-2-ones as ligands of vasopressin and oxytocin receptors.

It is an object of the present invention to provide further compounds for the treatment or prophylaxis of various vasopressin-dependent diseases.

The compounds were intended preferably to have advantages over known compounds, such as, for example, an improved metabolic stability and/or an improved pharmacological activity. The advantages can in this case be shown for example by using suitable models which make it possible to make a prognostic statement about the desired use in the treatment of patients.

DESCRIPTION OF THE INVENTION

The object is achieved by providing at least one compound of the general formula (I)

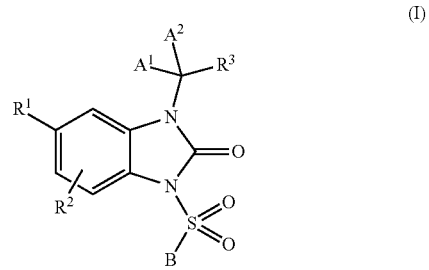

in which
A$^1$ is hydrogen, in each case optionally substituted C$_1$-C$_6$-alkyl, C$_2$-C$_6$-alkenyl, C$_2$-C$_6$-alkynyl, C$_3$-C$_6$-cycloalkyl, C$_3$-C$_6$-cycloalkenyl or C$_1$-C$_4$-alkylene-phenyl, or an aromatic, heteroaromatic, partly aromatic or partly heteroaromatic mono- or bicyclic ring having 1, 2, 3, 4, 5, 6, 7, 8, 9 or 10 carbon atoms as ring members, which may besides additionally comprise 0, 1, 2, 3 or 4 identical or different heteroatoms independently of one another selected from the group consisting of nitrogen, oxygen and sulfur as ring members, and which may be substituted by one, two or three radicals $R_A^{11}$, $R_A^{12}$ and/or $R_A^{13}$ which are selected independently of one another and independently of their respective occurrence from the group consisting of hydrogen, bromine, chlorine, iodine, fluorine, CN, $CF_3$, $OCF_3$, $OCHF_2$, OH, COOH, CO—$NH_2$, $NH_2$, NH—CO—$NH_2$ or in each case optionally substituted $C_1$-$C_6$-alkyl, O—$C_1$-$C_6$-alkyl, $C_2$-$C_6$-alkenyl, $C_2$-$C_6$-alkynyl, $C_3$-$C_6$-cycloalkyl, O—$C_3$-$C_6$-cycloalkyl, $C_3$-$C_6$-cycloalkenyl, $C_1$-$C_4$-alkylene-aryl, NH—($C_1$-$C_6$-alkyl), N($C_1$-$C_6$-alkyl)$_2$, $C_1$-$C_4$—$NH_2$, $C_1$-$C_4$-alkylene-NH—($C_1$-$C_6$-alkyl), $C_1$-$C_4$-alkylene-N($C_1$-$C_6$-alkyl)$_2$, $C_1$-$C_4$-alkylene-OH, $C_1$-$C_4$alkylene-O—$C_1$-$C_6$-alkyl, CO—$C_1$-$C_6$-alkyl, CO—O—$C_1$-$C_6$-alkyl, CO—NH($C_1$-$C_6$-alkyl), CO—N($C_1$-$C_6$-alkyl)$_2$, NH—CO—$C_1$-$C_6$-alkyl, NH—CO—N($C_1$-$C_6$-alkyl)$_2$, N($C_1$-$C_6$-alkyl)-CO—$C_1$-$C_6$-alkyl;

$A^2$ is hydrogen or in each case optionally substituted $C_1$-$C_6$-alkyl, $C_1$-$C_6$-alkenyl, $C_1$-$C_6$-alkynyl or $C_3$-$C_6$-cycloalkyl;

or where the radicals $A^1$ and $A^2$ may form together with the carbon atom to which they are bonded an in each case optionally substituted 3- to 7-membered carbocyclic ring (spiro linkage) which may additionally comprise a heteroatom as ring member selected from the group consisting of O, S and $NR_A^{14}$ in which $R_A^{14}$ is a radical selected from the group consisting of hydrogen and in each case optionally substituted $C_1$-$C_6$-alkyl, aryl and $C_1$-$C_4$-alkylene-aryl, and where the ring formed in this way may be substituted by one, two or three radicals $R_A^{11}$, $R_A^{12}$ and/or $R_A^{13}$ which may independently of one another and independently of their respective occurrence assume the aforementioned meanings;

B is an aromatic, heteroaromatic, partly aromatic or partly heteroaromatic mono- or bicyclic ring having 1, 2, 3, 4, 5, 6, 7, 8, 9 or 10 C atoms as ring members, which may additionally comprise 0, 1, 2, 3 or 4 identical or different heteroatoms independently of one another selected from the group consisting of nitrogen, oxygen and sulfur as ring members, and which may be substituted by one, two or three radicals $R_B^1$, $R_B^2$ and/or $R_B^3$, where $R_B^1$, $R_B^2$ and $R_B^3$ are selected independently of one another and independently of their respective occurrence from the group consisting of hydrogen, chlorine, bromine, fluorine, CN, $CF_3$, $OCF_3$, $OCHF_2$, $OCH_2F$, $OCH_2CF_3$, $OCH_2$—$CHF_2$, OH, and in each case optionally substituted O—$C_1$-$C_4$-alkyl, $C_1$-$C_4$-alkyl, $C_2$-$C_4$-alkenyl and $C_2$-$C_4$-alkynyl, $R^1$ is selected from the group consisting of hydrogen, bromine, chlorine, fluorine, iodine, CN, $CF_3$, $OCF_3$, $OCHF_2$, and in each case O—$C_1$-$C_4$-alkyl, $C_1$-$C_4$-alkyl, $C_1$-$C_4$-alkenyl and $C_2$-$C_4$-alkynyl; NH($C_1$-$C_4$-alkyl), N($C_1$-$C_4$-alkyl)($C_1$-$C_4$-alkyl), $NO_2$, NHCHO, NHCO ($C_1$-$C_4$-alkyl) or $NHCONH_2$ $R^2$ is selected from the group consisting of hydrogen, and in each case optionally substituted $C_1$-$C_4$-alkyl, O—$C_1$-$C_4$-alkyl, chlorine, fluorine, difluoromethyl ($CHF_2$) and trifluoromethyl;

$R^3$ is a radical (X)—(Y), where
X is CO, $SO_2$ or (C=NH), in particular CO,
Y is selected from the group consisting of
OH, $NH_2$, NH($C_1$-$C_4$-alkyl), N($C_1$-$C_4$-alkyl)($C_1$-$C_4$-alkyl), NH($C_2$-$C_4$-alkylene-OH), N($C_1$-$C_4$-alkyl) ($C_2$-$C_4$-alkylene-OH), NH($C_2$-$C_4$-alkylene-O—$C_1$-$C_4$-alkyl), N($C_1$-$C_4$-alkyl)($C_2$-$C_4$-alkylene-O—$C_1$-$C_4$-alkyl), NH($C_3$-$C_7$-cycloalkyl), N($C_1$-$C_4$-alkyl)($C_3$-$C_7$-cycloalkyl), NH($C_1$-$C_4$-haloalkyl), N($C_1$-$C_4$-alkyl)($C_1$-$C_4$-haloalkyl), N($R_Y^5$)($C_1$-$C_4$-alkylene)-$R_Y^3$, and radical $R_Y^1$;

$R_Y^1$ is selected independently of its respective occurrence from the group consisting of the respective individual radicals mentioned below

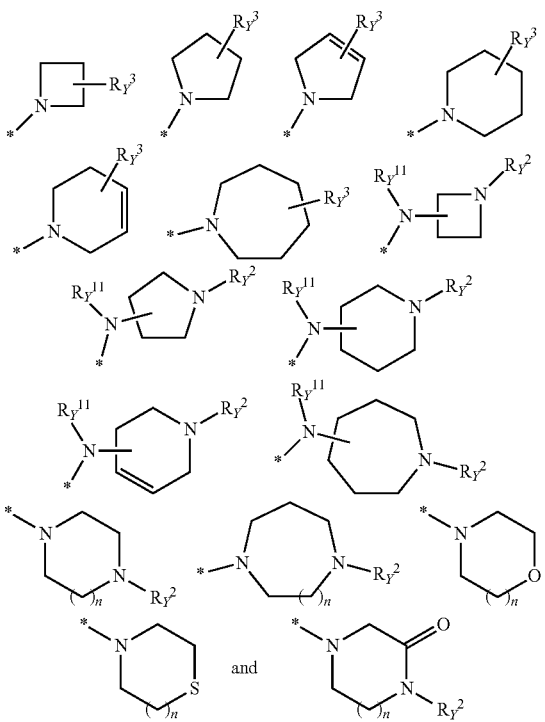

where n is independently of its occurrence the integer 1 or 2, where the aforementioned radicals may independently of one another each have one or two substituents $R_Y^{12}$ and/or $R_Y^{13}$ which are selected independently of one another and independently of their respective occurrence from the group consisting of hydrogen, fluorine, OH, in each case optionally substituted O—$C_1$-$C_4$-alkyl, phenyl and $C_1$-$C_4$-alkyl;

$R_Y^{11}$ is a radical selected from the group consisting of hydrogen, in each case optionally substituted $C_1$-$C_6$-alkyl, $C_2$-$C_6$-alkenyl and $C_2$-$C_6$-alkynyl.

$R_Y^2$ is a radical selected from the group consisting of hydrogen, in each case optionally substituted $C_1$-$C_6$-alkyl, $C_2$-$C_6$-alkenyl, $C_2$-$C_6$-alkynyl, phenyl, $C_1$-$C_4$-alkylene-phenyl, $C_1$-$C_4$-haloalkyl, $C_3$-$C_7$-cycloalkyl, pyridine, pyrimidine, pyrazine, pyridazine, furan, thiophene, pyrrole, oxazole, isoxazole, thiazole, imidazole, pyrazole, 1,2,4-oxadiazole, 1,2,5-oxadiazole, 1,3,4-oxadiazole, thiadiazole, triazole, 1,3,5-triazine, tetrazole, ($C_2$-$C_4$-alkylene)-$R_Y^3$ and ring radical $R_Y^{22}$, where $R_Y^{22}$ is selected independently of its respective occurrence from the group consisting of the respective individual radicals

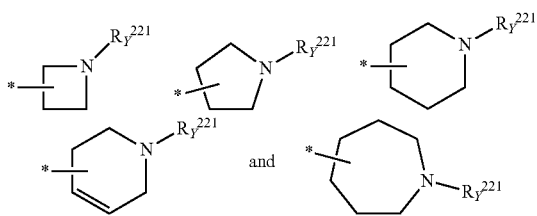

where the aforementioned radicals may independently of one another in each case have one or two substituents $R_Y^{222a}$ and/or $R_Y^{223a}$ which are selected independently of one another and independently of their respective occurrence from the group consisting of hydrogen, fluorine, OH and in each case optionally substituted O—$C_1$-$C_4$-alkyl, phenyl and $C_1$-$C_4$-alkyl.

$R_Y^{221}$ is a radical selected from the group consisting of hydrogen, and in each case optionally substituted $C_1$-$C_6$-alkyl, $C_2$-$C_6$-alkenyl $C_2$-$C_6$-alkynyl and $C_1$-$C_4$-alkylene-phenyl;

$R_Y^3$ is a radical selected from the group consisting of hydrogen, $NH_2$, $N(R_Y^{3a})R_Y^{3b}$, $NH(C_2$-$C_4$-alkylene)-$R_Y^8$, $N(R_Y^7)(C_2$-$C_4$-alkylene)-$R_Y^8$, $N(R_Y^7)R_Y^9$, $N(R_Y^7)CH_2R_Y^9$, a radical $R_Y^{33}$, a radical $CH_2R_Y^{33}$ and an aromatic radical, selected from phenyl, pyridine, pyrimidine, pyrazine, pyridazine, furan, thiophene, pyrrole, oxazole, isoxazole, thiazole, isothiazole, imidazole, pyrazole, 1,2,4-oxadiazole, 1,2,5-oxadiazole, 1,3,4-oxadiazole, thiadiazole, triazole, 1,3,5-triazine and tetrazole, the aromatic radical being substituted or carrying 1 or 2 substituents $R_Y^{331}$ and/or $R_Y^{332}$, where $R_Y^{33}$ is independently of its respective occurrence a radical selected from the group consisting of the respective individual radicals

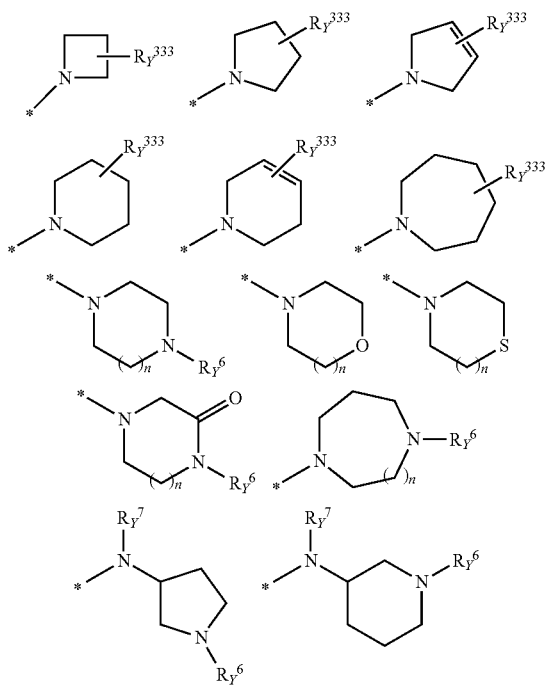

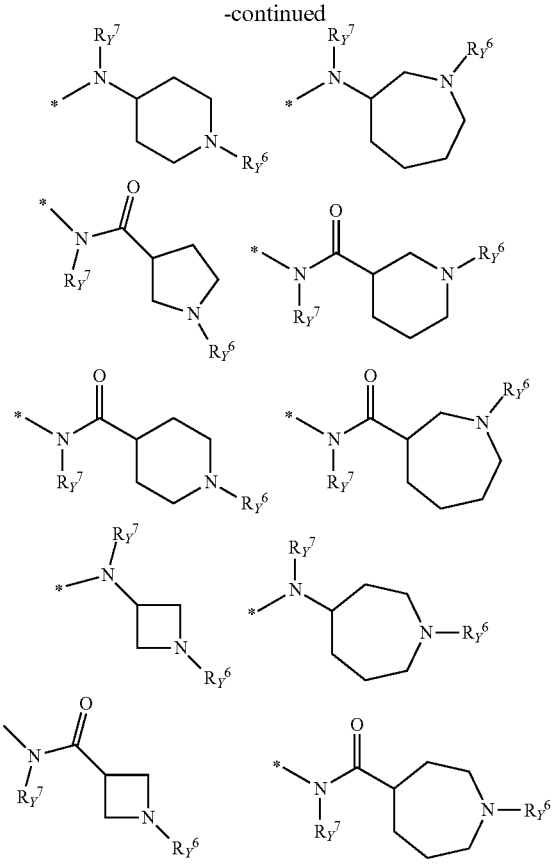

$n = 1, 2$ where n is independently of its occurrence the integer 1 or 2, where the aforementioned radicals $R_Y^{33}$ may independently of one another in each case have one or two substituents $R_Y^{331}$ and/or $R_Y^{332}$ which are selected independently of one another and independently of their respective occurrence from the group consisting of hydrogen, fluorine, OH, and in each case optionally substituted O—$C_1$-$C_4$-alkyl, phenyl and $C_1$-$C_4$-alkyl.

$R_Y^{333}$ is a radical selected from the group consisting of hydrogen and in each case optionally substituted $C_1$-$C_6$-alkyl, $C_2$-$C_6$-alkenyl, $C_2$-$C_6$-alkynyl, phenyl and $C_1$-$C_4$-alkylene-phenyl;

$R_Y^{3a}$ is a radical selected from the group consisting of hydrogen, and in each case optionally substituted $C_1$-$C_6$-alkyl, $C_3$-$C_7$-cycloalkyl, $C_2$-$C_6$-alkenyl, $C_2$-$C_6$-alkynyl, phenyl and $C_1$-$C_4$-alkylene-phenyl;

$R_Y^{3b}$ is a radical selected from the group consisting of in each case optionally substituted $C_1$-$C_6$-alkyl and $C_1$-$C_4$-alkylene-phenyl;

$R_Y^5$ is a radical selected from the group consisting of hydrogen and in each case optionally substituted $C_1$-$C_4$-alkyl;

$R_Y^6$ is a radical selected from the group consisting of hydrogen and in each case optionally substituted $C_1$-$C_6$-alkyl, $C_2$-$C_6$-alkenyl, $C_2$-$C_6$-alkynyl, phenyl and $C_1$-$C_4$-alkylene-phenyl;

$R_Y^7$ is a radical selected from the group consisting of hydrogen and in each case optionally substituted $C_1$-$C_6$-alkyl, $C_2$-$C_6$-alkenyl, $C_2$-$C_6$-alkynyl, phenyl and $C_1$-$C_4$-alkylene-phenyl;

$R_Y^8$ is a radical selected from the group consisting of OH, $NH_2$, and in each case optionally substituted $NH(C_1-C_4$-alkyl), $N(C_1-C_4$-alkyl)$(C_1-C_4$-alkyl), $NH(C_2-C_4$-alkylene-OH), $N(C_1-C_4$-alkyl)$(C_2-C_4$-alkylene-OH), $NH(C_2-C_4$-alkylene-O—$C_1-C_4$-alkyl), $N(C_1-C_4$-alkyl)$(C_2-C_4$-alkylene-O—$C_1-C_4$-alkyl), $NH(C_3-C_7$-cycloalkyl), $N(C_1-C_4$-alkyl)$(C_3-C_7$-cycloalkyl), $NH(C_1-C_4$-haloalkyl), $N(C_1-C_4$-alkyl)$(C_1-C_4$-haloalkyl), O—$C_1-C_4$-alkyl, and the ring radical $R_Y^{81}$, where $R_Y^{81}$ is a radical independently of its respective occurrence selected from the group consisting of the respective individual radicals

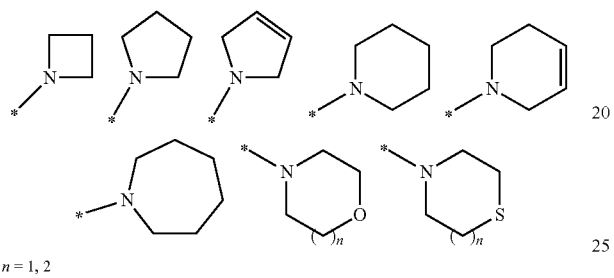

$n = 1, 2$ $R_Y^9$ is a 5- or 6-membered heteroaromatic radical having 2, 3, 4 or 5 carbon atom as ring members and 1, 2 or 3 heteroatoms, selected from O, S and N, wherein the 5- or 6-membered heteroaromatic radical may be unsubstituted or may have one or two substituents $R_Y^{331}$ and/or $R_Y^{332}$, the tautomeric, enantiomeric and/or diastereomeric forms thereof, and/or prodrugs thereof, and the physiologically tolerated salts of the aforementioned compound or compounds, where appropriate preferably with the proviso that $R^1 \neq H$ (is not hydrogen) when $A^1 = A^2 =$ hydrogen, and/or where appropriate particularly preferably with the proviso that $R^1$ is halogen, cyano, or in each case optionally substituted $C_1-C_6$-alkoxy and $C_1-C_6$-alkyl when $A^1 = A^2 =$ hydrogen.

Each of these aforementioned definitions of a variable can be combined with any of the aforementioned definitions of the remaining variables. This applies in particular to the combination of preferred definitions of a variable with any or preferred definitions of the remaining variables.

One embodiment of the invention (embodiment A) relates to compounds of the formula I, to the tautomeric, enantiomeric and/or diastereomeric forms thereof, the prodrugs thereof, and to the physiologically tolerated salts of the aforementioned compounds, wherein at least one or in particular all of the radicals $R^1$, $R^2$, $R^3$, $A^1$ and $A^2$ have one of the following meanings:

$A^1$ is an aromatic, heteroaromatic, partly aromatic or partly heteroaromatic mono- or bicyclic ring having 1, 2, 3, 4, 5, 6, 7, 8, 9 or 10 carbon atoms as ring members, which may besides additionally comprise 0, 1, 2, 3 or 4 identical or different heteroatoms independently of one another selected from the group consisting of nitrogen, oxygen and sulfur as ring members, and which may be substituted by one, two or three radicals $R_A^{11}$, $R_A^{12}$ and/or $R_A^{13}$ which are selected independently of one another and independently of their respective occurrence from the group consisting of hydrogen, bromine, chlorine, iodine, fluorine, CN, $CF_3$, $OCF_3$, $OCHF_2$, OH, COOH, CO—$NH_2$, $NH_2$, NH—CO—$NH_2$ or in each case optionally substituted $C_1-C_6$-alkyl, O—$C_1-C_6$-alkyl, $C_2-C_6$-alkenyl, $C_2-C_6$-alkynyl, $C_3-C_6$-cycloalkyl, O—$C_3-C_6$-cycloalkyl, $C_3-C_6$-cycloalkenyl, $C_1-C_4$-alkylene-aryl, NH—($C_1-C_6$-alkyl), N($C_1-C_6$-alkyl)$_2$, $C_1-C_4$—$NH_2$, $C_1-C_4$-alkylene-NH—($C_1-C_6$-alkyl), $C_1-C_4$-alkylene-N($C_1-C_6$-alkyl)$_2$, $C_1-C_4$-alkylene-OH, $C_1-C_4$alkylene-O—$C_1-C_6$-alkyl, CO—$C_1-C_6$-alkyl, CO—O—$C_1-C_6$-alkyl, CO—NH($C_1-C_6$-alkyl), CO—N($C_1-C_6$-alkyl)$_2$, NH—CO—$C_1-C_6$-alkyl, NH—CO—N($C_1-C_6$-alkyl)$_2$, N($C_1-C_6$-alkyl)-CO—$C_1-C_6$-alkyl;

$A^2$ is hydrogen or in each case optionally substituted $C_1-C_6$-alkyl, $C_1-C_6$-alkenyl, $C_1-C_6$-alkynyl or $C_3-C_6$-cycloalkyl;

or where the radicals $A^1$ and $A^2$ may form together with the carbon atom to which they are bonded an in each case optionally substituted 3- to 7-membered carbocyclic ring (spiro linkage) which may additionally comprise a heteroatom as ring member selected from the group consisting of O, S and $NR_A^{14}$ in which $R_A^{14}$ is a radical selected from the group consisting of hydrogen and in each case optionally substituted $C_1-C_6$-alkyl, aryl and $C_1-C_4$-alkylene-aryl, and where the ring formed in this way may be substituted by one, two or three radicals $R_A^{11}$, $R_A^{12}$ and/or $R_A^{13}$ which may independently of one another and independently of their respective occurrence assume the aforementioned meanings;

B is an aromatic, heteroaromatic, partly aromatic or partly heteroaromatic mono- or bicyclic ring having 1, 2, 3, 4, 5, 6, 7, 8, 9 or 10 C atoms as ring members, which may additionally comprise 0, 1, 2, 3 or 4 identical or different heteroatoms independently of one another selected from the group consisting of nitrogen, oxygen and sulfur as ring members, and which may be substituted by one, two or three radicals $R_B^1$, $R_B^2$ and/or $R_B^3$, where $R_B^1$, $R_B^2$ and $R_B^3$ are selected independently of one another and independently of their respective occurrence from the group consisting of hydrogen, chlorine, bromine, fluorine, CN, $CF_3$, $OCF_3$, $OCHF_2$, $OCH_2F$, $OCH_2CF_3$, $OCH_2$—$CHF_2$, OH, and in each case optionally substituted O—$C_1-C_4$-alkyl, $C_1-C_4$-alkyl, $C_2-C_4$-alkenyl and $C_2-C_4$-alkynyl, $R^1$ is selected from the group consisting of hydrogen, bromine, chlorine, fluorine, iodine, CN, $CF_3$, $OCF_3$, $OCHF_2$, and in each case O—$C_1-C_4$-alkyl, $C_1-C_4$-alkyl, $C_1-C_4$-alkenyl and $C_2-C_4$-alkynyl; NH($C_1-C_4$-alkyl), N($C_1-C_4$-alkyl)$(C_1-C_4$-alkyl), $NO_2$, NHCHO, NHCO($C_1-C_4$-alkyl) or $NHCONH_2$ $R^2$ is selected from the group consisting of hydrogen, and in each case optionally substituted $C_1-C_4$-alkyl, O—$C_1-C_4$-alkyl, chlorine, fluorine, difluoromethyl ($CHF_2$) and trifluoromethyl;

$R^3$ is a radical (X)—(Y), where
X is CO, $SO_2$ or (C=NH), in particular CO,
Y is selected from the group consisting of
OH, $NH_2$, NH($C_1-C_4$-alkyl), N($C_1-C_4$-alkyl)$(C_1-C_4$-alkyl), NH($C_2-C_4$-alkylene-OH), N($C_1-C_4$-alkyl)$(C_2-C_4$-alkylene-OH), NH($C_2-C_4$-alkylene-O—$C_1-C_4$-alkyl), N($C_1-C_4$-alkyl)$(C_2-C_4$-alkylene-O—$C_1-C_4$-alkyl), NH($C_3-C_7$-cycloalkyl), N($C_1-C_4$-alkyl)$(C_3-C_7$-cycloalkyl), NH($C_1-C_4$-haloalkyl), N($C_1-C_4$-alkyl)$(C_1-C_4$-haloalkyl), N($R_Y^5$)($C_1-C_4$-alkylene)$R_Y^3$, and radical $R_Y^1$;

$R_Y^1$ is selected independently of its respective occurrence from the group consisting of the respective individual radicals mentioned below

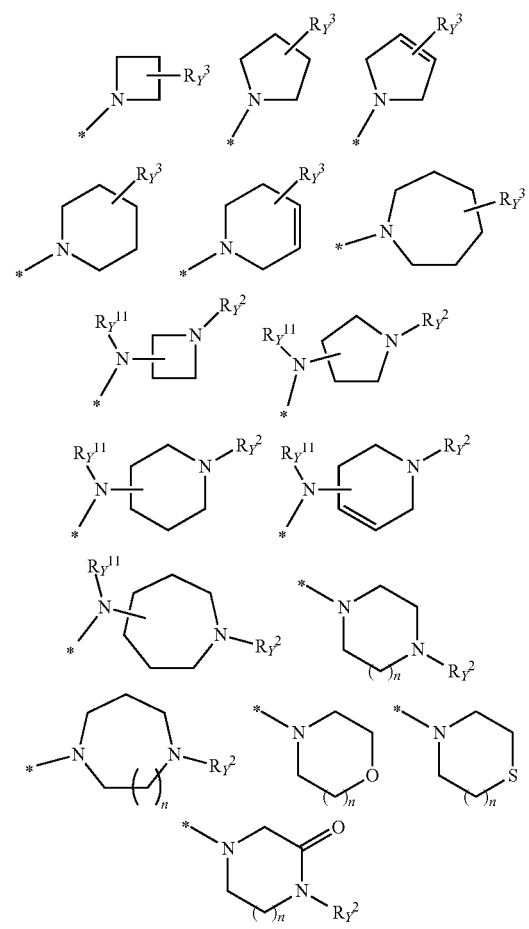

$n = 1, 2$ where the aforementioned radicals may independently of one another each have one or two substituents $R_Y^{12}$ and/or $R_Y^{13}$ which are selected independently of one another and independently of their respective occurrence from the group consisting of hydrogen, fluorine, OH, in each case optionally substituted O—$C_1$-$C_4$-alkyl, phenyl and $C_1$-$C_4$-alkyl;

$R_Y^{11}$ is a radical selected from the group consisting of hydrogen, in each case optionally substituted $C_1$-$C_6$-alkyl, $C_2$-$C_6$-alkenyl and $C_2$-$C_6$-alkynyl.

$R_Y^2$ is a radical selected from the group consisting of hydrogen, in each case optionally substituted $C_1$-$C_6$-alkyl, $C_2$-$C_6$-alkenyl, $C_2$-$C_6$-alkynyl, phenyl, $C_1$-$C_4$-alkylene-phenyl, $C_1$-$C_4$-haloalkyl, $C_3$-$C_7$-cycloalkyl, pyridine, pyrimidine, pyrazine, pyridazine, furan, thiophene, pyrrole, oxazole, isoxazole, thiazole, imidazole, pyrazole, 1,2,4-oxadiazole, 1,2,5-oxadiazole, 1,3,4-oxadiazole, thiadiazole, triazole, 1,3,5-triazine, tetrazole, ($C_2$-$C_4$-alkylene)-$R_Y^3$ and ring radical $R_Y^{22}$, where $R_Y^{22}$ is selected independently of its respective occurrence from the group consisting of the respective individual radicals

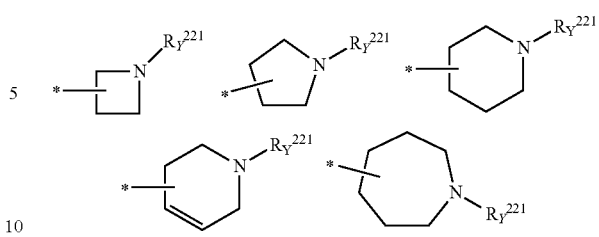

where the aforementioned radicals may independently of one another in each case have one or two substituents $R_Y^{222a}$ and/or $R_Y^{223a}$ which are selected independently of one another and independently of their respective occurrence from the group consisting of hydrogen, fluorine, OH and in each case optionally substituted O—$C_1$-$C_4$-alkyl, phenyl and $C_1$-$C_4$-alkyl.

$R_Y^{221}$ is a radical selected from the group consisting of hydrogen, and in each case optionally substituted $C_1$-$C_6$-alkyl, $C_2$-$C_6$-alkenyl and $C_2$-$C_6$-alkynyl;

$R_Y^3$ is a radical selected from the group consisting of hydrogen, $NH_2$ and in each case optionally substituted $NH(C_1$-$C_4$-alkyl), $N(C_1$-$C_4$-alkyl)($C_1$-$C_4$-alkyl), $NH(C_2$-$C_4$-alkylene-OH), $N(C_1$-$C_4$-alkyl)($C_2$-$C_4$-alkylene-OH), $NH(C_2$-$C_4$-alkylene-O—$C_1$-$C_4$-alkyl), $N(C_1$-$C_4$-alkyl)($C_2$-$C_4$-alkylene-O—$C_1$-$C_4$-alkyl), $NH(C_3$-$C_7$-cycloalkyl), $N(C_1$-$C_4$-alkyl)($C_3$-$C_7$-cycloalkyl), $NH(C_1$-$C_4$-haloalkyl), $N(C_1$-$C_4$-alkyl)($C_1$-$C_4$-haloalkyl), $NH(C_2$-$C_4$-alkylene)-$R_Y^8$, $N(R_Y^7)(C_2$-$C_4$-alkylene)-$R_Y^8$ an aromatic radical selected from phenyl, pyridine, pyrimidine, pyrazine, pyridazine, furan, thiophene, pyrrole, oxazole, isoxazole, thiazole, imidazole, pyrazole, 1,2,4-oxadiazole, 1,2,5-oxadiazole, 1,3,4-oxadiazole, thiadiazole, triazole, 1,3,5-triazine, tetrazole, the aromatic radical being unsubstituted or carrying 1 or 2 radicals $R_Y^{331}$ and/or $R_Y^{332}$, and a ring radical $R_Y^{33}$, where $R_Y^{33}$ is independently of its respective occurrence a radical selected from the group consisting of the respective individual radicals

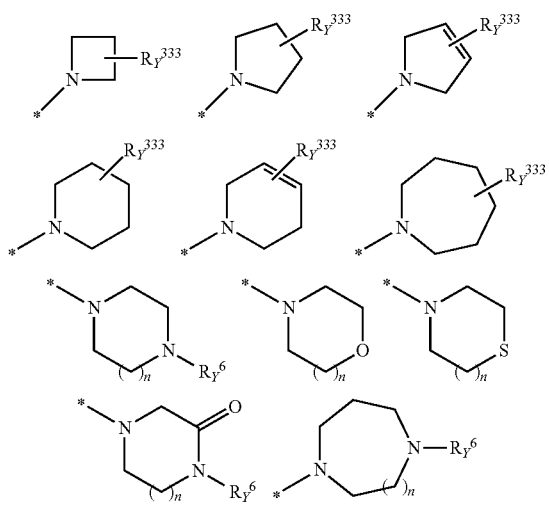

-continued

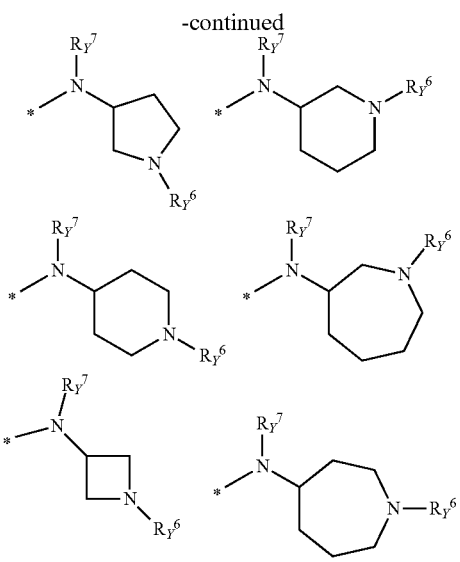

n = 1, 2 where the aforementioned radicals may independently of one another in each case have one or two substituents $R_Y^{331}$ and/or $R_Y^{332}$ which are selected independently of one another and independently of their respective occurrence from the group consisting of hydrogen, fluorine, OH, and in each case optionally substituted O—$C_1$-$C_4$-alkyl, phenyl and $C_1$-$C_4$-alkyl.

$R_Y^{333}$ is a radical selected from the group consisting of hydrogen and in each case optionally substituted $C_1$-$C_6$-alkyl, $C_2$-$C_6$-alkenyl, $C_2$-$C_6$-alkynyl, phenyl and $C_1$-$C_4$-alkylene-phenyl;

$R_Y^5$ is a radical selected from the group consisting of hydrogen and in each case optionally substituted $C_1$-$C_4$-alkyl;

$R_Y^6$ is a radical selected from the group consisting of hydrogen and in each case optionally substituted $C_1$-$C_6$-alkyl, $C_2$-$C_6$-alkenyl, $C_2$-$C_6$-alkynyl, phenyl and $C_1$-$C_4$-alkylene-phenyl;

$R_Y^7$ is a radical selected from the group consisting of hydrogen and in each case optionally substituted $C_1$-$C_6$-alkyl, $C_2$-$C_6$-alkenyl, $C_2$-$C_6$-alkynyl, phenyl and $C_1$-$C_4$-alkylene-phenyl;

$R_Y^8$ is a radical selected from the group consisting of OH, $NH_2$, and in each case optionally substituted $NH(C_1$-$C_4$-alkyl), $N(C_1$-$C_4$-alkyl)($C_1$-$C_4$-alkyl), $NH(C_2$-$C_4$-alkylene-OH), $N(C_1$-$C_4$-alkyl)($C_2$-$C_4$-alkylene-OH), $NH(C_2$-$C_4$-alkylene-O—$C_1$-$C_4$-alkyl), $N(C_1$-$C_4$-alkyl)($C_2$-$C_4$-alkylene-O—$C_1$-$C_4$-alkyl), $NH(C_3$-$C_7$-cycloalkyl), $N(C_1$-$C_4$-alkyl)($C_3$-$C_7$-cycloalkyl), $NH(C_1$-$C_4$-haloalkyl), $N(C_1$-$C_4$-alkyl)($C_1$-$C_4$-haloalkyl), O—C1-C4-alkyl, and the ring radical $R_Y^{81}$ where $R_Y^{81}$ is a radical independently of its respective occurrence selected from the group consisting of the respective individual radicals

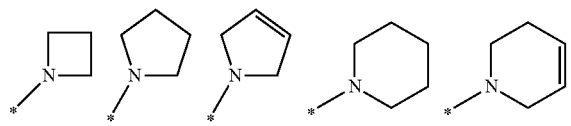

-continued

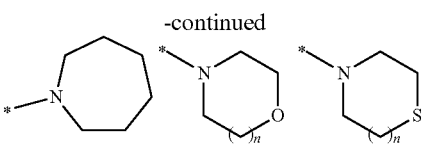

n = 1, 2

Another embodiment (embodiment B) of the invention relates to compounds of the formula I, to the tautomeric, enantiomeric and/or diastereomeric forms thereof, the prodrugs thereof, and to the physiologically tolerated salts of the aforementioned compounds, wherein the radicals $R^1$, $R^2$, $A^1$ and $A^2$ have one of meanings given for embodiment A or in claim 1 and wherein $R^3$ is a radical (X)—(Y), wherein X is as defined for embodiment A, X being in particular CO, Y is a radical $R_Y^1$, or a radical $NR_Y^5(C_1$-$C_4$-alkylene)-$R_Y^3$, where $R_Y^1$ is a cyclic radical selected from

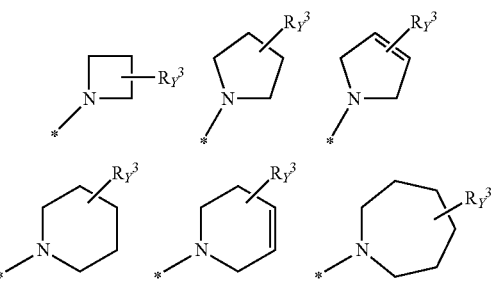

$R_Y^3$ is $N(R_Y^7)R_Y^9$, $N(R_Y^7)CH_2R_Y^9$, a radical $R_Y^{33a}$, a radical $CH_2R_Y^{33}$, wherein $R_Y^7$ and $R_Y^{33}$ are as defined herein or in claim 1 or 2, and wherein $R_Y^{33a}$ is one of the following radicals

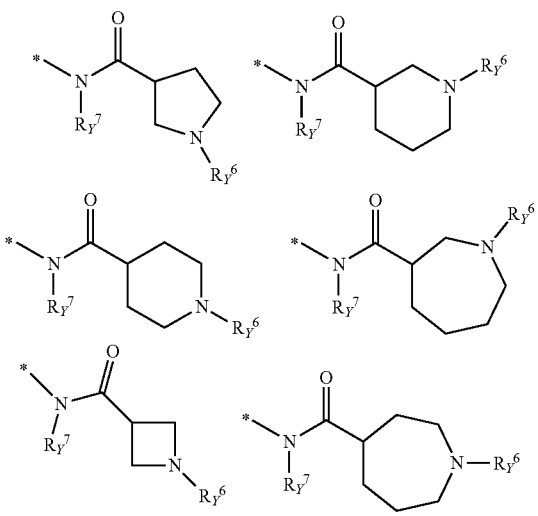

wherein $R_Y^6$ and $R_Y^7$ are as defined for embodiment A or in claim 1 and $R_Y^9$ is a 5- or 6-membered heteroaromatic radical having 2, 3, 4 or 5 carbon atom as ring members and 1, 2 or 3 heteroatoms, selected from O, S and N, wherein the 5- or 6-membered heteroaromatic radical may be unsubstituted or may have one or two substituents $R_Y^{331}$ and/or $R_Y^{332}$, wherein $R_Y^{331}$ and/or $R_Y^{332}$ are as defined for embodiment A or in claim 1.

In a preferred embodiment of the present invention, at least one compound of the general formula (I) as detailed above or in claim 1 or 2 is provided, in which $A^1$ is an aromatic, heteroaromatic, partly aromatic or partly heteroaromatic mono- or bicyclic ring having 1, 2, 3, 4, 5, 6, 7, 8, 9 or 10 carbon atoms as ring members, which may besides additionally comprise 0, 1, 2, 3 or 4 identical or different heteroatoms independently of one another selected from the group consisting of nitrogen, oxygen and sulfur as ring members, and which may be substituted by one, two or three radicals $R_A^{11}$, $R_A^{12}$ and/or $R_A^{13}$ which are selected independently of one another and independently of their respective occurrence from the group consisting of hydrogen, bromine, chlorine, fluorine, CN, $CF_3$, $OCF_3$, $OCHF_2$, OH, and in each case optionally substituted $O-C_1-C_4$-alkyl and $C_1-C_4$-alkyl; or in each case optionally substituted $C_1-C_6$-alkyl, $C_2-C_6$-alkenyl, $C_2-C_6$-alkynyl, $C_3-C_6$-cycloalkyl, $C_3-C_6$-cycloalkenyl, $C_1-C_4$-alkylene-phenyl.

$A^2$ is hydrogen or in each case optionally substituted $C_1-C_6$-alkyl, $C_1-C_6$-alkenyl, $C_1-C_6$-alkynyl and $C_3-C_6$-cycloalkyl;

or where

A1 and A2 form together with the carbon atom to which they are bonded an in each case optionally substituted 3- to 7-membered carbocyclic ring (spiro linkage) which may additionally comprise a heteroatom as ring member selected from the group consisting of O, S and $NR_A^{14}$ in which $R_A^{14}$ is a radical selected from the group consisting of hydrogen and in each case optionally substituted $C_1-C_6$-alkyl, aryl and $C_1-C_4$-alkylene-aryl, and where the carbo- or heterocarbocyclic ring formed in this way may be substituted by one, two or three radicals $R_A^{11}$, $R_A^{12}$ and/or $R_A^{13}$ which may independently of one another and independently of their respective occurrence assume the aforementioned meanings;

B is an aromatic, heteroaromatic, partly aromatic or partly heteroaromatic mono- or bicyclic ring having 1, 2, 3, 4, 5, 6, 7, 8, 9 or 10 C atoms as ring members, which may additionally comprise 0, 1, 2, 3 or 4 identical or different heteroatoms independently of one another selected from the group consisting of nitrogen, oxygen and sulfur as ring members, and which may be substituted by one, two or three radicals $R_B^1$, $R_B^2$ and/or $R_B^3$, where $R_B^1$, $R_B^2$ and $R_B^3$ are selected independently of one another and independently of their respective occurrence from the group consisting of hydrogen, chlorine, bromine, fluorine, CN, $CF_3$, $OCF_3$, $OCHF_2$, $OCH_2F$, $OCH_2CF_3$, $OCH_2-CHF_2$, OH, and in each case optionally substituted $O-C_1-C_4$-alkyl, $C_1-C_4$-alkyl, $C_2-C_4$-alkenyl and $C_2-C_4$-alkynyl, $R^1$ is a radical selected from the group consisting of hydrogen, bromine, chlorine, fluorine, iodine, CN, $CF_3$, $OCF_3$, $OCHF_2$, and/or in each case optionally substituted $O-C_1-C_4$-alkyl, $C_1-C_4$-alkyl, $C_1-C_4$-alkenyl, $C_2-C_4$-alkynyl; $NH(C_1-C_4$-alkyl), $N(C_1-C_4$-alkyl)($C_1-C_4$-alkyl), $NO_2$, NHCHO, $NHCO(C_1-C_4$-alkyl) and $NHCONH_2$;

$R^2$ is a radical selected from the group consisting of hydrogen, chlorine, fluorine and trifluoromethyl and/or in each case optionally substituted $C_1-C_4$-alkyl and $O-C_1-C_4$-alkyl;

$R^3$ is a radical (X)—(Y), where

X is CO, $SO_2$ or (C=NH), in particular CO,

Y is a radical selected from the group consisting of OH, $NH_2$, and/or in each case optionally substituted $NH(C_1-C_4$-alkyl), $N(C_1-C_4$-alkyl)($C_1-C_4$-alkyl), $NH(C_2-C_4$-alkylene-OH), $N(C_1-C_4$-alkyl)($C_2-C_4$-alkylene-OH), $NH(C_2-C_4$-alkylene-O—$C_1-C_4$-alkyl), $N(C_1-C_4$-alkyl)($C_2-C_4$-alkylene-O—$C_1-C_4$-alkyl), $NH(C_3-C_7$-cycloalkyl), $N(C_1-C_4$-alkyl) ($C_3-C_7$-cycloalkyl), $NH(C_1-C_4$-haloalkyl), $N(C_1-C_4$-alkyl)($C_1-C_4$-haloalkyl), $N(R_Y^5)(C1-C4$-alkylene)-$R_Y^3$, and the radical $R_Y^1$; in which $R_Y^1$ is independently of its respective occurrence a radical selected from the group consisting of the respective individual radicals mentioned below

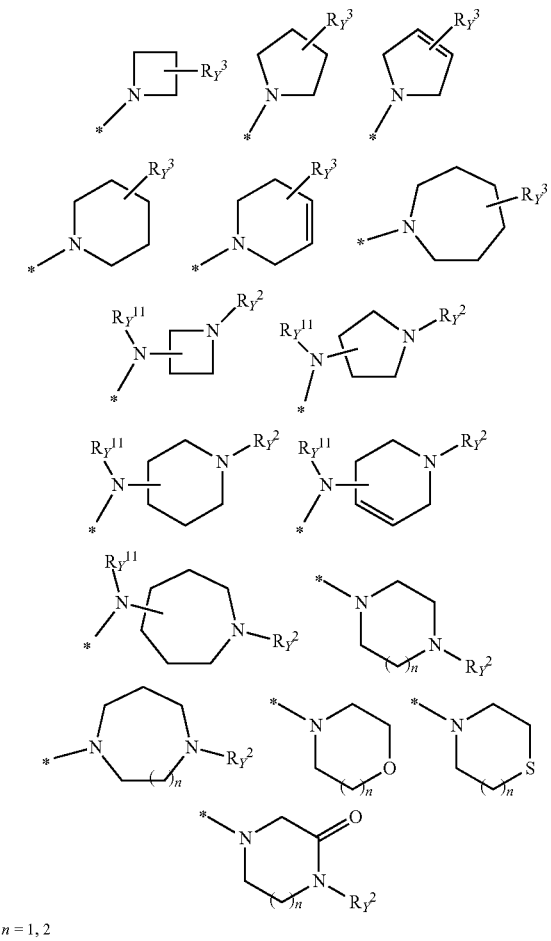

$n = 1, 2$ where the aforementioned radicals may in each case have one or two substituents $R_Y^{12}$ and/or $R_Y^{13}$ which are selected independently of one another and independently of their respective occurrence from the group consisting of hydrogen, fluorine, OH, and/or in each case optionally substituted $O-C_1-C_4$-alkyl, phenyl and $C_1-C_4$-alkyl;

$R_Y^{11}$ is a radical selected from the group consisting of hydrogen, and/or in each case optionally substituted $C_1-C_6$-alkyl, $C_2-C_6$-alkenyl or $C_2-C_6$-alkynyl;

$R_Y^2$ is a radical selected from the group consisting of hydrogen and/or in each case optionally substituted $C_1$-$C_6$-alkyl, $C_2$-$C_6$-alkenyl, $C_2$-$C_6$-alkynyl, phenyl, $C_1$-$C_4$-alkylene-phenyl, $C_1$-$C_4$-haloalkyl, $C_3$-$C_7$-cycloalkyl, pyridine, pyrimidine, pyrazine, pyridazine, furan, thiophene, pyrrole, oxazole, isoxazole, thiazole, imidazole, pyrazole, 1,2,4-oxadiazole, 1,2,5-oxadiazole, 1,3,4-oxadiazole, thiadiazole, triazole, 1,3,5-triazine, tetrazole, ($C_2$-$C_4$-alkylene)$R_Y^3$ and the ring radical $R_Y^{22}$, where $R_Y^{22}$ irrespective of its respective occurrence is a radical selected from the group consisting of the respective individual radicals mentioned below

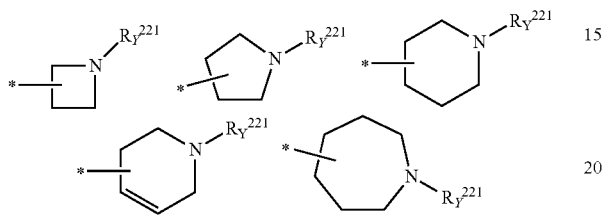

where the aforementioned radicals may in each case have one or two substituents $R_Y^{222}$ and/or $R_Y^{223}$ which are selected independently of one another and independently of their respective occurrence from the group consisting of hydrogen, fluorine, OH, and/or in each case optionally substituted O—$C_1$-$C_4$-alkyl, phenyl and $C_1$-$C_4$-alkyl; and where $R_Y^{221}$ is a radical selected from the group consisting of hydrogen, and/or in each case optionally substituted $C_1$-$C_6$-alkyl, $C_2$-$C_6$-alkenyl and $C_2$-$C_6$-alkynyl;

$R_Y^3$ is a radical selected from the group consisting of hydrogen, $NH_2$, and/or in each case optionally substituted $NH(C_1$-$C_4$-alkyl), $N(C_1$-$C_4$-alkyl)($C_1$-$C_4$-alkyl), $NH(C_2$-$C_4$-alkylene-OH), $N(C_1$-$C_4$-alkyl)($C_2$-$C_4$-alkylene-OH), $NH(C_2$-$C_4$-alkylene-O—$C_1$-$C_4$-alkyl), $N(C_1$-$C_4$-alkyl)($C_2$-$C_4$-alkylene-O—$C_1$-$C_4$-alkyl), $NH(C_3$-$C_7$-cycloalkyl), $N(C_1$-$C_4$-alkyl)($C_3$-$C_7$-cycloalkyl), $NH(C_1$-$C_4$-haloalkyl), $N(C_1$-$C_4$-alkyl)($C_1$-$C_4$-haloalkyl), phenyl, pyridine, pyrimidine, pyrazine, pyridazine, furan, thiophene, pyrrole, oxazole, isoxazole, thiazole, imidazole, pyrazole, 1,2,4-oxadiazole, 1,2,5-oxadiazole, 1,3,4-oxadiazole, thiadiazole, triazole, 1,3,5-triazine, tetrazole, $NH(C_2$-$C_4$-alkylene)-$R_Y^8$, $N(R_Y^7)(C_2$-$C_4$-alkylene)-$R_Y^8$, $N(R_Y^7)R_Y^9$, $N(R_Y^7)CH_2R_Y^9$, a radical $R_Y^{33}$, a radical $CH_2R_Y^{33}$ and an aromatic radical, selected from phenyl, pyridine, pyrimidine, pyrazine, pyridazine, furan, thiophene, pyrrole, oxazole, isoxazole, thiazole, isothiazole, imidazole, pyrazole, 1,2,4-oxadiazole, 1,2,5-oxadiazole, 1,3,4-oxadiazole, thiadiazole, triazole, 1,3,5-triazine and tetrazole, the aromatic radical being substituted or carrying 1 or 2 substitutents $R_Y^{331}$ and/or $R_Y^{332}$, in which $R_Y^{33}$ irrespective of its respective occurrence is a radical selected from the group consisting of the respective individual radicals mentioned below

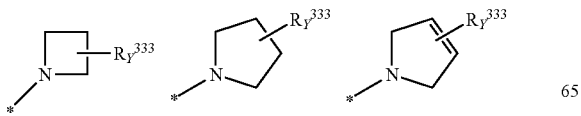

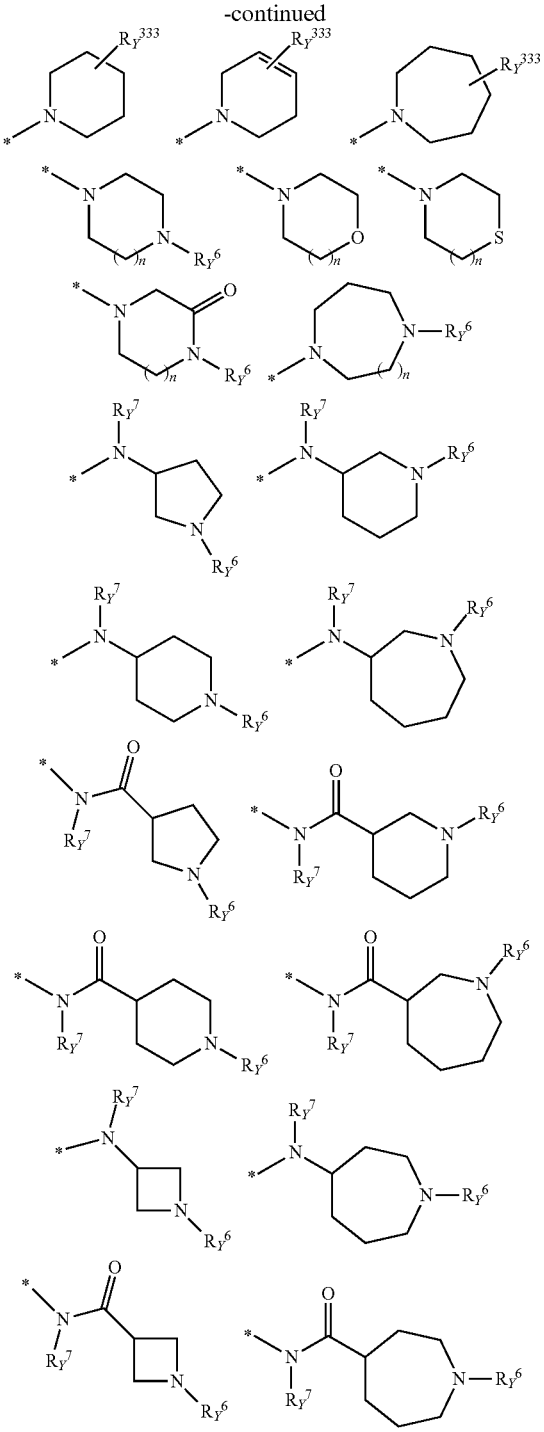

$n = 1, 2$ where the aforementioned radicals may in each case have one or two substituents $R_Y^{331}$ and/or $R_Y^{332}$ which are selected independently of one another and independently of their respective occurrence from the group consisting of hydrogen, fluorine, OH, and/or in each case optionally substituted O—$C_1$-$C_4$-alkyl, phenyl and $C_1$-$C_4$-alkyl;

$R_Y^{333}$ is a radical selected from the group consisting of hydrogen and/or in each case optionally substituted C$_1$-C$_6$-alkyl, C$_2$-C$_6$-alkenyl, C$_2$-C$_6$-alkynyl, phenyl and C$_1$-C$_4$-alkylene-phenyl;

R$_Y^5$ is a radical selected from the group consisting of hydrogen and optionally substituted C$_1$-C$_4$-alkyl;

R$_Y^6$ is a radical selected from the group consisting of hydrogen and/or in each case optionally substituted C$_1$-C$_6$-alkyl, C$_2$-C$_6$-alkenyl, C$_2$-C$_6$-alkynyl, phenyl and C$_1$-C$_4$-alkylene-phenyl;

R$_Y^7$ is a radical selected from the group consisting of hydrogen and/or in each case optionally substituted C$_1$-C$_6$-alkyl, C$_2$-C$_6$-alkenyl, C$_2$-C$_6$-alkynyl, phenyl and C$_1$-C$_4$-alkylene-phenyl;

R$_Y^8$ is a radical selected from the group consisting of OH, NH$_2$, and/or in each case optionally substituted NH(C$_1$-C$_4$-alkyl), N(C$_1$-C$_4$-alkyl)(C$_1$-C$_4$-alkyl), NH(C$_2$-C$_4$-alkylene-OH), N(C$_1$-C$_4$-alkyl)(C$_2$-C$_4$-alkylene-OH), NH(C$_2$-C$_4$-alkylene-O—C$_1$-C$_4$-alkyl), N(C$_1$-C$_4$-alkyl)(C$_2$-C$_4$-alkylene-O—C$_1$-C$_4$-alkyl), NH(C$_3$-C$_7$-cycloalkyl), N(C$_1$-C$_4$-alkyl)(C$_3$-C$_7$-cycloalkyl), NH(C$_1$-C$_4$-haloalkyl), N(C$_1$-C$_4$-alkyl)(C$_1$-C$_4$-haloalkyl), O—C$_1$-C$_4$-alkyl, and the ring radical R$_Y^{81}$, in which R$_Y^{81}$ is independently of its respective occurrence a radical selected from the group consisting of the respective individual radicals mentioned below

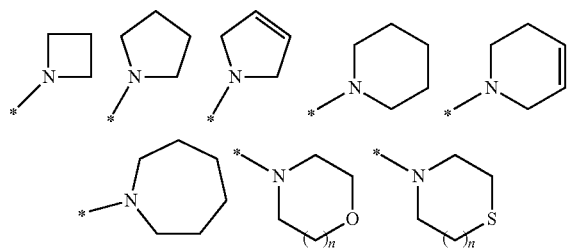

n = 1, 2

R$_Y^9$ is a 5- or 6-membered heteroaromatic radical having 2, 3, 4 or 5 carbon atom as ring members and 1, 2 or 3 heteroatoms, selected from O, S and N, wherein the 5- or 6-membered heteroaromatic radical may be unsubstituted or may have one or two substituents R$_Y^{331}$ and/or R$_Y^{332}$, and/or the tautomeric, enantiomeric and/or diastereomeric forms thereof, and/or prodrugs thereof, and the physiologically tolerated salts of the aforementioned compound or compounds.

Each of these aforementioned definitions of a variable can with any of the aforementioned definitions of the remaining variables. This applies in particular to the combination of preferred definitions of a variable with any or preferred definitions of the remaining variables.

A particular preferred embodiment of the invention relates to compounds of the formula I, to the tautomeric, enantiomeric and/or diastereomeric forms thereof, the prodrugs thereof, and to the physiologically tolerated salts of the aforementioned compounds, wherein the radicals R$^1$, R$^2$, A$^1$ and A$^2$ are as defined herein or in claim 1, 2 or 3 and wherein R$^3$ is a radical (X)—(Y), wherein X is as defined herein, in particular C(=O), Y is a radical R$_Y^1$, wherein R$_Y^1$ is as defined herein or in claim 1, 2 or 3 (embodiment C). In this embodiment R$_Y^1$ is preferably a cyclic radical selected from

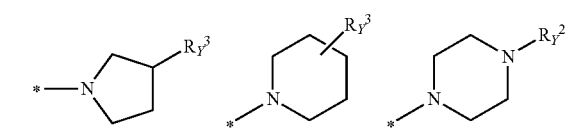

wherein R$_Y^2$ and R$_Y^3$ are as defined herein or in claim 1, 2 or 3.

Independently of its respective occurrence but in particular in this embodiment C, R$_Y^2$ is preferably selected from pyridyl, 2-methylpyridyl and a radical R$_Y^{22}$.

Independently of its respective occurrence but in particular in this embodiment C, R$_Y^{22}$ is preferably selected from the following radicals:

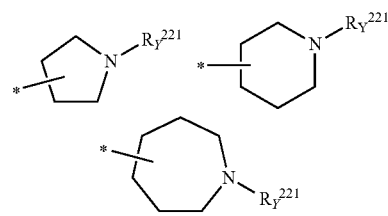

wherein R$_Y^{221}$ is as defined herein or in claim 1, 2 or 3 and in particular C$_1$-C$_6$-alkyl or hydrogen.

Independently of its respective occurrence but in particular in this embodiment C, R$_Y^3$ is preferably selected from the group consisting of NH$_2$, NH(C$_1$-C$_4$-alkyl), N(C$_1$-C$_4$-alkyl)(C$_1$-C$_4$-alkyl), NH(C$_2$-C$_4$-alkylene-OH), N(C$_1$-C$_4$-alkyl)(C$_2$-C$_4$-alkylene-OH), NH(C$_2$-C$_4$-alkylene-O—C$_1$-C$_4$-alkyl), N(C$_1$-C$_4$-alkyl)(C$_2$-C$_4$-alkylene-O—C$_1$-C$_4$-alkyl), NH(C$_3$-C$_7$-cycloalkyl), N(C$_1$-C$_4$-alkyl)(C$_3$-C$_7$-cycloalkyl), NH(C$_1$-C$_4$-haloalkyl), N(C$_1$-C$_4$-alkyl)(C$_1$-C$_4$-haloalkyl), N(R$_Y^7$)R$_Y^9$, N(R$_Y^7$)CH$_2$R$_Y^9$, a radical R$_Y^{33}$, a radical CH$_2$R$_Y^{33}$ and an aromatic radical, selected from pyridine, which optionally carries a C$_1$-C$_4$-alkyl radical. In this embodiment, R$_Y^7$, R$_Y^8$, R$_Y^9$, R$_Y^{33}$ are as defined herein or in claims 1 to 3.

Independently of its respective occurrence but in particular in this embodiment C, R$_Y^{33}$ is preferably selected from the following radicals:

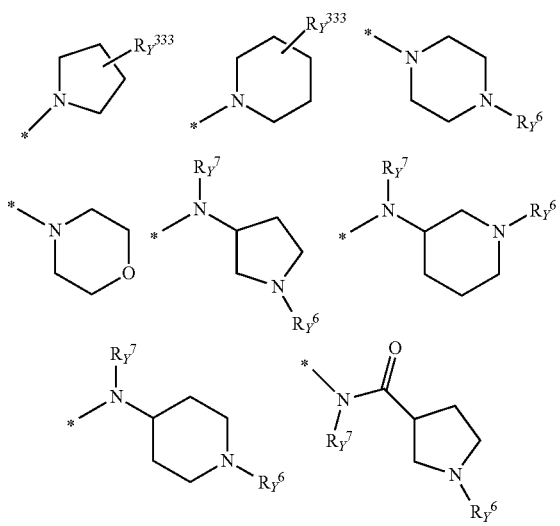

-continued

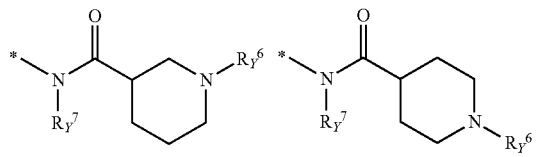

wherein $R_Y^{333}$, $R_Y^6$ and $R_Y^7$ are as defined herein or in claim 1, 2 or 3 and in particular $C_1$-$C_6$-alkyl or hydrogen.

Independently of its respective occurrence but in particular in this embodiment C, Y is one of the following radicals:

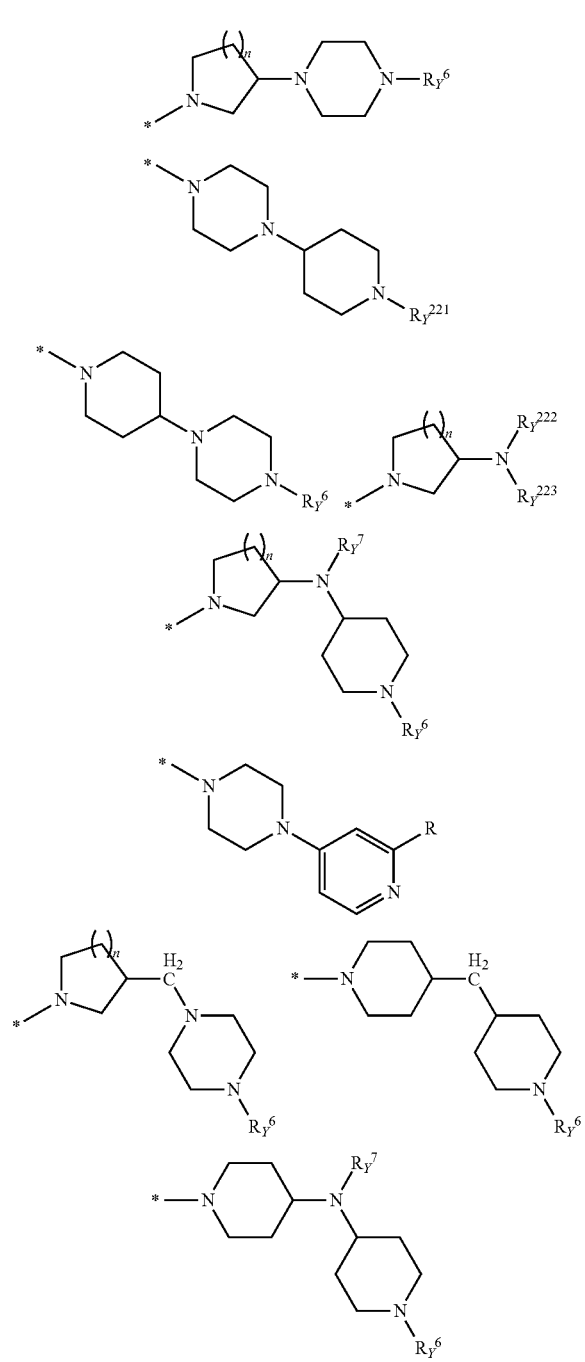

-continued

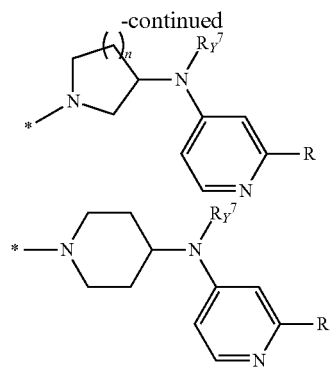

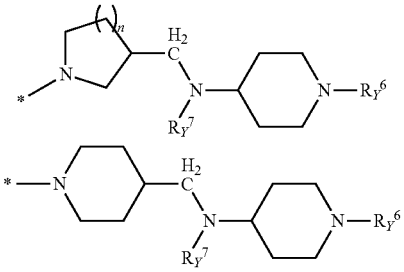

wherein n is 1 or 2, and wherein $R_Y^6$, $R_Y^7$, $R_Y^{221}$, $R_Y^{222}$ and $R_Y^{223}$ are as defined herein or in the claims. R is hydrogen or methyl, in particular hydrogen. In particular $R_Y^6$, $R_Y^7$, $R_Y^{221}$, $R_Y^{222}$ and $R_Y^{223}$ are selected independently of each other from the group consisting of hydrogen and/or in each case optionally substituted $C_1$-$C_6$-alkyl and $CH_2$-phenyl, in particular from hydrogen and $C_1$-$C_6$-alkyl. In particular, $R_Y^6$ is $C_1$-$C_6$-alkyl. In particular, $R_Y^7$ is hydrogen or $C_1$-$C_6$-alkyl. In particular, $R_Y^{221}$ is $C_1$-$C_6$-alkyl. In particular, $R_Y^{222}$ and $R_Y^{223}$ are selected independently of each other from the group consisting of hydrogen and $C_1$-$C_6$-alkyl.

In a preferred embodiment of the present invention, at least one compound of the general formula (I) as described above or according to claim 1 or 2 is provided in which the radicals $A^1$, $A^2$, B, X, Y, may in each case independently of one another, unless described otherwise hereinafter, assume one of the meanings mentioned in claim 1 or 2, wherein the radical $R^1$ and the radical $R^2$ have the following meanings:

$R^1$ is hydrogen, fluorine, chlorine, iodine, CN or ethynyl (acetylenyl), and $R^2$ is hydrogen and/or the tautomeric, enantiomeric and/or diastereomeric forms thereof, and/or prodrugs thereof, and the physiologically tolerated salts thereof. In this preferred embodiment, $R^1$ is particularly preferable chlorine or CN.

A particular preferred embodiment of the invention relates to compounds of the formula I, to the tautomeric, enantiomeric and/or diastereomeric forms thereof, the prodrugs thereof, and to the physiologically tolerated salts of the aforementioned compounds, wherein the radicals B, $R^1$, $R^2$, $R^3$ and $A^2$ are as defined herein or in the claims and wherein $A^1$ is an phenyl or a 5 or 6 membered heteroaromatic ring having 1, 2, 3, 4 or 5 carbon atoms as ring members additionally comprise 1, 2, 3 or 4 identical or different heteroatoms independently of one another selected from the group consisting of nitrogen, oxygen and sulfur as ring members, and which may be substituted by one, two or three radicals $R_A^{11}$, $R_A^{12}$ and/or $R_A^{13}$ as defined above is a radical

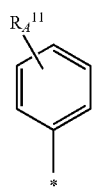

in which $R_A^{11}$ is as defined herein or in the claims and in particular a radical selected from the group consisting of hydrogen, chlorine, fluorine, or in each case optionally substituted O—$C_1$-$C_4$-alkyl and $C_1$-$C_4$-alkyl.

A particular preferred embodiment of the invention relates to compounds of the formula I, to the tautomeric, enantiomeric and/or diastereomeric forms thereof, the prodrugs thereof, and to the physiologically tolerated salts of the aforementioned compounds, wherein the radicals B, $R^1$, $R^2$, $R^3$ and $A^1$ are as defined herein or in the claims and wherein $A^2$ is hydrogen.

A particular preferred embodiment of the invention relates to compounds of the formula I, to the tautomeric, enantiomeric and/or diastereomeric forms thereof, the prodrugs thereof, and to the physiologically tolerated salts of the aforementioned compounds, wherein the radicals $R^1$, $R^2$, $R^3$, $A^1$ and $A^2$ are as defined herein or in the claims and wherein B is an aromatic or heteroaromatic radical, selected from phenyl, pyridyl, in particular 2-pyridyl, quinolinyl, in particular 8-quinolinyl, 2-thienyl and 3-thienyl, wherein the aromatic or heteroaromatic radical is unsubstituted or may carry 1 or 2 radicals $R_A^{11}$, $R_A^{12}$ which are as defined herein or in the claims. Preferably $R_A^{11}$, $R_A^{12}$ are selected independently of each other from the group consisting of hydrogen, chlorine, fluorine, O—$C_1$-$C_4$-alkyl and $C_1$-$C_4$-alkyl. Examples of particularly preferable radicals B include the following radicals.

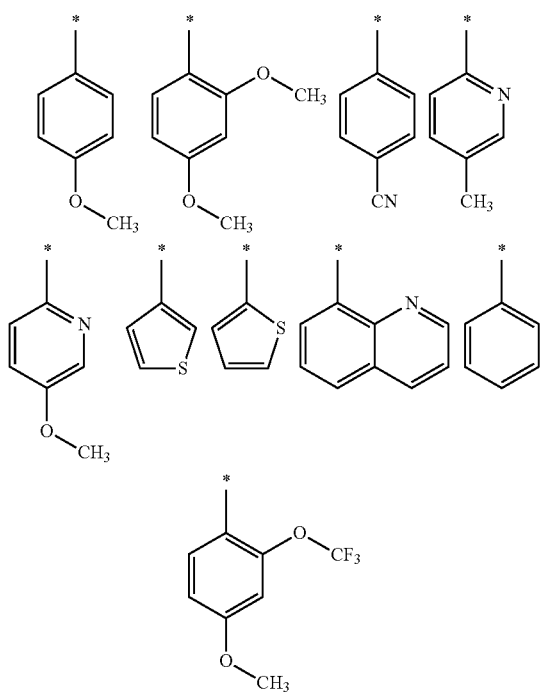

Each of these aforementioned definitions of a variable can with any of the aforementioned definitions of the remaining variables. This applies in particular to the combination of preferred definitions of a variable with any or preferred definitions of the remaining variables.

In a preferred embodiment of the present invention, at least one compound of the general formula (I) as detailed above or according to any of claims 1 to 3 is provided, in which the radicals $A^1$, $A^2$, B, Y, $R^1$ and $R^2$ may in each case independently of one another, unless described otherwise hereinafter, assume one of the meanings mentioned above or in any of claims 1 to 3, and in which $A^1$ is a radical selected from the group consisting of the in each case optionally substituted $C_1$-$C_6$-alkyl, $C_2$-$C_6$-alkenyl, $C_2$-$C_6$-alkynyl, $C_3$-$C_6$-cycloalkyl and the radical

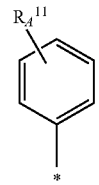

in which $R_A^{11}$ is a radical selected from the group consisting of hydrogen, chlorine, fluorine, or in each case optionally substituted O—$C_1$-$C_4$-alkyl and $C_1$-$C_4$-alkyl;

$A^2$ is hydrogen;

B is a radical selected from the group consisting of the respective individual radicals mentioned below

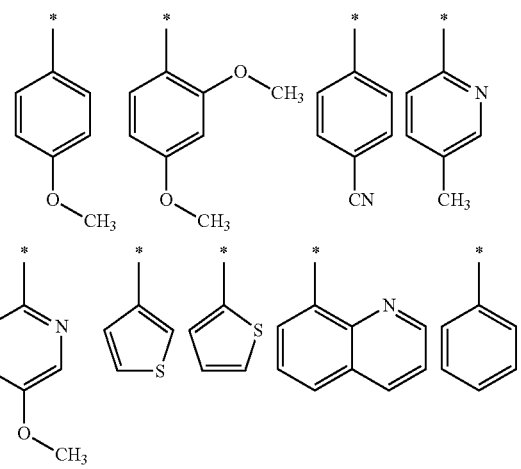

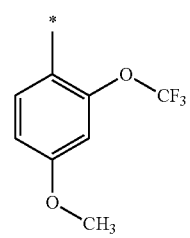

$R^1$ is selected from the group consisting of chlorine, bromine, iodine, fluorine, CN and acetylene;

$R^2$ is hydrogen $R^3$ is a radical (X)—(Y), where

X is CO;

Y is a radical selected from the group consisting of the respective individual radicals mentioned below

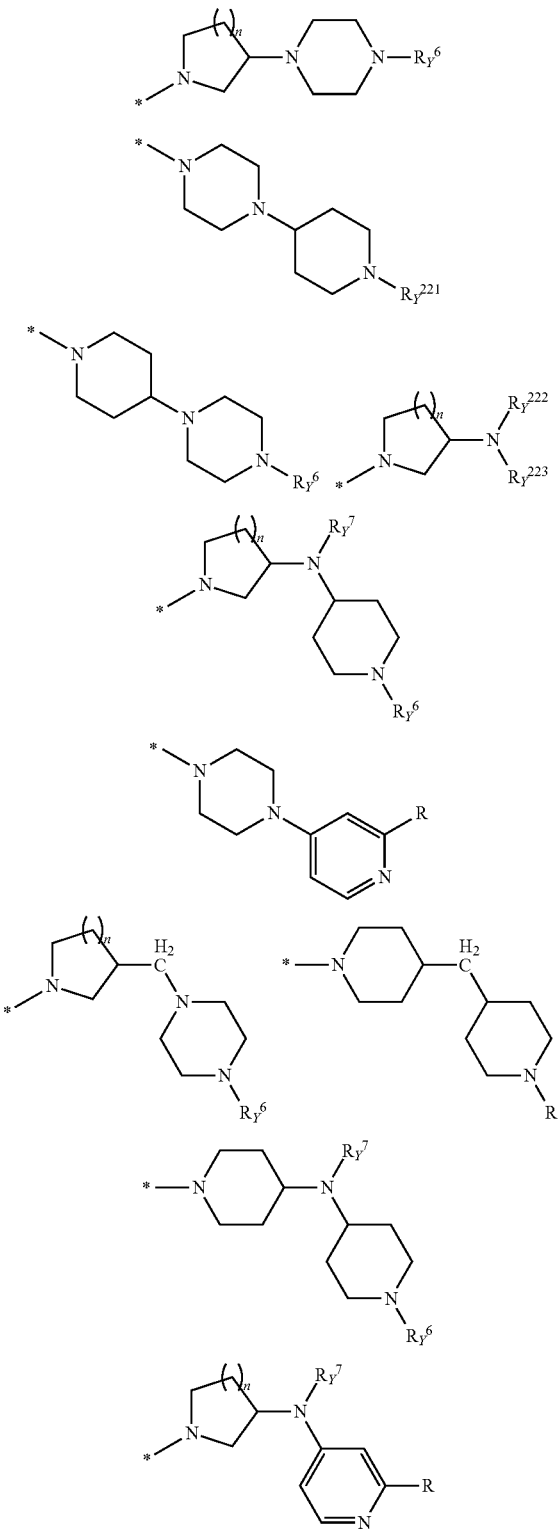

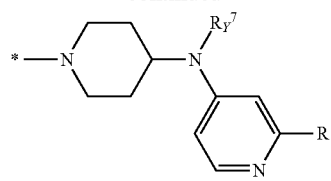

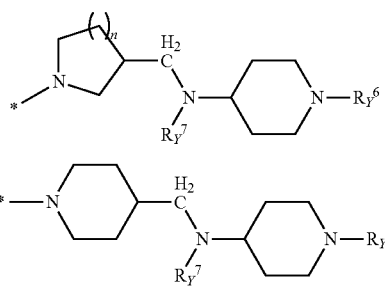

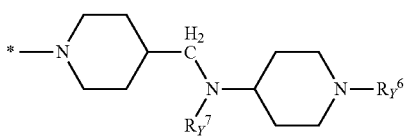

in which n is 1 or 2, R is hydrogen or methyl, $R_Y^6$ is a radical selected from the group consisting of hydrogen and/or in each case optionally substituted $C_1$-$C_6$-alkyl and $CH_2$-phenyl, in particular $C_1$-$C_6$-alkyl;

$R_Y^7$ is a radical selected from the group consisting of hydrogen and/or in each case optionally substituted $C_1$-$C_6$-alkyl and $CH_2$-phenyl, in particular hydrogen or $C_1$-$C_6$-alkyl;

$R_Y^{221}$ is a radical selected from the group consisting of hydrogen and/or in each case optionally substituted $C_1$-$C_6$-alkyl and $CH_2$-phenyl, in particular $C_1$-$C_6$-alkyl;

$R_Y^{222}$ is a radical selected from the group consisting of hydrogen and/or in each case optionally substituted $C_1$-$C_6$-alkyl and $CH_2$-phenyl, in particular hydrogen or $C_1$-$C_6$-alkyl; and $R_Y^{223}$ is a radical selected from the group consisting of hydrogen and/or in each case optionally substituted $C_1$-$C_6$-alkyl and $CH_2$-phenyl, in particular hydrogen or $C_1$-$C_6$-alkyl;

in particular Y is a radical of the following formulae

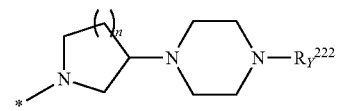

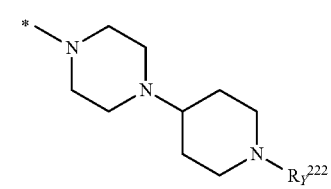

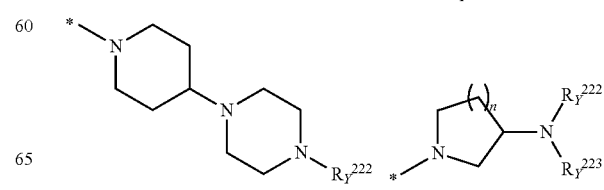

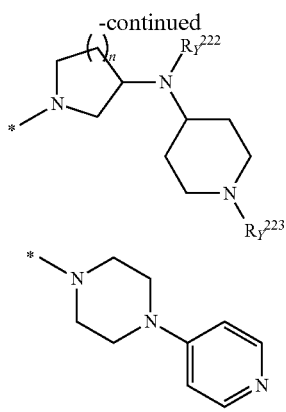

n = 1, 2 in which
R_Y^{222} is a radical selected from the group consisting of hydrogen and/or in each case optionally substituted $C_1$-$C_6$-alkyl and $CH_2$-phenyl; and
R_Y^{223} is a radical selected from the group consisting of hydrogen and/or in each case optionally substituted $C_1$-$C_6$-alkyl and $CH_2$-phenyl;
the tautomeric, enantiomeric and/or diastereomeric forms thereof, and/or the prodrugs thereof, and the physiologically tolerated salts of the aforementioned compound or compounds.

Each of these aforementioned definitions of a variable can with any of the aforementioned definitions of the remaining variables. This applies in particular to the combination of preferred definitions of a variable with any or preferred definitions of the remaining variables.

In a preferred embodiment of the present invention, at least one compound of the general formula (I) as detailed above or according to any of claims 1 to 4 is provided, in which the radicals $A^1$, $A^2$, B, Y, $R^1$ and $R^2$ may in each case independently of one another, unless described otherwise hereinafter, assume one of the meanings mentioned above or in any of claims 1 to 4, and in which $A^1$ is a radical selected from the group consisting of the respective individual radicals mentioned below

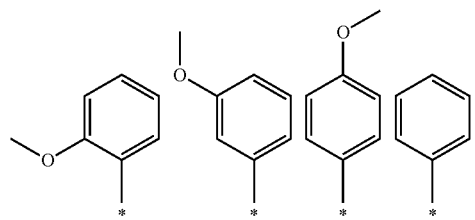

$A^2$ is hydrogen;
B is a radical selected from the group consisting of the respective individual radicals mentioned below

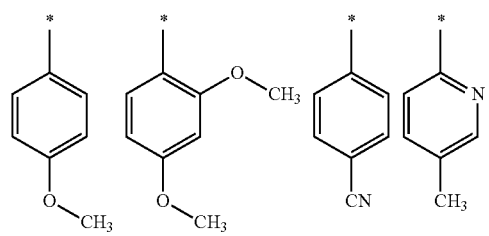

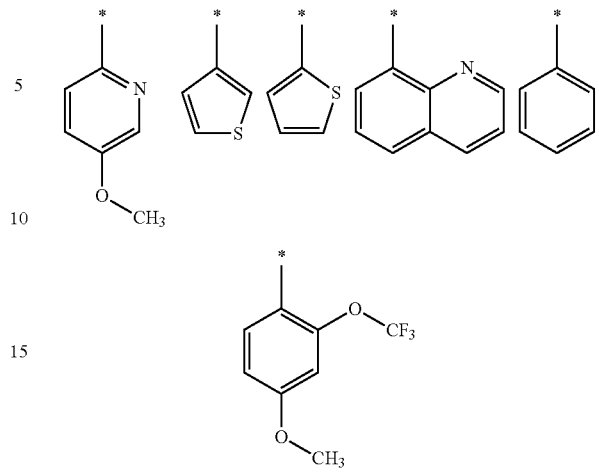

$R^1$ is selected from the group consisting of chlorine, iodine, CN and acetylene;

$R^2$ is hydrogen;

$R^3$ is a radical (X)—(Y), where
  X is CO;
  Y is a radical selected from the group consisting of the respective individual radicals mentioned below

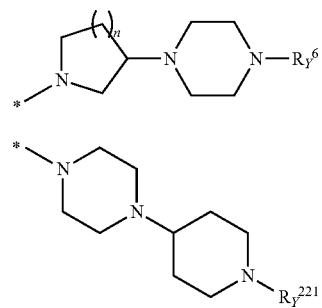

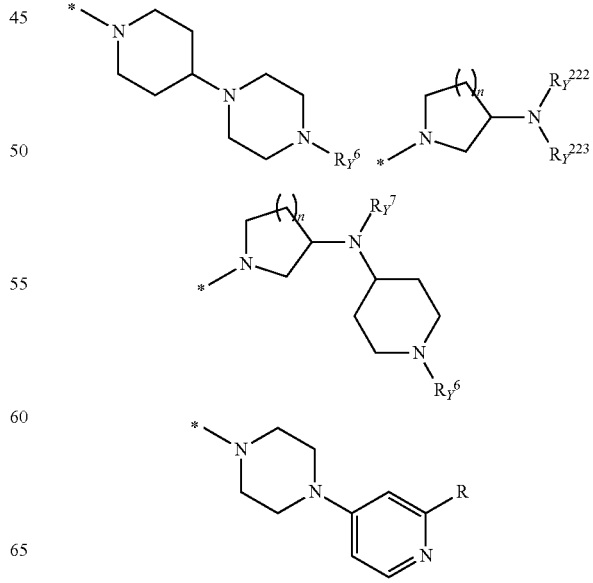

-continued

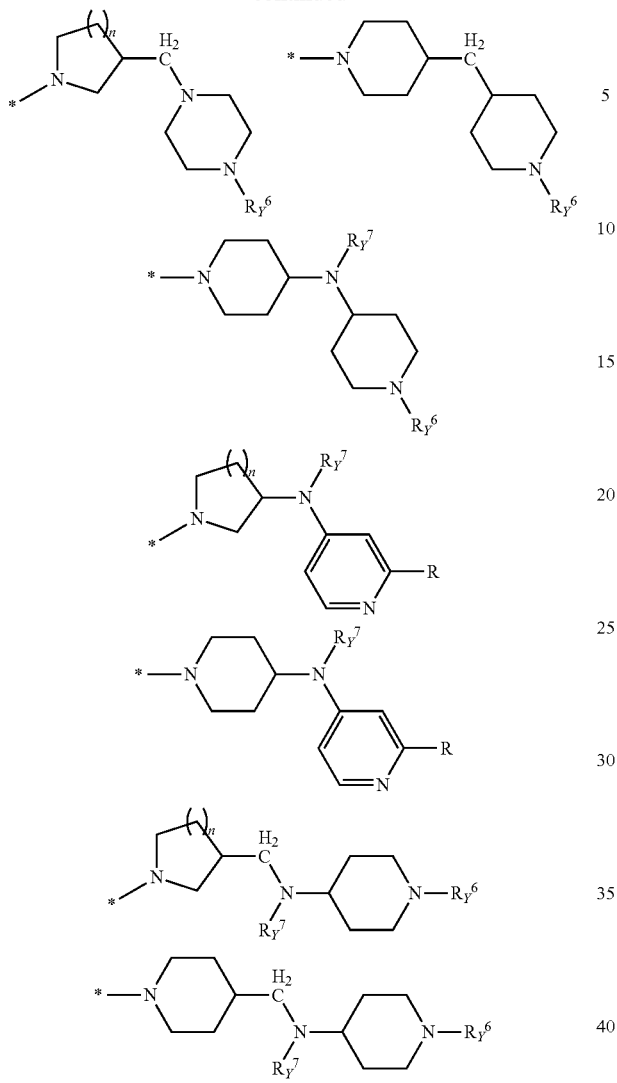

in which n is 1 or 2, R is hydrogen or methyl, $R_Y^6$ is a radical selected from the group consisting of hydrogen and/or in each case optionally substituted $C_1$-$C_6$-alkyl and $CH_2$-phenyl, in particular $C_1$-$C_6$-alkyl;

$R_Y^7$ is a radical selected from the group consisting of hydrogen and/or in each case optionally substituted $C_1$-$C_6$-alkyl and $CH_2$-phenyl, in particular hydrogen or $C_1$-$C_6$-alkyl;

$R_Y^{221}$ is a radical selected from the group consisting of hydrogen and/or in each case optionally substituted $C_1$-$C_6$-alkyl and $CH_2$-phenyl, in particular $C_1$-$C_6$-alkyl;

$R_Y^{222}$ is a radical selected from the group consisting of hydrogen and/or in each case optionally substituted $C_1$-$C_6$-alkyl and $CH_2$-phenyl, in particular hydrogen or $C_1$-$C_6$-alkyl; and $R_Y^{223}$ is a radical selected from the group consisting of hydrogen and/or in each case optionally substituted $C_1$-$C_6$-alkyl and $CH_2$-phenyl, in particular hydrogen or $C_1$-$C_6$-alkyl;

in particular Y is a radical of the following formulae

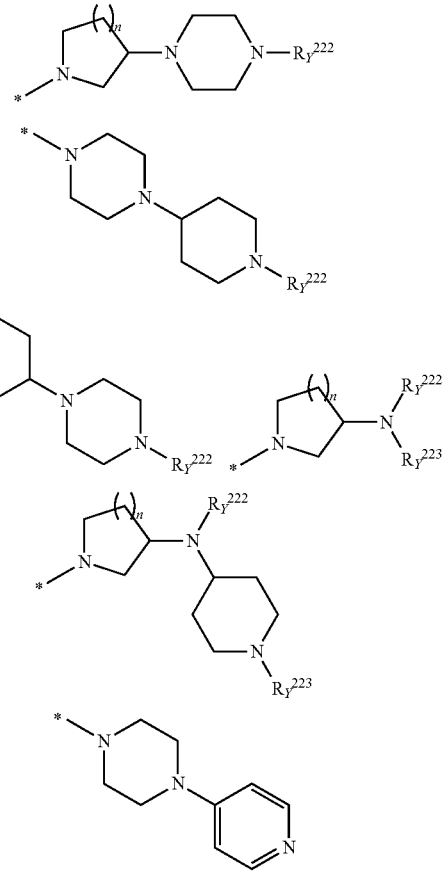

n = 1, 2 in which $R_Y^{222}$ is a radical selected from the group consisting of hydrogen, in each case optionally substituted $C_1$-$C_6$-alkyl and $CH_2$-phenyl;

$R_Y^{223}$ is a radical selected from the group consisting of hydrogen, in each case optionally substituted $C_1$-$C_6$-alkyl and $CH_2$-phenyl;

the tautomeric, enantiomeric and/or diastereomeric forms thereof, and/or the prodrugs thereof, and the physiologically tolerated salts of the aforementioned compound or compounds.

Each of these aforementioned definitions of a variable can with any of the aforementioned definitions of the remaining variables. This applies in particular to the combination of preferred definitions of a variable with any or preferred definitions of the remaining variables.

In a preferred embodiment of the present invention, at least one compound of the general formula (I) as detailed above according to any of claims 1 to 5 is provided in which the radicals $A^1$, $A^2$, B, Y, $R^1$ and $R^2$ may in each case independently of one another, unless described otherwise hereinafter, assume one of the meanings mentioned above or in any of claims 1 to 5, and in which

29

$A^1$ is a radical selected from the group consisting of the respective individual radicals mentioned below

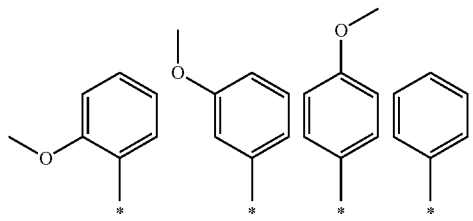

$A^2$ is hydrogen;
B is a radical selected from the group consisting of the respective individual radicals mentioned below

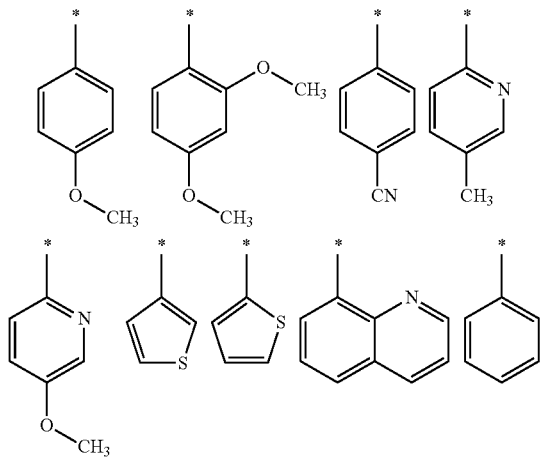

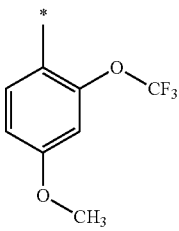

$R^1$ is CN;
$R^2$ is hydrogen;
$R^3$ is a radical (X)—(Y), where
  X is CO;
  Y is a radical selected from the group consisting of the respective individual radicals mentioned below

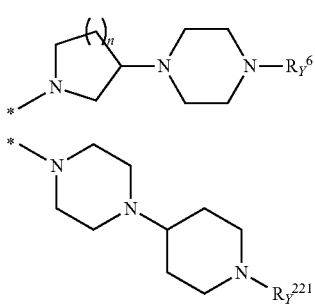

30

-continued

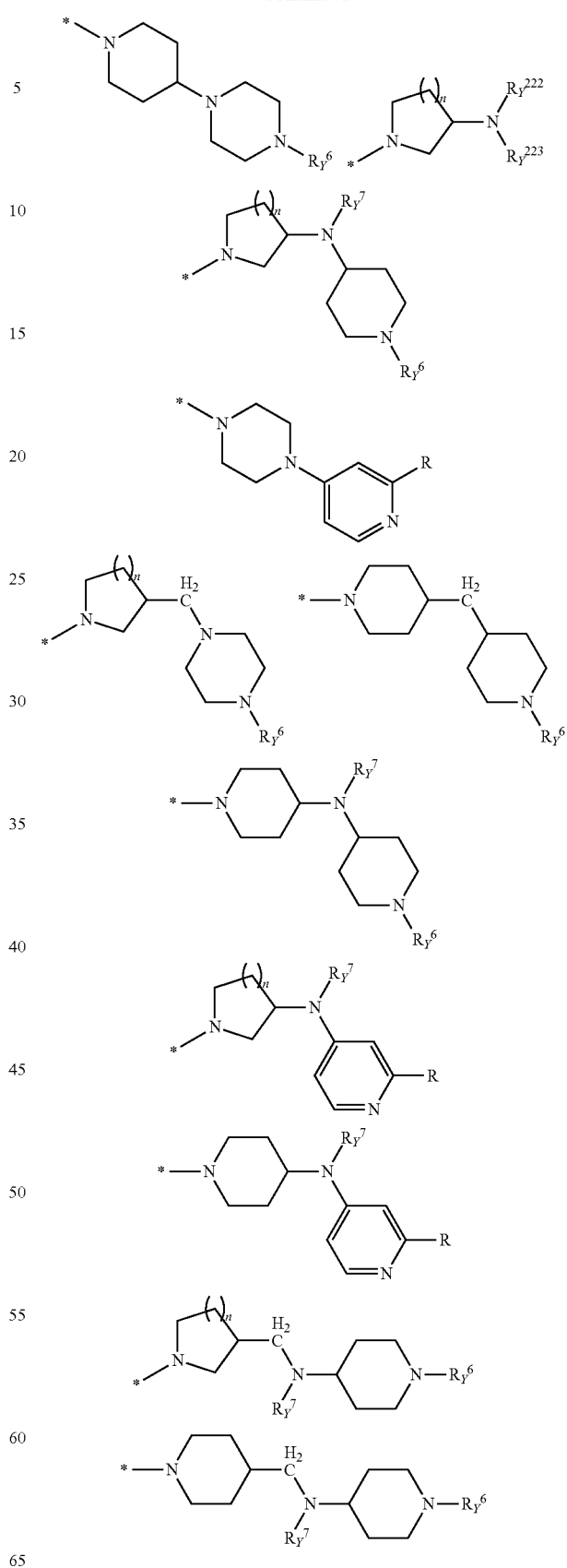

in which n is 1 or 2, R is hydrogen or methyl, $R_Y^6$ is a radical selected from the group consisting of hydrogen and/or in each case optionally substituted $C_1$-$C_6$-alkyl and $CH_2$-phenyl, in particular $C_1$-$C_6$-alkyl;

$R_Y^7$ is a radical selected from the group consisting of hydrogen and/or in each case optionally substituted $C_1$-$C_6$-alkyl and $CH_2$-phenyl, in particular hydrogen or $C_1$-$C_6$-alkyl;

$R_Y^{221}$ is a radical selected from the group consisting of hydrogen and/or in each case optionally substituted $C_1$-$C_6$-alkyl and $CH_2$-phenyl, in particular $C_1$-$C_6$-alkyl;

$R_Y^{222}$ is a radical selected from the group consisting of hydrogen and/or in each case optionally substituted $C_1$-$C_6$-alkyl and $CH_2$-phenyl, in particular hydrogen or $C_1$-$C_6$-alkyl; and $R_Y^{223}$ is a radical selected from the group consisting of hydrogen and/or in each case optionally substituted $C_1$-$C_6$-alkyl and $CH_2$-phenyl, in particular hydrogen or $C_1$-$C_6$-alkyl;

in particular Y is a radical of the following formulae

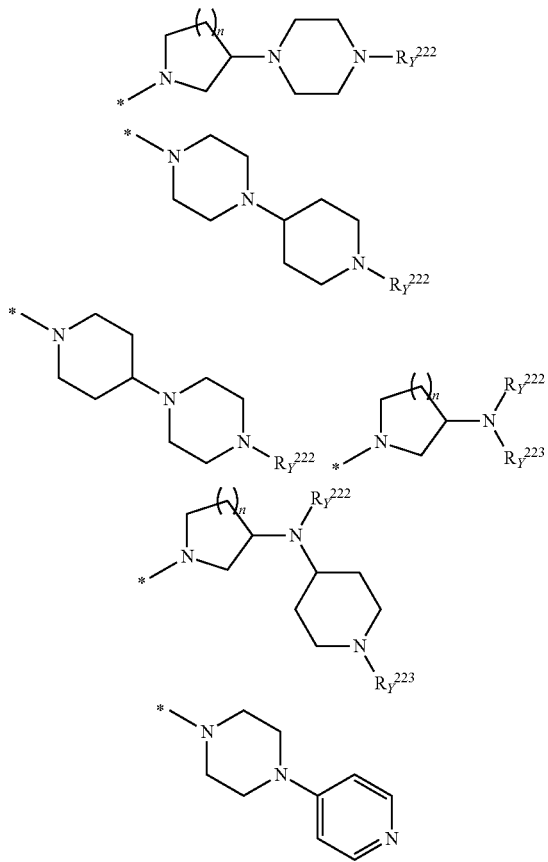

n = 1, 2 in which $R_Y^{222}$ is a radical selected from the group consisting of hydrogen, in each case optionally substituted $C_1$-$C_6$-alkyl and $CH_2$-phenyl;

$R_Y^{223}$ is a radical selected from the group consisting of hydrogen, in each case optionally substituted $C_1$-$C_6$-alkyl and $CH_2$-phenyl;

the tautomeric, enantiomeric and/or diastereomeric forms thereof, and/or the prodrugs thereof, and the physiologically tolerated salts of the aforementioned compound or compounds.

Each of these aforementioned definitions of a variable can with any of the aforementioned definitions of the remaining variables. This applies in particular to the combination of preferred definitions of a variable with any or preferred definitions of the remaining variables.

A further aspect of the present invention provides at least one compound of the general formula (I) as detailed above or according to any of claims 1 to 19 or a physiologically tolerated salt or a prodrug thereof for use as medicament.

A further aspect of the present invention provides a pharmaceutical composition comprising at least one compound of the general formula (I) as detailed above or according to any of claims 1 to 19 or of a physiologically tolerated salt or a prodrug thereof, where appropriate with one or more physiologically tolerated excipients and/or additives.

A further aspect of the present invention provides the use of at least one compound of the general formula (I) as detailed above or according to any of claims 1 to 19 or of a physiologically tolerated salt or a prodrug thereof for the treatment and/or prophylaxis of at least one vasopressin-dependent disease and/or for the manufacture of a medicament for the treatment and/or prophylaxis of at least one vasopressin-dependent disease.

A further aspect of the present invention provides the use of at least one compound of the general formula (I) as detailed above or according to any of claims 1 to 6, which has a binding affinity Ki for the vasopressin V1b receptor subtype of less than about 100 nM, preferably between about 10 nM and about 100 nM, particularly preferably less than or equal to about 10 nM.

A further aspect of the present invention provides the use of at least one compound of the general formula (I) as detailed above or according to any of claims 1 to 19 or of a physiologically tolerated salt or a prodrug thereof for the treatment and/or prophylaxis of at least one disorder selected from the group consisting of diabetes insipidus, nocturnal enuresis, incontinence, diseases in which blood coagulation disorders occur, and/or for delaying micturition and/or for the manufacture of a medicament for the treatment and/or prophylaxis of at least one of said diseases.

A further aspect of the present invention provides the use of at least one compound of the general formula (I) as detailed above or according to any of claims 1 to 19 or of a physiologically tolerated salt or a prodrug thereof for the treatment and/or prophylaxis of at least one disorder selected from the group consisting of hypertension, pulmonary hypertension, heart failure, myocardial infarction, coronary spasm, unstable angina, PTCA (percutaneous transluminal coronary angioplasty), ischemias of the heart, disorders of the renal system, edemas, renal vasospasm, necrosis of the renal cortex, hyponatremia, hypokalemia, Schwartz-Bartter syndrome, disorders of the gastrointestinal tract, gastric vasospasm, hepatocirrhosis, gastric and intestinal ulcer, emesis, emesis occurring during chemotherapy, and/or travel sickness and/or for the manufacture of a medicament for the treatment and/or prophylaxis of at least one of said diseases.

A further aspect of the present invention provides the use of at least one compound of the general formula (I) as detailed above or according to any of claims 1 to 19 or of a physiologically tolerated salt or a prodrug thereof for the treatment of affective disorders and/or for the manufacture of a medicament for the treatment of affective disorders.

A further aspect of the present invention provides the use of at least one compound of the general formula (I) as detailed above or according to any of claims 1 to 19 or of a physiologically tolerated salt or a prodrug thereof for the treatment of anxiety disorders and/or stress-related anxiety disorders and/or for the manufacture of a medicament for the treatment of anxiety disorders and/or stress-related anxiety disorders.

A further aspect of the present invention provides the use of at least one compound of the general formula (I) as detailed above or according to any of claims 1 to 19 or of a physiologically tolerated salt or a prodrug thereof for the treatment of memory impairments and/or Alzheimer's disease and/or for the manufacture of a medicament for the treatment of memory impairments and/or Alzheimer's disease.

A further aspect of the present invention provides the use of at least one compound of the general formula (I) as detailed above or according to any of claims 1 to 19 or of a physiologically tolerated salt or a prodrug thereof for the treatment of psychoses and/or psychotic disorders and/or for the manufacture of a medicament for the treatment of psychoses and/or psychotic disorders.

A further aspect of the present invention provides the use of at least one compound of the general formula (I) as detailed above or according to any of claims 1 to 19 or of a physiologically tolerated salt or a prodrug thereof for the treatment of Cushing's syndrome or other stress-related diseases and/or for the manufacture of a medicament for the treatment of Cushing's syndrome or other stress-related diseases.

A further aspect of the present invention provides the use of at least one compound of the general formula (I) as detailed above or according to any of claims 1 to 19 or of a physiologically tolerated salt or a prodrug thereof treatment of sleep disorders and/or for the manufacture of a medicament for the treatment of sleep disorders.

A further aspect of the present invention provides the use of at least one compound of the general formula (I) as detailed above or according to any of claims 1 to 19 or of a physiologically tolerated salt or a prodrug thereof treatment of depressive disorders and/or for the manufacture of a medicament for the treatment of depressive disorders.

A further aspect of the present invention provides the use of at least one compound of the general formula (I) as detailed above or according to any of claims 1 to 19 or of a physiologically tolerated salt or a prodrug thereof for the treatment of vasomotor symptoms and/or thermoregulatory dysfunctions such as, for example, the "hot flush" symptom.

A further aspect of the present invention provides the use of at least one compound of the general formula (I) as detailed above or according to any of claims 1 to 19 or of a physiologically tolerated salt or a prodrug thereof for the treatment and/or prophylaxis of drug dependencies, medicament dependencies and/or dependencies mediated by other factors, for the treatment and/or prophylaxis of stress caused by the withdrawal of one or more factors mediating the dependency and/or for the treatment and/or prophylaxis of stress-induced relapses into the drug dependencies, medicament dependencies and/or dependencies mediated by other factors.

A further aspect of the present invention provides the use of at least one compound of the general formula (I) as detailed above or according to any of claims 1 to 19 or of a physiologically tolerated salt or a prodrug thereof for the treatment and/or prophylaxis of schizophrenia and/or psychosis.

A further aspect of the present invention provides the use of at least one compound of the general formula (I) as detailed above or according to any of claims 1 to 19 or of a physiologically tolerated salt or a prodrug thereof for inhibiting the development of tolerance to analgesic effects elicited by the administration of analgesic agents such as morphines.

The term "inhibiting the development of tolerance to analgesic effects by administration of analgesic agents such as morphines" is to be understood in the sense of WO 2006/070742.

A further aspect of the present invention provides the use of at least one compound as detailed above or according to any of claims 1 to 6 as detailed above or according to any of claims 9 to 23, wherein the use takes place by administering at least one compound as detailed above or according to any of claims 1 to 6 in or to a patient, and the patient is a mammal, preferably a human or a nonhuman or a nonhuman transgenic mammal.

A further aspect of the present invention provides a method for the treatment and/or prophylaxis of at least one disorder whose treatment and/or prophylaxis relates to the use according to any of claims 9 to 23 of at least one compound of the general formula (I) as detailed above or according to any of claims 1 to 6, wherein for this purpose an effective amount of at least one compound of the general formula (I) as detailed above or according to any of claims 1 to 6 is administered to the patient requiring this.

A further aspect of the present invention provides a method for the preparation of at least one compound of the general formula (I) as detailed above or according to any of claims 1 to 6, wherein it can be prepared by the relevant skilled worker with knowledge of the technical teaching of the invention in implementation, where appropriate employing analogous procedures of process steps known per se.

A further preferred embodiment provides at least one compound of the general formula (I) as described above, which exhibits a selectivity for the vasopressin V1b receptor subtype over at least one of the closely related vasopressin/oxytocin receptor subtypes (for example vasopressin V1a, vasopressin V2 and/or oxytocin).

A further preferred embodiment provides at least one compound of the general formula (I) as described above, which has an improved metabolic stability.

The metabolic stability of a compound can be measured for example by incubating a solution of this compound with liver microsomes from particular species (for example rat, dog or human) and determining the half-life of the compound under these conditions (R S Obach, Curr Opin Drug Discov Devel. 2001, 4, 36-44). It is possible to conclude from larger half-lives that the metabolic stability of the compound is improved. The stability in the presence of human liver microsomes is of particular interest since it makes it possible to predict the metabolic degradation of the compound in the human liver. Compounds with increased metabolic stability are therefore probably also degraded more slowly in the liver (measured in the liver microsome test). The slower metabolic degradation in the liver can lead to higher and/or longer-lasting concentrations (effective levels) of the compound in the body, so that the elimination half-life of the compounds of the invention is increased. Increased and/or longer-lasting effective levels may lead to a better efficacy of the compound in the treatment or prophylaxis of various vasopressin-dependent or oxytocin-dependent diseases. An improved metabolic stability may additionally lead to an increased bioavailability after oral administration, because the compound is subjected, after being absorbed in the intestine, to less metabolic degradation in the liver (so-called first pass effect). An increased oral bioavailability may, because the concentration (effective level) of the compound is increased, lead to a better efficacy of the compound after oral administration.

A further preferred embodiment provides at least one compound of the general formula (I) as described above, which has an improved pharmacological activity in patients or relevant animal models which make prognostic statements possible for use in treatment.

Each of these preferred definitions of a variable can be combined with any definitions of the remaining variables.

A further embodiment provides at least one compound of the invention according to general formula (I) selected from the group consisting of examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 and 198, and the tautomeric, enantiomeric and diastereomeric forms thereof, and prodrugs thereof, and non-salt forms and other physiologically tolerated salts of the aforementioned compounds.

A further embodiment provides at least one compound of the invention according to general formula (I) selected from the group consisting of examples 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 245, 246, 247, 248, 249, 250, 251, 252, 253, 254, 255 and 256, and the tautomeric, enantiomeric and diastereomeric forms thereof, and prodrugs thereof, and non-salt forms and other physiologically tolerated salts of the aforementioned compounds.

The compounds of the invention may be in the form either of a mixture of enantiomers or of a mixture of diastereomers. The respective diastereomers may in turn be in the form either of a mixture of enantiomers.

Physiologically tolerated salts in the meaning of the description can, unless stated otherwise, be formed, for example, with the following anions: chloride, methanesulfonate, formate, trifluoroacetate and/or acetate. Further suitable acids are listed for example in "Fortschritte der Arzneimittelforschung", 1966, Birkhäuser Verlag, Vol. 10, pp. 224-285.

In the sense of the present description, unless stated otherwise, the terms "alkyl", "cycloalkyl", "alkoxy", "haloalkyl", "alkenyl", "alkynyl" or "alkylene" and radicals derived therefrom always include both unbranched and branched "alkyl", "cycloalkyl", "alkoxy", "haloalkyl", "alkenyl", "alkynyl" or "alkylene".

$C_0$-Alkylene or $(CH_2)_0$ or similar expressions designate in the sense of the description, unless stated otherwise, a single bond or hydrogen.

The terms $C_1$-$C_6$-alkyl and $C_1$-$C_4$-alkyl mean in the sense of the description, unless stated otherwise, an optionally substituted straight-chain or branched saturated hydrocarbon chain having the number of carbon atoms stated in each case, respectively from 1 to 6 and from 1 to 4 carbon atoms, such as, for example, methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, n-hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl, preferably methyl, ethyl, propyl, n-butyl or i-butyl. $C_1$-$C_4$-Alkyl is in the sense of the description, unless stated otherwise, preferably methyl, ethyl, n-propyl, i-propyl, n-butyl, sec-butyl or t-butyl.

The term "$C_1$-$C_6$-alkoxy" means in the sense of the description, unless stated otherwise, an optionally substituted $C_1$-$C_6$-alkyl group, as defined above, which is linked via oxygen.

The terms $C_1$-$C_6$-alkylene, $C_1$-$C_4$-alkylene and $C_0$-$C_4$-alkylene (with $C_0$-alkylene=single bond) mean in the sense of the description, unless stated otherwise, an optionally substituted alkyl group having 1 to 6, 1 to 4 or 0 to 4 C atoms, as defined above, in which one hydrogen atom is replaced by a bond. Particular examples which should be mentioned are methylene, eth-1,2-ylene, prop-1,2-ylene, prop-1,3-ylene, but-1,2-ylene, but-1,3-ylene, but-2,3-ylene, but-1,4-ylene, 2-methylprop-1,3-ylene, pent-1,2-ylene, pent-1,3-ylene, pent-1,4-ylene, pent-1,5-ylene, pent-2,3-ylene, pent-2,4-ylene, 1-methylbut-1,4-ylene, 2-methylbut-1,4-ylene, 2-methylbut-1,3-ylene, 2-ethylprop-1,3-ylene, hex-3,4-ylene, 3-methylpent-2,4-ylene, hept-3,5-ylene, 2-ethylpent-1,3-ylene, 3-ethylhept-3,5-ylene, etc., preferably methylene, eth-1,2-ylene and prop-1,2-ylene.

The term $C_3$-$C_7$-cycloalkyl means in the sense of the description, unless stated otherwise, an optionally substituted saturated hydrocarbon ring having 3 to 7, such as cyclopropyl, cyclobutyl, cyclopentyl, cyclohexyl or cycloheptyl.

$C_1$-$C_6$-Haloalkyl or $C_1$-$C_4$-haloalkyl is in the sense of the description, unless stated otherwise, an optionally substituted $C_1$-$C_6$-alkyl or $C_1$-$C_4$-alkyl, as defined above, in which one, more than one or all hydrogen atoms have been replaced by identical or different halogen atoms as defined below.

The term $C_2$-$C_6$-alkenyl means in the sense of the description, unless stated otherwise, an optionally substituted branched or unbranched hydrocarbon chain comprising at least one double bond, having 2 to 6 carbon atoms.

$C_2$-$C_6$-Alkenyl preferably comprises one or two double bonds, most preferably one double bond. Examples of the alkenyl groups are those mentioned above for alkyl, these groups comprising one or two double bonds such as, for example, vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-entenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl or 3-methyl-2-pentenyl.

The term $C_2$-$C_6$-alkynyl means in the sense of the description, unless indicated otherwise, an optionally substituted branched or unbranched hydrocarbon chain comprising at least one triple bond with 2 to 6 carbon atoms. $C_2$-$C_6$-Alkynyl preferably comprises one or two triple bonds, most preferably one triple bond. Examples of the alkynyl groups are those mentioned above for alkyl, these groups comprising one or two triple bonds, such as, for example, ethynyl, 1-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably ethynyl, 1-propynyl, 1-butynyl, 1-methyl-2-propynyl or 1-methyl-2-butynyl.

The terms "3- to 10-membered carbocycle" or "4 to 7 membered carbocyclic ring" or "carbocyclic ring having 2 to 10 C atoms" mean in the sense of the description, unless stated otherwise, an optionally substituted saturated or wholly or partly unsaturated hydrocarbon ring having 3 to 10 carbon atoms or 4 to 7 C atoms or 2-10 C atoms as ring atoms, such as, for example, cyclopropyl, cyclobutyl, cyclopentyl, cyclohexyl, cycloheptyl, cyclooctyl, cyclononyl or cyclodecanyl. Where explicitly mentioned or identified thus in the relevant structure formula, the carbocyclic ring may also comprise heteroatoms as ring atoms. Unless stated otherwise, the heteroatom ring members may optionally be present either in place of the C atom ring members or in addition to the C atom ring members.

Halogen is in the sense of the description, unless stated otherwise, a halogen atom selected from fluorine, chlorine, bromine or iodine, preferably fluorine, chlorine or bromine, more preferably fluorine or chlorine.

The expressions "$C_1$-$C_6$-haloalkyl" or "$C_1$-$C_4$-haloalkyl" designate in the sense of the description, unless stated otherwise, an optionally substituted alkyl radical, as defined above, which is partially or completely substituted by one or more identical or different radicals independently of one another selected from the group consisting of fluorine, chlorine, bromine and iodine, thus, for example, $CH_2F$, $CHF_2$, $CF_3$, $CH_2Cl$, 2-fluoroethyl, 2-chloroethyl, 2,2,2-trifluoroethyl.

Where described appropriately by use of the expression "substituted" or "optionally substituted", the radicals and groups may in the sense of the description, unless otherwise concerning this, be substituted preferably one or more times, more preferably once, twice or three times, most preferably once or twice. The expression "in each case optionally substituted" is intended to make it clear that not only the immediately following radical but all the radicals mentioned in the respective group may be substituted independently of one another.

Examples of suitable substituents in the sense of the description and of the expressions "substituted", "optionally substituted" and "in each case optionally substituted", unless stated otherwise, comprise: halogen, CN, $CF_3$, $CHF_2$, $OCF_3$, $OCHF_2$, $NO_2$, $NH_2$, OH, COOH, in each case branched or unbranched, optionally substituted $C_1$-$C_6$-alkyl, $C_3$-$C_7$-cycloalkyl, $C_1$-$C_6$-alkylene-O—$C_1$-$C_6$-alkyl or $C_1$-$C_6$-thioalkyl, O—$C_1$-$C_4$-alkyl, N($C_1$-$C_4$-alkyl)$_2$, NH($C_1$-$C_4$-alkyl), aryl, —O-aryl, $C_1$-$C_4$-alkylene-O-aryl, NHCO—$C_1$-$C_4$-alkyl, NH—$SO_2$—$C_1$-$C_4$-alkyl, CO—$C_1$-$C_4$-alkyl, $SO_2$—$C_1$-$C_4$-alkyl, and, optionally substituted in the aryl radical, NHCO-aryl, NHSO$_2$-aryl, CONH$_2$, SO$_2$NH$_2$, SO$_2$-aryl, SO—$C_1$-$C_4$-alkyl, SO-aryl, N-pyrrolidinyl, N-piperidinyl, and N-morpholinyl. Preferred substituents are F, Cl, $CF_3$, $OCF_3$, $NH_2$, $NO_2$, OH, COOH, $C_1$-$C_4$-alkyl, methoxy, acetyl, NH-acetyl and SO$_2$NH$_2$.

Expressions in parentheses with subscript integers are to be understood in the sense of the description, unless stated otherwise, in such a way that the meanings of the radicals in parentheses may in each case be identical or different. For example, N($C_1$-$C_4$-alkyl)$_2$ stands in the sense of the description for N($C_1$-$C_4$-alkyl)($C_1$-$C_4$-alkyl), where the two ($C_1$-$C_4$-alkyl) radicals may be identical or different.

The symbol (*) in the chemical formulae of $R_Y^1$, $R_Y^{22}$, $R_Y^{33}$, $R_Y^{81}$, $A^1$, B and Y in the general formula (I) describes in the sense of the description, unless stated otherwise, the points of linkage of said radicals to the benzimidazolone ring structure or a group connected to the benzimidazolone ring structure.

The symbol () describes in the sense of the description, unless stated otherwise, a single bond which—if linked to a center of chirality—is intended to mean that the corresponding compound are in the form either of an approximately 1:1 mixture (racemate, (R/S) form) of the two enantiomeric forms in relation to the center of chirality or else of separated (R) enantiomers and/or (S) enantiomers in relation to the center of chirality.

The symbol —SO— means in the sense of the description, unless stated otherwise, a sulfoxide group (—S(=O)—).

The symbol ( . . . )$_{1,2}$ means that the expression in parentheses occurs once or twice. For example, (CH$_2$)$_{1,2}$ (or a notation equivalent thereto) means optionally the radical (CH$_2$)$_1$(=(CH$_2$)) or (CH$_2$)$_2$.

The symbol ( . . . )$_0$ means that the expression in parentheses is a single bond.

The symbol —SO$_2$— means in the sense of the description, unless stated otherwise, optionally a radical selected from the group consisting of the sulfone (—(O=S=O)—) and the sulfinic acid group (—(S=O)—O—), with the meaning of the sulfone group being preferably meant.

The expression "aromatic, heteroaromatic, partly aromatic or partly heteroaromatic mono- or bicyclic ring" means in the sense of the description, unless stated otherwise, a mono- or bicyclic ring which is composed of C atoms ("aromatic" or "partly aromatic") or, in case of heteroaromatic or partly heteroaromatic, a combination of C atoms and heteroatoms ("heteroaromatic" or "partly heteroaromatic") in each case as ring members, and includes an aromatic number of double bonds in the ring ("monocyclic") or in the two rings ("bicyclic") ("aromatic" or "heteroaromatic") or only in one of the rings ("partly aromatic" or "partly heteroaromatic").

The aromatic carbocycles may be mono- bi or tricyclic and thus contain 6, 10 or 13 carbon atoms as ring members. In bicyclic and tricyclic aromatic carbocycles each ring includes an aromatic number of double bonds. Examples of aromatic rings are phenyl, naphthyl, and phenanthrenyl, preferably phenyl and naphthyl, which may be 1-naphthyl or 2-naphthyl. Phenyl is most preferred.

The heteroaromatic cycles may be mono- bi or tricyclic and may contain from 5 to 14 atoms as ring members, provided that at least one ring member, e.g. 1, 2, 3 or 4 ring member atoms are heteroatoms. Heteroaromatic bi- or tricycles include at least one aromatic 5 or 6 membered heterocycle and at least one further aromatic ring, selected from phenyl ring and a 5- or 6-heteroaromatic ring, the at least one further aromatic ring being fused to the aromatic 5 or 6 membered heterocycle. Examples of heteroaromatic rings are 2-furyl, 3-furyl, 2-pyrrolyl, 3-pyrrolyl, 2-thienyl, 3-thienyl, 2-pyridyl, 3-pyridyl, 4-pyridyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl, triazinyl, benzothienyl, naphthothienyl, benzofuranyl, indolyl, isoindolyl, indazolyl, quinolyl, isoquinolyl, phthalazinyl, quinoxalinyl, benzimidazolyl, benzoxazolyl, and 2,1,3-benzothiadiazolyl.

Examples of partly aromatic rings are: 5,6,7,8-tetrahydronaphthalen-1-yl, 5,6,7,8-tetrahydronaphthalen-2-yl, fluorenyl, indenyl and indan-4-yl, indan-5-yl.

Examples of partly heteroaromatic rings are: benzo[1,3]dioxol-4-yl, benzo[1,3]dioxol-5-yl, 2,3-dihydrobenzo[1,4]dioxin-5-yl, and 2,3-dihydro-benzo[1,4]dioxin-6-yl, chromanyl, chromenyl, indolinyl, 2,3-dihydro-1,4-benzodioxinyl and 1,3-benzodioxolyl.

The expressions "saturated or wholly or partly unsaturated carbocyclic ring" or "saturated or unsaturated carbocyclic ring" mean in the sense of the description, unless stated otherwise, a ring or ring system which is in each case formed of C atoms and optionally one or more heteroatoms and has no double bond located in the ring ("saturated") or has one or more double bonds which are conjugated or unconjugated or only in part conjugated with one another ("partly or wholly unsaturated" or "unsaturated"). The carbocyclic ring may be a mono-, bi- or tricyclic ring. A bi- or tricyclic saturated carbocycle may in the sense of the description, unless stated otherwise, be a bicycloalkyl or tricycloalkyl radical having up to 10 carbon atoms. In the case of a bicycloalkyl radical, the ring system may preferably comprise 5 to 10, more preferably 6 to 10, carbon atoms. In the case of a tricycloalkyl radical, the ring system preferably comprises 6 to 10, more preferably 6 to 10, carbon atoms. Examples of a bicycloalkyl radical include indanyl, camphyl and norbornyl. Examples of a tricycloalkyl radical include adamantyl.

The expression "in the sense of the description" includes the present application in all its parts, that is in particular the description, the claims, the drawings and the abstract.

The compounds of the invention are effective after administration by various routes (for example intravenous, intramuscular, oral), in particular oral.

The present invention also provides the use of the compounds of the invention for the treatment and/or prophylaxis of diseases in which the course of the disease is at least partly dependent on vasopressin, i.e. diseases which show an elevated vasopressin level which may contribute indirectly or indirectly to the pathological state.

The present invention further provides the use of the compounds of the invention for the treatment and/or prophylaxis of diseases such as, for example, diabetes insipidus, nocturnal enuresis, incontinence, diseases in which blood coagulation disorders occur and/or for delaying micturition.

The present invention also provides the use of the compounds of the invention for the treatment and/or prophylaxis of the following diseases: hypertension, pulmonary hypertension, heart failure, myocardial infarction, coronary spasm, unstable angina, PTCA (percutaneous transluminal coronary angioplasia), ischemias of the heart, disorders of the renal system, edemas, renal vasospasm, necrosis of the renal cortex, hyponatremia, hypokalemia, Schwartz-Bartter syndrome, disorders of the gastrointestinal tract, gastritic vasospasm, hepatocirrhosis, gastric and intestinal ulcer, emesis, emesis occurring during chemotherapy, and travel sickness.

The compounds of the invention can also be used for the treatment of various vasopressin-dependent complaints which exhibit central nervous causes or alterations in the HPA axis (hypothalamic pituitary adrenal axis), for example for affective disorders such as depressive disorders and bipolar disorders. These include for example dysthymic disorders, phobias, post-traumatic stress disorders, general anxiety disorders, panic disorders, seasonal depressions and sleep disorders.

The compounds of the invention can likewise be employed for treatment in cases of anxiety disorders and stress-dependent anxiety disorders such as, for example, generalized anxiety disorders, phobias, post-traumatic anxiety disorders, panic anxiety disorders, obsessive-compulsive anxiety disorders, acute stress-dependent anxiety disorders and social phobia. The compounds of the invention can further be employed also for the treatment of memory impairments, Alzheimer's disease, psychoses, psychotic disorders, sleep disorders and/or Cushing's syndrome, and all stress-dependent diseases.

The present invention also relates to pharmaceutical compositions which comprise an effective dose of a compound of the invention or of a pharmaceutically acceptable salt thereof and suitable drug carriers.

These drug carriers are chosen according to the pharmaceutical form and the desired mode of administration.

The compounds of the invention of the general formula (I) or, where appropriate, suitable salts of these compounds can be used to manufacture pharmaceutical compositions for oral, sublingual, subcutaneous, intramuscular, intravenous, topical, intratracheal, intranasal, transdermal, vaginal or rectal administration and be administered to animals or humans in unit dose forms mixed with conventional pharmaceutical carriers for the prophylaxis or treatment of the above disorders or diseases.

Suitable unit dose forms include forms for oral administration, such as tablets, gelatin capsules, powders, granules, solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active basic ingredient can vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose can be administered 1 to 5 times a day so that a daily dose of from 0.05 to 25 000 mg, preferably 1 to 5000 mg, is administered.

If a solid composition in the form of tablets is prepared, the main (i.e. the active) ingredient is mixed with a pharmaceutical carrier such as gelatin, starch, lactose, magnesium stearate, talc, silicon dioxide or the like.

The tablets can be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener which is preferably calorie-free, methylparaben or propylparaben as antiseptics, a flavoring and a suitable coloring.

The water-dispersible powders or granules may comprise the active ingredients mixed with dispersants, wetting agents or suspending agents, such as polyvinylpyrrolidones, and sweeteners or taste improvers.

Rectal or vaginal administration is achieved by the use of suppositories which are prepared with binders which melt at the rectal temperature, for example cocoa butter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active basic ingredient can also be formulated as microcapsules or centrosomes, if suitable with one or more carriers or additives.

In addition to the compounds of the general formula (I), or their pharmaceutically acceptable salts, the compositions of the invention may comprise further active basic ingredients which may be beneficial for the treatment of the impairments or disorders indicated above.

The present invention therefore further relates to pharmaceutical compositions which comprise a plurality of active basic ingredients, where at least one of these is a compound of the invention.

Preparation of the Compounds of the Invention

Examples of synthetic routes for preparing the compounds of the invention are described below.

SYNTHESIS SCHEME 1 ($R_4$ = methyl, ethyl or tert-butyl)

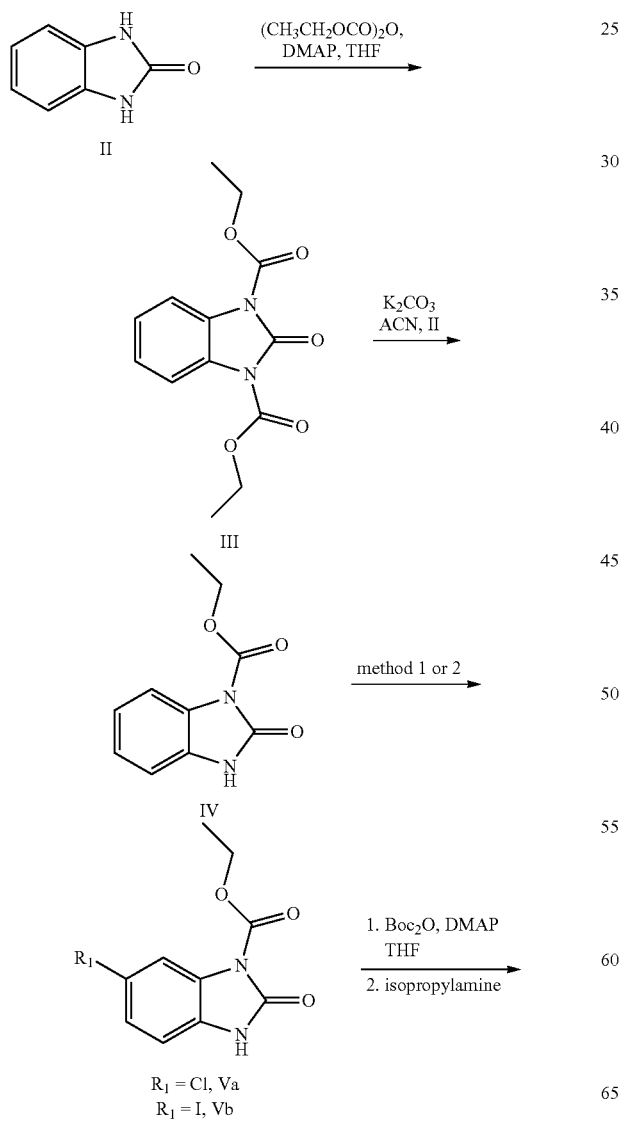
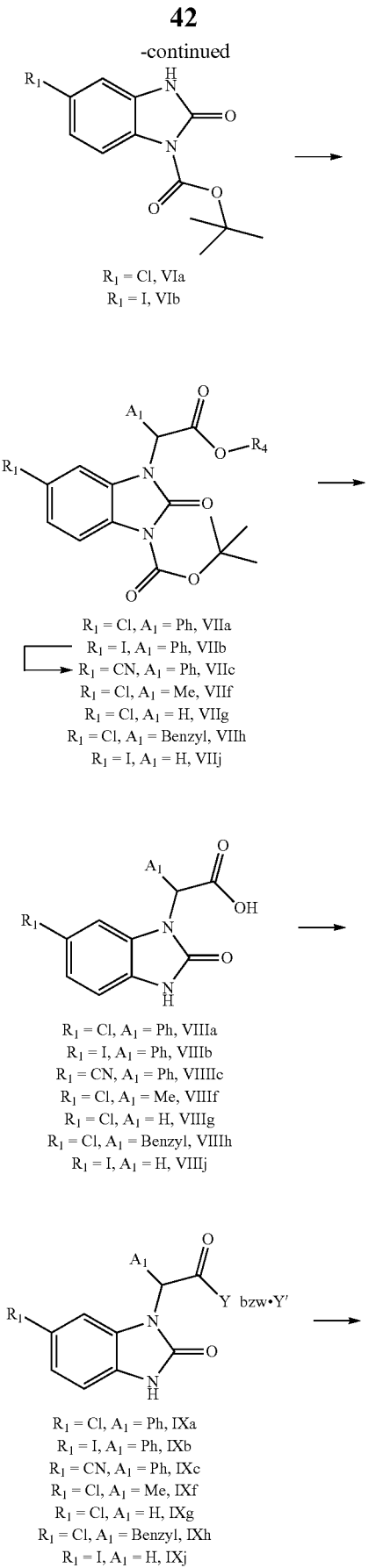

-continued

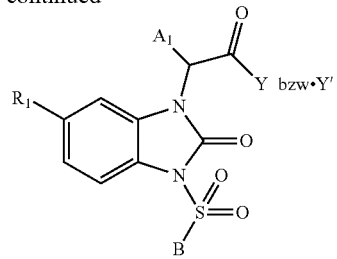

R₁ = Cl, A₁ = Ph, Xa
R₁ = I, A₁ = Ph, Xb
R₁ = CN, A₁ = Ph, Xc
R₁ = Cl, A₁ = Me, Xf
R₁ = Cl, A₁ = H, Xg
R₁ = Cl, A₁ = Benzyl, Xh
R₁ = I, A₁ = H, Xj In accordance with the nomenclature used, the following designations are chosen further for reaction stages with specific substitutions: k: R₁=Cl, A₁=o-methoxyphenyl; m: R₁=Cl, A₁=m-methoxyphenyl; n: R₁=Cl, A₁=p-methoxyphenyl; o: R₁=Cl, R₂=6-Cl, A₁=Ph; p: R₁=H, A₁=o-methoxyphenyl.

Compounds of the general formula X can be synthesized in the manner shown in synthesis scheme 1. The procedure depicted here is distinguished by carrying out the introduction of the sulfonamide in the last step after the carboxamide (IX) has already been formed. The synthesis and regioselective electrophilic substitution of the benzimidazolones II-VI are carried out in accordance with the literature (J. Org. Chem. 1995, 60, 1565-1582). The alkylation of the compounds VI can take place for example by treatment with alpha-halo carboxylic esters after deprotonation either with strong bases such as, for example, potassium tert-butoxide or sodium hydride, in a solvent such as, for example, N,N-dimethylformamide (DMF) or tetrahydrofuran (THF). The compound VIIg (A₁=H) can additionally be obtained by alkylation of compounds VI with haloacetic esters using a base such as, for example, cesium carbonate, in a solvent such as, for example, acetonitrile. The cyano group as radical R₁ can be introduced starting from the corresponding compounds with R₁=iodine, for example by heating compounds VIIb with zinc cyanide in DMF in the presence of catalytic amounts of palladium tetrakis(triphenylphosphine) or by heating with potassium cyanide and catalytic amounts of palladium tetrakis(triphenylphosphine) in THF (J. Med. Chem. 1996, 39, 5072-5082). Removal of the esters and of the tert-butoxycarbonyl (Boc) groups can be carried out either under acidic or alkaline reaction conditions. In the case where the radical R₄ is an ethyl or methyl ester, the deprotection to give the compounds VIII is carried out with 5N sodium hydroxide solution in a methanol/water mixture and subsequent aqueous workup. In the case where R₄=tert-butyl, deprotection takes place in a mixture of trifluoroacetic acid (TFA) in dichloromethane (DCM). The reaction step to give the carboxamides (IX or X) can be carried out using the respective amine either with (3-dimethylaminopropyl)ethylcarbodiimide hydrochloride (EDCl) or using solid phase-bound carbodiimide in a solvent such as, for example, DCM. Sulfonylation of the free benzimidazolone nitrogen in the compounds IX can take place by treatment with sulfonyl chlorides B—SO₂—Cl after deprotonation either with a strong base such as, for example, potassium tert-butoxide or sodium hydride, or with triethylamine or solid phase-bound tertiary amine bases in the presence of catalytic amounts of N,N-dimethyl-aminopyridine (DMAP) in a solvent such as, for example, DMF or THF.

SYNTHESIS SCHEME 1a: (R1 = CN)

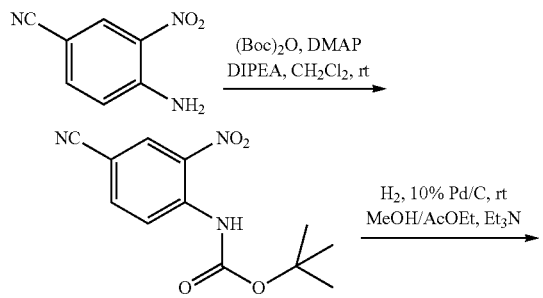

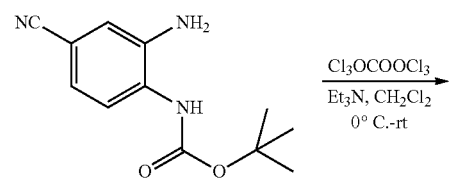

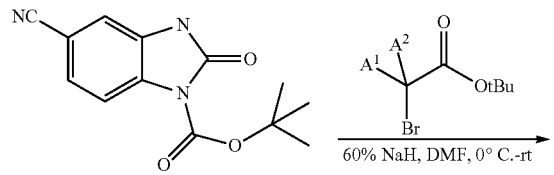

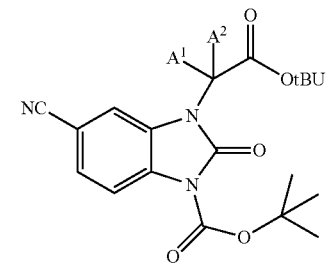

Compounds VIIc can also be prepared from commercially available 2-nitro-4-cyanoaniline by the method depicted in scheme 1a.

SYNTHESIS SCHEME 2

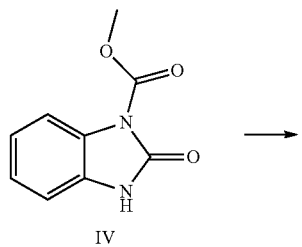

IV

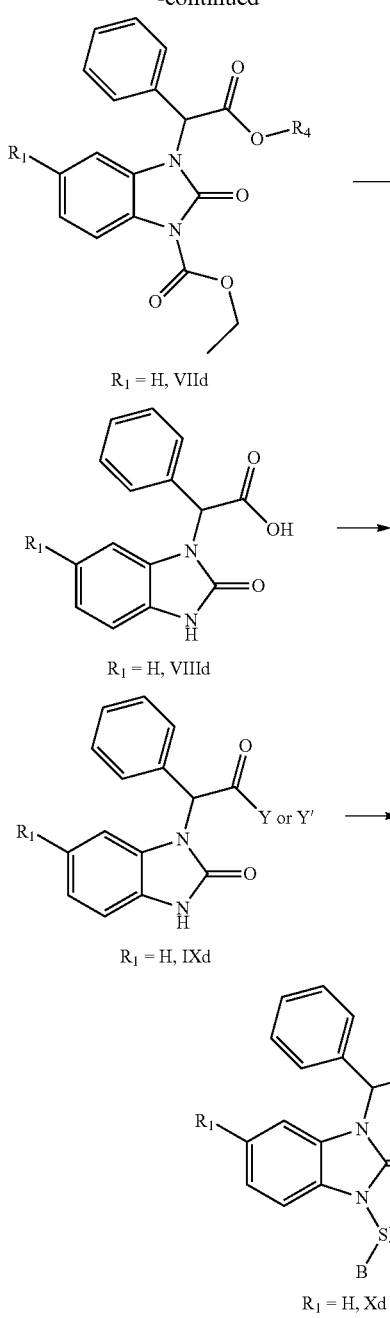

and inversion of reaction sequences (for example introduction of the sulfonamide first, before synthesis of the carboxamide).

SYNTHESIS SCHEME 3 ($R_4$ = tert-butyl; B e.g. 4-methoxybenzene)

$R_1$ = Cl, $A_1$ = Ph, VIIa
$R_1$ = I, $A_1$ = Ph, VIIb
$R_1$ = CN, $A_1$ = Ph, VIIc
$R_1$ = H, $A_1$ = Ph, VIId
$R_1$ = Cl, $A_1$ = Me, VIIf
$R_1$ = Cl, $A_1$ = H, VIIg
$R_1$ = Cl, $A_1$ = Benzyl, VIIh
$R_1$ = I, $A_1$ = H, VIIj 2% TFA in $CH_2Cl_2$ $R_1$ = Cl, $A_1$ = Ph, XIa
$R_1$ = I, $A_1$ = Ph, XIb
$R_1$ = CN, $A_1$ = Ph, XIc
$R_1$ = H, $A_1$ = Ph, XId
$R_1$ = Cl, $A_1$ = Me, XIf
$R_1$ = Cl, $A_1$ = H, XIg
$R_1$ = Cl, $A_1$ = Benzyl, XIh
$R_1$ = I, $A_1$ = H, XIj sulfonyl chloride
triethylamine
DMAP, THF $R_1$ = Cl, $A_1$ = Ph, XIIa
$R_1$ = I, $A_1$ = Ph, XIIb
$R_1$ = CN, $A_1$ = Ph, XIIc
$R_1$ = H, $A_1$ = Ph, XIId
$R_1$ = Cl, $A_1$ = Me, XIIf
$R_1$ = Cl, $A_1$ = H, XIIg
$R_1$ = Cl, $A_1$ = Benzyl, XIIh
$R_1$ = I, $A_1$ = H, XIIj TFA in $CH_2Cl_2$ Compounds Xd with unsubstituted benzimidazolone basic structures ($R_1$=hydrogen) can be synthesized (in analogy to synthesis scheme 1) as shown in synthesis scheme 2. Starting from compound IV, alkylation (see synthesis scheme 1) results in compound VIId. In the case where the radical $R_4$ is an ethyl or methyl ester, deprotection to give the compounds VIIId is carried out with 5N sodium hydroxide solution in a methanol/water mixture and subsequent aqueous workup. If $R_4$=tert-butyl, stepwise deprotection is also possible (first that of the ethyl carbamate with isopropylamine in THF, and then that of the tert-butyl ester with a mixture of trifluoroacetic acid (TFA) in dichloromethane (DCM). This stepwise selective deprotection strategy is further suitable also for derivatizations differing from the general synthesis scheme 2, -continued

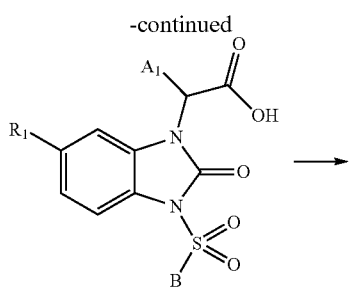

R₁ = Cl, A₁ = Ph, XIIIa
R₁ = I, A₁ = Ph, XIIIb
R₁ = CN, A₁ = Ph, XIIIc
R₁ = H, A₁ = Ph, XIIId
R₁ = Cl, A₁ = Me, XIIIf
R₁ = Cl, A₁ = H, XIIIg
R₁ = Cl, A₁ = Benzyl, XIIIh
R₁ = I, A₁ = H, XIIIj

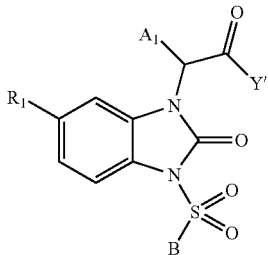

R₁ = Cl, A₁ = Ph, XIVa
R₁ = I, A₁ = Ph, XIVb
R₁ = CN, A₁ = Ph, XIVc
R₁ = H, A₁ = Ph, XIVd
R₁ = Cl, A₁ = Me, XIVf
R₁ = Cl, A₁ = H, XIVg
R₁ = Cl, A₁ = Benzyl, XIVh
R₁ = I, A₁ = H, XIVj

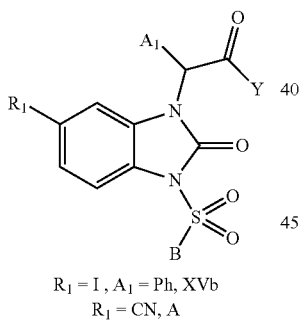

R₁ = I, A₁ = Ph, XVb
R₁ = CN, A

In accordance with the nomenclature used, the following designations are chosen further for reaction stages with specific substitutions: k: R₁=Cl, A₁=o-methoxyphenyl; m: R₁=Cl, A₁=m-methoxyphenyl; n: R₁=Cl, A₁=p-methoxyphenyl; o: R₁=Cl, R₂=6-Cl, A₁=Ph; p: R₁=H, A₁=o-methoxyphenyl.

As depicted in synthesis scheme 3, starting from the compounds VII with R₄=tert-butyl it is possible to remove the Boc protective group selectively with 2 percent TFA solution in DCM. The nitrogen atom of the benzimidazolone XI deprotected in this way can then be converted by treatment with sulfonyl chlorides B—SO₂Cl in the presence of triethylamine and catalytic amounts of DMAP in a solvent such as, for example, DMF or THF into compounds XII. After deprotection of the tert-butyl ester XII with a mixture of TFA and DCM to give the free carboxylic acids XIII, the reaction step to give the carboxamides (XIV or XV) can be carried out using the respective amine either with EDCl or with solid phase-bound carbodiimide in a solvent such as, for example, DCM. As already also indicated in synthesis scheme 1 it is possible to modify the initially introduced carboxamide (XIV) in further synthesis steps. This is possible by using a diamine synthon in the reaction step VIII→IX or XIII→XIV, in which in each case a nitrogen atom is protected by a protective group. After the amide coupling (VIII→IX or XIII→XIV), this protective group can be removed, and the nitrogen atom which has thus been deprotected can be further derivatized. Boc protective groups are deprotected in a mixture of TFA and DCM, and a benzyl protective group can be deprotected by reaction with 1-chloroethyl chloroformate in DCM and subsequent heating of the intermediate thus formed in methanol (MeOH). The amine obtained in this way can be reacted with aldehydes or ketones in the presence of a reducing agent such as, for example, sodium cyanoborohydride or solid phase-bound triacetoxyborohydride, in a solvent such as, for example, THF, to give the respective tertiary amines X and XV (reductive amination: J. March, Advanced Organic Chemistry, 1992, 4th edition., Wiley, New York, p. 411; 898).

SYNTHESIS SCHEME 4: (R₁ = Cl, R₂ = 6-Cl)

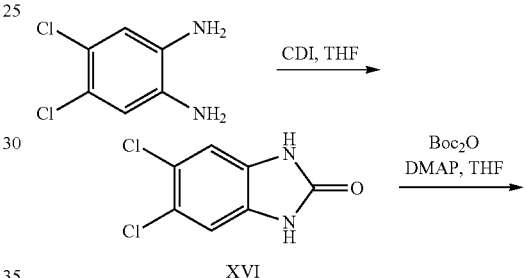

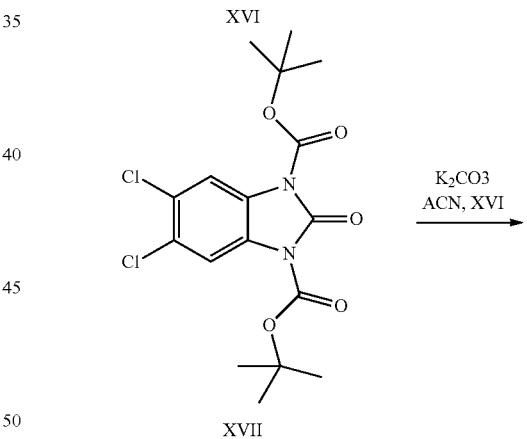

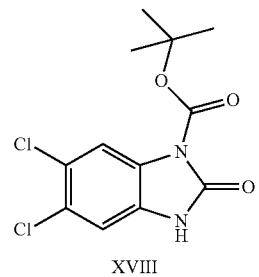

XVIII

Compounds of the general formula (I) with 5,6-dichloro-substituted benzimidazolone basic structure are obtained from reaction of 1,2-diamino-4,5-dichlorobenzene with CDI in THF. After reaction of the benzimidazolone XVI with Boc₂O in THF and subsequent disproportionation of the reaction product XVII with one equivalent XVI, the intermediate XVIII can be obtained and can be used in analogy to compounds VI in synthesis scheme 1 in further reaction steps to synthesize compounds of the invention.

SYNTHESIS SCHEME 5 ($R_1$ = H, $R_2$ = 6-Cl):

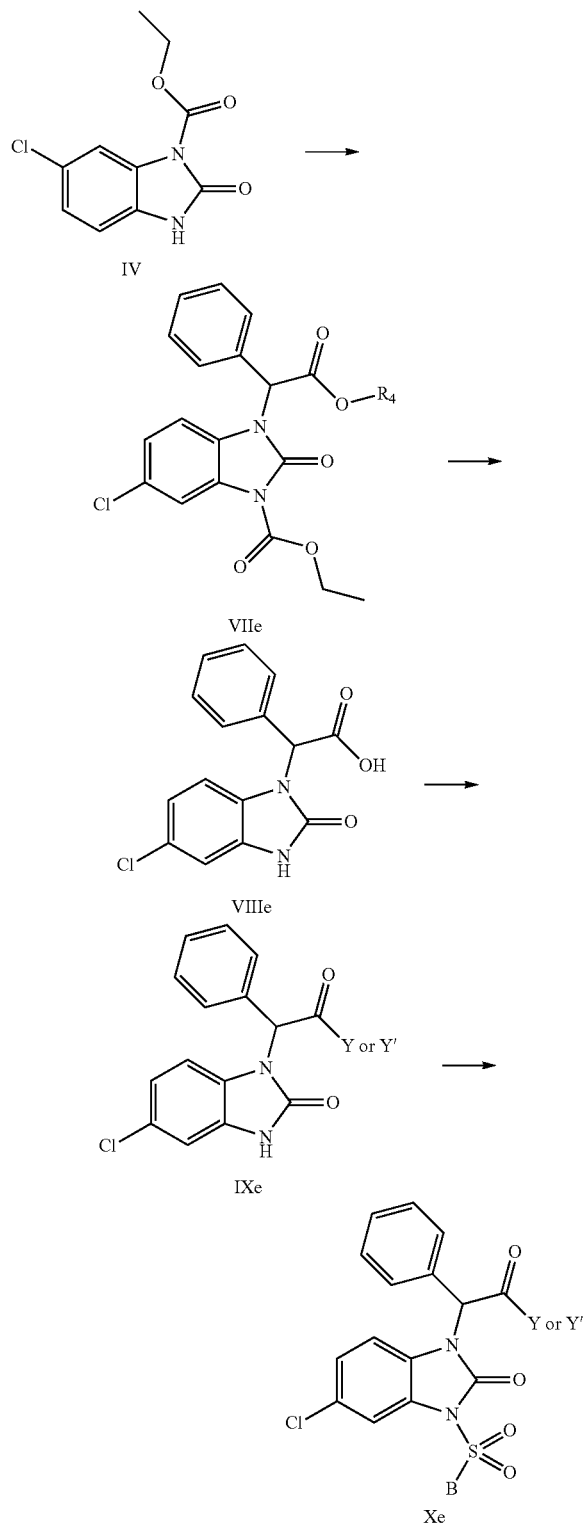

Compounds of the general formula (I) with 6-chloro-substituted benzimidazolone basic structure (synthesis scheme 5) are obtained from alkylation of compound IV in analogy to synthesis step VI→VII in synthesis scheme 1. The further reaction steps VIIe→Xe can then be carried out in analogy to general synthesis stages VII→X in synthesis scheme 1 or 2.

SYNTHESIS SCHEME 6:

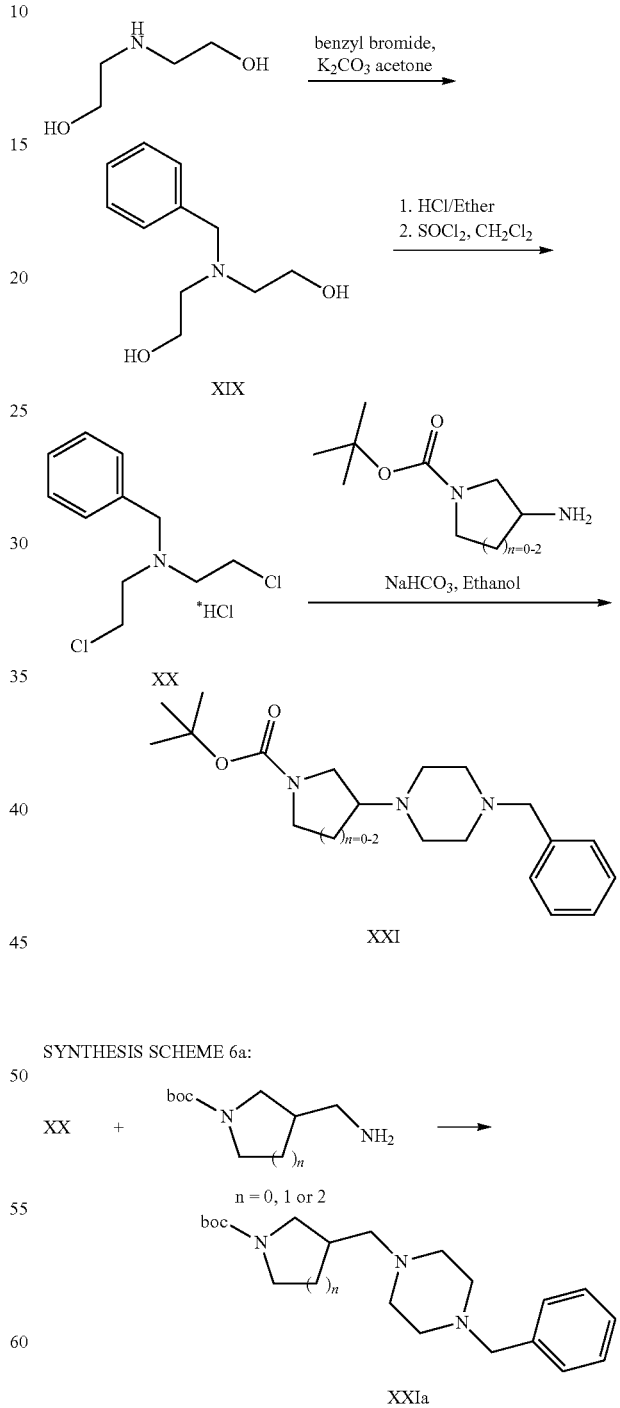

SYNTHESIS SCHEME 6a:

As depicted in synthesis schemes 6 and 6a, orthogonally protected triamines XXI and XXIa which have both a Boc and benzylamino protective group can be prepared from bis(2- hydroxyethyl)amine in three stages. Bis(2-hydroxyethyl) amine can be converted into the benzylamine XIX by treatment with benzyl bromide and potassium carbonate in a solvent such as, for example, acetone. After conversion into the hydrochloride, the dichloride XX is obtained by reacting with thionyl chloride in a solvent such as, for example, DCM. The orthogonally protected triamines XXI can be obtained from reaction of XX with the primary amino group of a Boc-protected diamine in the presence of a base such as, for example, sodium bicarbonate, in a solvent such as, for example, ethanol. This reaction route also makes it possible to synthesize enantiopure compounds XXI when the enantiopure amines (R)- and (S)-3-amino-1-Boc-pyrrolidine or (R)- and (S)-3-amino-1-Boc-piperidine are used in the reaction step XX→XXI or chiral compounds XXIa when the enantiopure amines (R)- and (S)-3-aminomethyl-1-Boc-pyrrolidine or (R)- and (S)-3-aminomethyl-1-Boc-piperidine are used in the reaction step XX→XXIa. The compounds XXI and XXIa make it possible for the two secondary amino groups to be selectively derivatized through chemical differentiation of the reaction conditions for removing the respective protective groups. The Boc protective group can be removed under acidic reaction conditions, such as, for example, with a mixture of TFA and DCM, whereas the benzyl group can be removed by hydrogenation either with hydrogen catalyzed by palladium/carbon, or can be removed with 1-chloroethyl chloroformate and by subsequent heating.

In the case where Y is a chiral radical, the compounds IX, X, XIV and XV may result as a mixture of diastereomers. If the compounds X and XV of the invention result as a mixture of diastereomers, the diastereomers may be separable by preparative HPLC using the suitable solvent and column material.

The invention is explained in more detail below by means of examples without being restricted to the examples mentioned.

EXPERIMENTAL SECTION

Diethyl 2-oxobenzimidazole-1,3-dicarboxylate (II)

25.0 g (154 mmol) of diethyl pyrocarbonate were added dropwise at room temperature with stirring to a suspension of 2-hydroxybenzimidazole and a catalytic amount of DMAP in dry THF (120 ml). A solution formed while the mixture was being stirred at room temperature for 1 h. The solvent was removed in vacuo, and the residue was slurried in heptane. The solid was filtered off, washed with heptane and dried in vacuo.
Yield: 16.6 g (96%) of pale brown solid
$^1$H-NMR (DMSO-d$_6$): 1.37 (t, 7.1 Hz, 6H), 4.43 (q, 7.1 Hz, 4H), 7.10-7.31 (m, 2H), 7.80-7.85 (m, 2H).
MS (API-ES, pos) m/z=279 [M+H]$^+$ Ethyl 2-oxo-2,3-dihydrobenzimidazole-1-carboxylate (IV)

A mixture of 11.0 g (39.5 mmol) of diethyl 2-oxobenzimidazole-1,3-dicarboxylate (III), 5.30 g (39.5 mmol) of 2-hydroxybenzimidazole and 6.55 g (47.4 mmol) of potassium carbonate in acetonitrile (200 ml) was heated under reflux with vigorous stirring for 2 h. Most of the solvent was then removed in vacuo, and the residue was mixed with 150 ml of 1N hydrochloric acid. The solid residue was filtered, washed with water, dried in vacuo and recrystallized from toluene.
Yield: 16.7 g (100%) of pale brown solid
$^1$H-NMR (DMSO-d$_6$): 1.35 (t, 7.1 Hz, 3H), 4.41 (q, 7.1 Hz, 2H), 7.01 (d, 8.3 Hz, 1H), 7.21 (dd, 8.4 Hz, 1.9 Hz, 1H), 7.69 (d, 1.9 Hz, 1H), 11.4 (bs, 1H).
MS (API-ES, pos) m/z=207 [M+H]$^+$ Ethyl 6-chloro-2-oxo-2,3-dihydrobenzimidazole-1-carboxylate (Va)

A mixture of 7.00 g (33.9 mmol) of ethyl 2-oxo-2,3-dihydrobenzimidazole-1-carboxylate (IV) and 3.02 ml (37.3 mmol) of sulfuryl chloride in acetic acid (90 ml) was stirred at 90° C. for 1 h. The cooled reaction mixture was poured into ice-water. The precipitated solid was filtered off, washed with water, dried in vacuo and recrystallized from ethyl acetate.
Yield: 5.90 g (72%) of colorless solid
$^1$H-NMR (DMSO-d$_6$): 1.32 (t, 7.1 Hz, 3H), 4.37 (q, 7.1 Hz, 2H), 6.98 (d, 8.3 Hz, 1H), 7.17 (d, 8.3 Hz, 1H), 7.66 (s, 1H), 11.4 (bs, 1H).
MS (API-ES, pos) m/z=241, 243 [M+H]$^+$ tert-Butyl 5-chloro-2-oxo-2,3-dihydrobenzimidazole-1-carboxylate (VIa)

A solution of 8.17 (33.9 mmol) of ethyl 6-chloro-2-oxo-2,3-dihydro-benzimidazole-1-carboxylate (Va) in tetrahydrofuran (120 ml) was mixed with 8.89 g (40.7 mmol) of Boc$_2$O and a catalytic amount of DMAP and stirred at room temperature for 1 h. Then 3.81 ml (44.1 mmol) of isopropylamine were added to the reaction solution, and it was stirred for a further 20 min. The reaction solution was concentrated in vacuo and slurried with heptane. The solid was filtered off, washed with heptane and dried in vacuo.
Yield: 8.30 g (91%) of colorless solid
$^1$H-NMR (DMSO-d$_6$): 1.58 (s, 9H), 7.01 (d, 2.0, 1H), 7.10 (dd, 8.6 Hz, 2.0 Hz, 1H), 7.62 (d, 8.6 Hz, 1H), 11.1 (bs, 1H).
MS (API-ES, pos) m/z=213, 215 [M+H−tBu]$^+$ 5,6-Dichloro-1,3-dihydrobenzimidazol-2-one (XVI)

5.49 g (33.9 mmol) of 1,1'-carbonyldiimidazole were added in portions to a stirred solution of 5.00 g (28.2 mmol) of 1,2-diamino-4,5-dichlorobenzene in THF (100 ml) at room temperature. The reaction solution was then stirred at room temperature overnight. The reaction mixture was mixed with water (60 ml) and cooled in an ice bath. The precipitate which separated out was filtered, washed with water and dried in vacuo.
Yield: 5.83 g (100%) of black solid
$^1$H-NMR (DMSO-d$_6$): 7.10 (s, 2H), 10.9 (s, 2H).
MS (API-ES, pos) m/z=203 [M+H]$^+$ di-tert-Butyl 5,6-dichloro-2-oxobenzimidazole-1,3-dicarboxylate (XVII)

3.70 g (17.0 mmol) of Boc$_2$O were added at room temperature to a stirred suspension of 1.38 g (6.80 mmol) of 5,6-dichloro-1,3-dihydrobenzimidazole-2-one (XVI) and a catalytic amount of DMAP in dry THF. The reaction solution was stirred at room temperature for 2 h, and the solvent was then removed in vacuo. The residue was slurried in heptane, filtered, washed with heptane and dried in vacuo.
Yield: 2.33 g (85%) of brown solid
$^1$H-NMR (DMSO-d$_6$): 1.59 (s, 18H), 7.91 (s, 2H).
MS (API-ES, pos) m/z=425 [M+Na]$^+$ tert-Butyl 5,6-dichloro-2-oxo-2,3-dihydrobenzimidazole-1-carboxylate (XVIII)

A mixture of 0.91 g (4.48 mmol) of 5,6-dichloro-1,3-dihydrobenzimidazol-2-one, 1.81 g (4.48 mmol) of di-tert-butyl 5,6-dichloro-2-oxobenzimidazole-1,3-dicarboxylate (XVIII) and 0.74 g (5.38 mmol) of potassium carbonate in acetonitrile (100 ml) was heated under reflux with vigorous stirring for 2.5 h. Most of the solvent was then removed in vacuo, and the residue was mixed with 80 ml of 1N hydrochloric acid. The solid residue was filtered, washed with water, dried in vacuo and recrystallized from ethyl acetate.
Yield: 1.38 g (100%) of black solid
$^1$H-NMR (DMSO-d$_6$): 1.58 (s, 9H), 7.19 (s, 1H), 7.77 (s, 1H), 11.5 (bs, 1H).
MS (API-ES, pos) m/z=247, 249 [M+H−tBu]$^+$

Ethyl 6-iodo-2-oxo-2,3-dihydrobenzimidazole-1-carboxylate (Vb)

A mixture of 9.00 g (43.6 mmol) of ethyl 2-oxo-2,3-dihydrobenzimidazole-1-carboxylate (IV) and 14.2 g (87.3 mmol) of iodine monochloride in acetic acid (100 ml) was stirred at room temperature for 5 min and then at 85° C. for 2.5 h. The cooled reaction mixture was poured into ice-water. The precipitated solid was filtered off, washed with water, dried in vacuo and recrystallized from THF.
Yield: 11.9 g (82%) of colorless solid
$^1$H-NMR (DMSO-d$_6$): 1.34 (t, 7.1 Hz, 3H), 4.39 (q, 7.1 Hz, 2H), 6.85 (d, 8.2 Hz, 1H), 7.48 (dd, 8.2 Hz, 1.5 Hz, 1H), 7.99 (d, 1.5 Hz, 1H), 11.4 (bs, 1H).
MS (API-ES, pos) m/z=333 [M+H]$^+$ tert-Butyl 5-iodo-2-oxo-2,3-dihydrobenzimidazole-1-carboxylate (VIb)

A solution of 9.90 (29.8 mmol) of ethyl 6-iodo-2-oxo-2,3-dihydrobenzimidazole-1-carboxylate (Vb) in tetrahydrofuran (120 ml) was mixed with 7.81 g (35.7 mmol) of Boc$_2$O and a catalytic amount of DMAP and stirred at room temperature for 1 h. Then, 3.33 ml (38.8 mmol) of isopropylamine were added to the reaction solution, and it was stirred for a further 45 min. The reaction solution was concentrated in vacuo and slurried with heptane. The solid was filtered off, washed with heptane and dried in vacuo.
Yield: 8.70 g (81%) of colorless solid
$^1$H-NMR (DMSO-d$_6$): 1.57 (s, 9H), 7.27 (s, 1H), 7.37-7.48 (m, 2H), 11.3 (bs, 1H).
MS (API-ES, pos) m/z=385 [M+Na]$^+$

Methyl bromo-(2-methoxyphenyl)acetate

A mixture of 14.6 g (81.2 mmol) of methyl (2-methoxyphenyl)acetate, 15.2 g (85.3 mmol) of N-bromosuccinimide and a catalytic amount of AIBN in tetrachloromethane (180 ml) was heated under reflux with stirring for 2 h. The cooled reaction solution was filtered, and the solvent was removed in vacuo. Yield: 21.6 g (100%) of yellow oil
$^1$H-NMR (CDCl$_3$): 3.78 (s, 3H), 3.87 (s, 3H), 5.90 (s, 1H), 6.88 (d, 8.31 Hz, 1H), 6.99 (t, 7.5 Hz, 1H), 7.32 (dt, 7.6 Hz, 1.5 Hz, 1H), 7.61 (dd, 7.6 Hz, 1.5 Hz).
MS (API-ES, pos) m/z=259 [M+H]$^+$

2-Bromo-3-phenylpropionic acid 15.0 g (165 mmol) of DL-phenylalanine and 37.8 g (317 mmol) were dissolved in 80 ml of water. 25 ml of conc. HBr in water were added at room temperature, and the reaction solution was then cooled to −10° C. While stirring at −10° C., 7.77 g (112 mmol) of sodium nitrite were added in portions over a period of 1 h, and the reaction solution was then stirred at 0° C. for 6 h. The reaction solution was extracted with diethyl ether (4×60 ml), the combined organic phases were dried over magnesium sulfate, and the solvent was removed in vacuo. Yield: 18.0 g (86%) of yellow oil
$^1$H-NMR (DMSO-d$_6$): 3.10-3.18 (m, 1H), 3.33-3.41 (m, 1H), 4.58-4.64 (m, 1H), 7.20-7.49 (m, 5H), 13.2 (bs, 1H).

tert-Butyl 2-bromo-3-phenylpropionate

A mixture of 10.1 g (44.1 mmol) of 2-bromo-3-phenylpropionic acid in tert-butyl acetate (150 ml) was cooled in an ice/water bath. 0.5 ml of perchloric acid was added, and the reaction solution was stirred at room temperature overnight. The reaction solution was slowly added to a saturated aqueous sodium bicarbonate solution (200 ml) and the organic phase was separated off. The aqueous phase was extracted twice with 60 ml of ethyl acetate each time, the combined organic phases were washed with saturated aqueous sodium bicarbonate solution and dried over magnesium sulfate, and the solvent was removed in vacuo. The residue was purified by chromatography on silica gel (mobile phase gradient 20% acetic acid in cyclohexane). Yield: 6.76 g (54%) of colorless oil
$^1$H-NMR (CDCl3): 1.40 (s, 9H), 3.20 (dd, 14.0 Hz, 6.9 Hz, 1H), 3.41 (dd, 14.0 Hz, 8.7 Hz, 1H), 4.30 (dd, 8.7 Hz, 6.9 Hz, 1H), 7.18-7.34 (m, 5H).
MS (API-ES, pos) m/z=307, 309 [M+Na]$^+$

Methyl (3-methoxyphenyl)acetate

A solution of 25.0 g (150 ml) of (3-methoxyphenyl)acetic acid in dry methanol (250 ml) was mixed with 2 ml of conc. sulfuric acid and heated under reflux for 16 h. The cooled reaction solution was concentrated in vacuo, added to ice-water and extracted four times with 70 ml of ethyl acetate each time. The combined organic extracts were washed with saturated NaCl solution and dried over magnesium sulfate, and the solvent was removed in vacuo. Yield: 28.3 g (100%) of colorless oil
$^1$H-NMR (DMSO-d$_6$): 3.61 (s, 3H), 3.64 (s, 2H), 3.74 (s, 3H), 6.80-6.86 (m, 3H), 7.19-7.25 (m, 1H).
MS (API-ES, pos) m/z=181 [M+H]$^+$

Methyl bromo(3-methoxyphenyl)acetate

A mixture of 15.7 g (87.1 mmol) of methyl (3-methoxyphenyl)acetate, 16.3 g (91.5 mmol) of N-bromosuccinimide and a catalytic amount of AIBN in tetrachloromethane (150 ml) was heated under reflux with stirring for 2 h. The cooled reaction solution was filtered and the solvent was removed in vacuo.
Yield: 21.8 g (100%) of yellow oil
$^1$H-NMR (DMSO-d$_6$): 3.72 (s, 3H), 3.76 (s, 3H), 5.90 (s, 1H), 6.92-6.97 (m, 1H), 7.08-7.13 (m, 2H), 7.28-7.34 (m, 1H).
MS (API-ES, pos) m/z=261 [M+H]$^+$

Methyl (4-methoxyphenyl)acetate

A solution of 25.3 g (152 ml) of (4-methoxyphenyl)acetic acid in dry methanol (250 ml) was mixed with 2 ml of conc. sulfuric acid and heated under reflux for 16 h. The cooled reaction solution was concentrated in vacuo, added to ice-water and extracted four times with 70 ml of ethyl acetate each time. The combined organic extracts were washed with saturated NaCl solution and dried over magnesium sulfate, and the solvent was removed in vacuo.

Yield: 26.4 g (96%) of colorless oil
$^1$H-NMR (DMSO-$d_6$): 3.59 (s, 2H), 3.60 (s, 3H), 3.73 (s, 3H), 6.87 (d, 8.6 Hz, 2H), 7.17 (d, 8.6 Hz, 2H).
MS (API-ES, pos) m/z=181 [M+H]$^+$ Methyl bromo(4-methoxyphenyl)acetate A mixture of 13.4 g (74.4 mmol) of methyl (4-methoxyphenyl)acetate, 13.9 g (78.1 mmol) of N-bromosuccinimide and a catalytic amount of AIBN in tetrachloromethane (120 ml) was heated under reflux with stirring for 2 h. The cooled reaction solution was filtered and the solvent was removed in vacuo.

Yield: 18.98 g (98%) of yellow oil
$^1$H-NMR (CDCl$_3$): 3.78 (s, 3H), 3.81 (s, 3H), 5.35 (s, 1H), 6.88 (d, 8.7 Hz, 2H), 7.48 (d, 8.7 Hz, 2H).
MS (API-ES, pos) m/z=179 [M+H−Br]$^+$ tert-Butyl bromo-phenylacetate A mixture of 7.9 g (44.1 mmol) of bromo-phenylacetic acid in tert-butyl acetate (100 ml) was cooled in an ice/water bath. 0.5 ml of perchloric acid was added, and the reaction solution was stirred at room temperature overnight. The reaction solution was slowly added to a saturated aqueous sodium bicarbonate solution (200 ml), and the organic phase was separated off. The aqueous phase was extracted twice with 60 ml of ethyl acetate each time, the combined organic phases were washed with saturated aqueous sodium bicarbonate solution and dried over magnesium sulfate, and the solvent was removed in vacuo. Yield: 8.41 g (84%) of colorless oil
$^1$H-NMR (CDCl3): 1.46 (s, 9H), 7.26 (s, 1H), 7.31-7.42 (m, 3H), 7.50-7.58 (m, 2H).
MS (API-ES, pos) m/z=134 [M+H−tBu−Br]$^+$ Ethyl 3-(tert-butoxycarbonylphenylmethyl)-2-oxo-2,3-dihydrobenzimidazole-1-carboxylate (VIId)

1.00 g (4.85 mmol) of ethyl 2-oxo-2,3-dihydrobenzimidazole-1-carboxylate (IV) was dissolved in dry DMF (20 ml) in a heat-dried flask under a nitrogen atmosphere. 203 mg (5.09 mmol) of sodium hydride (60% suspension in mineral oil) were added while stirring at 0° C., and the reaction solution was then stirred at room temperature for 30 min. After renewed cooling in an ice bath, 1.44 g (5.33 mmol) of tert-butyl bromophenylacetate were added, and the mixture was stirred while cooling in ice for 1 h, then at room temperature for 2 h. The reaction solution was diluted with ethyl acetate, mixed with 10% aqueous ammonium chloride solution and then extracted with ethyl acetate (3×). The combined organic phases were washed with water and saturated NaCl solution, dried over magnesium sulfate and concentrated in vacuo. The residue was purified by chromatography on silica gel (mobile phase gradient 15-30% ethyl acetate in cyclohexane). Yield: 1.49 g (78%) of colorless oil
$^1$H-NMR (DMSO-$d_6$): 1.37 (t, 7.0 Hz, 3H), 1.42 (s, 9H), 4.44 (q, 7.0 Hz, 2H), 6.30 (s, 1H), 6.94-7.00 (m, 1H), 7.08-7.16 (m, 2H), 7.32-7.42 (m, 3H), 7.43-7.47 (m, 2H), 7.76-7.82 (m, 1H).
MS (API-ES, pos) m/z=341 [M+H−tBu]$^+$ tert-Butyl (2-oxo-2,3-dihydrobenzimidazol-1-yl)phenylacetate (XId)

0.32 ml (3.72 ml) of isopropylamine was added to a stirred solution of 1.34 g (3.38 mmol) of ethyl 3-(tert-butoxycarbonylphenylmethyl)-2-oxo-2,3-dihydro-benzimidazole-1-carboxylate (VIId) in THF (18 ml) and then stirred for 1 h. The solvent was removed in vacuo and the residue was purified by chromatography on silica gel (mobile phase gradient 3-10% ethyl acetate in dichloromethane). Yield: 1.04 g (95%) of colorless oil
$^1$H-NMR (DMSO-$d_6$): 1.41 (s, 9H), 6.18 (s, 1H), 6.75-6.80 (m, 1H), 6.83-7.01 (m, 3H), 7.29-7.43 (m, 5H), 11.0 (bs, 1H).
MS (API-ES, pos) m/z=269 [M+H−tBu]$^+$ (2-Oxo-2,3-dihydrobenzimidazol-1-yl)phenylacetic acid (VIIId)

1.00 g (3.08 mmol) of tert-butyl (2-oxo-2,3-dihydrobenzimidazol-1-yl)acetate (XId) was dissolved in dichloromethane (10 ml) and, while stirring at room temperature, trifluoroacetic acid (6 ml) was added. The reaction solution was stirred for 2 h and then the solvent and excess trifluoroacetic acid were removed in vacuo. The residue was taken up again in toluene, concentrated in vacuo and then dried in vacuo. Yield: 827 mg (100%) of white solid
$^1$H-NMR (DMSO-$d_6$): 6.21 (s, 1H), 7.76-7.01 (m, 4H), 7.28-7.46 (m, 5H), 11.0 (bs, 1H), 13.3 (bs, 1H).
MS (API-ES, pos) m/z=269 [M+H]$^+$ tert-Butyl[3-(4-methoxybenzenesulfonyl)-2-oxo-2,3-dihydrobenzimidazol-1-yl]phenylacetate (XIId)

630 mg (3.05 mmol) of 4-methoxybenzenesulfonyl chloride were added to a solution of 900 mg (4.20 mmol) of tert-butyl (2-oxo-2,3-dihydrobenzimidazol-1-yl)phenylacetate (VIIId), 0.77 mg (5.55 mmol) of triethylamine and a catalytic amount of DMAP in tetrahydrofuran (25 ml) while stirring at room temperature, and the mixture was then stirred at room temperature for 16 h. The reaction solution was mixed with water and extracted with ethyl acetate (3×60 ml). The combined organic phases were washed with water and saturated brine, dried over magnesium sulfate and concentrated under reduced pressure. The residue was purified by chromatography on silica gel (mobile phase gradient 10-25% ethyl acetate in cyclohexane). Yield: 910 mg (66%) of colorless solid
$^1$H-NMR (DMSO-$d_6$): 1.22 (s, 9H), 3.85 (s, 3H), 6.22 (s, 1H), 7.06-7.12 (m, 1H), 7.14-7.22 (m, 4H), 7.29-7.35 (m, 5H), 7.82-7.87 (m, 1H), 7.98 (d, 8.9 Hz, 2H).
MS (API-ES, pos) m/z=439 [M+H−tBu]$^+$ tert-Butyl 3-tert-butoxycarbonylmethyl-5-chloro-2-oxo-2,3-dihydrobenzimidazole-1-carboxylate (VIIg)

A mixture of 4.00 g (14.9 mmol) of tert-butyl 5-chloro-2-oxo-2,3-dihydrobenzimidazole-1-carboxylate (VIa), 3.19 g (16.4 mmol) of tert-butyl bromoacetate and 7.28 g (22.3 mmol) of cesium carbonate in acetonitrile (80 ml) was heated under reflux for 3 h. The solvent was removed in vacuo, the residue was mixed with water, and the aqueous mixture was extracted four times with ethyl acetate. The combined organic phases were washed with saturated NaCl solution and dried over magnesium sulfate, and the solvent was removed in vacuo. The residue was purified by chromatography on silica gel (mobile phase gradient 0-5% ethyl acetate in dichloromethane).

Yield: 2.42 g of yellow solid.

$^1$H-NMR (DMSO-d$_6$): 1.42 (s, 9H), 1.59 (s, 9H), 4.62 (s, 2H), 7.19 (dd, 8.6 Hz, 2.0 Hz, 1H), 7.45 (d, 3.0 Hz), 7.70 (d, 8.6 Hz, 1H).

MS (API-ES, pos) m/z=271, 273 [M+H–2tBu]$^+$ tert-Butyl (6-chloro-2-oxo-2,3-dihydrobenzimidazol-1-yl)acetate (XIg)

A solution of 1.8 g (4.70 mmol) of tert-butyl 3-tert-butoxycarbonylmethyl-5-chloro-2-oxo-2,3-dihydrobenzimidazole-1-carboxylate (VIIg) in 100 ml of 2% trifluoroacetic acid in dichloromethane was stirred at room temperature for 16 h. The solvent was removed in vacuo and the residue was dried in vacuo. Yield: 1.32 g (100%) of colorless solid $^1$H-NMR (DMSO-d$_6$): 1.41 (s, 9H), 4.55 (s, 2H), 6.97-7.04 (m, 2H), 7.25 (d, 1.8 Hz, 1H), 11.1 (bs, 1H).

MS (API-ES, pos) m/z=305, 307 [M+H]$^+$ tert-Butyl[6-chloro-3-(4-methoxybenzenesulfonyl)-2-oxo-2,3-dihydrobenzimidazol-1-yl]acetate (XIIg)

0.96 g (4.62 mmol) of 4-methoxybenzenesulfonyl chloride was added to a solution of 1.18 g (4.20 mmol) of tert-butyl (6-chloro-2-oxo-2,3-dihydro-benzimidazol-1-yl)acetate (XIg), 1.16 g (8.40 mmol) of triethylamine and a catalytic amount of DMAP in tetrahydrofuran (20 ml) while stirring at room temperature, and the mixture was then stirred at room temperature for 16 h. The reaction solution was mixed with water and extracted with ethyl acetate (3×60 ml). The combined organic phases were washed with water and saturated brine, dried over magnesium sulfate and concentrated under reduced pressure. The residue was purified by chromatography on silica gel (mobile phase gradient 15-45% ethyl acetate in cyclohexane). Yield: 1.22 g (64%) of colorless solid $^1$H-NMR (DMSO-d$_6$): 1.30 (s, 9H), 3.84 (s, 3H), 4.56 (s, 2H), 7.17 (d, 8.8 Hz, 2H), 7.26 (dd, 8.6 Hz, 1.6 Hz, 1H), 7.49 (s, 1H), 7.81 (d, 8.6 Hz, 1H), 7.97 (d, 8.8 Hz, 2H).

MS (API-ES, pos) m/z=397, 399 [M+H–tBu]$^+$ (6-Chloro-2-oxo-2,3-dihydrobenzimidazol-1-yl)acetic acid (VIIIg)

1.92 g (5.02 mmol) of tert-butyl 3-tert-butoxycarbonylmethyl-5-chloro-2-oxo-2,3-dihydrobenzimidazole-1-carboxylate (VIIg) were dissolved in dichloromethane (40 ml) and, while stirring at room temperature, trifluoroacetic acid (15 ml) was added. The reaction solution was stirred for 2 h and then the solvent and excess trifluoroacetic acid were removed in vacuo. The residue was taken up again in toluene, concentrated in vacuo and then dried in vacuo. Yield: 1.50 g (100%) of white solid $^1$H-NMR (DMSO-d$_6$): 4.56 (s, 2H), 6.95-7.04 (m, 2H), 7.28 (s, 1H), 11.1 (s, 1H), 13.0 (bs, 1H).

MS (API-ES, pos) m/z=227, 229 [M+H]$^+$

[6-Chloro-3-(4-methoxybenzenesulfonyl)-2-oxo-2,3-dihydro-benzimidazol-1-yl]acetic acid (XIIIg)

1.10 g (2.43 mmol) of tert-butyl[6-chloro-3-(4-methoxybenzenesulfonyl)-2-oxo-2,3-dihydrobenzimidazol-1-yl]acetate (XIIg) were dissolved in dichloromethane (40 ml) and, while stirring at room temperature, trifluoroacetic acid (20 ml) was added. The reaction solution was stirred for 2 h and then the solvent and excess trifluoroacetic acid were removed in vacuo. The residue was taken up again in toluene, concentrated in vacuo and then dried in vacuo. Yield: 0.82 g (95%) of white solid MS (API-ES, pos) m/z=397, 399 [M+H]$^+$ tert-Butyl 5-chloro-3-(ethoxycarbonylphenylmethyl)-2-oxo-2,3-dihydrobenzimidazole-1-carboxylate (VIIa, R$_4$=ethyl)

2.00 g (7.44 mmol) of tert-butyl 5-chloro-2-oxo-2,3-dihydrobenzimidazole-1-carboxylate (VIa) were dissolved in dry DMF (20 ml) in a heat-dried flask under a nitrogen atmosphere. 313 mg (7.82 mmol) of sodium hydride (60% suspension in mineral oil) were added while stirring at 0° C. and the reaction solution was then stirred at room temperature for 30 min. After renewed cooling in an ice bath, 1.99 g (8.19 mmol) of ethyl bromo-phenylacetate were added, and the mixture was stirred while cooling in ice for 1 h and then at room temperature for 2 h. The reaction solution was diluted with ethyl acetate, mixed with 10% aqueous ammonium chloride solution and then extracted with ethyl acetate (3×). The combined organic phases were washed with water and saturated NaCl solution, dried over magnesium sulfate and concentrated in vacuo. The residue was purified by chromatography on silica gel (mobile phase gradient 20-60% ethyl acetate in cyclohexane). Yield: 3.40 g (100%) of yellow oil $^1$H-NMR (DMSO-d$_6$): 1.20 (t, 7.1 Hz, 3H), 1.60 (s, 9H), 4.26 (q, 7.1 Hz, 2H), 6.43 (s. 1H), 7.10 (s, 1H), 7.15-7.20 (m, 1H), 7.35-7.43 (m, 3H), 7.44-7.50 (m, 2H), 7.72 (d, 8.6 Hz, 1H).

MS (API-ES, pos) m/z=375, 377 [M+H–tBu]$^+$ tert-Butyl 3-(tert-butoxycarbonylphenylmethyl)-5-chloro-2-oxo-2,3-dihydrobenzimidazole-1-carboxylate (VIIa, R$_4$=tert-butyl)

4.00 g (14.9 mmol) of tert-butyl 5-chloro-2-oxo-2,3-dihydrobenzimidazole-1-carboxylate (VIa) were dissolved in dry DMF (60 ml) in a heat-dried flask under a nitrogen atmosphere. 625 mg (15.6 mmol) of sodium hydride (60% suspension in mineral oil) were added while stirring at 0° C., and the reaction solution was then stirred at room temperature for 30 min. After renewed cooling in an ice bath, 4.44 g (16.4 mmol) of tert-butyl bromo-phenylacetate were added, and the mixture was stirred while cooling in ice for 1 h and then at room temperature for 2 h. The reaction solution was diluted with ethyl acetate, mixed with 10% aqueous ammonium chloride solution and then extracted with ethyl acetate (3×). The combined organic phases were washed with water and saturated NaCl solution, dried over magnesium sulfate and concentrated in vacuo. The residue was purified by chromatography on silica gel (mobile phase gradient 15-35% ethyl acetate in cyclohexane). Yield: 6.91 g (100%) of yellow oil $^1$H-NMR (DMSO-d$_6$): 1.43 (s, 9H), 1.60 (s, 9H), 6.30 (s, 1H), 7.00-7.03 (m, 1H), 7.17 (dd, 8.6 Hz, 1.8 Hz, 1H), 7.34-7.48 (m, 5H), 7.71 (d, 8.6 Hz, 1H).

MS (API-ES, pos) m/z=347, 349 [M+H–2tBu]$^+$ (6-Chloro-2-oxo-2,3-dihydrobenzimidazol-1-yl)phenylacetic acid (VIIIa)

14.0 g (350 mmol) of sodium hydroxide were added to a stirred solution of 3.43 g (7.96 mmol) of tert-butyl 5-chloro-3-(ethoxycarbonylphenylmethyl)-2-oxo-2,3-dihydrobenzimidazole-1-carboxylate (VIIa, R$_4$=tert-butyl) in 80 ml of methanol/water (7:1) at 0° C. in order to obtain a 5N NaOH solution. The reaction solution was subsequently stirred at 0° C. for 1 h and then diluted with 100 ml of water and adjusted to pH=0 with concentrated hydrochloric acid. The aqueous phase was extracted with ethyl acetate (5×60 ml), the combined organic phases were dried over magnesium sulfate, and the solvent was removed in vacuo. Yield: 2.50 g (100%) of yellow solid $^1$H-NMR (DMSO-d$_6$): 6.21 (s, 1H), 6.84 (s, 1H), 6.99 (s, 2H), 7.31-7.45 (m, 5H), 11.22, (s, 1H), 13.4 (bs, 1H).

MS (API-ES, pos) m/z=303, 305 [M+H]$^+$ tert-Butyl (6-chloro-2-oxo-2,3-dihydrobenzimidazol-1-yl)phenylacetate (XIa)

3.00 (6.53 mmol) of tert-butyl 3-(tert-butoxycarbonylphenylmethyl)-5-chloro-2-oxo-2,3-dihydrobenzimidazole-1-carboxylate (VIIa) were dissolved in 100 ml of a 2 percent trifluoroacetic acid solution in dichloromethane and stirred at room temperature overnight. The solvent and excess trifluoroacetic acid were removed in vacuo, and the residue was taken up in toluene, concentrated in vacuo and dried.

Yield: 2.35 (100%) of white solid $^1$H-NMR (DMSO-d$_6$): 1.42 (s, 9H), 6.19 (s, 1H), 6.83 (s, 1H), 6.99 (s, 2H), 7.31-7.48 (m, 5H), 11.2 (bs, 1H).

MS (API-ES, pos) m/z=303, 305 [M+H–tBu]$^+$ tert-Butyl[6-chloro-3-(4-methoxybenzenesulfonyl)-2-oxo-2,3-dihydrobenzimidazol-1-yl]phenylacetate (XIIa)

2.36 g (11.4 mmol) of 4-methoxybenzenesulfonyl chloride were added at room temperature to a stirred solution of 3.72 g (10.4 mmol) of tert-butyl (6-chloro-2-oxo-2,3-dihydrobenzimidazol-1-yl)phenylacetate (XIa), 2.91 (20.7 mmol) of triethylamine and a catalytic amount of DMAP in tetrahydrofuran (40 ml), and the mixture was then stirred at room temperature for 16 h. The reaction solution was mixed with water and extracted with ethyl acetate (3×60 ml). The combined organic phases were washed with water and saturated brine, dried over magnesium sulfate and concentrated under reduced pressure. The residue was purified by chromatography on silica gel (mobile phase gradient 10-30% ethyl acetate in heptane). Yield: 4.18 g (76%) of colorless solid $^1$H-NMR (DMSO-d$_6$): 1.21 (s, 9H), 3.85 (s, 3H), 6.24 (s, 1H), 7.19 (d, 9.0 Hz, 2H), 7.24-7.29 (m, 2H), 7.33-7.37 (m, 5H), 7.84 (d, J=9.2 Hz, 1H), 7.98 (d, 9.0 Hz, 2H)

MS (API-ES, pos) m/z=473, 475 [M+H–tBu]$^+$

6-Chloro-3-(4-methoxybenzenesulfonyl)-2-oxo-2,3-dihydro-benzimidazol-1-yl]phenylacetic acid (XIIIa)

4.60 g (8.70 mmol) of tert-butyl[6-chloro-3-(4-methoxybenzenesulfonyl)-2-oxo-2,3-dihydrobenzimidazol-1-yl]phenylacetate (XIIa) were dissolved in dichloromethane (50 ml) and, while stirring at room temperature, trifluoroacetic acid (25 ml) was added. The reaction solution was stirred for 2 h and then the solvent and excess trifluoroacetic acid were removed in vacuo. The residue was taken up again in toluene, concentrated in vacuo and then dried in vacuo. Yield: 4.12 mg (100%) of white solid $^1$H-NMR (DMSO-d$_6$): 3.86 (s, 3H), 7.17 (d, 9.0 Hz, 2H), 7.16-7.27 (m, 2H), 7.30-7.34 (m, 5H), 7.82 (d, 8.7 Hz, 1H), 7.96 (d, 9.0 Hz, 2H).

MS (API-ES, pos) m/z=473, 475 [M+H]$^+$ tert-Butyl 3-(tert-butoxycarbonylphenylmethyl)-5-iodo-2-oxo-2,3-dihydrobenzimidazole-1-carboxylate (XIIb)

3.00 g (8.33 mmol) of tert-butyl 5-iodo-2-oxo-2,3-dihydrobenzimidazole-1-carboxylate (VIb) were dissolved in dry DMF (50 ml) in a heat-dried flask under a nitrogen atmosphere. 364 mg (5.09 mmol) of sodium hydride (60% suspension in mineral oil) were added at 0° C. while stirring, and the reaction solution was then stirred at room temperature for 30 min. After renewed cooling in an ice bath, 2.37 g (8.75 mmol) of tert-butyl bromo-phenylacetate were added, and the mixture was stirred while cooling in ice for 1 h and then at room temperature for 2 h. The reaction solution was diluted with ethyl acetate, mixed with 10% aqueous ammonium chloride solution and then extracted with ethyl acetate (3×). The combined organic phases were washed with water and saturated NaCl solution, dried over magnesium sulfate and concentrated in vacuo. The residue was purified by chromatography on silica gel (mobile phase gradient 10-30% ethyl acetate in cyclohexane). Yield: 4.20 g (91%) of colorless solid $^1$H-NMR (DMSO-d$_6$): 1.42 (s, 9H), 1.59 (s, 1H), 7.27 (s, 1H), 7.33-7.48 (m, 6H), 7.53 (m, 1H).

MS (API-ES, pos) m/z=438 [M+H–2tBu]$^+$ tert-Butyl 3-(ethoxycarbonylphenylmethyl)-5-iodo-2-oxo-2,3-dihydrobenzimidazol-1-carboxylate (VIIb, R$_4$=ethyl)

1.16 g (3.22 mmol) of tert-butyl 5-iodo-2-oxo-2,3-dihydrobenzimidazole-1-carboxylate (VIb) were dissolved in dry DMF (25 ml) in a heat-dried flask under a nitrogen atmosphere. 136 mg (3.38 mmol) of sodium hydride (60% suspension in mineral oil) were added at 0° C. while stirring, and the reaction solution was then stirred at room temperature for 30 min. After renewed cooling in an ice bath, 861 mg (3.54 mmol) of ethyl bromo-phenylacetate were added, and the mixture was stirred while cooling in ice for 1 h and then at room temperature for 2 h. The reaction solution was diluted with ethyl acetate, mixed with 10% aqueous ammonium chloride solution and then extracted with ethyl acetate (3×). The combined organic phases were washed with water and saturated NaCl solution, dried over magnesium sulfate and concentrated in vacuo. The residue was purified by chromatography on silica gel (mobile phase gradient 5-45% ethyl acetate in heptane). Yield: 1.53 g (91%) of colorless oil $^1$H-NMR (DMSO-d$_6$): 1.19 (t, 7.1 Hz, 3H), 1.59 (s, 9H), 4.21-4.28 (m, 2H), 6.41 (s, 1H), 7.32-7.55 (m, 8H).

MS (API-ES, pos) m/z=467 [M+H–tBu]$^+$ (6-Iodo-2-oxo-2,3-dihydrobenzimidazol-1-yl)phenylacetic acid (VIIIb)

1.50 g (2.73 mmol) of tert-butyl 3-(tert-butoxycarbonylphenylmethyl)-5-iodo-2-oxo-2,3-dihydrobenzimidazole-1-carboxylate (XIIb) were dissolved in dichloromethane (16 ml) and, while stirring at room temperature, trifluoroacetic acid (10 ml) was added. The reaction solution was stirred for 2 h and then the solvent and excess trifluoroacetic acid were removed in vacuo. The residue was taken up again in toluene, concentrated in vacuo and then dried in vacuo. Yield: 1.10 g (100%) of yellow solid.

$^1$H-NMR (DMSO-d$_6$): 6.14 (s, 1H), 6.83 (d, 8.1 Hz, 1H), 7.09 (s, 1H), 7.23-7.43 (m, 6H), 11.2 (s, 1H).

MS (API-ES, pos) m/z=396 [M+H]$^+$ tert-Butyl 3-tert-butoxycarbonylmethyl-5-iodo-2-oxo-2,3-dihydro-benzimidazole-1-carboxylate (VIIj)

A mixture of 1.90 g (5.27 mmol) of tert-butyl 5-iodo-2-oxo-2,3-dihydro-benzimidazole-1-carboxylate (VIb), 1.13 g (5.80 mmol) of tert-butyl bromoacetate and 2.23 g (6.86 mmol) of cesium carbonate in acetonitrile (60 ml) was heated under reflux for 3 h. The solvent was removed in vacuo, water was added to the residue, and the aqueous mixture was extracted four times with ethyl acetate. The combined organic phases were washed with saturated NaCl solution and dried over magnesium sulfate, and the solvent was removed in vacuo. The residue was purified by chromatography on silica gel (mobile phase gradient 15-40% ethyl acetate in heptane). Yield: 2.26 g (90%) of white solid.
$^1$H-NMR (DMSO-$d_6$): 1.43 (s, 9H), 1.59 (s, 9H), 4.60 (s, 2H), 7.47-7.53 (m, 2H), 7.67 (s, 1H).
MS (API-ES, pos) m/z=363 [M+H−2tBu]$^+$

(6-Iodo-2-oxo-2,3-dihydrobenzimidazol-1-yl)acetic acid (VIIIj)

2.10 g (4.43 mmol) of tert-butyl 3-tert-butoxycarbonylmethyl-5-iodo-2-oxo-2,3-dihydrobenzimidazole-1-carboxylate (VIIj) were dissolved in dichloromethane (50 ml) and, while stirring at room temperature, trifluoroacetic acid (25 ml) was added. The reaction solution was stirred for 2 h and then the solvent and excess trifluoroacetic acid were removed in vacuo. The residue was taken up again in toluene, concentrated in vacuo and then dried in vacuo. Yield: 1.39 g (99%) of white solid.
MS (API-ES, pos) m/z=319 [M+H]$^+$ tert-Butyl 3-(tert-butoxycarbonylphenylmethyl)-5-cyano-2-oxo-2,3-dihydrobenzimidazole-1-carboxylate (VIIc)

1.74 (3.16 mmol) of tert-butyl 3-(tert-butoxycarbonylphenylmethyl)-5-iodo-2-oxo-2,3-dihydrobenzimidazole-1-carboxylate (XIIb) were dissolved in 20 ml of dry DMF and stirred under a stream of nitrogen for 20 min. 482 mg (4.11 mmol) of zinc(II) cyanide and 292 mmol (0.25 mmol) of Pd[P(Ph)$_3$]$_4$ were added, and the reaction solution was stirred at 80° C. for 1.5 h. The cooled reaction solution was mixed with 70 ml of water and extracted with ethyl acetate (3×). The combined organic phases were washed with saturated NaCl solution and dried over magnesium sulfate, and the solvent was removed in vacuo. The residue was purified by chromatography on silica gel (mobile phase gradient 10-30% ethyl acetate in cyclohexane). Yield: 1.08 g (76%) of white solid
$^1$H-NMR (DMSO-$d_6$): 1.43 (s, 9H), 1.61 (s, 9H), 6.32 (s, 1H), 7.34-7.51 (m, 6H), 7.61 (d, 8.4 Hz, 1H), 7.88 (d, 8.4 Hz, 1H).
MS (API-ES, pos) m/z=338 [M+H−2tBu]$^+$ tert-Butyl (6-cyano-2-oxo-2,3-dihydrobenzimidazol-1-yl)phenylacetate (XIc)

2.40 (5.34 mmol) of tert-butyl 3-(tert-butoxycarbonylphenylmethyl)-5-cyano-2-oxo-2,3-dihydrobenzimidazole-1-carboxylate (VIIc) were dissolved in 200 ml of a 2-percent strength trifluoroacetic acid solution in dichloromethane and stirred at room temperature overnight. The solvent and excess trifluoroacetic acid were removed in vacuo, and the residue was taken up in toluene, concentrated in vacuo and dried.

Yield: 2.10 (100%) of white solid
$^1$H-NMR (DMSO-$d_6$): 1.43 (s, 9H), 6.23 (s, 1H), 7.16 (d, 8.1 Hz, 1H), 7.21 (s, 1H), 7.34-7.48 (m, 6H), 11.7 (bs, 1H).
MS (API-ES, pos) m/z=372 [M+Na]$^+$ tert-Butyl[6-cyano-3-(4-methoxybenzenesulfonyl)-2-oxo-2,3-dihydrobenzimidazol-1-yl]phenylacetate (XIIc)

1.63 g (7.87 mmol) of 4-methoxybenzenesulfonyl chloride were added to a solution of 2.50 g (7.16 mmol) of tert-butyl (6-cyano-2-oxo-2,3-dihydro-benzimidazol-1-yl)phenylacetate (XIc), 1.98 ml (14.3 mmol) of triethylamine and a catalytic amount of DMAP in tetrahydrofuran (60 ml) while stirring at room temperature, and the mixture was then stirred at room temperature for 16 h. The reaction solution was mixed with water and extracted with ethyl acetate (3×60 ml). The combined organic phases were washed with water and saturated brine, dried over magnesium sulfate and concentrated under reduced pressure. The residue was purified by chromatography on silica gel (mobile phase gradient 10-40% ethyl acetate in cyclohexane). Yield: 2.90 g (78%) of colorless solid
$^1$H-NMR (DMSO-$d_6$): 1.21 (s, 9H), 3.86 (s, 3H), 6.27 (s, 1H), 7.19 (d, 9.0 Hz, 2H), 7.32-7.44 (m, 5H), 7.67-7.74 (m, 2H), 7.98-8.04 (m, 3H).
MS (API-ES, pos) m/z=542 [M+Na]$^+$

3-(tert-Butoxycarbonyl-phenylmethyl)-5-cyano-2-oxo-2,3-dihydro-benzoimidazole-1-carboxylic acid tert-butyl ester (VIIc) (alternative route)

1. (4-Cyano-2-nitrophenyl)-carbamic acid tert-butyl ester

To a chilled suspension of 4-amino-3-nitrobenzonitrile (5.0 g, 30.7 mmol), 4-dimethylaminopyridine (catalytic amount) in CH$_2$Cl$_2$ (87 mL) and N,N-diisopropylethylamine (5.3 mL, 30.7 mmol) was added a solution of di-tert-butyldicarbonate (6.7 g, 30.7 mmol) in CH$_2$Cl$_2$ (38 mL) dropwise over 10 min. The suspension was stirred at room temperature for 4 hours. Then, di-tert-butyldicarbonate (0.34 g, 1.53 mmol) was added and the resulting solution was stirred for another hour. The reaction mixture was washed with 10% citric acid aqueous solution, brine, dried over Na$_2$SO$_4$, filtered and concentrated in vacuo. The residue was purified by flash chromatography in silica gel using 30% ethyl acetate in n-heptane as eluent to afford (4-cyano-2-nitrophenyl)-carbamic acid tert-butyl ester (6.4 g, 79%) as a light yellow solid.
$^1$H-NMR (400 MHz, DMSO-$d_6$): δ 1.46 (s, 9H), 7.87 (d, 8.6 Hz, 1H), 8.07 (dm, 8.6 Hz, 1H), 8.49 (br s, 1H), 10.0 (br s, NH).
MS (API-ES, pos) m/z=264.30 [M+H]$^+$.

2. (2-Amino-4-cyanophenyl)-carbamic acid tert-butyl ester

To solution of (4-cyano-2-nitrophenyl)-carbamic acid tert-butyl ester (3.6 g, 13.8 mmol) in methanol (18 mL), ethyl acetate (28 mL) and triethylamine (1.9 mL, 13.6 mmol) was added 10% Pd on carbon (0.73 g, 0.69 mmol). The reaction mixture was hydrogenated under 1 atm H$_2$ for 24 hours, filtered through Celite and concentrated in vacuo. The residue was purified by flash chromatography in silica gel using 20% ethyl acetate in n-heptane as eluent to afford (2-amino-4-cyanophenyl)-carbamic acid tert-butyl ester (2.6 g, 82%) as a light yellow solid.

¹H-NMR (400 MHz, DMSO-d₆): δ 1.48 (s, 9H), 6.93 (dm, 8.3 Hz, 1H), 6.99 (br s, 1H), 7.57 (d, 8.3 Hz, 1H), 8.56 (br s, NH).

MS (API-ES, pos) m/z=178.10 [M+H−$^t$Bu]⁺.

3. 5-Cyano-2-oxo-2,3-dihydro-benzoimidazole-1-carboxylic acid tert-butyl ester To a chilled solution of (2-amino-4-cyanophenyl)-carbamic acid tert-butyl ester (2.1 g, 8.8 mmol) in CH₂Cl₂ (50 mL) and triethylamine (1.22 mL, 8.8 mmol) was added a solution of triphosgene (0.94 g, 3.2 mmol) in CH₂Cl₂ (50 mL) slowly. The reaction was stirred at room temperature for 3 hours, diluted with CH₂Cl₂, washed with water, brine, dried over Na₂SO₄, filtered and concentrated in vacuo. The residue was purified by flash chromatography in silica gel using a gradient from 30% to 60% ethyl acetate in n-heptane as eluent to afford 5-cyano-2-oxo-2,3-dihydro-benzoimidazole-1-carboxylic acid tert-butyl ester (1.7 g, 75%) as a white solid.

¹H-NMR (400 MHz, DMSO-d₆): δ 1.59 (s, 9H), 7.39 (d, 1.5 Hz, 1H), 7.53 (dd, 8.3 Hz, 1.5 Hz, 1H), 7.76 (d, 8.3 Hz, 1H), 11.59 (br s, NH).

MS (API-ES, pos) m/z=260.15 [M+H]⁺.

4. 3-(tert-Butoxycarbonyl-phenylmethyl)-5-cyano-2-oxo-2,3-dihydro-benzoimidazole-1-carboxylic acid tert-butyl ester (VIIc)

To a chilled solution of 5-cyano-2-oxo-2,3-dihydro-benzoimidazole-1-carboxylic acid tert-butyl ester (808 mg, 3.1 mmol) in dry DMF (15 mL) was added NaH (60% dispersion mineral oil, 131 mg, 3.3 mmol) under N₂ atmosphere. The reaction was stirred at room temperature for 15 min. Then at 0° C., a solution of bromophenylacetic acid tert-butyl ester (887 mg, 3.3 mmol) in DMF (5 mL) was added. The reaction was stirred at room temperature for 2 hours, diluted with ethyl acetate, washed with water, with a saturated NH₄Cl aqueous solution, brine, dried over Na₂SO₄, filtered and concentrated in vacuo. The residue was purified by flash chromatography in silica gel using 15% ethyl acetate in n-heptane as eluent to afford 3-(tert-butoxycarbonyl-phenyl methyl)-5-cyano-2-oxo-2,3-dihydro-benzoimidazole-1-carboxylic acid tert-butyl ester (VIIc) (1.1 g, 78%) as a white solid.

[6-Cyano-3-(4-methoxybenzenesulfonyl)-2-oxo-2,3-dihydro-benzimidazol-1-yl]phenylacetic acid (XIIIc)

1.75 g (3.37 mmol) of tert-butyl[6-cyano-3-(4-methoxy-benzenesulfonyl)-2-oxo-2,3-dihydrobenzimidazol-1-yl]phenylacetate (XIIc) were dissolved in dichloromethane (20 ml) and, while stirring at room temperature, trifluoroacetic acid (10 ml) was added. The reaction solution was stirred for 2 h and then the solvent and excess trifluoroacetic acid were removed in vacuo. The residue was taken up again in toluene, concentrated in vacuo and then dried in vacuo. Yield: 1.49 g (96%) of white solid ¹H-NMR (DMSO-d₆): 3.87 (s, 3H), 6.28 (s, 1H), 7.18 (d, 9.0 Hz, 2H), 7.29-7.41 (m, 5H), 7.64 (s, 1H), 7.69 (d, 8.5 Hz, 1H), 7.95-8.03 (m, 3H), 13.7 (bs, 1H).

MS (API-ES, pos) m/z=464 [M+H]⁺

(6-Cyano-2-oxo-2,3-dihydrobenzimidazol-1-yl)phenylacetic acid (VIIIc)

tert-Butyl 3-(tert-butoxycarbonylphenylmethyl)-5-cyano-2-oxo-2,3-dihydro-benzoimidazole-1-carboxylate 695 mg (1.55 mmol) of tert-butyl 3-(tert-butoxycarbonylphenylm-ethyl)-5-cyano-2-oxo-2,3-dihydrobenzimidazole-1-carboxylate (VIIc) were dissolved in dichloromethane (30 ml) and, while stirring at room temperature, trifluoroacetic acid (20 ml) was added. The reaction solution was stirred for 2 h and then the solvent and excess trifluoroacetic acid were removed in vacuo. The residue was taken up again in toluene, concentrated in vacuo and then dried in vacuo. Yield: 449 mg (99%) of white solid ¹H-NMR (DMSO-d₆): 6.25 (s, 1H), 7.15 (d, 8.1 Hz, 1H), 7.25 (s, 1H), 7.33-7.52 (m, 6H), 11.65 (s, 1H), 13.53 (bs, 1H).

MS (API-ES, pos) m/z=294 [M+H]⁺ tert-Butyl 5-chloro-3-[methoxycarbonyl-(3-methoxyphenyl)methyl]-2-oxo-2,3-dihydrobenzimidazole-1-carboxylate (VIIm, R₄=methyl)

2.50 g (9.30 mmol) of tert-butyl 5-chloro-2-oxo-2,3-dihydrobenzimidazole-1-carboxylate (VIa) were dissolved in DMF (50 ml) in a heat-dried flask under a nitrogen atmosphere. 391 mg (9.77 mmol) of sodium hydride (60% suspension in mineral oil) were added while stirring at 0° C., and the reaction solution was then stirred at room temperature for 30 min. After renewed cooling in an ice bath, 2.65 g (10.2 mmol) of methyl bromo(3-methoxyphenyl)acetate were added, and the mixture was stirred while cooling in ice for 1 h and then at room temperature for 2 h. The reaction solution was diluted with ethyl acetate, mixed with 10% aqueous ammonium chloride solution and then extracted with ethyl acetate (3×). The combined organic phases were washed with water and saturated NaCl solution, dried over magnesium sulfate and concentrated in vacuo. The residue was purified by chromatography on silica gel (mobile phase gradient 15-40% ethyl acetate in heptane). Yield: 3.23 g (78%) of yellow oil ¹H-NMR (DMSO-d₆): 1.60 (s, 9H), 3.74 (s, 3H), 3.77 (s, 3H), 6.39 (s, 1H), 6.96 (dd, 8.2 Hz, 2.2 Hz, 1H), 7.02-7.07 (m, 2H), 7.13-7.21 (m, 2H), 7.29-7.36 (m, 1H), 7.72 (d, 8.6 Hz, 1H).

MS (API-ES, pos) m/z=391, 393 [M+H−tBu]⁺

(6-Chloro-2-oxo-2,3-dihydrobenzimidazol-1-yl)-(3-methoxyphenyl)acetic acid (VIIIm)

10.0 g (250 mmol) of sodium hydroxide were added to a solution of 1.46 g (3.27 mmol) of tert-butyl 5-chloro-3-[methoxycarbonyl-(3-methoxyphenyl)-methyl]-2-oxo-2,3-dihydrobenzimidazole-1-carboxylate (VIIm) in 50 ml of methanol/water (4:1) while stirring at 0° C. in order to obtain a 5N NaOH solution. The reaction solution was subsequently stirred at 0° C. for 2 h, then diluted with 100 ml of water and adjusted to pH=0 with concentrated hydrochloric acid. The aqueous phase was extracted with ethyl acetate (5×60 ml), the combined organic phases were dried over magnesium sulfate, and the solvent was removed in vacuo. Yield: 950 mg (87%) of white solid ¹H-NMR (DMSO-d₆): 3.73 (s, 3H), 6.17 (s, 1H), 6.88-6.95 (m, 2H), 6.97-7.04 (m, 4H), 7.27-7.34 (m, 1H), 11.2 (s, 1H).

MS (API-ES, pos) m/z=333, 335 [M+H]⁺ tert-Butyl 5-chloro-3-[methoxycarbonyl-(4-methoxyphenyl)methyl]-2-oxo-2,3-dihydrobenzimidazole-1-carboxylate (VIIn, R₄=methyl)

1.34 g (4.99 mmol) of tert-butyl 5-chloro-2-oxo-2,3-dihydrobenzimidazole-1-carboxylate (VIa) were dissolved in dry DMF (20 ml) in a heat-dried flask under a nitrogen atmosphere. 210 mg (5.24 mmol) of sodium hydride (60% suspension in mineral oil) were added while stirring at 0° C., and the reaction solution was then stirred at room temperature for 30 min. After renewed cooling in an ice bath, 1.42 g (5.49 mmol) of methyl bromo-(4-methoxyphenyl)acetate were added, and the mixture was stirred while cooling in ice for 1 h and then at room temperature for 2 h. The reaction solution was diluted with ethyl acetate, mixed with 10% aqueous ammonium chloride solution and then extracted with ethyl acetate (3×). The combined organic phases were washed with water and saturated NaCl solution, dried over magnesium sulfate and concentrated in vacuo. The residue was purified by chromatography on silica gel (mobile phase gradient 15-30% ethyl acetate in heptane). Yield: 2.02 g (91%) of colorless solid $^1$H-NMR (DMSO-$d_6$): 1.59 (s, 9H), 3.75 (s, 3H), 3.76 (s, 3H), 6.37 (s, 1H), 6.95 (d, 8.7 Hz, 2H), 7.15-7.20 (m, 2H), 7.41 (d, 8.7 Hz, 2H), 7.71 (d, 8.6 Hz, 1H).

MS (API-ES, pos) m/z=391, 393 [M+H–tBu]$^+$ (6-Chloro-2-oxo-2,3-dihydrobenzimidazol-1-yl)-(4-methoxyphenyl)acetic acid (VIIIn)

12.0 g (300 mmol) of sodium hydroxide were added to a solution of 1.92 g (4.30 mmol) of tert-butyl 5-chloro-3-[methoxycarbonyl-(4-methoxyphenyl)-methyl]-2-oxo-2,3-dihydrobenzimidazole-1-carboxylate (VIIn) in 70 ml of methanol/water (5:2) at 0° C. while stirring in order to obtain a 5N NaOH solution. The reaction solution was subsequently stirred at 0° C. for 1 h, then diluted with 100 ml of water and adjusted to pH=0 with concentrated hydrochloric acid. The aqueous phase was extracted with ethyl acetate (5×60 ml), the combined organic phases were washed with 2N HCl and dried over magnesium sulfate, and the solvent was removed in vacuo. Yield: 1.42 g (100%) of yellow solid $^1$H-NMR (DMSO-$d_6$): 3.74 (s, 3H), 6.14 (s. 1H), 6.85 (s, 1H), 6.91-7.00 (m, 4H), 7.36 (d, 8.7 Hz, 2H), 11.2 (s, 1H).

MS (API-ES, pos) m/z=333, 335 [M+H]$^+$ tert-Butyl 5,6-dichloro-3-(ethoxycarbonylphenylmethyl)-2-oxo-2,3-dihydrobenzimidazole-1-carboxylate $R_4$=ethyl)

was prepared in analogy to compound (VIIa, $R_4$=tert-butyl).

$^1$H-NMR (DMSO-$d_6$): 1.20 (t, 7.1 Hz, 3H), 1.60 (s, 9H), 4.27 (q, 7.1 Hz, 2H), 6.43 (s, 1H), 7.28 (s, 1H), 7.36-7.44 (m, 3H), 7.46-7.50 (m, 2H), 7.88 (s, 1H).

MS (API-ES, pos) m/z=464 [M+H]$^+$ (5,6-Dichloro-2-oxo-2,3-dihydrobenzimidazol-1-yl)phenylacetic acid (VIIIo)

8.00 g (200 mmol) of sodium hydroxide were added to a solution of 610 mg (1.31 mmol) of tert-butyl 5,6-dichloro-3-(ethoxycarbonylphenylmethyl)-2-oxo-2,3-dihydrobenzimidazole-1-carboxylate (VIIo) in 50 ml of methanol/water (3:2) at 0° C. while stirring in order to obtain a 5N NaOH solution. The reaction solution was subsequently stirred at room temperature for 30 min, then diluted with 100 ml of water and adjusted to pH=0 with concentrated hydrochloric acid. The aqueous phase was extracted with ethyl acetate (4×60 ml), the combined organic phases were dried over magnesium sulfate, and the solvent was removed in vacuo. Yield: 455 g (100%) of colorless solid $^1$H-NMR (DMSO-$d_6$): 6.22 (s, 1H), 7.01 (s, 1H), 7.20 (s, 1H), 7.31-7.44 (m, 5H), 11.4 (s, 1H), 13.53 (bs, 1H).

MS (API-ES, pos) m/z=337, 339 [M+H]$^+$

Ethyl 6-chloro-3-(ethoxycarbonylphenyl methyl)-2-oxo-2,3-dihydrobenzimidazole-1-carboxylate (VIIe, $R_4$=ethyl)

1.38 g (5.73 mmol) of ethyl 6-chloro-2-oxo-2,3-dihydrobenzimidazole-1-carboxylate (Va) were dissolved in dry DMF (20 ml) in a heat-dried flask under a nitrogen atmosphere. 240 mg (6.02 mmol) of sodium hydride (60% suspension in mineral oil) were added while stirring at 0° C., and the reaction solution was then stirred at room temperature for 30 min. After renewed cooling in an ice bath, 1.53 g (6.31 mmol) of ethyl bromo-phenylacetate were added, and the mixture was stirred while cooling in ice for 1 h and then at room temperature for 2 h. The reaction solution was diluted with ethyl acetate, mixed with 10% aqueous ammonium chloride solution and then extracted with ethyl acetate (4×). The combined organic phases were washed with water and saturated NaCl solution, dried over magnesium sulfate and concentrated in vacuo. The residue was purified by chromatography on silica gel (mobile phase 50% ethyl acetate in heptane). Yield: 2.03 g (88%) of colorless oil $^1$H-NMR (DMSO-$d_6$): 1.19 (t, 7.1 Hz, 3H), 1.37 (t, 7.1 Hz, 3H), 4.25 (q, 7.1 Hz, 2H), 4.44 (q, 7.1 Hz, 2H), 6.44 (s, 1H), 7.02 (d, 8.6 Hz, 1H), 7.23 (dd, 8.6 Hz, 2.1 Hz, 1H), 7.32-7.50 (m, 5H), 7.79 (d, 2.1 Hz).

MS (API-ES, pos) m/z=403 [M+H]$^+$ (5-Chloro-2-oxo-2,3-dihydrobenzimidazol-1-yl)phenylacetic acid (VIIIe)

16.0 g (400 mmol) of sodium hydroxide were added to a solution of 3.43 g (7.96 mmol) of ethyl 6-chloro-3-(ethoxycarbonylphenylmethyl)-2-oxo-2,3-dihydrobenzimidazole-1-carboxylate (VIIe, $R_4$=ethyl) in 90 ml of methanol/1,4-dioxane (8:1) while stirring at 0° C. in order to obtain a 5N NaOH solution. The reaction solution was subsequently stirred at 0° C. for 1 h, then diluted with 100 ml of water and adjusted to pH=0 with concentrated hydrochloric acid. The aqueous phase was extracted with ethyl acetate (5×60 ml), the combined organic phases were dried over magnesium sulfate, and the solvent was removed in vacuo. Yield: 1.90 g (100%) of yellow solid $^1$H-NMR (DMSO-$d_6$): 6.22 (s, 1H), 6.77 (d, 8.5 Hz, 1H), 6.93 (dd, 8.5 Hz, 2.0 Hz, 1H), 7.02 (d, 2.0 Hz, 1H), 7.31-7.44 (m, 5H).

MS (API-ES, pos) m/z=303, 305 [M+H]$^+$

Ethyl 3-[methoxycarbonyl-(2-methoxyphenyl)methyl]-2-oxo-2,3-dihydrobenzimidazole-1-carboxylate (VIIp, $R_4$=methyl)

2.61 g (12.7 mmol) of ethyl 2-oxo-2,3-dihydrobenzimidazole-1-carboxylate (IV) were dissolved in dry DMF (40 ml) in a heat-dried flask under a nitrogen atmosphere. 532 mg (13.3 mmol) of sodium hydride (60% suspension in mineral oil) were added while stirring at 0° C., and the reaction solution was then stirred at room temperature for 30 min. After renewed cooling in an ice bath, 3.54 g (13.7 mmol) of methyl bromo-(2-methoxyphenyl)acetate were added and the mixture was stirred while cooling in ice for 1 h and then at room temperature for 2 h. The reaction solution was diluted with ethyl acetate, mixed with 10% aqueous ammonium chloride solution and then extracted with ethyl acetate (3×). The combined organic phases were washed with water and saturated NaCl solution, dried over magnesium sulfate and concentrated in vacuo. The residue was purified by chromatography on silica gel (mobile phase 50% ethyl acetate in heptane). Yield: 3.21 g (66%) of colorless oil $^1$H-NMR (DMSO-d$_6$): 1.37 (t, 7.1 Hz, 3H), 3.75 (s, 3H), 3.77 (s, 3H), 4.43 (q, 7.1 Hz, 2H), 5.75 (s, 1H), 6.41 (s, 1H), 6.94-7.01 (m, 2H), 7.07 (d, 8.2 Hz, 1H), 7.35-7.41 (m, 1H), 7.27-7.31 (m, 1H).

MS (API-ES, pos) m/z=385 [M+H]$^+$

(2-Methoxyphenyl)-(2-oxo-2,3-dihydrobenzimidazol-1-yl)acetic acid (VIIIp)

8.0 g (200 mmol) of sodium hydroxide were added to a solution of 2.61 g (6.78 mmol) of ethyl 3-[methoxycarbonyl-(2-methoxyphenyl)methyl]-2-oxo-2,3-dihydrobenzimidazole-1-carboxylate (VIIp, R$_4$=methyl) in 60 ml of methanol/water (5:1) while stirring at 0° C. in order to obtain a 5N NaOH solution. The reaction solution was subsequently stirred at 0° C. for 1 h, then diluted with 100 ml of water and adjusted to pH=0 with concentrated hydrochloric acid. The aqueous phase was extracted with ethyl acetate (5×60 ml), the combined organic phases were dried over magnesium sulfate, and the solvent was removed in vacuo. Yield: 1.70 g (84%) of colorless solid $^1$H-NMR (DMSO-d$_6$): 3.77 (s, 3H), 6.24 (s, 1H), 6.73 (d, 7.8 Hz, 1H), 6.83-6.88 (m, 1H), 6.91-7.01 (m, 3H), 7.05 (d, 8.2 Hz, 1H), 7.25 (d, 7.5 Hz, 1H), 7.32-7.38 (m, 1H), 10.97 (s, 1H).

MS (API-ES, pos) m/z=299 [M+H]$^+$ tert-Butyl 5-chloro-3-[methoxycarbonyl-(2-methoxyphenyl)methyl]-2-oxo-2,3-dihydrobenzimidazole-1-carboxylate (VIIk, R$_4$=methyl)

2.00 g (7.44 mmol) of tert-butyl 5-chloro-2-oxo-2,3-dihydrobenzimidazole-1-carboxylate (VIa) were dissolved in dry DMF (50 ml) in a heat-dried flask under a nitrogen atmosphere. 313 mg (7.82 mmol) of sodium hydride (60% suspension in mineral oil) were added while stirring at 0° C., and the reaction solution was then stirred at room temperature for 30 min. After renewed cooling in an ice bath, 2.12 g (8.19 mmol) of methyl bromo-(2-methoxyphenyl)acetate were added, and the mixture was stirred while cooling in ice for 1 h and then at room temperature for 2 h. The reaction solution was diluted with ethyl acetate, mixed with 10% aqueous ammonium chloride solution and then extracted with ethyl acetate (3×). The combined organic phases were washed with water and saturated NaCl solution, dried over magnesium sulfate and concentrated in vacuo. The residue was purified by chromatography on silica gel (mobile phase gradient 10-45% ethyl acetate in heptane). Yield: 2.79 g (84%) of colorless solid $^1$H-NMR (DMSO-d$_6$): 1.59 (s, 9H), 3.77 (s, 6H), 6.43 (s, 1H), 6.97-7.04 (m, 2H), 7.09 (d, 8.2 Hz, 1H), 7.16 (dd, 8.7 Hz, 2.0 Hz, 1H), 7.33-7.44 (m, 2H), 7.71 (d, 8.6 Hz, 1H).

MS (API-ES, pos) m/z=391, 393 [M+H−tBu]$^+$

(6-Chloro-2-oxo-2,3-dihydrobenzimidazol-1-yl)-(2-methoxyphenyl)acetic acid (VIIIk)

8.0 g (200 mmol) of sodium hydroxide were added to a solution of 2.45 g (5.48 mmol) of tert-butyl 5-chloro-3-[methoxycarbonyl-(2-methoxyphenyl)-methyl]-2-oxo-2,3-dihydrobenzimidazole-1-carboxylate (VIIk, R$_4$=methyl) in 80 ml of methanol/water/1,4-dioxane (5:2:1) while stirring at 0° C. in order to obtain a 5N NaOH solution. The reaction solution was subsequently stirred at 0° C. for 1 h, then diluted with 100 ml of water and adjusted to pH=0 with concentrated hydrochloric acid. The aqueous phase was extracted with ethyl acetate (5×60 ml), the combined organic phases were dried over magnesium sulfate, and the solvent was removed in vacuo.

Yield: 1.91 g (100%) of pale violet solid $^1$H-NMR (DMSO-d$_6$): 3.76 (s, 3H), 6.23 (s, 1H), 6.70 (s, 1H), 6.95-7.04 (m, 3H), 7.05-7.00 (m, 1H), 7.24-7.30 (m, 1H), 7.36-7.42 (m, 1H), 11.2 (s, 1H).

MS (API-ES, pos) m/z=333, 335 [M+H]$^+$ tert-Butyl 3-(1-tert-butoxycarbonyl-2-phenylethyl)-5-chloro-2-oxo-2,3-dihydrobenzimidazole-1-carboxylate (VIIh)

1.20 g (4.47 mmol) of tert-butyl 5-chloro-2-oxo-2,3-dihydrobenzimidazole-1-carboxylate (VIa) were dissolved in dry DMF (15 ml) in a heat-dried flask under a nitrogen atmosphere. 187 mg (4.69 mmol) of sodium hydride (60% suspension in mineral oil) were added while stirring at 0° C., and the reaction solution was then stirred at room temperature for 30 min. After renewed cooling in an ice bath, 1.40 g (4.91 mmol) of tert-butyl 2-bromo-3-phenylpropionate were added, and the mixture was stirred while cooling in ice for 1 h and then at room temperature for 2 h. The reaction solution was diluted with ethyl acetate, mixed with 10% aqueous ammonium chloride solution and then extracted with ethyl acetate (3×). The combined organic phases were washed with water and saturated NaCl solution, dried over magnesium sulfate and concentrated in vacuo. The residue was purified by chromatography on silica gel (mobile phase gradient 15-30% ethyl acetate in heptane). Yield: 1.3 g (62%) of colorless oil $^1$H-NMR (DMSO-d$_6$): 1.38 (s, 9H), 1.57 (s, 9H), 3.38-3.47 (m, 2H), 5.38-5.43 (m, 1H), 7.07-7.23 (m, 7H), 7.59 (d, J=8.6 Hz, 1H).

MS (API-ES, pos) m/z=361, 363 [M+H−2tBu]$^+$

2-(6-Chloro-2-oxo-2,3-dihydrobenzimidazol-1-yl)-3-phenylpropionic acid (VIIIh)

950 mg (2.01 mmol) of tert-butyl 3-(1-tert-butoxycarbonyl-2-phenylethyl)-5-chloro-2-oxo-2,3-dihydrobenzimidazole-1-carboxylate (VIIh) were dissolved in dichloromethane (10 ml) and, while stirring at room temperature, trifluoroacetic acid (10 ml) was added. The reaction solution was stirred for 2 h and then the solvent and excess trifluoroacetic acid were removed in vacuo. The residue was taken up again in toluene, concentrated in vacuo and then dried in vacuo. Yield: 609 mg (96%) of white solid $^1$H-NMR (DMSO-d$_6$): 3.35-3.53 (m, 2H), 5.27-5.34 (m, 1H), 6.82-6.96 (m, 2H), 7.02-7.19 (m, 6H), 10.9 (s, 1H), 13.2 (bs, 1H).

MS (API-ES, pos) m/z=317, 319 [M+H]$^+$ tert-Butyl 5-chloro-3-(1-methoxycarbonylethyl)-2-oxo-2,3-dihydrobenzimidazol-1-carboxylate (VIIIf, R$_4$=methyl)

1.30 g (4.84 mmol) of tert-butyl 5-chloro-2-oxo-2,3-dihydrobenzimidazole-1-carboxylate (VIa) were dissolved in dry DMF (35 ml) in a heat-dried flask under a nitrogen atmosphere. 203 mg (5.09 mmol) of sodium hydride (60% suspension in mineral oil) were added while stirring at 0° C., and the reaction solution was then stirred at room temperature for 30 min. After renewed cooling in an ice bath, 0.89 g (5.33 mmol) of methyl 2-bromopropionate was added, and the mixture was stirred while cooling in ice for 1 h and then at room temperature for 2 h. The reaction solution was diluted with ethyl acetate, mixed with 10% aqueous ammonium chloride solution and then extracted with ethyl acetate (3×). The combined organic phases were washed with water and saturated NaCl solution, dried over magnesium sulfate and concentrated in vacuo. The residue was purified by chromatography on silica gel (mobile phase gradient 15-30% ethyl acetate in heptane). Yield: 1.32 g (77%) of colorless solid $^1$H-NMR (DMSO-d$_6$): 1.59 (s, 9H), 1.61 (s, 3H), 3.67 (s, 3H), 5.27-5.35 (m, 1H), 7.20 (dd, 8.6 Hz, 2.0 Hz, 1H), 7.41 (d, 2.0 Hz, 1H), 7.71 (d, 8.6 Hz, 1H).

MS (API-ES, pos) m/z=299, 301 [M+H–tBu]$^+$ 2-(6-Chloro-2-oxo-2,3-dihydrobenzimidazol-1-yl) propionic acid (VIIIf)

14.0 g (350 mmol) of sodium hydroxide were added to a solution of 1.20 g (3.38 mmol) of tert-butyl 5-chloro-3-(1-methoxycarbonylethyl)-2-oxo-2,3-dihydrobenzimidazole-1-carboxylate (VIIIf, R$_4$=methyl) in 70 ml of methanol/water (5:2) while stirring at 0° C. in order to obtain a 5N NaOH solution. The reaction solution was subsequently stirred at room temperature for 1 h, then diluted with 100 ml of water and adjusted to pH=0 with concentrated hydrochloric acid. The aqueous phase was extracted with ethyl acetate (5×60 ml), the combined organic phases were washed with 2N HCl and dried over magnesium sulfate, and the solvent was removed in vacuo. Yield: 770 mg (95%) of colorless solid $^1$H-NMR (DMSO-d$_6$): 1.56 (d, 7.3 Hz, 3H), 5.09 (q, 7.3 Hz, 1H), 7.00 (m, 2H), 7.17-7.19 (m, 1H), 11.0 (s, 1H).

MS (API-ES, pos) m/z=241, 243 [M+H–tBu]$^+$

1-[2-Oxo-1-phenyl-2-(4-pyridin-4-ylpiperazin-1-yl) ethyl]-1,3-dihydrobenzimidazol-2-one (IXd-1)

179 mg (0.94 mmol) of EDCl were added to a solution of 193 mg (0.72 mmol) of (2-oxo-2,3-dihydrobenzimidazol-1-yl)phenylacetic acid (VIIId), 106 mg (0.79 mmol) of HOBt, 117 mg (0.72 mmol) of 1-pyridin-4-ylpiperazine and 0.49 ml (2.87 mmol) of ethyldiisopropylamine in dichloromethane (8 ml) while stirring in an ice-water bath. The reaction solution was slowly warmed and stirred at room temperature for 16 h. Half-saturated aqueous potassium carbonate solution was added, and the organic phase was separated off. The aqueous phase was extracted with ethyl acetate (4×50 ml) and the combined organic phases were washed with sat. NaHCO$_3$ solution, dried over magnesium sulfate and concentrated under reduced pressure. The reaction product was used without further purification for the next reaction step. Yield: 292 mg (98%) of yellow solid MS (API-ES, pos) m/z=414 [M+H]$^+$ 1-{2-[4-(1-Methyl piperidin-4-yl)piperazin-1-yl]-2-oxo-1-phenylethyl}-1,3-dihydrobenzimidazol-2-one (IXd-2)

was prepared in an analogous manner to 1-[2-oxo-1-phenyl-2-(4-pyridin-4-ylpiperazin-1-yl)ethyl]-1,3-dihydrobenzimidazol-2-one (IXd-1) from compound VIIId and employed without further purification in the next reaction step.

MS (API-ES, pos) m/z=434 [M+H]$^+$

1-{2-[4-(4-Methylpiperazin-1-yl)piperidin-1-yl]-2-oxo-1-phenylethyl}-1,3-dihydrobenzimidazol-2-one (IXd-3)

was prepared in an analogous manner to 1-[2-oxo-1-phenyl-2-(4-pyridin-4-ylpiperazin-1-yl)ethyl]-1,3-dihydrobenzimidazol-2-one (IXd-1) from compound VIIId and employed without further purification in the next reaction step.

MS (API-ES, pos) m/z=434 [M+H]$^+$

2-Oxo-3-{2-oxo-1-phenyl-2-[(S)-3-(4-propyl-piperazin-1-yl)-pyrrolidin-1-yl]-ethyl}-2,3-dihydro-1H-benzoimidazole-5-carbonitrile (IXd-4)

A mixture of (6-cyano-2-oxo-2,3-dihydro-benzoimidazol-1-yl)-phenyl-acetic acid VIIIc (465 mg, 1.59 mmol), 1-hydroxybenzotriazole (321 mg, 2.38 mmol) and PS-carbodiimide resin (Argonaut; 1.18 mmol/g; 1.61 g, 1.90 mmol) in CH$_2$Cl$_2$ (15 mL) was agitated for 10 min at room temperature. Then, 1-propyl-4-(S)-pyrrolidin-3-yl-piperazine (344 mg, 1.74 mmol) was added and the reaction mixture was agitated at room temperature overnight. To this was then added MP-carbonate resin (Argonaut; 2.69 mmol/g; 1.77 g, 4.76 mmol) and the reaction mixture was agitated for another 2 hours, filtered and concentrated in vacuo. The residue was purified by flash chromatography in silica gel using from 3% to 12% MeOH in CH$_2$Cl$_2$ as eluent to afford 2-oxo-3-{2-oxo-1-phenyl-2-[(S)-3-(4-propyl-piperazin-1-yl)-pyrrolidin-1-yl]-ethyl}-2,3-dihydro-1H-benzoimidazole-5-carbonitrile (IXd-) (424 mg, 57%) as a white solid.

$^1$H-NMR (400 MHz, DMSO-d$_6$): δ 0.81-0.87 (m, 3H), 1.24 (m, 2H), 1.37-1.45 (m, 2H), 1.61-1.80 (m, 1H), 2.04 (m, 2H), 2.18-2.40 (m, 5H), 2.67-2.90 (m, 2H), 3.11-3.43 (m, 2H), 3.49-3.81 (m, 2H), 4.07 (m, 1H), 6.38-6.46 (m, 1H), 6.76-6.85 (m, 1H), 7.10-7.15 (m, 1H), 7.26-7.32 (m, 2H), 7.35-7.43 (m, 4H), 11.68 (br s, NH).

MS (API-ES, pos) m/z=473.35 [M+H]$^+$.

23. 3-{2-[(S)-3-(4-Benzyl-piperazin-1-yl)-pyrrolidin-1-yl]-2-oxo-1-phenyl-ethyl}-2-oxo-2,3-dihydro-1H-benzoimidazole-5-carbonitrile (IXd-)

It was synthesized in a similar manner to 2-oxo-3-{2-oxo-1-phenyl-2-[(S)-3-(4-propylpiperazin-1-yl)-pyrrolidin-1-yl]-ethyl}-2,3-dihydro-1H-benzoimidazole-5-carbonitrile (IXd-4).

MS (API-ES, pos) m/z=521.60 [M+H]$^+$.

3-{2-[(S)-3-(4-Benzyl-piperazin-1-ylmethyl)-pyrrolidin-1-yl]-2-oxo-1-phenylethyl}-2-oxo-2,3-dihydro-1H-benzoimidazole-5-carbonitrile (IXd-5)

To a chilled solution of (6-cyano-2-oxo-2,3-dihydro-benzoimidazol-1-yl)-phenyl-acetic acid VIIIc (251 mg, 0.86 mmol), 1-benzyl-4-(S)-1-pyrrolidin-3-ylmethyl-piperazine (266 mg, 1.03 mmol, 996 mg as TFA salt), 1-hydroxybenzotriazole (174 mg, 1.28 mmol) and N,N-diisopropylethylamine (1.33 mL, 7.70 mmol) in CH$_2$Cl$_2$ (45 mL) EDC (180 mg, 0.94 mmol) was added. The reaction mixture was allowed to warm up to room temperature while stirring overnight. Then, the reaction mixture was diluted with water and extracted with CH$_2$Cl$_2$ (3×). The combined organic phases were washed successively with a saturated aqueous solution of NaHCO$_3$, brine, dried over Na$_2$SO$_4$, filtered and concentrated in vacuo. The residue was purified by flash chromatography in silica gel using 5% MeOH in CH$_2$Cl$_2$ as eluent to afford 3-{2-[(S)-3-(4-benzyl-piperazin-1-ylmethyl)-pyrrolidin-1-yl]-2-oxo-1-phenyl-ethyl}-2-oxo-2,3-dihydro-1H-benzoimidazole-5-carbonitrile (IXd-) (283 mg, 62%) as a white solid.

$^1$H-NMR (400 MHz, DMSO-d$_6$): δ 1.49-1.64 (m, 1H), 1.94 (m, 1H), 2.13-2.37 (m, 1H), 2.97-3.65 (m, 6H), 6.36-

6.41 (m, 1H), 6.77-6.89 (m, 1H), 7.10-7.14 (m, 1H), 7.23-7.32 (m, 7H), 7.35-7.42 (m, 4H), 11.66 (br s, NH).
MS (API-ES, pos) m/z=535.30 [M+H]$^+$.

{(S)-1-[2-(6-Cyano-2-oxo-2,3-dihydro-benzoimidazol-1-yl)-2-phenyl-acetyl]-pyrrolidin-3-yl}-carbamic acid tert-butyl ester (IXd-6)

It was synthesized in a similar manner to 3-{2-[(S)-3-(4-benzyl-piperazin-1-ylmethyl)-pyrrolidin-1-yl]-2-oxo-1-phenyl-ethyl}-2-oxo-2,3-dihydro-1H-benzoimidazole-5-carbonitrile (IXd-6).

$^1$H-NMR (400 MHz, DMSO-d$_6$): δ 1.35 (d, 8.6 Hz, 9H) [+1.39 (d, 9.5 Hz, 9H) other diastereomer], 1.71-1.83 (m, 1H), 1.95-2.08 (m, 1H), 3.06-3.71 (m, 4H), 4.00 (m, 1H), 6.37-6.42 (m, 1H), 6.79-6.89 (m, 1H), 7.13 (d, 8.1 Hz, 2H), 7.29 (m, 2H), 7.34-7.40 (m, 3H+NH), 11.66 (br s, NH).
MS (API-ES, pos) m/z=462.15 [M+H]$^+$.

6-Chloro-1-[2-oxo-1-phenyl-2-(4-pyridin-4-ylpiperazin-1-yl)ethyl]-1,3-dihydrobenzimidazol-2-one (IXa-1)

was prepared in an analogous manner to 1-[2-oxo-1-phenyl-2-(4-pyridin-4-ylpiperazin-1-yl)ethyl]-1,3-dihydrobenzimidazol-2-one (IXd-1) from compound VIIIa and employed without further purification in the next reaction step.

$^1$H-NMR (methanol-d4): 3.34-3.40 (m, 2H), 3.44-3.53 (m, 3H), 3.70-3.78 (m, 1H), 3.84-3.95 (m, 2H), 6.55 (d, 1.6 Hz, 1H), 6.74 (s, 1H), 6.84 (d, 6.6 Hz, 2H), 6.95-7.02 (m, 5H), 8.15 (d, 6.6 Hz, 2H).
MS (API-ES, pos) m/z=448, 450 [M+H]$^+$

6-Chloro-1-{2-[4-(1-methylpiperidin-4-yl)piperazin-1-yl]-2-oxo-1-phenylethyl}-1,3-dihydrobenzimidazol-2-one (IXa-2)

was prepared in an analogous manner to 1-[2-oxo-1-phenyl-2-(4-pyridin-4-ylpiperazin-1-yl)ethyl]-1,3-dihydrobenzimidazol-2-one (IXd-1) from compound VIIIa and employed without further purification in the next reaction step.
MS (API-ES, pos) m/z=468, 470 [M+H]$^+$

6-Chloro-1-{2-[4-(4-methylpiperazin-1-yl)piperidin-1-yl]-2-oxo-1-phenyl-ethyl}-1,3-dihydrobenzimidazol-2-one (IXa-3)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIa and employed without further purification in the next reaction step.
MS (API-ES, pos) m/z=468, 470 [M+H]$^+$

6-Chloro-1-{2-oxo-1-phenyl-2-[4-(4-propylpiperazin-1-yl)piperidin-1-yl]-ethyl}-1,3-dihydrobenzimidazol-2-one (IXa-4)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIa and employed without further purification in the next reaction step.
MS (API-ES, pos) m/z=496, 498 [M+H]$^+$

5,6-Dichloro-1-[2-oxo-1-phenyl-2-(4-pyridin-4-ylpiperazin-1-yl)ethyl]-1,3-dihydrobenzimidazol-2-one (IXo-1)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIo and employed without further purification in the next reaction step.
(API-ES, pos) m/z=482, 484 [M+H]$^+$

5,6-Dichloro-1-{2-[4-(1-methylpiperidin-4-yl)piperazin-1-yl]-2-oxo-1-phenylethyl}-1,3-dihydrobenzimidazol-2-one (IXo-2)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIo and employed without further purification in the next reaction step.
MS (API-ES, pos) m/z=502, 504 [M+H]$^+$

5,6-Dichloro-1-{2-[4-(4-methylpiperazin-1-yl)piperidin-1-yl]-2-oxo-1-phenylethyl}-1,3-dihydrobenzimidazol-2-one (IXo-3)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIo and employed without further purification in the next reaction step.
MS (API-ES, pos) m/z=502, 504 [M+H]$^+$

6-Iodo-1-[2-oxo-1-phenyl-2-(4-pyridin-4-ylpiperazin-1-yl)ethyl]-1,3-dihydrobenzimidazol-2-one (IXb-1)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIb and employed without further purification in the next reaction step.
MS (API-ES, pos) m/z=540 [M+H]$^+$

6-Iodo-1-[2-oxo-2-(4-pyridin-4-ylpiperazin-1-yl)ethyl]-1,3-dihydrobenzimidazol-2-one (IXj-1)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIj and employed without further purification in the next reaction step.
MS (API-ES, pos) m/z=464 [M+H]$^+$

5-Chloro-1-[2-oxo-1-phenyl-2-(4-pyridin-4-ylpiperazin-1-yl)ethyl]-1,3-dihydrobenzimidazol-2-one (IXe-1)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIe and employed without further purification in the next reaction step.
MS (API-ES, pos) m/z=448, 450 [M+H]$^+$

5-Chloro-1-{2-[4-(1-methylpiperidin-4-yl)piperazin-1-yl]-2-oxo-1-phenyl-ethyl}-1,3-dihydrobenzimidazol-2-one (IXe-2)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIe and employed without further purification in the next reaction step.

MS (API-ES, pos) m/z=468, 470 [M+H]$^+$

2-oxo-3-[2-oxo-1-phenyl-2-(4-pyridin-4-ylpiperazin-1-yl)ethyl]-2,3-dihydro-1H-benzimidazol-5-carbonitrile (IXc-1)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIc and employed without further purification in the next reaction step.

MS (API-ES, pos) m/z=439 [M+H]$^+$

3-{2-[4-(1-Methylpiperidin-4-yl)piperazin-1-yl]-2-oxo-1-phenylethyl}-2-oxo-2,3-dihydro-1H-benzimidazol-5-carbonitrile (IXc-2)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIc and employed without further purification in the next reaction step.

MS (API-ES, pos) m/z=460 [M+H]$^+$

1-[1-(2-Methoxyphenyl)-2-oxo-2-(4-pyridin-4-ylpiperazin-1-yl)ethyl]-1,3-dihydrobenzimidazol-2-one (IXp-1)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIp and employed without further purification in the next reaction step.

MS (API-ES, pos) m/z=444 [M+H]$^+$

1-{1-(2-Methoxyphenyl)-2-[4-(1-methylpiperidin-4-yl)piperazin-1-yl]-2-oxo-ethyl}-1,3-dihydrobenzimidazol-2-one (IXp-2)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIp and employed without further purification in the next reaction step.

MS (API-ES, pos) m/z=464 [M+H]$^+$

6-Chloro-1-[1-(2-methoxyphenyl)-2-oxo-2-(4-pyridin-4-ylpiperazin-1-yl)-ethyl]-1,3-dihydrobenzimidazol-2-one (IXk-1)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIk and employed without further purification in the next reaction step.

MS (API-ES, pos) m/z=478, 480 [M+H]$^+$

6-Chloro-1-{(1-(2-methoxyphenyl)-2-[4-(1-methylpiperidin-4-yl)piperazin-1-yl]-2-oxoethyl}-1,3-dihydrobenzimidazol-2-one (IXk-2)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIk and employed without further purification in the next reaction step.

MS (API-ES, pos) m/z=498, 500 [M+H]$^+$

6-Chloro-1-[1-(3-methoxyphenyl)-2-oxo-2-(4-pyridin-4-ylpiperazin-1-yl)-ethyl]-1,3-dihydrobenzimidazol-2-one (IXm-1)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIm and employed without further purification in the next reaction step.

MS (API-ES, pos) m/z=478, 480 [M+H]$^+$

6-Chloro-1-{(1-(3-methoxyphenyl)-2-[4-(1-methylpiperidin-4-yl)piperazin-1-yl]-2-oxoethyl}-1,3-dihydrobenzimidazol-2-one (IXm-2)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIm and employed without further purification in the next reaction step.

MS (API-ES, pos) m/z=498, 500 [M+H]$^+$

6-Chloro-1-[2-oxo-2-(4-pyridin-4-ylpiperazin-1-yl)ethyl]-1,3-dihydrobenzimidazol-2-one (1×g-1)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIg and employed without further purification in the next reaction step.

MS (API-ES, pos) m/z=372, 374 [M+H]$^+$

1-[1-Benzyl-2-oxo-2-(4-pyridin-4-ylpiperazin-1-yl)ethyl]-6-chloro-1,3-dihydrobenzimidazol-2-one (IXh-1)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIh and employed without further purification in the next reaction step.

MS (API-ES, pos) m/z=462, 464 [M+H]$^+$

6-Chloro-1-[1-methyl-2-oxo-2-(4-pyridin-4-ylpiperazin-1-yl)ethyl]-1,3-dihydrobenzimidazol-2-one (IXf-1)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIf and employed without further purification in the next reaction step.

MS (API-ES, pos) m/z=386, 388 [M+H]$^+$

6-Chloro-1-[1-(4-methoxyphenyl)-2-oxo-2-(4-pyridin-4-ylpiperazin-1-yl)-ethyl]-1,3-dihydrobenzimidazol-2-one (IXn-1)

was prepared in an analogous manner to 1-[2-oxo-1-phenyl-2-(4-pyridin-4-yl-piperazin-1-yl)ethyl]-1,3-dihydrobenzimidazol-2-one (IXd-1) from compound VIIIn and employed without further purification in the next reaction step.

$^1$H-NMR (DMSO-$d_6$): 3.14-3.48 (m, 5H), 3.51-3.60 (m, 1H), 3.62-3.71 (m, 1H), 3.74-3.82 (m, 1H), 3.76 (s, 3H), 6.52 (s, 1H), 6.56 (s, 1H), 6.80 (d, 5.9 Hz, 2H), 6.94-7.04 (m, 3H), 7.27 (d, 8.4 Hz, 2H), 11.2 (s, 1H).

MS (API-ES, pos) m/z=478, 480 [M+H]$^+$

5-Chloro-1-{2-oxo-1-phenyl-2-[3-(4-propylpiperazin-1-yl)pyrrolidin-1-yl]-ethyl}-1,3-dihydrobenzimidazol-2-one (IXe-4)

110 mg (0.36 mmol) of (5-chloro-2-oxo-2,3-dihydrobenzimidazol-1-yl)phenyl-acetic acid (VIIIe), 69.1 mg (0.51 mmol) of HOBt and 335 mg (0.44 mmol, 1.3 mmol/g) of solid phase-bound PS-carbodiimide were dissolved in 6 ml of dry dichloromethane in a screw-cap tube and shaken mechanically at room temperature for 10 min. 78.9 mg (0.40 mmol) of 1-propyl-4-pyrrolidin-3-ylpiperazine were added, and the mixture was then shaken mechanically overnight. Three equivalents of solid phase-bound MP-carbonate were then added to the reaction mixture, and shaking was continued for 2 h. The solid phase-bound reagents were filtered off and washed with dichloromethane. The filtrate was concentrated in vacuo and the residue was dried in vacuo. The reaction product was used without further purification for the next reaction step.

MS (API-ES, pos) m/z=482, 484 [M+H]$^+$

6-Chloro-1-{(1-(2-methoxyphenyl)-2-oxo-2-[3-(4-propylpiperazin-1-yl)-pyrrolidin-1-yl]ethyl}-1,3-dihydrobenzimidazol-2-one (IXk-4)

was prepared in an analogous manner to 5-chloro-1-{2-oxo-1-phenyl-2-[3-(4-propylpiperazin-1-yl)pyrrolidin-1-yl]ethyl}-1,3-dihydrobenzimidazol-2-one (IXe-4) from compound VIIIk and employed without further purification in the next reaction step.

MS (API-ES, pos) m/z=512, 514 [M+H]$^+$

6-Chloro-1-{1-methyl-2-oxo-2-[3-(4-propylpiperazin-1-yl)pyrrolidin-1-yl]-ethyl}-1,3-dihydrobenzimidazol-2-one (IXf-4)

was prepared in an analogous manner to 5-chloro-1-{2-oxo-1-phenyl-2-[3-(4-propylpiperazin-1-yl)pyrrolidin-1-yl]ethyl}-1,3-dihydrobenzimidazol-2-one (IXe-4) from compound VIIIf and employed without further purification in the next reaction step.

MS (API-ES, pos) m/z=420, 422 [M+H]$^+$

2-Oxo-3-{2-oxo-1-phenyl-2-[3-(4-propylpiperazin-1-yl)pyrrolidin-1-yl]-ethyl}-2,3-dihydro-1H-benzimidazole-5-carbonitrile (IXc-4)

was prepared in an analogous manner to 5-chloro-1-{2-oxo-1-phenyl-2-[3-(4-propylpiperazin-1- yl)pyrrolidin-1-yl]ethyl}-1,3-dihydrobenzimidazol-2-one (IXe-4) from compound VIIIc and employed without further purification in the next reaction step.

MS (API-ES, pos) m/z=473 [M+H]$^+$

6-Iodo-1-{2-oxo-1-phenyl-2-[3-(4-propylpiperazin-1-yl)pyrrolidin-1-yl]-ethyl}-1,3-dihydrobenzimidazol-2-one (IXb-4)

was prepared in an analogous manner to 5-chloro-1-{2-oxo-1-phenyl-2-[3-(4-propylpiperazin-1-yl)pyrrolidin-1-yl]ethyl}-1,3-dihydrobenzimidazol-2-one (IXe-4) from compound VIIIb and employed without further purification in the next reaction step.

MS (API-ES, pos) m/z=574 [M+H]$^+$

6-Chloro-1-{1-(3-methoxyphenyl)-2-oxo-2-[3-(4-propylpiperazin-1-yl)-pyrrolidin-1-yl]ethyl}-1,3-dihydrobenzimidazol-2-one (IXm-4)

was prepared in an analogous manner to 5-chloro-1-{2-oxo-1-phenyl-2-[3-(4-propylpiperazin-1-yl)pyrrolidin-1-yl]ethyl}-1,3-dihydrobenzimidazol-2-one (IXe-4) from compound VIIIm and employed without further purification in the next reaction step.

MS (API-ES, pos) m/z=512, 514 [M+H]$^+$

1-{1-Benzyl-2-oxo-2-[3-(4-propylpiperazin-1-yl)pyrrolidin-1-yl]ethyl}-6-chloro-1,3-dihydrobenzimidazol-2-one (IXh-4)

was prepared in an analogous manner to 5-chloro-1-{2-oxo-1-phenyl-2-[3-(4-propylpiperazin-1-yl)pyrrolidin-1-yl]ethyl}-1,3-dihydrobenzimidazol-2-one (IXe-4) from compound VIIIh and employed without further purification in the next reaction step.

MS (API-ES, pos) m/z=496, 498 [M+H]$^+$

6-Chloro-1-{1-(4-methoxyphenyl)-2-oxo-2-[3-(4-propylpiperazin-1-yl)-pyrrolidin-1-yl]ethyl}-1,3-dihydrobenzimidazol-2-one (IXn-4)

was prepared in an analogous manner to 5-chloro-1-{2-oxo-1-phenyl-2-[3-(4-propylpiperazin-1-yl)pyrrolidin-1-yl]ethyl}-1,3-dihydrobenzimidazol-2-one (IXe-4) from compound VIIIn and employed without further purification in the next reaction step.

MS (API-ES, pos) m/z=512, 514 [M+H]$^+$

Benzyl 4-(1-tert-butoxycarbonylpiperidin-4-yl)piperazine-1-carboxylate 1.89 g (30.1 mmol) of sodium cyanoborohydride were added to a stirred solution of 3.00 g (15.1 mmol) of tert-butyl 4-oxo-1-piperidinecarboxylate and 3.48 g (15.8 mmol) of 1-Z-piperazine in methanol (60 ml) at room temperature. The pH of the solution was adjusted to about pH 7 by dropwise addition of acetic acid and was monitored during the course of the reaction. The reaction mixture was stirred at room temperature overnight and then concentrated in vacuo. The residue was mixed with water (60 ml) and extracted with dichloromethane (4×60 ml). The combined organic phases were washed with saturated NaCl solution, dried over magnesium sulfate and concentrated in vacuo. The residue was purified by chromatography on silica gel (mobile phase gradient 3-10% methanol in dichloromethane). Yield: 3.41 g (56%) of colorless oil MS (API-ES, pos) m/z=404 [M+H]$^+$ tert-Butyl 4-piperazin-1-ylpiperidine-1-carboxylate A suspension of 3.01 g (7.46 mmol) of benzyl 4-(1-tert-butoxycarbonylpiperidin-4-yl)piperazine-1-carboxylate and 300 mg of Pd—C (5%) in 100 ml of methanol was mixed with 4 ml of formic acid and stirred under a hydrogen atmosphere (1 bar) at room temperature overnight. The reaction mixture was filtered through Celite, the residue on the filter was washed with methanol, and the solvent was then removed in vacuo. The residue was used without further purification in the next reaction step.
Yield: 2.41 g of colorless oil
MS (API-ES, pos) m/z=270 [M+H]$^+$ tert-Butyl 4-{4-[2-(6-chloro-2-oxo-2,3-dihydrobenz-imidazol-1-yl)-2-phenyl-acetyl]piperazin-1-yl}piperidine-1-carboxylate (IXa-5)

2.99 mg (1.56 mmol) of EDCl were added to a solution of 430 mg (1.42 mmol) of (6-chloro-2-oxo-2,3-dihydrobenz-imidazol-1-yl)phenylacetic acid (VIIIa), 289 mg (2.13 mmol) of HOBt, 459 mg (0.1.70 mmol) of 1-pyridin-4-ylpiperazine and 1.24 ml (7.10 mmol) of ethyldiisopropylamine in dichloromethane (25 ml) while stirring in an ice-water bath. The reaction solution was slowly warmed and stirred at room temperature for 16 h. Half-saturated aqueous potassium carbonate solution was added, and the organic phase was separated off. The aqueous phase was extracted with ethyl acetate (4×50 ml), and the combined organic phases were washed with sat. NaHCO3 solution, dried over magnesium sulfate and concentrated under reduced pressure. The reaction product was used without further purification for the next reaction step. Yield: 439 mg (56%) of white solid
MS (API-ES, pos) m/z=554, 556 [M+H]$^+$ The following compounds XIX, XX and XXIa-e were prepared as shown in synthesis scheme 6 by the following reaction procedures.

2-[Benzyl-(2-hydroxyethyl)amino]ethanol (XIX)

16.9 ml (142 mmol) of benzyl bromide were added to a stirred solution of 15.0 g (142 mmol) of diethanolamine and 39.4 g (285 mmol) of potassium carbonate in 200 ml of acetone, and the solution was then heated under reflux for 3 h. The cooled reaction mixture was filtered and concentrated in vacuo. 100 ml of water were added, and the aqueous mixture was extracted with chloroform (3×60). The combined organic phases were washed with water and saturated NaCl solution and dried over magnesium sulfate, and the solvent was removed in vacuo. Yield: 26.9 g (96%) of colorless oil
The reaction product was converted into the hydrochloride by dissolving the residue in 70 ml of 5N ethereal HCl and removing the solvent in vacuo. The residue was then coevaporated with toluene twice. Yield: 31.7 g (99%) of colorless oil
$^1$H-NMR (DMSO-d$_6$): 2.51-2.59 (m, 2H), 3.41-3.48 (m, 4H), 3.65 (s, 2H), 4.34 (bs, 2H), 7.16-7.36 (m, 5H).
MS (API-ES, pos) m/z=196 [M+H]$^+$ Benzylbis(2-chloroethyl)amine hydrochloride (XX)

7.70 g (64.7 mmol) of thionyl chloride were added dropwise to a stirred solution of 5.00 g (21.6 mmol) of (2-[benzyl-(2-hydroxyethyl)amino]ethanol hydrochloride (XIX) in 100 ml of dry dichloromethane at 0° C., and the resulting reaction solution was then stirred at room temperature for 1 h. The solvent and excess thionyl chloride were removed in vacuo, and the reaction product was used without further purification.
Yield: 5.00 g (99%)

tert-Butyl (R)-3-(4-benzylpiperazin-1-yl)pyrrolidine-1-carboxylate (XXIa)

4.99 g (21.5 mmol) of benzylbis(2-chloroethyl)amine hydrochloride (XX) were dissolved in ethanol (120 ml) and, while stirring, 4.00 g (21.5 mmol) of (R)-(+)-N-Boc-3-aminopyrrolidine and 7.22 g (85.9 mmol) of sodium bicarbonate were added. The resulting reaction solution was heated under reflux for 4 h. The cooled reaction mixture was concentrated in vacuo, 100 ml of water were added, and the aqueous phase was extracted with ethyl acetate (4×60 ml). The combined organic phases were washed with saturated aqueous NaHCO$_3$ solution, dried over magnesium sulfate and concentrated in vacuo. The residue was purified by chromatography on silica gel (mobile phase gradient 0-5% methanol in dichloromethane). Yield: 4.48 g (60%) of yellow solid
$^1$H-NMR (DMSO-d$_6$): 1.38 (m, 9H), 1.52-1.68 (m, 1H), 1.93-2.03 (m, 1H), 2.19-2.52 (m, 7H), 2.64-2.78 (m, 1H), 2.48-2.96 (m, 1H), 3.06-3.21 (m, 1H), 3.30-3.49 (m, 5H), 7.19-7.36 (m, 5H).
MS (API-ES, pos) m/z=346 [M+H]$^+$ tert-Butyl (S)-3-(4-benzylpiperazin-1-yl)pyrrolidine-1-carboxylate (XXIb)

6.23 g (26.8 mmol) of benzylbis(2-chloroethyl)amine hydrochloride were dissolved in ethanol (100 ml) and, while stirring, 5.00 g (26.8 mmol) of (S)-(−)-N-Boc-3-aminopyrrolidine and 9.02 g (107 mmol) of sodium bicarbonate were added. The resulting reaction solution was heated under reflux for 4 h. The cooled reaction mixture was concentrated in vacuo, 100 ml of water were added, and the aqueous phase was extracted with ethyl acetate (4×60 ml). The combined organic phases were washed with saturated aqueous NaHCO$_3$ solution, dried over magnesium sulfate and concentrated in vacuo. The residue was purified by chromatography on silica gel (mobile phase gradient 0-5% methanol in dichloromethane). Yield: 6.99 g (75%) of yellow solid
$^1$H-NMR (DMSO-d$_6$): 1.38 (m, 9H), 1.52-1.68 (m, 1H), 1.93-2.03 (m, 1H), 2.19-2.52 (m, 7H), 2.64-2.78 (m, 1H), 2.48-2.96 (m, 1H), 3.06-3.21 (m, 1H), 3.30-3.49 (m, 5H), 7.19-7.36 (m, 5H).
MS (API-ES, pos) m/z=346 [M+H]$^+$ tert-Butyl 3-(4-benzylpiperazin-1-yl)piperidine-1-carboxylate (XXIc)

4.90 g (21.1 mmol) of benzylbis(2-chloroethyl)amine hydrochloride were dissolved in ethanol (120 ml) and, while stirring, 5.00 g (21.1 mmol) of tert-butyl 3-aminopiperidine-1-carboxylate hydrochloride and 14.2 g (169 mmol) of sodium bicarbonate were added. The resulting reaction solution was heated under reflux for 4 h. The cooled reaction mixture was concentrated in vacuo, 100 ml of water were added, and the aqueous phase was extracted with ethyl acetate (4×60 ml). The combined organic phases were washed with saturated aqueous NaHCO$_3$ solution, dried over magnesium sulfate and concentrated in vacuo. The residue was purified by chromatography on silica gel (mobile phase gradient 0-5% methanol in dichloromethane). Yield: 6.99 g (75%) of yellow solid
Yield: 5.82 g (77%) of yellow oil
MS (API-ES, pos) m/z=360 [M+H]$^+$ tert-Butyl 3-(4-benzylpiperazin-1-yl)pyrrolidine-1-carboxylate (XXId)

6.23 g (26.8 mmol) of benzylbis(2-chloroethyl)amine hydrochloride were dissolved in ethanol (100 ml) and, while stirring, 5.00 g (26.8 mmol) of N-Boc-3-aminopyrrolidine and 9.02 g (107 mmol) of sodium bicarbonate were added. The resulting reaction solution was heated under reflux for 4 h. The cooled reaction mixture was concentrated in vacuo, 100 ml of water were added, and the aqueous phase was extracted with ethyl acetate (4×60 ml). The combined organic phases were washed with saturated aqueous $NaHCO_3$ solution, dried over magnesium sulfate and concentrated in vacuo. The residue was purified by chromatography on silica gel (mobile phase gradient 0-5% methanol in dichloromethane). Yield: 6.15 g (66%) of yellow solid $^1$H-NMR (DMSO-$d_6$): 1.38 (m, 9H), 1.52-1.68 (m, 1H), 1.93-2.03 (m, 1H), 2.19-2.52 (m, 7H), 2.64-2.78 (m, 1H), 2.48-2.96 (m, 1H), 3.06-3.21 (m, 1H), 3.30-3.49 (m, 5H), 7.19-7.36 (m, 5H).

MS (API-ES, pos) m/z=346 [M+H]$^+$ tert-Butyl 3-(4-benzylpiperazin-1-yl)azetidine-1-carboxylate (XXIe)

6.33 g (29.0 mmol) of benzylbis(2-chloroethyl)amine hydrochloride were dissolved in ethanol (100 ml) and, while stirring, 5.00 g (29.0 mmol) of tert-butyl 3-aminoazetidine-1-carboxylate and 9.76 g (116 mmol) of sodium bicarbonate were added. The resulting reaction solution was heated under reflux for 4 h. The cooled reaction mixture was concentrated in vacuo, 100 ml of water were added and the aqueous phase was extracted with ethyl acetate (4×60 ml). The combined organic phases were washed with saturated aqueous $NaHCO_3$ solution, dried over magnesium sulfate and concentrated in vacuo. The residue was purified by chromatography on silica gel (mobile phase gradient 2.5-5% methanol in dichloromethane). Yield: 6.27 g (65%) of yellow oil $^1$H-NMR (DMSO-$d_6$): 1.37 (s, 9H), 2.15-2.46 (m, 8H), 2.96-3.04 (m, 1H), 3.45 (s, 2H), 3.56-3.65 (m, 2H), 3.74-3.84 (m, 2H), 7.16-7.35 (m, 5H).

MS (API-ES, pos) m/z=332 [M+H]$^+$

(S)-3-(4-Propyl-piperazin-1-yl)-pyrrolidine-1-carboxylic acid tert-butyl ester To a solution of (S)-3-(4-benzyl-piperazin-1-yl)-pyrrolidine-1-carboxylic acid tert-butyl ester (3.7 g, 10.83 mmol) in EtOH (75 mL) and acetic acid (50 mL) 10% Pd on carbon (0.58 g, 0.54 mmol) was added. The reaction mixture was hydrogenated under 1 atm $H_2$ for 18 hours, filtered through Celite and concentrated in vacuo to afford (S)-3-piperazin-1-yl-pyrrolidine-1-carboxylic acid tert-butyl ester as an orange oil. The product was used without further purification.

$^1$H-NMR (400 MHz, DMSO-$d_6$): δ 1.39 (s, 9H), 1.61 (m, 1H), 1.98 (m, 1H), 2.25 (m, 2H), 2.33 (m, 2H), 2.66 (m, 5H), 2.91 (m, 1H), 3.15 (m, 1H), 3.29-3.38 (m, 1H), 3.47 (dd, 9.5 Hz, 7.6 Hz, 1H).

MS (API-ES, pos) m/z=257.15 [M+2H]$^+$.

To a chilled solution of (S)-3-piperazin-1-yl-pyrrolidine-1-carboxylic acid tert-butyl ester (2.8 g, 10.81 mmol) in MeOH (100 mL) propionalhedyde (1.17 mL, 16.21 mmol) and sodium cyanoborohydride (747 mg, 11.89 mmol) were added. The pH of the solution was kept to 4-5. The reaction mixture was allowed to warm up to room temperature and stirred for 2 hours. Then, the reaction mixture was concentrated in vacuo, water was added and 1N HCl aqueous solution was added until pH 2, and the mixture was extracted three times with $CH_2Cl_2$. The aqueous phase was brought to pH>10 with 1N NaOH aqueous solution and extracted three times with $CH_2Cl_2$. The combined organic phases were dried over $Na_2SO_4$, filtered and concentrated in vacuo to afford (S)-3-(4-propyl-piperazin-1-yl)-pyrrolidine-1-carboxylic acid tert-butyl ester (3.1 g, 98%) as an orange oil.

$^1$H-NMR (400 MHz, CDCl$_3$): δ 0.89 (q, 6.7 Hz, 3H), 1.30 (m, 2H), 1.46 (s, 9H), 1.51 (m, 1H), 1.61 (m, 1H), 1.77 (m, 1H), 2.08 (m, 1H), 2.31 (t, 7.6 Hz, 1H), 2.48-2.57 (m, 7H), 2.78 (m, 1H), 3.10 (t, 9.5 Hz, 1H), 3.28 (m, 1H), 3.46-3.73 (m, 2H).

MS (API-ES, pos) m/z=298.25 [M+H]$^+$.

1-Propyl-4-(S)-pyrrolidin-3-yl-piperazine

A solution of (S)-3-(4-propyl-piperazin-1-yl)-pyrrolidine-1-carboxylic acid tert-butyl ester (3.14 g, 10.56 mmol) in $CH_2Cl_2$ (20 mL) was treated with trifluoroacetic acid (20 mL). The reaction mixture was stirred at room temperature for 2 hours, concentrated in vacuo and co-evaporated the solvent with toluene (3×). The residue was dissolved in $CH_2Cl_2$ (30 mL) and treated with solid $K_2CO_3$. The reaction mixture was stirred at room temperature for 1 hour, filtered and concentrated in vacuo to afford 1-propyl-4-(S)-pyrrolidin-3-yl-piperazine (1.14 g, 55%) as an orange oil.

MS (API-ES, pos) m/z=198.15 [M+H]$^+$.

(R)-3-(4-Benzyl-piperazin-1ylmethyl)-pyrrolidine-1-carboxylic acid tert-butyl ester To a stirred solution of benzyl-bis-(2-chloro-ethyl)-amine (990 mg, 4.26 mmol) in ethanol (20 mL) (R)-3-(aminomethyl)-1-N-pyrrolidine (854 mg, 4.26 mmol) and $NaHCO_3$ (1.43 g, 17.06 mmol) were added and the mixture was refluxed for 3 hours. The cooled reaction mixture was concentrated in vacuo, water was added and the aqueous phase was extracted with ethyl acetate (3×). The combined organic phases were washed with saturated $NaHCO_3$ aqueous solution, dried over $Na_2SO_4$ and concentrated in vacuo. The residue was purified by flash chromatography on silica gel using 2% MeOH in $CH_2Cl_2$ as eluent to afford (R)-3-(4-benzyl-piperazin-1ylmethyl)-pyrrolidine-1-carboxylic acid tert-butyl ester (980 mg, 64%) as an orange oil.

MS (API-ES, pos) m/z=360.20 [M+H]$^+$.

(S)-3-(4-Benzyl-piperazin-1ylmethyl)-pyrrolidine-1-carboxylic acid tert-butyl ester The title compound was synthesized in a similar manner to (R)-3-(4-benzyl-piperazin-1-ylmethyl)-pyrrolidine-1-carboxylic acid tert-butyl ester.

MS (API-ES, pos) m/z=360.20 [M+H]$^+$.

1-Benzyl-4-(S)-1-pyrrolidin-3-ylmethyl-piperazine; compound with trifluoroacetic acid To a stirred solution of (R)-3-(4-benzyl-piperazin-1-ylmethyl)-pyrrolidine-1-carboxylic acid tert-butyl ester (300 mg, 0.84 mmol) in $CH_2Cl_2$ (3 mL) trifluoroacetic acid (3 mL) were added. The reaction mixture was stirred at room temperature for 2 hours, concentrated in vacuo and co-evaporated the solvent with toluene (3×) to afford 1-benzyl-4-(S)-1-pyrrolidin-3-ylmethyl-piperazine; compound with trifluoroacetic acid as an orange oil. The residue was used without further purification.

MS (API-ES, pos) m/z=260.20 [M+H]$^+$.

1-Benzyl-4-(R)-1-pyrrolidin-3-ylmethyl-piperazine; compound with trifluoroacetic acid The title compound was synthesized in a similar manner to 1-benzyl-4-(S)-1-pyrrolidin-3-ylmethyl-piperazine; compound with trifluoroacetic acid.

MS (API-ES, pos) m/z=260.40 [M+H]$^+$.

(S)-3-(2-Methyl-pyridin-4-ylamino)-pyrrolidine-1-carboxylic acid tert-butyl ester 4-Bromo-2-methylpyridine (165 mg, 0.96 mmol), (S)-(−)-N-Boc-3-aminopyrrolidine (214 mg, 1.15 mmol), Pd(OAc)$_2$ (8.6 mg, 0.04 mmol), (rac)-BINAP (23.9 mg, 0.04 mmol) and NaOtBu (129 mg, 1.34 mmol) in dry toluene (5 mL) were heated at 70° C. in a flask under nitrogen atmosphere for 4 hours. The reaction mixture was allowed to cool down to room temperature, taken up in diethyl ether (10 mL), washed with brine, dried over Na$_2$SO$_4$, filtered and concentrated in vacuo. The residue was purified by flash chromatography on silica gel using 15% MeOH in CH$_2$Cl$_2$ as eluent to afford (S)-3-(2-methyl-pyridin-4-ylamino)-pyrrolidine-1-carboxylic acid tert-butyl ester (255 mg, 96%) as an orange oil.

$^1$H-NMR (400 MHz, DMSO-d$_6$): δ 1.39 (s, 9H), 1.76 (m, 1H), 2.10 (m, 1H), 2.26 (s, 3H), 3.09 (m, 1H), 3.28-3.41 (m, 2H), 3.53 (m, 1H), 4.01 (m, 1H), 6.33 (dd, 5.7 Hz, 2.1 Hz, 1H), 6.37 (m, 1H), 6.55 (d, 6.6 Hz, 1H), 7.89 (d, 5.7 Hz, 1H).

MS (API-ES, pos) m/z=278.20 [M+H]$^+$.

(2-Methyl-pyridin-4-yl)-(S)-pyrrolidin-3-yl-amine; compound with trifluoroacetic acid To a stirred solution of (S)-3-(2-methyl-pyridin-4-ylamino)-pyrrolidine-1-carboxylic acid tert-butyl ester 11 (255 mg, 0.92 mmol) in CH$_2$Cl$_2$ (10 mL) trifluoroacetic acid (8 mL) was added. The reaction mixture was stirred at room temperature for 2 hours, concentrated in vacuo and co-evaporated the solvent with toluene (3×) to afford (2-methyl-pyridin-4-yl)-(S)-pyrrolidin-3-yl-amine; compound with trifluoroacetic acid as an orange oil. The residue was used without further purification.

MS (API-ES, pos) m/z=178.10 [M+H]$^+$.

(S)-3-(2-Pyridin-4-ylamino)-pyrrolidine-1-carboxylic acid tert-butyl ester

4-Bromopyridine hydrochloride (150 mg, 0.77 mmol), (S)-(−)-N-Boc-3-aminopyrrolidine (172 mg, 0.93 mmol), Pd(OAc)$_2$ (6.9 mg, 0.03 mmol), (rac)-BINAP (19.2 mg, 0.03 mmol) and NaOtBu (178 mg, 1.85 mmol) in dry toluene (5 mL) were heated for 4 hours to 70° C. in a flask under nitrogen atmosphere. The reaction mixture was allowed to cool to room temperature, taken up in diethyl ether (10 mL), washed with brine, dried over Na$_2$SO$_4$, filtered and concentrated in vacuo. The residue was purified by flash chromatography on silica gel using 12% MeOH in CH$_2$Cl$_2$ as eluent to afford (S)-3-(2-pyridin-4-ylamino)-pyrrolidine-1-carboxylic acid tert-butyl ester (200 mg, 99%) as an orange oil.

$^1$H-NMR (400 MHz, DMSO-d$_6$): δ 1.40 (s, 9H), 1.80 (m, 1H), 2.12 (m, 1H), 3.11 (m, 1H), 3.29-3.41 (m, 2H), 3.54 (m, 1H), 4.02 (m, 1H), 6.50 (d, 6.0 Hz, 1H), 6.70 (br d, 6.3 Hz, 1H), 8.02 (br d, 6.0 Hz, 2H).

MS (API-ES, pos) m/z=264.20 [M+H]$^+$.

Pyridin-4-yl-(S)-pyrrolidin-3-yl-amine; compound with trifluoroacetic acid

To a stirred solution of (S)-3-(2-pyridin-4-ylamino)-pyrrolidine-1-carboxylic acid tert-butyl ester 13 (70 mg, 0.27 mmol) in CH$_2$Cl$_2$ (2 mL) trifluoroacetic acid (2 mL) was added. The reaction mixture was stirred at room temperature for 4 hours, concentrated in vacuo and co-evaporated the solvent with toluene (3×) to afford pyridin-4-yl-(S)-pyrrolidin-3-yl-amine; compound with trifluoroacetic acid as an orange oil. The residue was used without further purification.

MS (API-ES, pos) m/z=164.10 [M+H]$^+$.

(S)-3-(1-Methyl-piperidin-4-ylamino)-pyrrolidine-1-carboxylic acid tert-butyl ester To a solution of (S)-(−)-N-Boc-3-aminopyrrolidine (500 mg, 2.68 mmol) and 1-methyl-4-piperidone (0.34 mL, 2.95 mmol) in THF (10 mL) MP-(OAc)$_3$BH resin (Argonaut; 2.55 mmol/g; 2.63 g, 6.71 mmol) was added and the reaction mixture was agitated at room temperature for 18 hours. Then, 1-methyl-4-piperidone (0.28 mL, 2.42 mmol) was added and the reaction mixture was agitated for 24 hours more. The reaction mixture was filtered and concentrated in vacuo. The residue was purified by flash chromatography on silica gel using 12% MeOH in CH$_2$Cl$_2$ as eluent to afford (S)-3-(1-methyl-piperidin-4-ylamino)-pyrrolidine-1-carboxylic acid tert-butyl ester (750 mg, 99%) as an orange oil.

$^1$H-NMR (400 MHz, CDCl$_3$): δ 1.46 (s, 9H), 1.65 (m, 1H), 1.89 (m, 2H), 2.02-2.13 (m, 4H), 2.31 (s, 3H), 2.53 (m, 1H), 2.80-2.90 (m, 4H), 3.01 (m, 1H), 3.31 (m, 1H), 3.41-3.60 (m, 3H).

MS (API-ES, pos) m/z=284.25 [M+H]$^+$.

(S)-3-[Methyl-(1-methyl-piperidin-4-yl)-amino]-pyrrolidine-1-carboxylic acid tert-butyl ester To a solution of (S)-3-(1-methyl-piperidin-4-ylamino)-pyrrolidine-1-carboxylic acid tert-butyl ester (100 mg, 0.35 mmol) and paraformaldehyde (21 mg, 0.71 mmol) in THF (3 mL) MP-(OAc)$_3$BH resin (Argonaut; 2.55 mmol/g; 346 mg, 0.88 mmol) was added and the reaction mixture was agitated at room temperature for 96 hours. Then, the reaction mixture was filtered and concentrated in vacuo to afford (S)-3-[methyl-(1-methyl-piperidin-4-yl)-amino]-pyrrolidine-1-carboxylic acid tert-butyl ester (100 mg, 99%) as an orange oil. The residue was used without further purification.

MS (API-ES, pos) m/z=298.25 [M+H]$^+$.

Methyl-(1-methyl-piperidin-4-yl)-(S)-pyrrolidin-3-yl-amine; compound with trifluoroacetic acid To a stirred solution of (S)-3-[methyl-(1-methyl-piperidin-4-yl)-amino]-pyrrolidine-1-carboxylic acid tert-butyl ester 16 (100 mg, 0.34 mmol) in CH$_2$Cl$_2$ (1 mL) trifluoroacetic acid (1 mL) was added. The reaction mixture was stirred at room temperature for 5 hours, concentrated in vacuo and co-evaporated the solvent with toluene (3×) to afford methyl-(1-methyl-piperidin-4-yl)-(S)-pyrrolidin-3-yl-amine; compound with trifluoroacetic acid as an orange oil. The residue was used without further purification.

MS (API-ES, pos) m/z=198.20 [M+H]$^+$.

(R)-3-[(1-Methyl-piperidin-4-ylamino)-methyl]-pyrrolidine-1-carboxylic acid tert-butyl ester To a solution of (R)-3-(aminomethyl)-1-N-Boc-pyrrolidine (252 mg, 1.26 mmol) and 1-methyl-4-piperidone (0.16 mL, 1.38 mmol) in THF (10 mL) MP-(OAc)₃BH resin (Argonaut; 2.33 mmol/g; 1.35 g, 3.15 mmol) was added and the reaction mixture was agitated at room temperature for 24 hours. Then, the reaction mixture was filtered and concentrated in vacuo to afford (R)-3-[(1-methyl-piperidin-4-ylamino)-methyl]-pyrrolidine-1-carboxylic acid tert-butyl ester (370 mg, 99%) as an orange oil. The product was used without further purification.

$^1$H-NMR (400 MHz, CDCl₃): δ 1.46 (s, 9H), 1.45-1.58 (m, 1H), 1.86-2.01 (m, 5H), 2.25 (m, 2H), 2.36 (s, 3H), 2.48-2.74 (m, 3H), 2.97 (m, 2H), 3.28-3.56 (m, 2H), 3.75 (m, 1H), 4.60 (m, 2H).

MS (API-ES, pos) m/z=298.25 [M+H]⁺.

(1-Methyl-piperidin-4-yl)-(S)-pyrrolidin-3-ylmethyl-amine; compound with trifluoroacetic acid To a stirred solution of (R)-3-[(1-methyl-piperidin-4-ylamino)-methyl]-pyrrolidine-1-carboxylic acid tert-butyl ester 18 (361 mg, 1.21 mmol) in CH₂Cl₂ (3 mL) trifluoroacetic acid (3 mL) was added. The reaction mixture was stirred at room temperature for 24 hours, concentrated in vacuo and co-evaporated the solvent with toluene (3×) to afford (1-methyl-piperidin-4-yl)-(S)-pyrrolidin-3-ylmethyl-amine; compound with trifluoroacetic acid as an orange oil. The residue was used without further purification.

MS (API-ES, pos) m/z=198.20 [M+H]⁺.

(R)-3-{[Methyl-(1-methyl-piperidin-4-yl)-amino]-methyl}-pyrrolidine-1-carboxylic acid tert-butyl ester To a solution of (R)-3-[(1-methyl-piperidin-4-ylamino)-methyl]-pyrrolidine-1-carboxylic acid tert-butyl ester (100 mg, 0.34 mmol) and paraformaldehyde (20 mg, 0.67 mmol) in THF (4 mL) was added MP-(OAc)₃BH resin (Argonaut; 2.55 mmol/g; 330 mg, 0.84 mmol) and the reaction mixture was agitated at room temperature for 96 hours. Then, the reaction mixture was filtered and concentrated in vacuo to afford (R)-3-{[methyl-(1-methyl-piperidin-4-yl)-amino]-methyl}-pyrrolidine-1-carboxylic acid tert-butyl ester (96 mg, 92%) as an orange oil. The residue was used without further purification.

MS (API-ES, pos) m/z=312.25 [M+H]⁺.

Methyl-(1-methyl-piperidin-4-yl)-(S)-1-pyrrolidin-3-ylmethyl-amine; compound with trifluoroacetic acid To a stirred solution of (R)-3-{[methyl-(1-methyl-piperidin-4-yl)-amino]-methyl}-pyrrolidine-1-carboxylic acid tert-butyl ester 20 (96 mg, 0.31 mmol) in CH₂Cl₂ (3 mL) trifluoroacetic acid (3 mL) was added. The reaction mixture was stirred at room temperature for 24 hours, concentrated in vacuo and co-evaporated the solvent with toluene (3×) to afford methyl-(1-methyl-piperidin-4-yl)-(S)-1-pyrrolidin-3-ylmethylamine; compound with trifluoroacetic acid as an orange oil. The residue was used without further purification.

MS (API-ES, pos) m/z=212.25 [M+H]⁺.

The following compounds (examples 1-81) were prepared as shown in synthesis schemes 1 and 2 from the respective intermediates IX by one of the following reaction procedures:

1) A solution of the respective intermediate IX in dry THF or DMF was mixed with triethylamine (3 eq.) and a catalytic amount of DMAP. 1.3 eq. of the respective arylsulfonyl chloride or heteroarylsulfonyl chloride were added, and the resulting solution was then stirred at room temperature overnight. The reaction solution was mixed with water and extracted with ethyl acetate (3×60 ml). The combined organic phases were washed with water and saturated brine, dried over magnesium sulfate and concentrated under reduced pressure. The residue was purified by chromatography either on silica gel (mobile phase: gradients of methanol in dichloromethane) or by preparative RP-HPLC (mobile phase: gradient from 10% to 80% acetonitrile in water, 0.1 trifluoroacetic acid as modulator)

2) A solution of the respective intermediate IX in dry THF or DMF was mixed with a catalytic amount of DMAP, 1.3 eq. of the respective arylsulfonyl chloride or heteroarylsulfonyl chloride and 3-4 eq. of Si-diethylamines (Silicycle, 1.04 mmol/g) and shaken overnight. The solid phase reagent was filtered off and washed with dichloromethane. The filtrate was concentrated under reduced pressure, and the residue was purified by chromatography either on silica gel (mobile phase: gradients of methanol in dichloromethane) or by preparative RP-HPLC (mobile phase: gradient from 10% to 80% acetonitrile in water, 0.1 trifluoroacetic acid as modulator).

3) 1.05 eq. of sodium hydride (60% suspension in mineral oil) were added to a solution of the respective intermediate IX in dry DMF at 0° C. in a heat-dried flask under a nitrogen atmosphere, and the mixture was then stirred at room temperature. After renewed cooling in an ice bath, 1.1 eq. of the respective arylsulfonyl chloride or heteroarylsulfonyl chloride were added, and the mixture was stirred while cooling in ice for 1 h and then at room temperature for 2 h. The reaction solution was mixed with saturated sodium bicarbonate solution and water and then extracted with ethyl acetate (3×). The combined organic phases were washed with saturated sodium bicarbonate solution, dried over magnesium sulfate and concentrated in vacuo. The residue was purified by chromatography either on silica gel (mobile phase: gradients of methanol in dichloromethane) or by preparative RP-HPLC (mobile phase: gradient from 10% to 80% acetonitrile in water, 0.1 trifluoroacetic acid as modulator).

If not stated otherwise, the compounds of the following examples, e.g. examples 1, 2, 3, 9, 11, 15, 16, 18 to 34, 36, 37, 42, 46, 51, 53, 55 to 58, 62 to 64, 68, 69, 71 to 76, 78, 79, 81, 85, 86, 88, 91, 92, 94, 95, 96, 106, 107, 108, 111 to 115, 117 to 126, 131 to 141, 145, 146, 148 to 157, 159 to 163, 165, 167 to 175, 177, 179, 191, 193 and 211, may be obtained either as the free base or as the acid addition salt with trifluoroacetic acid.

Example 1

5-Chloro-1-(2,4-dimethoxybenzenesulfonyl)-3-[1-(4-methoxyphenyl)-2-oxo-2-(4-pyridin-4-ylpiperazin-1-yl)ethyl]-1,3-dihydrobenzimidazol-2-one $^1$H-NMR (DMSO-d₆): 3.28-3-40 (m, 1H), 3.45 (s, 3H), 3.52-3.63 (m, 3H), 3.67-3.75 (m, 3H), 3.76 s, 3H), 3.79-3.92 (m, 1H), 3.86 (s, 3H), 6.56 (s, 1H), 6.68 (s, 1H), 6.75 (m, 2H), 6.97 (d, 8.1 Hz, 2H), 7.12-7.25 (m, 5H), 7.66 (d, 8.7 Hz, 1H), 7.93 (d, 8.9 Hz, 1H), 8.26 (d, 6.9 Hz, 2H), 13.4 (s, 1H).

MS (API-ES, pos) m/z=678, 680 [M+H]⁺

Example 2

5-Chloro-1-(furan-2-sulfonyl)-3-[2-oxo-1-phenyl-2-(4-pyridin-4-ylpiperazin-1-yl)ethyl]-1,3-dihydrobenzimidazol-2-one $^1$H-NMR (DMSO-d₆): 3.53-3.93 (m, 8H), 6.71 (s, 1H), 6.74 (s, 1H), 6.81-6.83 (m, 1H), 7.12-7.23 (m, 3H), 7.32-7.38 (m, 2H), 7.40-7.47 (m, 3H), 7.67-7.73 (m, 2H), 8.13 (s, 1H), 8.26 (d, 2H), 13.4 (s, 1H).

MS (API-ES, pos) m/z=578, 580 [M+H]⁺

Example 3

5-Chloro-3-{2-[4-(4-methylpiperazin-1-yl)piperidin-1-yl]-2-oxo-1-phenyl-ethyl}-1-(quinoline-8-sulfonyl)-1,3-dihydrobenzimidazol-2-one MS (API-ES, pos) m/z=659, 661 [M+H]$^+$

Example 4

5-Iodo-1-(4-methoxybenzenesulfonyl)-3-[2-oxo-1-phenyl-2-(4-pyridin-4-ylpiperazin-1-yl)ethyl]-1,3-dihydrobenzimidazol-2-one $^1$H-NMR (DMSO-d$_6$): 3.05-3.14 (m, 2H), 3.24-3.47 (m, 4H), 3.56-3.73 (m, 2H), 3.82 (s, 3H), 6.61 (s, 1H), 6.76 (d, 6.4 Hz, 2H), 6.96 (m, 1H), 7.17 (d, 9.0 Hz, 2H), 7.21-7.28 (m, 2H), 7.35-7.42 (m, 3H), 7.48 (dd, 8.5 Hz, 1.4 Hz, 1H), 7.62 (d, 8.5 Hz, 1H), 7.97 (d, 9.0 Hz, 2H), 8.16 (d, 6.3 Hz, 2H).
MS (API-ES, pos) m/z=710 [M+H]$^+$

Example 5

5-Chloro-3-[2-oxo-1-phenyl-2-(4-pyridin-4-ylpiperazin-1-yl)ethyl]-1-(thiophene-3-sulfonyl)-1,3-dihydrobenzimidazol-2-one $^1$H-NMR (methanol-d4): 3.48-3.65 (m, 5H), 3.76-3.90 (m, 3H), 6.59 (d, 1.9 Hz, 1H), 6.67 (s, 1H), 6.81 (d, 6.6 Hz, 2H), 7.10 (dd, 8.7 Hz, 2.0 Hz, 1H), 7.26-7.33 (m, 2H), 7.40-7.45 (m, 3H), 7.49-7.52 (m, 1H), 7.61-7.66 (m, 1H), 7.83 (d, 8.7 Hz, 1H), 8.13 (d, 6.6 Hz, 2H), 8.51-8.54 (m, 1H).
MS (API-ES, pos) m/z=594, 596 [M+H]$^+$

Example 6

5-Chloro-1-(4-methoxybenzenesulfonyl)-3-[1-(2-methoxyphenyl)-2-oxo-2-(4-pyridin-4-ylpiperazin-1-yl)ethyl]-1,3-dihydrobenzimidazol-2-one $^1$H-NMR (methanol-d4): 3.20-3.41 (m, 3H), 3.42-3.58 (m, 3H), 3.53 (s, 3H), 3.79-3.85 (m, 2H), 3.87 (s, 3H), 6.63 (s, 1H), 6.70 (d, 1.9 Hz, 1H), 6.77-6.84 (m, 2H), 6.96-7.14 (m, 5H), 7.32 (d, 7.4 Hz, 1H), 7.39-7.46 (m, 1H), 7.85 (d, 8.7 Hz, 1H), 8.04 (d, 9 Hz, 2H), 8.07-8.18 (m, 2H).
MS (API-ES, pos) m/z=649, 651 [M+H]$^+$

Example 7

5-Chloro-1-(5-chlorothiophene-2-sulfonyl)-3-[2-oxo-1-phenyl-2-(4-pyridin-4-ylpiperazin-1-yl)ethyl]-1,3-dihydrobenzimidazol-2-one $^1$H-NMR (DMSO-d$_6$): 3.14-3.21 (m, 2H), 3.28-3.38 (m, 2H), 3.42-3.53 (m, 2H), 3.64-3.75 (m, 2H), 6.69 (s, 1H), 6.71-6.82 (m, 3H), 7.21 (dd, 8.8 Hz, 2.0 Hz, 1H), 7.30-7.45 (m, 6H), 7.72 (d, 8.7 Hz, 1H), 7.94 (d, 4.2 Hz, 1H), 8.16 (m, 2H).
MS (API-ES, pos) m/z=628, 630 [M+H]$^+$

Example 8

5-Chloro-1-(2,4-dimethoxybenzenesulfonyl)-3-{1-(2-methoxyphenyl)-2-[4-(1-methylpiperidin-4-yl)piperazin-1-yl]-2-oxoethyl}-1,3-dihydrobenzimidazol-2-one $^1$H-NMR (methanol-d4): 1.42-1.58 (m, 2H), 1.76-1.84 (m, 2H), 1.97-2.08 (m, 2H), 2.20-2.28 (m, 1H), 2.26 (s, 3H), 2.32-2.47 (m, 2H), 2.50-2.68 (m, 2H), 2.85-2.96 (m, 2H), 3.13-3.25 (m, 1H), 3.30-3.40 (m, 1H), 3.49 (s, 3H), 3.61 (s, 3H), 3.64-3.72 (m, 2H), 3.89 (s, 3H), 6.57 (s, 1H), 6.60 (d, 2.1 Hz, 1H), 6.68-6.75 (m, 2H), 6.97-7.10 (m, 3H), 7.29 (d, 7.5 Hz, 1H), 7.40-7.47 (m, 1H), 7.72 (d, 8.7 Hz, 1H), 8.03 (d, 8.9 Hz, 1H).
MS (API-ES, pos) m/z=698, 700 [M+H]$^+$

Example 9

5-Chloro-1-(4-methoxybenzenesulfonyl)-3-{1-(2-methoxyphenyl)-2-[4-(1-methylpiperidin-4-yl)piperazin-1-yl]-2-oxoethyl}-1,3-dihydrobenzimidazol-2-one $^1$H-NMR (DMSO-d$_6$): 1.51-1.78 (m, 2H), 2.05-2.20 (m, 2H), 2.76 (s, 3H), 2.85-3.79 (m, 13H), 3.37 (s, 3H), 3.87 (s, 3H), 6.51 (s, 1H), 6.68 (d, 1.5 Hz, 1H), 6.98 (d, 8.3 Hz, 1H), 7.03 (t, 7.5 Hz, 1H), 7.15 (dd, 8.7 Hz, 2.0 Hz, 1H), 7.21 (d, 9 Hz, 2H), 7.26-7.46 (m, 1H), 7.41 (t, 7.4 Hz, 1H), 7.79 (d, 8.7 Hz, 1H), 7.99 (d, 9 Hz, 2H), 9.43-9.65 (bs, 1H).
MS (API-ES, pos) m/z=668, 670 [M+H]$^+$

Example 10

1-(2,4-Dimethoxybenzenesulfonyl)-3-{2-[4-(1-methylpiperidin-4-yl)piperazin-1-yl]-2-oxo-1-phenyl-ethyl}-2-oxo-2,3-dihydro-1H-benzimidazole-5-carbonitrile $^1$H-NMR (methanol-d4): 1.44-1.58 (m, 2H), 1.76-1.85 (m, 2H), 1.98-2.13 (m, 2H), 2.20-2.30 (m, 1H), 2.27 (s, 3H), 2.36-2.71 (m, 2H), 2.92 (m, 2H), 3.24-3.32 (m, 1H), 3.45 (s, 3H), 3.43-3.52 (m, 1H), 3.62-3.80 (m, 2H), 3.90 (s, 3H), 6.58-6.64 (m, 2H), 6.73 (m, 1H), 6.84 (s, 1H), 7.28-7.35 (m, 2H), 7.42-7.51 (m, 4H), 7.93 (d, 8.5 Hz, 1H), 8.04 (d, 9.0 Hz, 1H).
MS (API-ES, pos) m/z=659 [M+H]$^+$

Example 11

1-(4-Methoxybenzenesulfonyl)-3-{2-[4-(1-methylpiperidin-4-yl)piperazin-1-yl]-2-oxo-1-phenylethyl}-2-oxo-2,3-dihydro-1H-benzimidazole-5-carbonitrile $^1$H-NMR (DMSO-d$_6$): 1.57-1.75 (m, 2H), 2.03-2.20 (m, 2H), 2.76 (s, 3H), 2.70-3.77 (m, 13H), 3.88 (s, 3H), 6.68 (bs, 1H), 7.03 (s, 1H), 7.20 (d, 9.0 Hz, 2H), 7.28-7.36 (m, 2H), 7.37-7.45 (m, 3H), 7.64 (dd, 8.5 Hz, 1.3 Hz, 1H), 7.98 (d, 8.5 Hz, 1H), 8.01 (d, 9.0 Hz, 2H), 9.48 (bs, 1H).
MS (API-ES, pos) m/z=629 [M+H]$^+$

Example 12

5-Chloro-1-(2,4-dimethoxybenzenesulfonyl)-3-[1-(2-methoxyphenyl)-2-oxo-2-(4-pyridin-4-ylpiperazin-1-yl)ethyl]-1,3-dihydrobenzimidazol-2-one $^1$H-NMR (methanol-d4): 3.18-3.58 (m, 6H), 3.48 (s, 3H), 3.63 (s, 3H), 3.79-3.85 (m, 2H), 3.87 (s, 3H), 6.59 (d, 2.1 Hz, 1H), 6.62 (s, 1H), 6.68-6.84 (m, 4H), 6.99-7.10 (m, 3H), 7.34 (d, 7.1 Hz, 1H), 7.42-7.48 (m, 1H), 7.74 (d, 8.7 Hz, 1H), 8.04 (d, 8.9 Hz, 1H), 8.07-8.16 (m, 2H).
MS (API-ES, pos) m/z=678, 680 [M+H]$^+$

Example 13

5-Chloro-3-[1-(2-methoxyphenyl)-2-oxo-2-(4-pyridin-4-ylpiperazin-1-yl)-ethyl]-1-(quinoline-8-sulfonyl)-1,3-dihydrobenzimidazol-2-one $^1$H-NMR (DMSO-d$_6$): 3.04 (s, 3H), 3.07-3.19 (m, 2H), 3.25-3.44 (m, 4H), 3.53-3.62 (m, 1H), 3.67-3.75 (m, 1H), 6.35 (s, 1H), 6.70 (d, 2.0 Hz, 1H), 6.74 (d, 6.4 Hz, 2H), 6.88 (d, 8.3 Hz, 1H), 6.93-6.99 (m, 1H), 7.17 (d, 7.4 Hz, 1H), 7.20-7.24 (m, 1H), 7.32-7.38 (m, 1H), 7.55-7.62 (m, 1H), 7.87-7.96 (m, 2H), 8.15 (d, 6.2 Hz, 2H), 8.45 (d, 8.3 Hz, 1H), 8.48-8.56 (m, 2H), 8.67 (d, 7.4 Hz, 1H).
MS (API-ES, pos) m/z=669, 671 [M+H]$^+$

Example 14

4-{5-Chloro-3-[1-(2-methoxyphenyl)-2-oxo-2-(4-pyridin-4-ylpiperazin-1-yl)ethyl]-2-oxo-2,3-dihydrobenzimidazole-1-sulfonyl}benzonitrile $^1$H-NMR (DMSO-d$_6$): 3.03-3.11 (m, 1H), 3.12-3.20 (m, 1H), 3.23-3.48 (m, 4H), 3.40 (s, 3H), 3.56-3.66 (m, 1H), 3.72-3.82 (m, 1H), 6.49 (s, 1H), 6.73-6.80 (m, 3H), 6.95-7.06 (m, 2H), 7.19 (dd, 8.7 Hz, 2.0 Hz, 1H), 7.35 (d, 7.6 Hz, 1H), 7.37-7.44 (m, 1H), 7.80 (d, 8.7 Hz, 1H), 8.12-8.28 (m, 6H).
MS (API-ES, pos) m/z=643, 645 [M+H]$^+$

Example 15

5-Chloro-3-{1-(2-methoxyphenyl)-2-[4-(1-methylpiperidin-4-yl)piperazin-1-yl]-2-oxoethyl}-1-(quinoline-8-sulfonyl)-1,3-dihydrobenzimidazol-2-one $^1$H-NMR (DMSO-d$_6$): 1.56-1.74 (m, 2H), 2.02-2.16 (m, 2H), 2.71-3.67 (m, 13H), 2.75 (s, 3H), 3.01 (s, 3H), 6.36 (s, 1H), 6.67 (d, 1.5 Hz, 1H), 6.89 (d, 8.3 Hz, 1H), 6.93-6.99 (m, 1H), 7.15 (bs, 1H), 7.22 (dd, 8.8 Hz, 2.0 Hz, 1H), 7.33-7.39 (m, 1H), 7.59-7.66 (m, 1H), 7.86-7.97 (m, 2H), 8.47 (d, 8.3 Hz, 1H), 8.49-8.57 (m, 2H), 8.66 (d, 7.4 Hz, 1H), 9.46 (bs, 1H).
MS (API-ES, pos) m/z=689, 691 [M+H]$^+$

Example 16

4-(5-Chloro-3-{1-(2-methoxyphenyl)-2-[4-(1-methylpiperidin-4-yl)piperazin-1-yl]-2-oxoethyl}-2-oxo-2,3-dihydrobenzoimidazole-1-sulfonyl)benzonitrile $^1$H-NMR (DMSO-d$_6$): 1.60-1.75 (m, 2H), 2.04-2.18 (m, 2H), 2.71-3.66 (m, 13H), 2.76 (s, 3H), 3.38 (s, 3H), 6.50 (s, 1H), 6.76 (s, 1H), 6.99 (d, 8.3 Hz, 1H), 7.01-7.07 (m, 1H), 7.19 (dd, 8.7 Hz, 2.0 Hz, 1H), 7.33 (bs, 1H), 7.38-7.441 (m, 1H), 7.80 (d, 8.7 Hz, 1H), 8.18-8.26 (m, 4H).
MS (API-ES, pos) m/z=663, 665 [M+H]$^+$

Example 17

5-Chloro-1-(4-methoxybenzenesulfonyl)-3-{2-oxo-1-phenyl-2-[4-(4-propylpiperazin-1-yl)piperidin-1-yl]ethyl}-1,3-dihydrobenzimidazol-2-one $^1$H-NMR (DMSO-d$_6$): 0.73-1.10 (m, 5H), 1.31-1.48 (m, 3H), 1.66-1.79 (m, 1H), 2.10-2.44 (m, 11H), 2.62-2.75 (m, 1H), 2.78-2.90 (m, 1H), 3.46-3.62 (m, 1H), 3.87 (s, 3H), 4.30-4.39 (m, 1H), 6.52 u. 6.57 (2s, 1H), 6.64 u. 6.67 (2d, 1.8 Hz, 1H), 7.12-7.24 (m, 4H), 7.25-7.32 (m, 1H), 7.34-7.43 (m, 3H), 7.79 u. 7.83 (2d, 8.7 Hz, 1H), 7.94-8.03 (m, 1H).
MS (API-ES, pos) m/z=666, 668 [M+H]$^+$

Example 18

5-Chloro-1-(4-methoxybenzenesulfonyl)-3-{2-[4-(4-methylpiperazin-1-yl)piperidin-1-yl]-2-oxo-1-phenyl-ethyl}-1,3-dihydrobenzimidazol-2-one $^1$H-NMR (DMSO-d$_6$): 0.72-1.48 (m, 3H), 1.66-1.78 (m, 1H), 2.12 (s, 3H), 2.16-2.46 (m, 9H), 2.62-2.75 (m, 1H), 2.78-2.88 (m, 1H), 3.47-3.60 (m, 1H), 3.87 (s, 3H), 4.29-4.38 (m, 1H), 6.51 u. 6.57 (2s, 1H), 6.64 u. 6.67 (2d, 1.8 Hz, 1H), 7.12-7.24 (m, 4H), 7.26-7.32 (m, 1H), 7.33-7.45 (m, 3H), 7.77-7.86 (m, 1H), 7.95-8.03 (m, 2H).
MS (API-ES, pos) m/z=638, 640 [M+H]$^+$

Example 19

5-Chloro-1-(4-methoxybenzenesulfonyl)-3-{1-(3-methoxyphenyl)-2-[4-(1-methylpiperidin-4-yl)piperazin-1-yl]-2-oxo-ethyl}-1,3-dihydrobenzimidazol-2-one $^1$H-NMR (DMSO-d$_6$): 1.22-1.46 (m, 2H), 1.51-1.60 (m, 2H), 1.73-1.85 (m, 2H), 1.98-2.20 (m, 3H), 2.11 (s, 3H), 2.27-2.37 (m, 1H), 2.44-2.54 (m, 1H), 2.69-2.78 (m, 2H), 3.05-3.14 (m, 1H), 3.16-3.25 (m, 1H), 3.43-3.55 (m, 2H), 3.68 (s, 3H), 3.87 (s, 3H), 6.49 (s, 1H), 6.72 (d, 1.8 Hz, 2H), 6.79 (d, 7.7 Hz, 1H), 6.95 (dd, 8.2 Hz, 2.2 Hz, 1H), 7.15-7.23 (m, 3H), 7.31 (t, 8 Hz, 1H), 7.81 (d, 8.7 Hz, 1H), 7.99 (d, 9.0 Hz, 2H).
MS (API-ES, pos) m/z=668, 670 [M+H]$^+$

Example 20

5-Chloro-1-(4-methoxybenzenesulfonyl)-3-[1-(3-methoxyphenyl)-2-oxo-2-(4-pyridin-4-ylpiperazin-1-yl)ethyl]-1,3-dihydrobenzimidazol-2-one $^1$H-NMR (DMSO-d$_6$): 3.07-3.16 (m, 2H), 3.22-3.45 (m, 4H), 3.58-3.70 (m, 2H), 3.67 (s, 3H), 3.82 (s, 3H), 6.57 (s, 1H), 6.72-6.79 (m, 4H), 6.86 (d, 7.7 Hz, 1H), 6.94-6.98 (m, 1H), 7.17 (d, 9.0 Hz, 2H), 7.21 (dd, 8.7 Hz, 2.0 Hz, 1H), 7.31 (t, 8.0 Hz, 1H), 7.81 (d, 8.7 Hz, 1H), 7.98 (d, 9.0 Hz, 2H), 8.16 (d, 6.4 Hz, 2H).
MS (API-ES, pos) m/z=648, 650 [M+H]$^+$

Example 21

5-Chloro-1-(2,4-dimethoxybenzenesulfonyl)-3-[1-(3-methoxyphenyl)-2-oxo-2-(4-pyridin-4-ylpiperazin-1-yl)-ethyl]-1,3-dihydrobenzimidazol-2-one $^1$H-NMR (DMSO-d$_6$): 3.13-3.20 (m, 2H), 3.25-3.35 (m, 2H), 3.38-3.48 (m, 2H), 3.43 (s, 3H), 3.60-3.70 (m, 2H), 3.71 (s, 3H), 3.84 (s, 3H), 6.56 (s, 1H), 6.66 (m, 1H), 6.72-6.81 (m, 5H), 6.86 (d, 7.6 Hz, 1H), 6.98 (d, 7.7 Hz, 1H), 7.16-7.21 (m, 1H), 7.32-7.38 (m, 1H), 7.66 (d, 8.7 Hz, 1H), 7.93 (d, 8.9 Hz, 1H), 8.15 (d, 5.9 Hz, 2H).
MS (API-ES, pos) m/z=678, 680 [M+H]$^+$

Example 22

4-(5-Chloro-3-{1-(3-methoxyphenyl)-2-[4-(1-methylpiperidin-4-yl)piperazin-1-yl]-2-oxoethyl}-2-oxo-2,3-dihydrobenzimidazol-1-sulfonyl)benzonitrile ¹H-NMR (DMSO-d₆): 1.22-1.38 (m, 2H), 1.52-1.63 (m, 2H), 1.73-1.87 (m, 2H), 2.01-2.23 (m, 3H), 2.12 (s, 3H), 2.27-2.39 (m, 1H), 2.44-2.53 (m, 1H), 2.70-2.80 (m, 2H), 3.05-3.14 (m, 1H), 3.17-3.27 (m, 1H), 3.44-3.52 (m, 2H), 3.70 (s, 3H), 6.49 (s, 1H), 6.68-6.75 (m, 2H), 6.81 (d, 7.8 Hz, 1H), 6.94-6.99 (m, 1H), 7.23 (dd, 8.8 Hz, 2.0 Hz, 1H), 7.29-7.25 (m, 1H), 7.82 (d, 1H), 8.14-8.25 (m, 4H).
MS (API-ES, pos) m/z=663, 665 [M+H]⁺

Example 23

1-(4-Cyanobenzenesulfonyl)-3-{2-[4-(1-methylpiperidin-4-yl)piperazin-1-yl]-2-oxo-1-phenylethyl}-2-oxo-2,3-dihydro-1H-benzimidazole-5-carbonitrile ¹H-NMR (DMSO-d₆): 1.62-1.80 (m, 2H), 2.08-2.22 (m, 2H), 2.70-3.58 (m, 13H), 2.76 (s, 3H), 6.70 (s, 1H), 7.11 (s, 1H), 7.30-7.46 (m, 5H), 7.67 (d, 8.5 Hz, 1H), 7.99 (d, 8.5 Hz, 1H), 8.20 (d, 8.5 Hz, 2H), 8.27 (d, 8.5 Hz, 2H).
MS (API-ES, pos) m/z=624 [M+H]⁺

Example 24

5-Chloro-1-(4-methoxybenzenesulfonyl)-3-[2-oxo-2-(4-pyridin-4-ylpiperazin-1-yl)-ethyl]-1,3-dihydrobenzimidazol-2-one ¹H-NMR (DMSO-d₆): 3.32-3.39 (m, 2H), 3.44-3.49 (m, 2H), 3.49-3.57 (m, 2H), 3.59-3.67 (m, 2H), 3.85 (s, 3H), 4.81 (s. 2H), 6.84 (d, 6.4 Hz, 2H), 7.17 (d, 9.0 Hz, 2H), 7.23 (dd, 6.6 Hz, 2.0 Hz, 1H), 7.42 (d, 2.0 Hz, 1H), 7.79 (d, 8.6 Hz, 1H), 7.98 (d, 9.0 hz, 2H), 8.18 (d, 6.4 Hz, 2H).
MS (API-ES, pos) m/z=542, 544 [M+H]⁺

Example 25

5-Chloro-1-(2,4-dimethoxybenzenesulfonyl)-3-[2-oxo-2-(4-pyridin-4-ylpiperazin-1-yl)-ethyl]-1,3-dihydrobenzimidazol-2-one ¹H-NMR (DMSO-d₆): 3.50 (s, 3H), 3.56-3.64 (m, 2H), 3.68-3.77 (m, 4H), 3.81-3.87 (m, 2H), 3.86 (s, 3H), 4.82 (s, 2H), 6.68 (d, 2.0 Hz, 1H), 6.73 (dd, 9.0 Hz, 1.1 Hz, 1H), 7.20 (d, 7.1 Hz, 2H), 7.23 (dd, 8.6 Hz, 2.0 Hz, 1H), 7.41 (d, 1.8 Hz, 1H), 7.67 (d, 8.6 Hz, 1H), 7.91 (d, 8.8 Hz, 1H), 8.29 (d, 7.3 Hz, 2H).
MS (API-ES, pos) m/z=572, 574 [M+H]⁺

Example 26

4-{5-Chloro-2-oxo-3-[2-oxo-2-(4-pyridin-4-ylpiperazin-1-yl)ethyl]-2,3-dihydrobenzimidazole-1-sulfonyl}benzonitrile ¹H-NMR (DMSO-d₆): 3.56-3.62 (m, 2H), 3.68-3.76 (m, 4H), 3.80-3.87 (m, 2H), 4.84 (s, 2H), 7.19 (d, 7.1 Hz, 2H), 7.28 (d, 8.6 Hz, 1H), 7.46 (s, 1H), 7.81 (d, 8.6 Hz, 1H), 8.17 (d, 8.4 Hz, 2H), 8.21 (d, 8.6 Hz, 2H), 8.29 (d, 7.1 Hz, 2H).
MS (API-ES, pos) m/z=537, 539 [M+H]⁺

Example 27

3-[1-Benzyl-2-oxo-2-(4-pyridin-4-ylpiperazin-1-yl)ethyl]-5-chloro-1-(4-methoxybenzenesulfonyl)-1,3-dihydrobenzimidazol-2-one ¹H-NMR (DMSO-d₆): 3.62-3.75 (m, 10H), 3.82 (s, 3H), 5.52-5.62 (m, 1H), 6.81 (d, 7.0 Hz, 2H), 6.89-6.98 (m, 3H), 7.07-7.16 (m, 4H), 7.23 (d, 8.7 Hz, 1H), 7.35 (s, 1H), 7.75 (d, 8.7 Hz, 1H), 7.81 (d, 8.7 Hz, 2H), 8.27 (d, 7.0 Hz, 2H).
MS (API-ES, pos) m/z=632, 634 [M+H]⁺

Example 28

3-[1-Benzyl-2-oxo-2-(4-pyridin-4-ylpiperazin-1-yl)ethyl]-5-chloro-1-(2,4-dimethoxybenzenesulfonyl)-1,3-dihydrobenzimidazol-2-one ¹H-NMR (DMSO-d₆): 3.17-3.74 (m, 10H), 3.39 (s, 3H), 3.85 (s, 3H), 5.53-5.62 (m, 1H), 6.58 (d, 1.8 Hz, 1H), 6.68-6.72 (m, 1H), 6.88-6.95 (m, 2H), 6.97-7.04 (m, 3H), 7.13 (d, 7.3 Hz, 2H), 7.24 (dd, 8.7 Hz, 1.8 Hz, 1H), 7.41 (s, 1H), 7.66 (d, 8.7 Hz, 1H), 7.81 (d, 8.9 Hz, 1H), 8.27 (d, 7.3 Hz, 2H).
MS (API-ES, pos) m/z=662, 664 [M+H]⁺

Example 29

4-{3-[1-Benzyl-2-oxo-2-(4-pyridin-4-ylpiperazin-1-yl)ethyl]-5-chloro-2-oxo-2,3-dihydrobenzimidazol-1-sulfonyl}-benzonitrile ¹H-NMR (DMSO-d₆): 3.13-3.75 (m, 10H), 5.57-5.62 (m, 1H), 6.80 (d, 6.6 Hz, 2H), 6.87-6.96 (m, 3H), 7.12 (d, 7.2 Hz, 2H), 7.28 (d, 8.7 Hz, 1H), 7.45 (d, 1.3 Hz, 1H), 7.78 (d, 8.7 Hz, 1H), 8.03 (d, 8.3 Hz, 2H), 8.13 (d, 8.3 Hz, 2H), 8.26 (d, 7.1 Hz, 2H).
MS (API-ES, pos) m/z=627, 629 [M+H]⁺

Example 30

5-Chloro-1-(4-methoxybenzenesulfonyl)-3-[1-methyl-2-oxo-2-(4-pyridin-4-ylpiperazin-1-yl)-ethyl]-1,3-dihydrobenzimidazol-2-one ¹H-NMR (DMSO-d₆): 1.43 (d, 6.9 Hz, 3H), 3.08-3.23 (m, 2H), 3.34-3.75 (m, 6H), 3.75 (s, 3H), 5.40-5.48 (m, 1H), 7.05-7.16 (m, 4H), 7.29 (dd, 8.9 Hz, 1.9 Hz, 1H), 7.39 (d, 1.8 Hz, 1H), 7.84 (d, 8.7 Hz, 1H), 7.96 (d, 8.9 Hz, 2H), 8.27 (d, 7.3 Hz, 2H).
MS (API-ES, pos) m/z=556, 558 [M+H]⁺

Example 31

5-Chloro-1-(2,4-dimethoxybenzenesulfonyl)-3-[1-methyl-2-oxo-2-(4-pyridin-4-ylpiperazin-1-yl)ethyl]-1,3-dihydrobenzimidazol-2-one ¹H-NMR (DMSO-d₆): 1.44 (d, 6.9 Hz, 3H), 3.25-3.76 (m, 8H), 3.46 (s, 3H), 3.81 (s, 3H), 5.44 (q, 7.0 Hz, 1H), 6.58 (d, 1.5 Hz, 1H), 6.75 (dd, 9.0 Hz, 1.7 Hz, 1H), 7.12 (d, 7.2 Hz, 2H), 7.28 (d, 8.7 Hz, 1H), 7.40 (d, 1.3 Hz, 1H), 7.69 (d, 8.7 Hz, 1H), 7.92 (d, 8.9 Hz, 1H), 8.27 (d, 7.1 Hz, 2H).
MS (API-ES, pos) m/z=586, 588 [M+H]⁺

Example 32

4-{5-Chloro-3-[1-methyl-2-oxo-2-(4-pyridin-4-ylpiperazin-1-yl)ethyl]-2-oxo-2,3-dihydrobenzimidazole-1-sulfonyl}benzonitrile $^1$H-NMR (DMSO-d$_6$): 1.46 (d, 6.9 Hz, 3H), 3.19-3.74 (m, 8H), 5.46 (q, 7.0 Hz, 1H), 7.12 (d, 7.1 Hz, 2H), 7.31 (d, 8.7 Hz, 1H), 7.43 (s, 1H), 7.84 (d, 8.7 Hz, 1H), 8.13 (d, 8.2 Hz, 2H), 8.21 (d, 8.4 Hz, 2H), 8.27 (d, 7.1 Hz, 2H).
MS (API-ES, pos) m/z=551, 553 [M+H]$^+$

Example 33

5-Chloro-1-(4-methoxybenzenesulfonyl)-3-[1-(4-methoxyphenyl)-2-oxo-2-(4-pyridin-4-ylpiperazin-1-yl)-ethyl]-1,3-dihydrobenzimidazol-2-one $^1$H-NMR (DMSO-d$_6$): 3.24-3.35 (m, 1H), 3.47-3.58 (m, 3H), 3.66-3.74 (m, 3H), 3.75 (s, 3H), 3.78-3.87 (m, 1H), 3.84 (s, 3H), 6.57 (s, 1H), 6.75 (d, 1.8 Hz, 1H), 6.93 (d, 8.7 Hz, 2H), 7.09-7.26 (m, 7H), 7.81 (d, 8.7 Hz, 1H), 7.98 (d, 8.9 Hz, 2H), 8.27 (d, 7.3 Hz, 2H).
MS (API-ES, pos) m/z=648, 650 [M+H]$^+$

Example 34

4-{5-Chloro-3-[1-(4-methoxyphenyl)-2-oxo-2-(4-pyridin-4-ylpiperazin-1-yl)-ethyl]-2-oxo-2,3-dihydrobenzimidazole-1-sulfonyl}-benzonitrile $^1$H-NMR (DMSO-d$_6$): 3.24-3.35 (m, 1H), 3.45-3.60 (m, 3H), 3.66-3.86 (m, 4H), 3.76 (s, 3H), 6.58 (s, 1H), 6.79 (s, 1H), 6.94 (d, 8.5 Hz, 2H), 7.10-7.18 (m, 2H), 7.21-7.27 (m, 3H), 7.81 (d, 8.7 Hz, 1H), 8.15-8.29 (m, 6H).
MS (API-ES, pos) m/z=618, 620 [M+H]$^+$

Example 35

5,6-Dichloro-1-{2-[4-(1-methylpiperidin-4-yl)piperazin-1-yl]-2-oxo-1-phenylethyl}-3-(quinoline-8-sulfonyl)-1,3-dihydrobenzimidazol-2-one $^1$H-NMR (Methanol-d4): 1.41-1.55 (m, 2H), 1.73-1.82 (m, 2H), 1.98-2.08 (m, 2H), 2.15-2.36 (m, 3H), 2.26 (s, 3H), 2.42-2.49 (m, 1H), 2.56-2.66 (m, 1H), 2.86-2.95 (m, 2H), 3.14-3.24 (m, 1H), 3.52-3.67 (m, 2H), 6.43 (s, 1H), 6.71 (s, 1H), 7.01 (d, 7.3 Hz, 2H), 7.28-7.40 (m, 3H), 7.52-7.57 (m, 1H), 7.83 (t, 7.8 Hz, 1H), 8.13 (s, 1H), 8.34 (d, 8.2 Hz, 1H), 8.44 (m, 2H), 8.72 (d, 7.4 Hz, 1H).
MS (API-ES, pos) m/z=693, 694, 695, 696 [M+H]$^+$

Example 36

5,6-Dichloro-1-(4-methoxybenzenesulfonyl)-3-{2-[4-(1-methylpiperidin-4-yl)piperazin-1-yl]-2-oxo-1-phenylethyl}-1,3-dihydrobenzimidazol-2-one $^1$H-NMR (methanol-d4): 1.77-1.97 (m, 2H), 2.18-2.33 (m, 2H), 2.78-3.15 (m, 7H), 2.89 (s, 3H), 3.36-3.47 (m, 1H), 3.56-3.77 (m, 4H), 3.92-4.05 (m, 1H), 3.93 (s, 3H), 6.62 (d, 8.2 Hz, 2H), 7.16 (d, 9.0 Hz, 2H), 7.24-7.31 (m, 2H), 7.42-7.48 (m, 3H), 8.03 (s, 1H), 8.06 (d, 9.0 Hz, 2H).
MS (API-ES, pos) m/z=672, 673, 674, 675 [M+H]$^+$

Example 37

5-Chloro-3-(2,4-dimethoxybenzenesulfonyl)-1-{2-[4-(1-methylpiperidin-4-yl)piperazin-1-yl]-2-oxo-1-phenylethyl}-1,3-dihydrobenzimidazol-2-one $^1$H-NMR (Methanol-d4): 1.80-1.98 (m, 2H), 2.18-2.35 (m, 2H), 2.88 (s, 3H), 2.88-3.23 (m, 6H), 3.37-3.51 (m, 2H), 3.47 (s, 3H), 3.56-3.75 (m, 4H), 3.90 (s, 3H), 3.99-4.12 (m, 1H), 6.53-6.64 (m, 3H), 6.73 (dd, 8.7 Hz, 2.0 Hz, 1H), 6.97 (dd, 8.7 Hz, 2.0 Hz, 1H), 7.24-7.29 (m, 2H), 7.40-7.46 (m, 3H), 7.78-7.80 (m, 1H), 8.17 (d, 8.9 Hz, 1H).
MS (API-ES, pos) m/z=668, 670 [M+H]$^+$

Example 38

5-Chloro-3-(4-methoxybenzenesulfonyl)-1-{2-[4-(1-methylpiperidin-4-yl)piperazin-1-yl]-2-oxo-1-phenylethyl}-1,3-dihydrobenzimidazol-2-one $^1$H-NMR (methanol-d4): 1.47-1.60 (m, 2H), 1.78-1.87 (m, 2H), 2.18-2.39 (m, 8H), 2.43-2.54 (m, 1H), 2.60-2.68 (m, 1H), 2.99-3.06 (m, 2H), 3.21-3.29 (m, 1H), 3.37-3.45 (m, 1H), 3.54-3.64 (m, 1H), 3.68-3.76 (m, 1H), 3.90 (s, 3H), 6.56-6.59 (m, 2H), 6.97 (dd, 8.7 Hz, 2.0 Hz, 1H), 7.13 (d, 9.0 Hz, 2H), 7.20-7.24 (m, 2H), 7.36-7.39 (m, 3H), 7.89-7.91 (m, 1H), 8.04 (d, 9.0 Hz, 2H).
MS (API-ES, pos) m/z=638, 640 [M+H]$^+$

Example 39

4-(6-Chloro-3-{2-[4-(1-methylpiperidin-4-yl)piperazin-1-yl]-2-oxo-1-phenylethyl}-2-oxo-2,3-dihydrobenzimidazole-1-sulfonyl)benzonitrile $^1$H-NMR (DMSO-d$_6$): 1.24-1.39 (m, 2H), 1.53-1.65 (m, 2H), 1.79-2.35 (m, 9H), 2.43-2.51 (m, 1H), 2.74-2.38 (m, 2H), 3.02-3.14 (m, 1H), 3.16-3.26 (m, 1H), 3.40-3.56 (m, 2H), 6.55 (s, 1H), 6.65 (d, 8.7 Hz, 1H), 7.17 (dd, 8.7 Hz, 2 Hz, 1H), 7.19 (m, 2H), 7.34-7.41 (m, 3H), 7.83 (d, 1.9 Hz, 1H), 8.19 (d, 8.5 Hz, 2H), 8.31 (d, 8.7 Hz, 2H).
MS (API-ES, pos) m/z=633, 635 [M+H]$^+$

Example 40

5,6-Dichloro-1-[2-oxo-1-phenyl-2-(4-pyridin-4-ylpiperazin-1-yl)ethyl]-3-(quinoline-8-sulfonyl)-1,3-dihydrobenzimidazol-2-one $^1$H-NMR (Methanol-d4): 3.02-3.11 (m, 1H), 3.16-3.38 (m, 3H), 3.40-3.55 (m, 2H), 3.67-3.83 (m, 2H), 6.51 (s, 1H), 6.73-6.79 (m, 3H), 7.10 (d, 7.4 Hz, 2H), 7.31-7.44 (m, 3H), 7.50-7.56 (m, 1H), 7.85 (t, 7.8 Hz, 1H), 8.10-8.18 (m, 3H), 8.32 (d, 8.0 Hz, 1H), 8.37 (dd, 8.3 Hz, 1.3 Hz, 1H), 8.43-8.47 (m, 1H), 8.74 (d, 7.5 Hz, 1H).
MS (API-ES, pos) m/z=673, 674, 675, 676 [M+H]$^+$

Example 41

1-(4-Methoxybenzenesulfonyl)-3-[2-oxo-1-phenyl-2-(4-pyridin-4-ylpiperazin-1-yl)ethyl]-1,3-dihydrobenzimidazol-2-one $^1$H-NMR (DMSO-d$_6$): 2.97-3.06 (m, 1H), 3.08-3.17 (m, 1H), 3.22-3.48 (m, 4H), 3.61-3.69 (m, 2H), 3.81 (s, 3H), 6.61

(s, 1H), 6.69-6.69 (m, 3H), 7.01-7.07 (m, 1H), 7.09-7.20 (m, 3H), 7.21-7.28 (m, 2H), 7.32-7.39 (m, 3H), 7.82 (d, 8.1 Hz, 1H), 7.99 (d, 9.0 Hz, 2H), 8.16 (d, 6.4 Hz, 2H).
MS (API-ES, pos) m/z=584 [M+H]$^+$

Example 42

5-Chloro-3-[2-oxo-1-phenyl-2-(4-pyridin-4-ylpiperazin-1-yl)ethyl]-1-(4-trifluoromethoxybenzenesulfonyl)-1,3-dihydrobenzimidazol-2-one $^1$H-NMR (Methanol-d4): 3.34-3.45 (m, 1H), 3.48-3.85 (m, 7H), 6.44 (d, 1.9 Hz, 1H), 6.54 (s, 1H), 6.97-7.06 (m, 3H), 7.17-7.24 (m, 2H), 7.28-7.37 (m, 3H), 7.43 (d, 8.5 Hz, 2H), 7.77 (d, 8.7 Hz, 1H), 8.05 (d, 7.4 Hz, 2H), 8.11 (d, 8.9 Hz, 2H).
MS (API-ES, pos) m/z=672, 674 [M+H]$^+$

Example 43

5-Chloro-1-(2-methoxy-4-methyl-benzenesulfonyl)-3-[2-oxo-1-phenyl-2-(4-pyridin-4-ylpiperazin-1-yl)ethyl]-1,3-dihydrobenzimidazol-2-one $^1$H-NMR (methanol-d4): 2.40 (s, 3H), 3.46 (s, 3H), 3.46-3.90 (m, 8H), 6.63 (s, 2H), 6.94-7.01 (m, 4H), 7.10 (dd, 8.7 Hz, 2.0 Hz, 1H), 7.30-7.34 (m, 2H), 7.43-7.47 (m, 3H), 7.73 (d, 8.8 Hz, 1H), 7.96 (d, 8.1 Hz, 1H), 8.14 (d, 6.7 Hz, 2H).
MS (API-ES, pos) m/z=632, 634 [M+H]$^+$

Example 44

5-Chloro-3-[2-oxo-1-phenyl-2-(4-pyridin-4-ylpiperazin-1-yl)ethyl]-1-(thiophene-2-sulfonyl)-1,3-dihydrobenzimidazol-2-one $^1$H-NMR (Methanol-d4): 3.35-3.43 (m, 2H), 3.47-3.58 (m, 2H), 3.60-3.74 (m, 2H), 3.84-3.98 (m, 2H), 6.70 (s, 1H), 6.77 (s, 1H), 6.90 (d, 6.55 Hz, 2H), 7.21 (dd, 8.7 Hz, 1.9 Hz, 1H), 7.26-7.33 (m, 1H), 7.35-7.43 (m, 2H), 7.47-7.56 (m, 3H), 7.90 (d, 8.7 Hz, 1H), 8.03-8.08 (m, 2H), 8.22 (d, 6.5 Hz, 2H).
MS (API-ES, pos) m/z=594, 596 [M+H]$^+$

Example 45

5-Chloro-1-(2-methoxybenzenesulfonyl)-3-[2-oxo-1-phenyl-2-(4-pyridin-4-ylpiperazin-1-yl)ethyl]-1,3-dihydrobenzimidazol-2-one $^1$H-NMR (methanol-d4): 3.28-3.35 (m, 2H), 3.38-3.53 (m, 2H), 3.51 (s, 3H), 3.55-3.70 (m, 2H), 3.78-3.93 (m, 2H), 6.64-6.71 (m, 2H), 6.81-6.87 (m, 2H), 7.12-7.23 (m, 3H), 7.32-7.49 (m, 2H), 7.45-7.52 (m, 3H), 7.66-7.72 (m, 1H), 7.78 (d, 8.7 Hz, 1H), 8.12-8.22 (m, 3H).
MS (API-ES, pos) m/z=618, 620 [M+H]$^+$

Example 46

1-(4-Methoxybenzenesulfonyl)-2-oxo-3-[2-oxo-1-phenyl-2-(4-pyridin-4-ylpiperazin-1-yl)ethyl]-2,3-dihydro-1H-benzimidazole-5-carbonitrile $^1$H-NMR (Methanol-d4): 3.46-3.56 (m, 1H), 3.61-3.72 (m, 2H), 3.73-3.98 (m, 5H), 3.89 (s, 3H), 6.69 (s, 1H), 6.82 (s, 1H), 7.08-7.16 (m, 4H), 7.31-7.37 (m, 2H), 7.41-7.52 (m, 4H), 8.03-8.09 (m, 3H), 8.16 (d, 7.4 Hz, 2H).
MS (API-ES, pos) m/z=609 [M+H]$^+$

Example 47

1-Benzenesulfonyl-5-chloro-3-[2-oxo-1-phenyl-2-(4-pyridin-4-ylpiperazin-1-yl)ethyl]-1,3-dihydrobenzimidazol-2-one $^1$H-NMR (Methanol-d4): 3.19-3.28 (m, 2H), 3.35-3.48 (m, 2H), 3.50-3.61 (m, 2H), 3.73-3.87 (m, 2H), 6.59 (d, 1.9 Hz, 1H), 6.64 (s, 1H), 6.76-6.84 (m, 2H), 7.12 (dd, 8.7 Hz, 2.0 Hz, 1H), 7.24-7.31 (m, 2H), 7.38-7.45 (m, 3H), 7.56-7.64 (m, 2H), 7.68-7.75 (m, 1H), 7.88 (d, 8.8 Hz, 1H), 8.08 (d, 7.6 Hz, 2H), 8.09-8.18 (m, 2H).
MS (API-ES, pos) m/z=588, 590 [M+H]$^+$

Example 48

1-(2,4-Dimethoxybenzenesulfonyl)-2-oxo-3-[2-oxo-1-phenyl-2-(4-pyridin-4-ylpiperazin-1-yl)-ethyl]-2,3-dihydro-1H-benzimidazole-5-carbonitrile $^1$H-NMR (DMSO-d$_6$): 3.09-3.23 (m, 2H), 3.25-3.36 (m, 2H), 3.39-3.52 (m, 2H), 3.41 (s, 3H), 3.59-3.76 (m, 2H), 3.85 (s, 3H), 6.66 (s, 1H), 6.68 (d, 2.1 Hz, 1H), 6.73-6.82 (m, 3H), 7.07 (s, 1H), 7.27-7.35 (m, 2H), 7.38-7.45 (m, 3H), 7.60-7.64 (m, 1H), 7.84 (d, 8.5 Hz, 1H), 7.94 (d, 8.9 Hz, 1H), 8.15 (d, 6.0 Hz, 2H).
MS (API-ES, pos) m/z=639 [M+H]$^+$

Example 49

5-Chloro-3-[2-oxo-1-phenyl-2-(4-pyridin-4-ylpiperazin-1-yl)ethyl]-1-(4-trifluoromethylbenzenesulfonyl)-1,3-dihydrobenzimidazol-2-one $^1$H-NMR (methanol-d4): 3.18-3.31 (m, 2H), 3.33-3.44 (m, 2H), 3.45-3.60 (m, 2H), 3.72-3.78 (m, 2H), 6.49 (d, 1.9 Hz, 1H), 6.59 (s, 1H), 6.75 (d, 6.2 Hz, 2H), 7.08 (dd, 8.7 Hz, 2.0 Hz, 1H), 7.22-7.28 (m, 2H), 7.34-7.42 (m, 3H), 7.83 (d, 8.8 Hz, 1H), 7.90 (d, 8.4 Hz, 2H), 8.07 (d, 5.8 Hz, 2H), 8.22 (d, 8.4 Hz, 2H).
MS (API-ES, pos) m/z=656, 658 [M+H]$^+$

Example 50

2-Oxo-3-[2-oxo-1-phenyl-2-(4-pyridin-4-ylpiperazin-1-yl)ethyl]-1-(quinoline-8-sulfonyl)-2,3-dihydro-1H-benzimidazole-5-carbonitrile $^1$H-NMR (DMSO-d$_6$): 2.96-3.10 (m, 2H), 3.16-3.25 (m, 2H), 3.26-3.42 (m, 2H), 3.52-3.66 (m, 2H), 6.53 (s, 1H), 6.68-6.77 (m, 2H), 7.02 (d, 7.4 Hz, 2H), 7.07 (s, 1H), 7.24-7.37 (m, 3H), 7.55-7.62 (m, 1H), 7.69 (dd, 8.5 Hz, 1.3 Hz, 1H), 7.85-7.93 (m, 1H), 8.08 (d, 8.5 Hz, 1H), 8.10-8.21 (m, 2H), 8.34-8.39 (m, 1H), 8.44 (d, 8.2 Hz, 1H), 8.49 (dd, 8.4 Hz, 1.3 Hz, 1H), 8.68 (d, 7.4 Hz, 1H).
MS (API-ES, pos) m/z=630 [M+H]$^+$

Example 51

1-(4-Cyanobenzenesulfonyl)-2-oxo-3-[2-oxo-1-phenyl-2-(4-pyridin-4-yl piperazin-1-yl)ethyl]-2,3-dihydro-1H-benzimidazole-5-carbonitrile $^1$H-NMR (methanol-d4): 7.44-3.54 (m, 1H), 3.58-3.94 (m, 7H), 6.69 (s, 1H), 6.81 (s, 1H), 7.13 (d, 8.1 Hz, 2H), 7.34-7.42

(m, 2H), 7.44-7.55 (m, 4H), 8.02 (d, 8.5 Hz, 2H), 8.07 (d, 8.5 Hz, 1H), 8.16 (d, 7.4 Hz, 2H), 8.29 (d, 8.5 Hz, 2H).
MS (API-ES, pos) m/z=604 [M+H]$^+$

Example 52

1-(4-Methoxybenzenesulfonyl)-2-oxo-3-{2-oxo-1-phenyl-2-[3-(4-propylpiperazin-1-yl)-pyrrolidin-1-yl]-ethyl}-2,3-dihydro-1H-benzimidazole-5-carbonitrile $^1$H-NMR (DMSO-d$_6$): 0.76-0.88 (m, 3H), 1.29-1.45 (m, 2H), 1.46-1.70 (m, 1H), 1.84-2.05 (m, 1H), 2.08-3.74 (m, 15H), 3.86 (s, 3H), 6.30-6.44 (m, 1H), 6.95-7.30 (m, 5H), 7.32-7.44 (m, 3H), 7.58-7.75 (m, 1H), 7.93-8.06 (m, 3H).
MS (API-ES, pos) m/z=643 [M+H]$^+$

Example 53

5-Chloro-3-[2-oxo-1-phenyl-2-(4-pyridin-4-ylpiperazin-1-yl)ethyl]-1-(quinoline-8-sulfonyl)-1,3-dihydrobenzimidazol-2-one $^1$H-NMR (DMSO-d$_6$): 3.35-3.71 (m, 7H), 3.74-3.83 (m, 1H), 6.53 (s, 1H), 6.73 (d, 1.9 Hz, 1H), 6.99 (d, 7.4 Hz, 2H), 7.10 (d, 7.2 Hz, 2H), 7.22-7.37 (m, 4H), 7.58-7.65 (m, 1H), 7.85-7.93 (m, 2H), 8.26 (d, 7.2 Hz, 2H), 8.41-8.47 (m, 2H), 8.52 (dd, 8.4 Hz, 1.3 Hz, 1H), 8.67 (d, 7.5 Hz, 1H).
MS (API-ES, pos) m/z=639, 641 [M+H]$^+$

Example 54

5-Chloro-1-(2,4-dimethoxybenzenesulfonyl)-3-{2-[4-(1-methylpiperidin-4-yl)piperazin-1-yl]-2-oxo-1-phenylethyl}-1,3-dihydrobenzimidazol-2-one $^1$H-NMR (DMSO-d$_6$): 1.25-1.39 (m, 2H), 1.55-1.64 (m, 2H), 1.73-1.82 (m, 2H), 2.02-2.12 (m, 1H), 2.10 (s, 3H), 2.17-2.29 (m, 2H), 2.33-2.42 (m, 1H), 2.69-2.78 (m, 2H), 3.07-3.17 (m, 1H), 3.46 (s, 3H), 3.48-3.56 (m, 2H), 3.88 (s, 3H), 6.53 (s, 1H), 6.62 (d, 1.9 Hz, 1H), 6.70 (d, 2.1 Hz, 1H), 6.76 (dd, 8.9 Hz, 2.0 Hz, 1H), 7.16 (dd, 8.7 Hz, 2.0 Hz, 1H), 7.18-7.24 (m, 2H), 7.37-7.44 (m, 3H), 7.65 (d, 8.7 Hz, 1H), 7.93 (d, 8.9 Hz, 1H).
MS (API-ES, pos) m/z=668, 670 [M+H]$^+$

Example 55

5-Chloro-1-(4-methoxybenzenesulfonyl)-3-{2-[4-(1-methylpiperidin-4-yl)piperazin-1-yl]-2-oxo-1-phenylethyl}-1,3-dihydrobenzimidazol-2-one $^1$H-NMR (DMSO-d$_6$): 1.60-1.77 (m, 2H), 2.06-2.18 (m, 2H), 2.76 (s, 3H), 2.86-2.98 (m, 2H), 3.88 (s, 3H), 6.65 (s, 1H), 6.67 (s, 1H), 7.16-7.27 (m, 5H), 7.35-7.43 (m, 3H), 7.81 (d, 8.7 Hz, 1H), 7.98 (d, 9.0 Hz, 2H).
MS (API-ES, pos) m/z=638, 640 [M+H]$^+$

Example 56

5-Chloro-1-(2,4-dimethoxybenzenesulfonyl)-3-[2-oxo-1-phenyl-2-(4-pyridin-4-ylpiperazin-1-yl)-ethyl]-1,3-dihydrobenzimidazol-2-one $^1$H-NMR (DMSO-d$_6$): 3.44 (s, 3H), 3.51-3.87 (m, 8H), 3.85 (s, 3H), 6.64-6.73 (m, 3H) 6.76 (dd, 8.9 Hz, 2.1 Hz, 1H), 7.09-7.15 (m, 2H), 7.19 (dd, 8.7 Hz, 2.0 Hz, 1H), 7.22-7.28 (m, 2H), 7.37-7.45 (m 3H), 7.66 (d, 8.7 Hz, 1H), 7.93 (d, 9.0 Hz, 1H), 8.26 (d, 7.2 Hz, 2H).
MS (API-ES, pos) m/z=648, 650 [M+H]$^+$

Example 57

4-{5-Chloro-2-oxo-3-[2-oxo-1-phenyl-2-(4-pyridin-4-ylpiperazin-1-yl)-ethyl]-2,3-dihydrobenzimidazole-1-sulfonyl}-benzonitrile $^1$H-NMR (DMSO-d$_6$): 3.50-3.88 (m, 8H), 6.67 (s, 1H), 6.75 (d, 1.8 Hz, 1H), 7.11-7.16 (m, 2H), 7.24 (dd, 8.7 Hz, 2.0 Hz, 1H), 7.27-7.34 (m, 2H), 7.37-7.45 (m, 3H), 7.82 (d, 8.7 Hz, 1H), 8.14-8.28 (m, 6H).
MS (API-ES, pos) m/z=613, 615 [M+H]$^+$

Example 58

5-Chloro-1-(4-methoxybenzenesulfonyl)-3-[2-oxo-1-phenyl-2-(4-pyridin-4-ylpiperazin-1-yl)ethyl]-1,3-dihydrobenzimidazol-2-one $^1$H-NMR (DMSO-d$_6$): 3.18-3.24 (m, 2H), 3.32-3.47 (m, 3H), 3.48-3.56 (m, 1H), 3.61-3.73 (m, 2H), 3.83 (s, 3H), 6.64 (s, 1H), 6.70 (d, 1.9 Hz, 1H), 6.82-6.88 (m, 2H), 7.14-7.22 (m, 3H), 7.23-7.30 (m, 2H), 7.36-7.42 (m, 3H), 7.81 (d, 8.6 Hz, 1H), 7.98 (d, 9.0 Hz, 2H), 8.18 (d, 6.5 Hz, 2H).
MS (API-ES, pos) m/z=618, 620 [M+H]$^+$

Example 59

5,6-Dichloro-1-(2,4-dimethoxybenzenesulfonyl)-3-[2-oxo-1-phenyl-2-(4-pyridin-4-ylpiperazin-1-yl)ethyl]-1,3-dihydrobenzoimidaz $^1$H-NMR (DMSO-d$_6$): 3.32-3.40 (m, 3H), 3.46-3.56 (m, 2H), 3.47 (s, 3H), 3.58-3.73 (m, 3H), 3.86 (s, 3H), 6.65 (s, 1H), 6.70 (d, 2.0 Hz, 1H), 6.77 (dd, 8.9 Hz, 2.1 Hz, 1H), 6.85 (s, 1H), 6.95 (d, 6.8 Hz, 2H), 7.25-7.32 (m, 2H), 7.39-7.47 (m, 3H), 7.81 (s, 1H), 7.94 (d, 8.9 Hz, 1H), 8.21 (d, 6.8 Hz, 2H).
MS (API-ES, pos) m/z=682, 684 [M+H]$^+$

Example 60

1-(4-Methoxybenzenesulfonyl)-3-{2-[4-(1-methylpiperidin-4-yl)piperazin-1-yl]-2-oxo-1-phenyl-ethyl}-1,3-dihydrobenzimidazol-2-one $^1$H-NMR (DMSO-d$_6$): 1.17-1.22 (m, 2H), 1.46-1.55 (m, 2H), 1.71-1.82 (m, 2H), 1.87-2.04 (m, 2H), 2.06-2.13 (m, 1H), 2.10 (s, 3H), 2.18-2.28 (m, 1H), 2.41-2.47 (m, 1H), 2.68-2.76 (m, 2H), 3.02-3.19 (m, 2H), 3.34-3.45 (m, 1H), 3.48-3.56 (m, 1H), 3.87 (s, 3H), 6.52 (s, 1H), 6.71 (d, 7.9 Hz, 1H), 7.03-7.08 (m, 1H), 7.10-7.22 (m, 5H), 7.31-7.38 (m, 3H), 7.83 (d, 7.9 Hz, 1H), 7.99 (d, 9.0 Hz, 2H).
MS (API-ES, pos) m/z=604 [M+H]$^+$

Example 61

5,6-Dichloro-1-[2-oxo-1-phenyl-2-(4-pyridin-4-ylpiperazin-1-yl)-ethyl]-3-(quinoline-8-sulfonyl)-1,3-dihydrobenzimidazol-2-one MS (API-ES, pos) m/z=673, 675 [M+H]$^+$

Example 62

4-{5,6-Dichloro-2-oxo-3-[2-oxo-1-phenyl-2-(4-pyridin-4-ylpiperazin-1-yl)-ethyl]-2,3-dihydrobenzimidazol-1-sulfonyl}benzonitrile $^1$H-NMR (DMSO-d$_6$): 3.49-3.91 (m, 8H), 6.67 (s, 1H), 6.90 (s, 1H), 7.13 (d, 7.1 Hz, 2H), 7.28-7.34 (m, 2H), 7.38-7.44 (m, 3H), 7.98 (s, 1H), 8.18 (d, 8.5 Hz, 2H), 8.26 (d, 7.3 Hz, 2H), 8.30 (d, 8.6 Hz, 2H).
MS (API-ES, pos) m/z=647, 649 [M+H]$^+$

Example 63

5-Chloro-1-(2,4-dimethoxybenzenesulfonyl)-3-{2-[4-(4-methylpiperazin-1-yl)piperidin-1-yl]-2-oxo-1-phenylethyl}-1,3-dihydrobenzimidazol-2-one $^1$H-NMR (DMSO-d$_6$): 0.90-1.90 (m, 4H), 2.63-3.50 (m, 12H), 2.75 (s, 3H), 3.45 (s, 3H), 3.88 (s, 3H), 4.38-4.47 (m, 1H), 6.52-6.65 (m, 2H), 6.68-6.78 (m, 2H), 7.12-7.18 (m, 2H), 7.25-7.32 (m, 1H), 7.36-7.47 (m, 3H), 7.65 (d, 8.6 Hz, 1H), 7.93 (dd, 8.8 Hz, 2.0 Hz, 1H).
MS (API-ES, pos) m/z=668, 670 [M+H]$^+$

Example 64

5-Chloro-1-(4-methoxybenzenesulfonyl)-3-{2-[4-(4-methylpiperazin-1-yl)piperidin-1-yl]-2-oxo-1-phenylethyl}-1,3-dihydrobenzimidazol-2-one $^1$H-NMR (Methanol-d4): 1.07-2.00 (m, 4H), 2.64-3.31 (m, 16H), 3.69-3.82 (m, 1H), 3.88-3.91 (m, 3H), 6.50-6.62 (m, 2H), 7.08-7.19 (m, 4H), 7.28-7.45 (m, 4H), 7.84-7.89 (m, 1H), 7.98-8.05 (m, 2H).
MS (API-ES, pos) m/z=638, 640 [M+H]$^+$

Example 65

4-(5-Chloro-3-{2-[4-(4-methylpiperazin-1-yl)piperidin-1-yl]-2-oxo-1-phenylethyl}-2-oxo-2,3-dihydrobenzimidazole-1-sulfonyl)benzonitrile $^1$H-NMR (Methanol-d4): 1.06-2.00 (m, 4H), 2.64-3.31 (m, 16H), 3.68-3.81 (m, 1H), 6.43-6.62 (m, 2H), 7.11-7.16 (m, 1H), 7.21-7.25 (m, 1H), 7.32-7.48 (m, 4H), 7.85-7.89 (m, 1H), 7.98-8.05 (m, 2H), 8.22-8.27 (m, 2H).
MS (API-ES, pos) m/z=633, 635 [M+H]$^+$

Example 66

5-Chloro-3-(2,4-dimethoxybenzenesulfonyl)-1-[2-oxo-1-phenyl-2-(4-pyridin-4-ylpiperazin-1-yl)ethyl]-1,3-dihydrobenzimidazol-2-one $^1$H-NMR (Methanol-d4): 3.46 (s, 3H), 3.47-3.77 (m, 5H), 3.78-3.97 (m, 3H), 3.88 (s, 3H), 6.58-6.63 (m, 3H), 6.72 (dd, 8.9 Hz, 2.1 Hz, 1H), 6.97 (dd, 8.7 Hz, 2.1 Hz, 1H), 7.08 (d, 7.4 Hz, 2H), 7.29-7.34 (m, 2H), 7.41-7.46 (m, 3H), 7.79 (d, 2 Hz, 1H), 8.03 (d, 9.0 Hz, 1H), 8.15 (d, 7.4 Hz, 2H).
MS (API-ES, pos) m/z=648, 650 [M+H]$^+$

Example 67

1-(2,4-Dimethoxybenzenesulfonyl)-3-{2-[4-(1-methylpiperidin-4-yl)piperazin-1-yl]-2-oxo-1-phenylethyl}-1,3-dihydrobenzimidazol-2-one $^1$H-NMR (DMSO-d$_6$): 1.24-1.37 (m, 2H), 1.54-1.62 (m, 2H), 1.74-1.83 (m, 2H), 2.02-2.19 (m, 2H), 2.11 (s, 3H), 2.21-2.28 (m, 1H), 2.30-2.38 (m, 1H), 2.69-2.77 (m, 2H), 3.08-3.17 (m, 1H), 3.18-3.25 (m, 1H), 3.42 (s, 3H), 3.47-3.53 (m, 2H), 3.87 (s, 3H), 6.51 (s, 1H), 6.64-6.69 (m, 2H), 6.75 (dd, 8.9 Hz, 2.1 Hz, 1H), 6.97-7.03 (m, 1H), 7.07-7.12 (m, 1H), 7.17-7.21 (m, 2H), 7.34-7.71 (m, 3H), 7.67 (d, 8.0 Hz, 1H), 7.94 (d, 8.9 Hz, 1H).
MS (API-ES, pos) m/z=634 [M+H]$^+$

Example 68

4-(5-Chloro-3-{2-[4-(1-methylpiperidin-4-yl)piperazin-1-yl]-2-oxo-1-phenylethyl}-2-oxo-2,3-dihydrobenzimidazol-1-sulfonyl)benzonitrile MS (API-ES, pos) m/z=633, 635 [M+H]$^+$

Example 69

5,6-Dichloro-1-(2,4-dimethoxybenzenesulfonyl)-3-{2-[4-(1-methylpiperidin-4-yl)piperazin-1-yl]-2-oxo-1-phenyl-ethyl}-1,3-dihydrobenzimidazol-2-one $^1$H-NMR (methanol-d4): 1.76-1.94 (m, 2H), 2.18-2.32 (m, 2H), 2.78-3.15 (m, 7H), 2.88 (s, 3H), 3.34-3.43 (m, 1H), 3.51 (s, 3H), 3.55-3.74 (m, 4H), 3.91 (s, 3H), 3.94-4.06 (m, 1H), 6.57-6.65 (m, 3H), 6.74 (dd, 9.0 Hz, 2.1 Hz, 1H), 7.26-7.33 (m, 2H), 7.43-7.51 (m, 3H), 7.91 (s, 1H), 8.03 (d, 9.0 Hz, 1H).
MS (API-ES, pos) m/z=702, 704 [M+H]$^+$

Example 70

1-(2,4-Dimethoxybenzenesulfonyl)-3-[2-oxo-1-phenyl-2-(4-pyridin-4-ylpiperazin-1-yl)ethyl]-1,3-dihydrobenzimidazol-2-one $^1$H-NMR (DMSO-d$_6$): 3.05-3.46 (m, 6H), 3.39 (s, 3H), 3.62-3.69 (m, 2H), 3.84 (s, 3H), 6.60 (s, 1H), 6.65 (s, 1H), 6.68-6.80 (m, 4H), 6.96-7.03 (m, 1H), 7.06-7.12 (m, 1H), 7.21-7.27 (m, 2H), 7.33-7.42 (m, 3H), 7.67 (d, 8.1 Hz, 1H), 7.94 (d, 9.0 Hz, 1H), 8.16 (d, 5.2 Hz, 2H).
MS (API-ES, pos) m/z=614 [M+H]$^+$

Example 71

5-Chloro-1-{2-[4-(1-methylpiperidin-4-yl)piperazin-1-yl]-2-oxo-1-phenyl-ethyl}-3-(quinoline-8-sulfonyl)-1,3-dihydrobenzimidazol-2-one $^1$H-NMR (methanol-d4): 1.77-1.94 (m, 2H), 2.17-2.30 (m, 2H), 2.76-3.17 (m, 7H), 2.88 (s, 3H), 3.32-3.43 (m, 1H), 3.54-3.69 (m, 4H), 3.92-4.06 (m, 1H), 6.47 (s, 1H), 6.57 (d, 8.7 Hz, 1H), 6.96-7.03 (m, 3H), 7.24-7.37 (m, 3H), 7.53-7.57 (m, 1H), 7.81-7.88 (m, 1H), 8.00 (d, 2.0 Hz, 1H), 8.35 (d, 8.2 Hz, 1H), 8.41-8.47 (m, 2H), 8.73 (d, 7.4 Hz, 1H).
MS (API-ES, pos) m/z=559, 661 [M+H]$^+$

Example 72

1-(2,4-Dimethoxybenzenesulfonyl)-3-{2-[4-(4-methylpiperazin-1-yl)piperidin-1-yl]-2-oxo-1-phenylethyl}-1,3-dihydrobenzimidazol-2-one $^1$H-NMR (DMSO-d$_6$): 0.96-1.88 (m, 4H), 2.35-3.95 (m, 12H), 2.74 (s, 3H), 3.40 (s, 3H), 3.87 (s, 3H), 4.36-4.48 (m, 1H), 6.50-6.56 (m, 1H), 6.62-6.71 (m, 2H), 6.73-6.77 (m, 1H), 6.95-7.02 (m, 1H), 7.05-7.15 (m, 2H), 7.23-7.27 (m, 1H), 7.34-7.42 (m, 3H), 7.64-7.68 (m, 1H), 7.93 (d, 8.9 Hz, 1H).
MS (API-ES, pos) m/z=634 [M+H]$^+$ Example 73

5-Chloro-3-(4-methoxybenzenesulfonyl)-1-[2-oxo-1-phenyl-2-(4-pyridin-4-ylpiperazin-1-yl)-ethyl]-1,3-dihydrobenzimidazol-2-one $^1$H-NMR (DMSO-d$_6$): 3.28-3.88 (m, 8H), 3.84 (s, 3H), 6.65 (s, 1H), 6.69 (d, 8.7 Hz, 1H), 7.09-7.20 (m, 5H), 7.22-7.28 (m, 2H), 7.34-7.40 (m, 3H), 7.81 (d, 2.0 Hz, 1H), 8.03 (d, 9.0 Hz, 2H), 8.27 (d, 7.3 Hz, 2H).
MS (API-ES, pos) m/z=618, 620 [M+H]$^+$ Example 74

5-Chloro-3-(4-methoxybenzenesulfonyl)-1-{2-oxo-1-phenyl-2-[3-(4-propylpiperazin-1-yl)-pyrrolidin-1-yl]ethyl}-1,3-dihydrobenzimidazol-2-one $^1$H-NMR (methanol-d4): 0.97-1.06 (m, 3H), 1.66-1.98 (m, 3H), 2.07-2.22 (m, 1H), 2.29-3.88 (m, 15H), 3.90 (s, 3H), 6.34-6.45 (m, 1H), 6.52-6.61 (m, 1H), 6.92-7.00 (m, 1H), 7.08-7.26 (m, 4H), 7.33-7.44 (m, 3H), 7.91 (s, 1H), 7.99-8.07 (m, 2H).
MS (API-ES, pos) m/z=652, 654 [M+H]$^+$ Example 75

5-Chloro-1-(4-methoxybenzenesulfonyl)-3-{1-methyl-2-oxo-2-[3-(4-propylpiperazin-1-yl)-pyrrolidin-1-yl]ethyl}-1,3-dihydrobenzimidazol-2-one $^1$H-NMR (methanol-d4): 0.97-1.06 (m, 3H), 1.42-1.51 (m, 3H), 1.54-3.98 (m, 19H), 3.89 (s, 3H), 5.17-5.32 (m, 1H), 7.07-7.16 (m, 2H), 7.21-7.37 (m, 2H), 7.88-7.94 (m, 1H), 7.96-8.08 (m, 2H).
MS (API-ES, pos) m/z=590, 592 [M+H]$^+$ Example 76

5-Chloro-1-(4-methoxybenzenesulfonyl)-3-{1-(2-methoxyphenyl)-2-oxo-2-[3-(4-propylpiperazin-1-yl)pyrrolidin-1-yl]ethyl}-1,3-dihydrobenzimidazol-2-one $^1$H-NMR (methanol-d4): 0.97-1.05 (m, 3H), 1.67-1.99 (m, 3H), 2.06-2.22 (m, 1H), 2.28-3.88 (m, 18H), 3.89 (s, 3H), 6.38-6.46 (m, 1H), 6.63-6.68 (m, 1H), 6.93-6.98 (m, 1H), 7.00-7.16 (m, 4H), 7.22-7.30 (m, 1H), 7.38-7.45 (m, 1H), 7.82-7.86 (m, 1H), 8.01-8.07 (m, 2H).
MS (API-ES, pos) m/z=682, 684 [M+H]$^+$ Example 77

5-Iodo-1-(4-methoxybenzenesulfonyl)-3-[2-oxo-2-(4-pyridin-4-ylpiperazin-1-yl)ethyl]-1,3-dihydrobenzimidazol-2-one $^1$H-NMR (methanol-d4): 3.34-3.66 (m, 8H), 3.85 (s, 3H), 4.79 (s, 2H), 6.84 (d, 6.2 Hz, 2H), 7.17 (d, 9.0 Hz, 2H), 7.50-7.65 (m, 3H), 7.97 (d, 9.0 Hz, 2H), 8.15-8.21 (m, 2H).
MS (API-ES, pos) m/z=643 [M+H]$^+$ Example 78

5-Chloro-1-(4-methoxybenzenesulfonyl)-3-{1-(4-methoxyphenyl)-2-oxo-2-[3-(4-propylpiperazin-1-yl)pyrrolidin-1-yl]ethyl}-1,3-dihydrobenzimidazol-2-one $^1$H-NMR (methanol-d4): 0.96-1.06 (m, 3H), 1.67-1.99 (m, 3H), 2.07-2.21 (m, 1H), 2.27-3.86 (m, 15H), 3.80 (s, 3H), 3.90 (s, 3H), 6.28-6.38 (m, 1H), 6.54-6.62 (m, 1H), 6.91-6.98 (m, 2H), 7.07-7.19 (m, 5H), 7.82-7.87 (m, 1H), 7.97-8.05 (m, 2H).
MS (API-ES, pos) m/z=682, 684 [M+H]$^+$ Example 79

5-Chloro-1-(4-methoxybenzenesulfonyl)-3-{1-(3-methoxyphenyl)-2-oxo-2-[3-(4-propylpiperazin-1-yl)pyrrolidin-1-yl]-ethyl}-1,3-dihydrobenzimidazol-2-one $^1$H-NMR (methanol-d4): 0.96-1.06 (m, 3H), 1.67-1.99 (m, 3H), 2.07-2.21 (m, 1H), 2.25-3.86 (m, 15H), 3.68-3.75 (m, 3H), 3.90 (s, 3H), 6.32-6.42 (m, 1H), 6.59-6.84 (m, 3H), 6.94-7.02 (m, 1H), 7.07-7.15 (m, 3H), 7.27-7.36 (m, 1H), 7.83-7.89 (m, 1H), 7.97-8.05 (m, 2H).
MS (API-ES, pos) m/z=682, 684 [M+H]$^+$ Example 80

5-Iodo-1-(4-methoxybenzenesulfonyl)-3-{2-oxo-1-phenyl-2-[3-(4-propylpiperazin-1-yl)pyrrolidin-1-yl]ethyl}-1,3-dihydrobenzimidazol-2-one $^1$H-NMR (methanol-d4): 0.97-1.07 (m, 3H), 1.65-1.99 (m, 3H), 2.06-2.21 (m, 1H), 2.26-2.72 (m, 2H), 2.87-3.88 (m, 13H), 3.90 (s, 3H), 6.34-6.45 (m, 1H), 6.84-6.92 (m, 1H), 7.08-7.25 (m, 4H), 7.34-7.47 (m, 4H), 7.64-7.71 (m, 1H), 7.97-8.04 (m, 2H)
MS (API-ES, pos) m/z=744 [M+H]$^+$ Example 81

3-{1-Benzyl-2-oxo-2-[3-(4-propylpiperazin-1-yl)pyrrolidin-1-yl]ethyl}-5-chloro-1-(4-methoxybenzenesulfonyl)-1,3-dihydrobenzimidazol-2-one $^1$H-NMR (methanol-d4): 0.96-1.07 (m, 3H), 1.64-1.85 (m, 3H), 1.94-2.16 (m, 1H), 2.26-3.83 (m, 17H), 3.91-3.96 (m, 3H), 5.28-5.41 (m, 1H), 6.73-6.80 (m, 2H), 6.82-6.96 (m, 3H), 7.05-7.13 (m, 2H), 7.16-7.24 (m, 1H), 7.28-7.57 (m, 1H), 7.81-7.91 (m, 3H).
MS (API-ES, pos) m/z=666, 668 [M+H]$^+$ Example 82

5-Chloro-1-(4-methoxybenzenesulfonyl)-3-[2-oxo-1-phenyl-2-(4-pyridin-2-ylpiperazin-1-yl)ethyl]-1,3-dihydrobenzimidazol-2-one 70.0 mg (0.15 mmol) of 6-chloro-3-(4-methoxybenzenesulfonyl)-2-oxo-2,3-dihydrobenzimidazol-1-yl]phenylacetic acid (XIIIa), 24.1 mg (0.18 mmol) of HOBt and 120 mg (0.17 mmol) solid phase-bound PS-carbodiimide (Argonaut, 1.3 mmol/g) were dissolved in 5 ml of dry dichloromethane in a screw-cap tube and shaken mechanically at room temperature for 10 min. 29.0 mg (0.18 mmol) of 1-(2-pyridyl)piperazine were added, and the mixture was then shaken mechanically overnight. Three equivalents of solid phase-bound MP-carbonate were then added to the reaction mixture, and it was shaken for a further 2 h. The solid phase-bound reagents were filtered off and washed with dichloromethane. The filtrate was concentrated in vacuo, and the residue was dried in vacuo. The residue was purified by chromatography on silica gel (mobile phase gradient 5-16% ethyl acetate in dichloromethane). Yield: 47.1 mg (52%) of white solid $^1$H-NMR (DMSO-$d_6$): 3.15-3.75 (m, 8H), 3.83 (s, 3H), 6.62-6.72 (m, 2H), 6.76-6.87 (m, 1H), 6.96-7.07 (m, 1H), 7.14-7.23 (m, 3H), 7.24-7.32 (m, 2H), 7.36-7.44 (m, 3H), 7.58-7.77 (m, 1H), 7.81 (d, 8.3 Hz, 1H), 7.98 (d, 7.8 Hz, 2H), 8.05-8.12 (m, 1H)

MS (API-ES, pos) m/z=618, 620 [M+H]$^+$

The following compounds (Examples 83-126) were prepared as shown in synthesis scheme 3 (step XIII→XIV) in an analogous manner to that described in Example 82.

Example 83

5-Chloro-1-(4-methoxybenzenesulfonyl)-3-[2-oxo-1-phenyl-2-(2-phenylpyrrolidin-1-yl)ethyl]-1,3-dihydrobenzimidazol-2-one MS (API-ES, pos) m/z=602, 604 [M+H]$^+$

Example 84

3-(2-Azetidin-1-yl-2-oxo-1-phenylethyl)-5-chloro-1-(4-methoxybenzenesulfonyl)-1,3-dihydrobenzimidazol-2-one $^1$H-NMR (DMSO-$d_6$): 2.03-2.20 (m, 2H), 3.69-3.78 (m, 2H), 3.86 (s, 3H), 3.86-3.93 (m, 1H), 3.94-4.03 (m, 1H), 6.16 (s, 1H), 6.88 (s, 1H), 7.17-7.26 (m, 5H), 7.33-7.49 (m, 3H), 7.82 (d, 8.7 Hz, 1H), 7.97 (d, 8.0 Hz, 2H)

MS (API-ES, pos) m/z=512, 514 [M+H]$^+$

Example 85

5-Chloro-1-(4-methoxybenzenesulfonyl)-3-[2-(4-methylpiperazin-1-yl)-2-oxoethyl]-1,3-dihydrobenzimidazol-2-one $^1$H-NMR (DMSO-$d_6$): 2.84 (s, 3H), 2.89-3.67 (m, 6H), 3.85 (s, 3H), 3.99-4.15 (m, 1H), 4.23-4.40 (m, 1H), 4.68-5.02 (m, 2H), 7.17 (d, 9.0 Hz, 2H), 7.25 (dd, 8.6 Hz, 1.8 Hz, 1H), 7.37 (m, 1H), 7.79 (d, 8.6 Hz, 1H), 7.98 (d, 8.9 Hz, 2H), 9.90 (bs, 1H)

MS (API-ES, pos) m/z=479, 481 [M+H]$^+$

Example 86

5-Chloro-1-(4-methoxybenzenesulfonyl)-3-{2-[4-(1-methylpiperidin-4-yl)piperazin-1-yl]-2-oxoethyl}-1,3-dihydrobenzimidazol-2-one $^1$H-NMR (DMSO-$d_6$): 1.71-1.87 (m, 2H), 2-16-2.29 (m, 2H), 2.72-2.83 (m, 4H), 2.90-3.91 (m, 12H), 3.85 (s, 3H), 4.74-4.91 (m, 2H), 7.17 (d, 8.9 Hz, 2H), 7.25 (d, 8.7 Hz, 1H), 7.38 (s, 1H), 7.79 (d, 8.7 Hz, 1H), 7.98 (d, 8.9 Hz, 2H).

MS (API-ES, pos) m/z=562, 564 [M+H]$^+$

Example 87

5-Chloro-1-(4-methoxybenzenesulfonyl)-3-(2-oxo-2-piperidin-1-yl-ethyl)-1,3-dihydrobenzimidazol-2-one $^1$H-NMR (DMSO-$d_6$): 1.38-1.47 (m, 2H), 1.51-1.62 (m, 4H), 3.32-3.43 (m, 4H), 4.72 (s, 2H), 7.17 (d, 8.8 Hz, 2H), 7.23 (d, 8.7 Hz, 1H), 7.39 (s, 1H), 7.78 (d, 8.7 Hz, 1H), 7.97 (d, 8.8 Hz, 2).

MS (API-ES, pos) m/z=464, 466 [M+H]$^+$

Example 88

5-Chloro-3-[2-(4-imidazol-1-ylpiperidin-1-yl)-2-oxo-1-phenylethyl]-1-(4-methoxybenzenesulfonyl)-1,3-dihydrobenzimidazol-2-one $^1$H-NMR (DMSO-$d_6$): 1.70-1.96 (m, 1H), 2.01-2.22 (m, 2H), 2.78-2.96 (m, 2H), 3.65-3.74 (m, 1H), 3.79-3.88 (m, 1H), 3.86 (s, 3H), 4.47-4.62 (m, 2H), 6.52-6.69 (m, 2H), 7.12-7.23 (m, 4H), 7.29-7.43 (m, 4H), 7.72 (s, 1H), 7.80 (d, 8.7 Hz, 1H), 7.85 (s, 1H), 7.99 (d, 8.2 Hz, 2H), 9.12 (d, 9.2 Hz, 1H).

MS (API-ES, pos) m/z=606, 608 [M+H]$^+$

Example 89

5-Chloro-1-(4-methoxybenzenesulfonyl)-3-[2-oxo-1-phenyl-2-(4-[1,3,5]triazin-2-ylpiperazin-1-yl)-ethyl]-1,3-dihydrobenzimidazol-2-one $^1$H-NMR (DMSO-$d_6$): 3.18-3.29 (m, 1H), 3.32-3.43 (m, 2H), 3.53-3.70 (m, 5H), 3.83 (s, 3H), 6.62 (s, 1H), 6.71 (s, 1H), 7.12-7.22 (m, 3H), 7.23-7.29 (m, 2H), 7.34-7.42 (m, 3H), 7.81 (d, 8.7 Hz, 1H), 7.99 (d, 8.8 Hz, 2H), 8.54-8.63 (m, 2H).

MS (API-ES, pos) m/z=620, 622 [M+H]$^+$

Example 90

5-Chloro-1-(4-methoxybenzenesulfonyl)-3-(2-oxo-2-pyrrolidin-1-yl-ethyl)-1,3-dihydrobenzimidazol-2-one $^1$H-NMR (DMSO-$d_6$): 1.72-1.81 (m, 2H), 1.86-1.96 (m, 2H), 3.22-3.28 (m, 2H), 3.44-3.52 (m, 2H), 3.85 (s, 3H), 4.62 (s, 2H), 7.17 (d, 8.7 Hz, 2H), 7.23 (d, 8.5 Hz, 1H), 7.41 (s, 1H), 7.78 (d, 8.5 Hz, 1H), 7.97 (d, 8.7 Hz, 2H).

MS (API-ES, pos) m/z=450, 452 [M+H]$^+$

Example 91

5-Chloro-1-(4-methoxybenzenesulfonyl)-3-{2-oxo-1-phenyl-2-[3-(4-propylpiperazin-1-yl)-pyrrolidin-1-yl]ethyl}-1,3-dihydrobenzimidazol-2-one $^1$H-NMR (DMSO-$d_6$): 0.84-0.95 (m, 3H), 1.56-1.74 (m, 3H), 1.94-2.11 (m, 1H), 2.23-2.44 (m, 2H), 2.63-3.70 (m, 13H), 3.87 (s, 3H), 6.31-6.42 (m, 1H), 6.56-6.61 and 6.67-6.71 (m, 1H), 7.13-7.23 (m, 5H), 7.33-7.42 (m, 3H), 7.77-7.83 (m, 1H), 7.94-8.02 (m, 2H).

MS (API-ES, pos) m/z=652, 654 [M+H]$^+$

Example 92

5-Chloro-1-(4-methoxybenzenesulfonyl)-3-[2-oxo-1-phenyl-2-(3-pyridin-4-yl-pyrrolidin-1-yl)ethyl]-1,3-dihydrobenzimidazol-2-one $^1$H-NMR (DMSO-d$_6$): 1.88-2.06 (m, 1H), 2.22-2.37 (m, 1H), 3.00-4.05 (m, 5H), 3.86 (s, 3H), 6.35-6.45 (m, 1H), 6.63-6.78 (m, 1H), 7.12-7.28 (m, 5H), 7.31-7.42 (m, 3H), 7.48-7.51 and 7.63-7.70 (m, 1H), 7.52-7.58 (m, 1H), 7.78-7.86 (m, 1H), 7.94-8.01 (m, 2H), 8.58-8.71 (m, 2H).
MS (API-ES, pos) m/z=603, 605 [M+H]$^+$

Example 93

1-{2-[6-Chloro-3-(4-methoxybenzenesulfonyl)-2-oxo-2,3-dihydrobenzimidazol-1-yl]-2-phenylacetyl}pyrrolidine-2-dimethylcarboxamide MS (API-ES, pos) m/z=597, 599 [M+H]$^+$

Example 93a

1-{2-[6-Chloro-3-(4-methoxybenzenesulfonyl)-2-oxo-2,3-dihydrobenzimidazol-1-yl]-2-phenylacetyl}pyrrolidine-2(S)-dimethylcarboxamide MS (API-ES, pos) m/z=597, 599 [M+H]$^+$

Example 94

5-Chloro-1-(4-methoxybenzenesulfonyl)-3-[2-oxo-1-phenyl-2-(4-pyridin-3-ylpiperazin-1-yl)ethyl]-1,3-dihydrobenzimidazol-2-one $^1$H-NMR (DMSO-d$_6$): 3.11-3.20 (m, 2H), 3.27-3.48 (m, 2H), 3.41-3.52 (m, 2H), 3.64-3.76 (m, 2H), 3.28 (s, 3H), 6.66 (s, 1H), 6.70 (s, 1H), 7.12-7.22 (m, 3H), 7.23-7.30 (m, 2H), 7.35-7.42 (m, 3H), 7.63-7.71 (m, 1H), 7.78-7.85 (m, 2H), 7.98 (d, 8.8 Hz, 2H), 8.16 (d, 5.0 Hz, 1H), 8.36 (s, 1H).
MS (API-ES, pos) m/z=618, 620 [M+H]$^+$

Example 95

5-Chloro-1-(4-methoxybenzenesulfonyl)-3-{2-[4-(4-methylpiperazin-1-yl)piperidin-1-yl]-2-oxo-ethyl}-1,3-dihydrobenzimidazol-2-one $^1$H-NMR (DMSO-d$_6$): 1.20-1.38 (m, 1H), 1.41-1.57 (m, 1H), 1.76-1.95 (m, 2H), 2.52-4.28 (m, 12H), 2.76 (s, 3H), 3.85 (s, 3H), 4.65-4.83 (m, 2H), 7.17 (d, 8.9 Hz, 2H), 7.24 (dd, 8.6 Hz, 1.7 Hz, 1H), 7.38 (d, 1.6 Hz, 1H), 7.79 (d, 8.7 Hz, 1H), 7.97 (d, 8.9 Hz, 2H).
MS (API-ES, pos) m/z=562, 564 [M+H]$^+$

Example 96

5-Chloro-1-(4-methoxybenzenesulfonyl)-3-{2-[4-(1-methylpiperidin-3-ylmethyl)piperazin-1-yl]-2-oxo-1-phenylethyl}-1,3-dihydrobenzimidazol-2-one $^1$H-NMR (DMSO-d$_6$): 0.95-1.11 (m, 1H), 1.51-1.91 (m, 3H), 1.98-2.15 (m, 1H), 2.51-3.85 (m, 14H), 2.76 (s, 3H), 3.87 (s, 3H), 6.65 (s, 2H), 7.15-7.26 (m, 5H), 7.34-7.43 (m, 3H), 7.81 (d, 8.7 Hz, 1H), 7.98 (d, 8.9 Hz, 2H).
MS (API-ES, pos) m/z=652, 654 [M+H]$^+$

Example 97

2-[6-Chloro-3-(4-methoxybenzenesulfonyl)-2-oxo-2,3-dihydrobenzimidazol-1-yl]-N,N-dimethyl-2-phenylacetamide $^1$H-NMR (DMSO-d$_6$): 2.80 (s, 3H), 2.92 (s, 3H), 3.87 (s, 3H), 6.52 (s, 1H), 6.55 (d, 1.9 Hz, 1H), 7.14-7.23 (m, 5H), 7.35-7.42 (m, 3H), 7.80 (d, 8.7 Hz, 1H), 7.98 (d, 8.9 Hz, 2H).
MS (API-ES, pos) m/z=500, 502 [M+H]$^+$

Example 98

5-Chloro-1-(4-methoxybenzenesulfonyl)-3-[2-(4-methylpiperazin-1-yl)-2-oxo-1-phenylethyl]-1,3-dihydrobenzimidazol-2-one $^1$H-NMR (DMSO-d$_6$): 1.85-1.94 (m, 1H), 1.96-2.05 (m, 1H), 2.08 (s, 3H), 2.09-2.17 (m, 1H), 2.28-2.37 (m, 1H), 3.06-3.15 (m, 1H), 3.21-3.28 (m, 1H), 3.45-3.56 (m, 2H), 3.87 (s, 3H), 6.56 (s, 1H), 6.63 (d, 1.9 Hz, 1H), 7.16-7.24 (m, 5H), 7.35-7.42 (m, 3H), 7.82 (d, 8.7 Hz, 1H), 7.98 (d, 8.9 Hz, 2H).
MS (API-ES, pos) m/z=555, 557 [M+H]$^+$

Example 99

5-Chloro-1-(4-methoxybenzenesulfonyl)-3-(2-morpholin-4-yl-2-oxo-1-phenylethyl)-1,3-dihydrobenzimidazol-2-one $^1$H-NMR (DMSO-d$_6$): 3.06-3.15 (m, 1H), 3.20-3.32 (m, 3H), 3.43-3.66 (m, 4H), 3.87 (s, 3H), 6.57 (s, 1H), 6.64 (d, 1.9 Hz, 1H), 7.20 (d, 8.9 Hz, 2H), 7.21-7.27 (m, 3H), 7.35-7.42 (m, 3H), 7.81 (d, 8.7 Hz, 1H), 7.98 (d, 8.9 Hz, 2H).
MS (API-ES, pos) m/z=542, 544 [M+H]$^+$

Example 100

N-Benzyl-2-[6-chloro-3-(4-methoxybenzenesulfonyl)-2-oxo-2,3-dihydrobenzimidazol-1-yl]-2-phenylacetamide $^1$H-NMR (DMSO-d$_6$): 3.86 (s, 3H), 4.35 (d, 5.6 Hz, 2H), 6.22 (s, 1H), 6.82 (d, 1.9 Hz, 1H), 7.14-7.20 (m, 5H), 7.22-7.27 (m, 3H), 7.28-7.36 (m, 5H), 7.79 (d, 8.7 Hz, 1H), 7.98 (d, 8.9 Hz, 2H), 9.03-9.07 (m, 1H).
MS (API-ES, pos) m/z=562, 564 [M+H]$^+$

Example 101

5-Chloro-1-(4-methoxybenzenesulfonyl)-3-(2-oxo-1-phenyl-2-piperidin-1-ylethyl)-1,3-dihydrobenzimidazol-2-one $^1$H-NMR (DMSO-d$_6$): 1.02-1.21 (m, 2H), 1.29-1.41 (m, 1H), 1.43-1.55 (m, 3H), 3.06-3.24 (m, 2H), 3.43-3.54 (m, 2H), 3.87 (s, 3H), 6.52 (s, 1H), 6.65 (s, 1H), 7.16-7.26 (m, 5H), 7.34-7.42 (m, 3H), 7.81 (d, 8.7 Hz, 1H), 7.98 (d, 8.8 Hz, 2H).
MS (API-ES, pos) m/z=540, 542 [M+H]$^+$

Example 102

5-Chloro-1-(4-methoxybenzenesulfonyl)-3-(2-oxo-1-phenyl-2-pyrrolidin-1-ylethyl)-1,3-dihydrobenzimidazol-2-one $^1$H-NMR (CDCl3): 1.80-1.99 (m, 4H), 3.14-3.23 (m, 1H), 3.50-3.62 (m, 3H), 3.88 (s, 3H), 6.44 (s, 1H), 6.81 (d, 1.7 Hz, 1H), 6.96-7.03 (m, 3H), 7.17-7.24 (m, 2H), 7.31-7.38 (m, 3H), 7.79 (d, 8.7 Hz, 1H), 8.05 (d, 8.9 Hz, 2H).
MS (API-ES, pos) m/z=526, 528 [M+H]$^+$

Example 103

2-[6-Chloro-3-(4-methoxybenzenesulfonyl)-2-oxo-2,3-dihydrobenzimidazol-1-yl]-2,N-diphenylacetamide $^1$H-NMR (CDCl3): 3.84 (s, 3H), 6.21 (s, 1H), 6.90-6.97 (m, 3H), 7.07-7.16 (m, 2H), 7.27-7.46 (m, 9H), 7.87 (d, 8.7 Hz, 1H), 7.88-7.93 (m, 1H), 8.01 (d, 8.9 Hz, 2H).
MS (API-ES, pos) m/z=548, 550 [M+H]$^+$

Example 104

2-[6-Chloro-3-(4-methoxybenzenesulfonyl)-2-oxo-2,3-dihydrobenzimidazol-1-yl]-N,N-diethyl-2-phenylacetamide $^1$H-NMR (CDCl3): 1.12-1.26 (m, 6H), 3.18-3.33 (m, 3H), 3.56-3.68 (m, 1H), 3.88 (s, 3H), 6.54 (s, 1H), 6.74 (s, 1H), 6.97-7.03 (m, 3H), 7.16-7.22 (m, 2H), 7.32-7.38 (m, 3H), 7.78 (d, 8.7 Hz, 1H), 8.02-8.07 (m, 2H).
MS (API-ES, pos) m/z=528, 530 [M+H]$^+$

Example 105

5-Chloro-1-(4-methoxybenzenesulfonyl)-3-[2-oxo-1-phenyl-2-(4-phenylpiperazin-1-yl)ethyl]-1,3-dihydrobenzimidazol-2-one $^1$H-NMR (CDCl3): 2.85-2.99 (m, 1H), 3.03-3.14 (m, 1H), 3.18-3.27 (m, 2H), 3.40-3.64 (m, 2H), 3.78-3.88 (m, 1H), 3.86 (s, 3H), 3.91-4.01 (m, 1H), 6.60 (s, 1H), 6.73 (s, 1H), 6.88-7.05 (m, 6H), 7.22-7.33 (m, 3H), 7.34-7.41 (m, 3H), 7.82 (d, 8.7 Hz, 1H), 8.04 (d, 7.5 Hz, 2H).
MS (API-ES, pos) m/z=617, 619 [M+H]$^+$

Example 106

2-[6-Chloro-3-(4-methoxybenzenesulfonyl)-2-oxo-2,3-dihydrobenzimidazol-1-yl]-N-(2-dimethylaminoethyl)-N-methyl-2-phenylacetamide $^1$H-NMR (methanol-d4): 2.97-3.07 (m, 9H), 3.36-3.43 (m, 1H), 3.44-3.55 (m, 2H), 3.96 (s, 3H), 4.26-4.38 (m, 1H), 6.58 (s, 1H), 6.66 (s, 1H), 7.14-7.30 (m, 5H), 7.40-7.53 (m, 3H), 7.94 (d, 8.7 Hz, 2H), 8.08 (d, 8.8 Hz, 2H).
MS (API-ES, pos) m/z=557, 559 [M+H]$^+$

Example 107

1-(4-Methoxybenzenesulfonyl)-3-{2-oxo-1-phenyl-2-[3-(4-propylpiperazin-1-yl)-pyrrolidin-1-yl]ethyl}-1,3-dihydrobenzimidazol-2-one $^1$H-NMR (methanol-d4): 0.99-1.08 (m, 3H), 1.68-1.98 (m, 3H), 2.06-2.23 (m, 1H), 2.25-2.68 (m, 2H), 2.85-3.88 (m, 13H), 3.91 (s, 3H), 6.36-6.48 (m, 1H), 6.59-6.72 (m, 1H), 6.92-7.03 (m, 1H), 7.08-7.26 (m, 5H), 7.31-7.43 (m, 3H), 7.88-7.96 (m, 1H), 8.00-8.07 (m, 2H).
MS (API-ES, pos) m/z=618 [M+H]$^+$

Example 108

5-Chloro-1-(4-methoxybenzenesulfonyl)-3-{2-oxo-2-[3-(4-propylpiperazin-1-yl)-pyrrolidin-1-yl]-ethyl}-1,3-dihydrobenzimidazol-2-one $^1$H-NMR (DMSO-d$_6$): 0.86-0.94 (m, 3H), 1.56-1.87 (m, 3H), 2.00-2.24 (m, 1H), 2.34-2.48 (m, 1H), 2.89-4.13 (m, 14H), 4.55-4.70 (m, 2H), 7.14-7.19 (m, 2H), 7.24 (dd, 8.7 Hz, 2.0 Hz, 1H), 7.36-7.40 (m, 1H), 7.89 (d, 8.6 Hz, 1H), 7.97 (d, 8.9 Hz, 2H).
MS (API-ES, pos) m/z=576, 578 [M+H]$^+$

Example 109

5-Chloro-1-(4-methoxybenzenesulfonyl)-3-[2-((S)-2-oxazol-2-yl-pyrrolidin-1-yl)-2-oxo-1-phenylethyl]-1,3-dihydrobenzimidazol-2-one MS (API-ES, pos) m/z=593, 595 [M+H]$^+$

Example 110

5-Chloro-1-(4-methoxybenzenesulfonyl)-3-[2-((S)-2-[1,2,4]oxadiazol-3-ylpyrrolidin-1-yl)-2-oxo-1-phenylethyl]-1,3-dihydrobenzimidazol-2-one MS (API-ES, pos) m/z=594, 596 [M+H]$^+$

Example 111

2-[6-Chloro-3-(4-methoxybenzenesulfonyl)-2-oxo-2,3-dihydrobenzimidazol-1-yl]-2-phenyl-N-pyridin-2-ylmethylacetamide MS (API-ES, pos) m/z=563, 565 [M+H]$^+$

Example 112

2-[6-Chloro-3-(4-methoxybenzenesulfonyl)-2-oxo-2,3-dihydrobenzimidazol-1-yl]-2-phenyl-N-pyridin-3-ylmethylacetamide MS (API-ES, pos) m/z=563, 565 [M+H]$^+$

Example 113

2-[6-Chloro-3-(4-methoxybenzenesulfonyl)-2-oxo-2,3-dihydrobenzimidazol-1-yl]-N-(3-morpholin-4-ylpropyl)-2-phenyl-acetamide MS (API-ES, pos) m/z=599, 601 [M+H]$^+$

Example 114

2-[6-Chloro-3-(4-methoxybenzenesulfonyl)-2-oxo-2,3-dihydrobenzimidazol-1-yl]-2-phenyl-N-(2-piperidin-1-ylethyl)acetamide MS (API-ES, pos) m/z=583, 585 [M+H]$^+$

Example 115

2-[6-Chloro-3-(4-methoxybenzenesulfonyl)-2-oxo-2,3-dihydrobenzimidazol-1-yl]-N-[2-(4-methylpiperazin-1-yl)ethyl]-2-phenylacetamide MS (API-ES, pos) m/z=598, 600 [M+H]$^+$

Example 116

2-[6-Chloro-3-(4-methoxybenzenesulfonyl)-2-oxo-2,3-dihydrobenzimidazol-1-yl]-N-[2-1H-imidazol-4-yl)ethyl]-2-phenylacetamide MS (API-ES, pos) m/z=566, 568 [M+H]$^+$

Example 117

2-[6-Chloro-3-(4-methoxybenzenesulfonyl)-2-oxo-2,3-dihydrobenzimidazol-1-yl]-N-(3-dimethylaminopropyl)-N-methyl-2-phenylacetamide MS (API-ES, pos) m/z=571, 573 [M+H]$^+$

Example 118

2-[6-Chloro-3-(4-methoxybenzenesulfonyl)-2-oxo-2,3-dihydrobenzimidazol-1-yl]-N-(2-dimethylaminoethyl)-N-ethyl-2-phenylacetamide MS (API-ES, pos) m/z=571, 573 [M+H]$^+$

Example 119

2-[6-Chloro-3-(4-methoxybenzenesulfonyl)-2-oxo-2,3-dihydrobenzimidazol-1-yl]-N-(2-diethylaminoethyl)-N-methyl-2-phenylacetamide MS (API-ES, pos) m/z=585, 587 [M+H]$^+$

Example 120

2-[6-Chloro-3-(4-methoxybenzenesulfonyl)-2-oxo-2,3-dihydrobenzimidazol-1-yl]-N-methyl-2-phenyl-N-(2-pyridin-2-ylethyl)acetamide MS (API-ES, pos) m/z=591, 593 [M+H]$^+$

Example 121

2-[6-Chloro-3-(4-methoxybenzenesulfonyl)-2-oxo-2,3-dihydrobenzimidazol-1-yl]-N-(3-hydroxypropyl)-2-phenylacetamide MS (API-ES, pos) m/z=530, 532 [M+H]$^+$

Example 122

2-[6-Chloro-3-(4-methoxybenzenesulfonyl)-2-oxo-2,3-dihydrobenzimidazol-1-yl]-2-phenyl-N-(2-propoxyethyl)acetamide MS (API-ES, pos) m/z=558, 560 [M+H]$^+$

Example 123

2-[6-Chloro-3-(4-methoxybenzenesulfonyl)-2-oxo-2,3-dihydrobenzimidazol-1-yl]-N-(2-diethylaminoethyl)-2-phenylacetamide MS (API-ES, pos) m/z=571, 573 [M+H]$^+$

Example 124

2-[6-Chloro-3-(4-methoxybenzenesulfonyl)-2-oxo-2,3-dihydrobenzimidazol-1-yl]—N-(4-dimethylaminobutyl)-2-phenylacetamide MS (API-ES, pos) m/z=571, 573 [M+H]$^+$

Example 125

2-[6-Chloro-3-(4-methoxybenzenesulfonyl)-2-oxo-2,3-dihydrobenzimidazol-1-yl]-N-[3-(2-oxopyrrolidin-1-yl)propyl]-2-phenylacetamide MS (API-ES, pos) m/z=597, 599 [M+H]$^+$

Example 126

5-Chloro-1-(4-methoxybenzenesulfonyl)-3-[2-(4-methyl-[1,4]diazepan-1-yl)-2-oxo-1-phenylethyl]-1,3-dihydrobenzoimidazol-2-one MS (API-ES, pos) m/z=569, 571 [M+H]$^+$

Example 127 tert-Butyl 4-(4-{2-[6-chloro-3-(4-methoxybenzenesulfonyl)-2-oxo-2,3-dihydrobenzimidazol-1-yl]-2-phenylacetyl}piperazin-1-yl)piperidin-1-carboxylate 167 mg (0.81 mmol) of 4-methoxybenzenesulfonyl chloride were added to a solution of 460 mg (0.73 mmol) of tert-butyl 4-{4-[2-(6-chloro-2-oxo-2,3-dihydrobenzimidazol-1-yl)-2-phenylacetyl]-piperazin-1-yl}piperidin-1-carboxylate (XIIIa), 0.21 ml (1.47 mmol) of triethylamine and a catalytic amount of DMAP in tetrahydrofuran (8 ml) while stirring at room temperature, and the mixture was then stirred at room temperature for 16 h. The reaction solution was mixed with water and extracted with ethyl acetate (3×60 ml). The combined organic phases were washed with water and saturated brine, dried over magnesium sulfate and concentrated under reduced pressure. The residue was purified by chromatography on silica gel (mobile phase gradient 5-10% methanol in dichloromethane). Yield: 517 g (97%) of colorless oil $^1$H-NMR (DMSO-d$_6$): 1.06-1.20 (m, 2H), 1.39 (s, 9H), 1.54-1.63 (m, 2H), 2.03-2.20 (m, 2H), 2.22-2.38 (m, 2H), 2.59-2.72 (m, 2H), 3.04-3.14 (m, 1H), 3.16-3.25 (m, 1H), 3.41-3.56 (m, 2H), 3.87 (s, 3H), 3.86-3.95 (m, 2H), 6.54 (s, 1H), 6.65 (d, 1.9 Hz, 1H), 7.15-7.24 (m, 5H), 7.33-7.40 (m, 3H), 7.81 (d, 8.7 Hz, 1H), 7.96 (d, 9.4 Hz, 1H), 7.98 (d, 8.9 Hz, 2H).

MS (API-ES, pos) m/z=724, 726 [M+H]$^+$

Example 128

5-Chloro-1-(4-methoxybenzenesulfonyl)-3-[2-oxo-1-phenyl-2-(4-piperidin-4-ylpiperazin-1-yl)ethyl]-1,3-dihydrobenzimidazol-2-one 122 mg (0.17 mmol) of tert-butyl 4-(4-{2-[6-chloro-3-(4-methoxybenzenesulfonyl)-2-oxo-2,3-dihydrobenzimidazol- 1-yl]-2-phenylacetyl}piperazin-1-yl)piperidine-1-carboxylate (Example 127) were dissolved in dichloromethane (3 ml) and while stirring at room temperature, trifluoroacetic acid (3 ml) was added. The reaction solution was stirred for 2 h and then the solvent and excess trifluoroacetic acid were removed in vacuo. The residue was taken up again in toluene, concentrated in vacuo and then dried in vacuo. The residue was dissolved in 15 ml of dichloromethane/methanol (9:1), mixed with 4 eq. of Si-carbonate (Silicycle, 0.69 mmol/g) and stirred at room temperature for 2 h. The solid phase reagent was filtered off and washed with dichloromethane. The filtrate was concentrated under reduced pressure and dried in vacuo. Yield: 105 mg (100%) of colorless oil.

MS (API-ES, pos) m/z=624, 626 [M+H]$^+$

Example 129

5-Chloro-1-(4-methoxybenzenesulfonyl)-3-{2-oxo-1-phenyl-2-[4-(1-propylpiperidin-4-yl)piperazin-1-yl]ethyl}-1,3-dihydrobenzimidazol-2-one A solution of 52 mg (0.08 mmol) of 5-chloro-1-(4-methoxybenzenesulfonyl)-3-[2-oxo-1-phenyl-2-(4-piperidin-4-ylpiperazin-1-yl)-ethyl]-1,3-dihydrobenzimidazol-2-one (Example 128) in 3 ml of THF was mixed with 5.32 mg (0.09 mmol) of propionaldehyde and 70 mg of MP-triacetoxyborohydride resin (Argonaut, 2.55 mmol/g, 0.17 mmol) and shaken at room temperature overnight. The solid phase reagent was filtered off and washed with dichloromethane. The filtrate was concentrated under reduced pressure. The residue was purified by chromatography on silica gel (mobile phase gradient 8-11% methanol in dichloromethane). Yield: 33.2 mg (60%) of colorless solid $^1$H-NMR (DMSO-d$_6$): 0.83 (t, 7.3 Hz, 3H), 1.24-1.49 (m, 4H), 1.55-1.67 (m, 2H), 2.04-2.38 (m, 6H), 2.82-3.58 (m, 9H), 3.87 (s, 3H), 6.55 (s, 1H), 6.64 (d, 1.9 Hz, 1H), 7.07-7.12 (m, 5H), 7.16-7.21 (m, 3H), 7.81 (d, 8.8 Hz, 1H), 7.98 (d, 8.9 Hz, 2H).

MS (API-ES, pos) m/z=666, 668 [M+H]$^+$

Example 130 tert-Butyl 4-(2-{2-[6-chloro-3-(4-methoxybenzenesulfonyl)-2-oxo-2,3-dihydrobenzimidazol-1-yl]-2-phenylacetylamino}ethyl)piperazine-1-carboxylate 474 mg (1.00 mmol) of 6-chloro-3-(4-methoxybenzenesulfonyl)-2-oxo-2,3-dihydrobenzimidazol-1-yl]phenylacetic acid (XIIIa), 204 mg (1.50 mmol) of HOBt and 850 mg (1.10 mmol) of solid phase-bound PS-carbodiimide (Argonaut, 1.3 mmol/g) were dissolved in 10 ml of dry dichloromethane in a screw-cap tube and checked mechanically at room temperature for 10 min. 241 mg (1.05 mmol) of 1-Boc-(2-aminoethyl)piperazine were added, and the mixture was then checked mechanically overnight. Three equivalents of solid phase-bound MP-carbonate were then added to the reaction mixture, and checking was continued for 2 h. The solid phase-bound reagents were filtered off and washed with dichloromethane. The filtrate was concentrated in vacuo, and the residue was dried in vacuo. The residue was purified by chromatography on silica gel (mobile phase gradient 0.5-5% methanol in dichloromethane). Yield: 574 mg (84%) of colorless oil.

$^1$H-NMR (methanol-d4): 1.46 (s, 9H), 2.28-2.52 (m, 6H), 3.32-3.50 (m, 6H), 3.89 (s, 3H), 6.20 (s, 1H), 6.80 (s, 1H), 7.07-7.14 (m, 3H), 7.24-7.38 (m, 5H), 7.86 (d, J=8.6 Hz, 1H), 8.01 (d, J=8.8 Hz, 2H).

MS (API-ES, pos) m/z=684, 686 [M+H]$^+$

Example 131

2-[6-Chloro-3-(4-methoxybenzenesulfonyl)-2-oxo-2,3-dihydrobenzimidazol-1-yl]-2-phenyl-N-(2-piperazin-1-ylethyl)acetamide 520 (0.76 mmol) of tert-butyl 4-(2-{2-[6-chloro-3-(4-methoxybenzenesulfonyl)-2-oxo-2,3-dihydrobenzimidazol-1-yl]-2-phenyl-acetylamino}-ethyl)piperazine-1-carboxylate (Example 130) were dissolved in dichlormethane (6 ml) and, while stirring at room temperature, trifluoroacetic acid (4 ml) was added. The reaction solution was stirred for 2 h and then the solvent and excess trifluoroacetic acid were removed in vacuo. The residue was taken up once again in toluene, concentrated in vacuo and then dried in vacuo. The residue was dissolved in 6 ml of dichloromethane, mixed with 3 eq. of MP carbonate (Argonaut, 1.69 mmol/g) and stirred at room temperature for 2 h. The solid phase reagent was filtered off and washed with dichloromethane. The filtrate was concentrated under reduced pressure and dried in vacuo. Yield: 430 mg (97%) of colorless oil.

A sample of the reaction product was further purified by preparative RP-HPLC (mobile phase: gradient from 10% to 80% acetonitrile in water, 0.1% trifluoroacetic acid as modulator)

$^1$H-NMR (methanol-d4): 2.75-2.81 (m, 2H), 2.89-3.02 (m, 4H), 3.45-3.52 (m, 2H), 3.90 (s, 3H), 6.16 (s, 1H), 6.80 (s, 1H), 7.08-7.17 (m, 3H), 7.18-7.24 (m, 2H), 7.30-7.38 (m, 3H), 7.87 (d, 8.7 Hz, 1H), 8.01 (d, 8.7 Hz, 2H).

MS (API-ES, pos) m/z=584, 586 [M+H]$^+$

Example 132

2-[6-Chloro-3-(4-methoxybenzenesulfonyl)-2-oxo-2,3-dihydrobenzimidazol-1-yl]-N-[2-(4-methylpiperazin-1-yl)ethyl]-2-phenyl-acetamide A solution of 98.0 mg (0.17 mmol) 2-[6-chloro-3-(4-methoxybenzenesulfonyl)-2-oxo-2,3-dihydrobenzimidazol-1-yl]-2-phenyl-N-(2-piperazin-1-yl-ethyl)acetamide (Example 131) in 4 ml of THF was mixed with 5.54 mg (0.19 mmol) of paraformaldehyde and 170 mg of MP-triacetoxyborohydride resin (Argonaut, 2.55 mmol/g, 0.42 mmol) and shaken at room temperature overnight. The solid phase reagent was filtered off and washed with dichloromethane. The filtrate was concentrated under reduced pressure. The residue was purified by preparative RP-HPLC (mobile phase: gradient from 10% to 80% acetonitrile in water, 0.1% trifluoroacetic acid as modulator). Yield: 69.6 mg (69%) of colorless solid $^1$H-NMR (methanol-d4): 2.65-2.72 (m, 2H), 2.74-3.08 (m, 6H), 3.19-3.54 (m, 7H), 3.90 (s, 3H), 6.16 (s, 1H), 6.77 (s, 1H), 7.08-7.17 (m, 3H), 7.19-7.24 (m, 2H), 7.31-7.39 (m, 3H), 7.87 (d, 8.7 Hz, 1H), 8.01 (d, 8.7 Hz, 2H).

MS (API-ES, pos) m/z=598, 600 [M+H]$^+$

Example 133

2-[6-Chloro-3-(4-methoxybenzenesulfonyl)-2-oxo-2,3-dihydrobenzimidazol-1-yl]-2-phenyl-N-[2-(4-propylpiperazin-1-yl)-ethyl]-acetamide was prepared in an analogous manner to that described in Example 132.

$^1$H-NMR (methanol-d4): 1.04 (t, 7.3 Hz, 3H), 1.70-1.82 (m, 2H), 2.66-3.56 (m, 14H), 3.90 (s, 3H), 6.16 (s, 1H), 6.77

(s, 1H), 7.08-7.17 (m, 3H), 7.19-7.24 (m, 2H), 7.31-7.39 (m, 3H), 7.87 (d, 8.7 Hz, 1H), 8.01 (d, 8.7 Hz, 2H).
MS (API-ES, pos) m/z=626, 628 [M+H]$^+$ Example 134 tert-Butyl 4-(3-{2-[6-chloro-3-(4-methoxybenzene-sulfonyl)-2-oxo-2,3-dihydrobenzimidazol-1-yl]-2-phenyl-acetylamino}-propyl)piperazine-1-carboxylate was prepared in an analogous manner to that described in Example 130.
MS (API-ES, pos) m/z=698, 700 [M+H]$^+$ Example 135

2-[6-Chloro-3-(4-methoxybenzenesulfonyl)-2-oxo-2,3-dihydrobenzimidazol-1-yl]

2-phenyl-N-(3-piperazin-1-ylpropyl)acetamide was prepared in an analogous manner to that described in Example 131. $^1$H-NMR (methanol-d4): 1.88-1.98 (m, 2H), 3.03-3.15 (m, 2H), 3.27-3.53 (m, 10H), 3.90 (s, 3H), 6.09 (s, 1H), 6.80 (s, 1H), 7.08-7.18 (m, 3H), 7.20-7.26 (m, 2H), 7.30-7.40 (m, 3H), 7.87 (d, 8.7 Hz, 1H), 8.01 (d, 8.6 Hz, 2H).
MS (API-ES, pos) m/z=598, 600 [M+H]$^+$ Example 136

2-[6-Chloro-3-(4-methoxybenzenesulfonyl)-2-oxo-2,3-dihydrobenzimidazol-1-yl]-2-phenyl-N-[3-(4-propylpiperazin-1-yl)propyl]-acetamide was prepared in an analogous manner to that described in Example 132.
$^1$H-NMR (methanol-d4): 0.98-1.05 (m, 3H), 1.67-1.93 (m, 4H), 2.83-3.50 (m, 14H), 3.90 (s, 3H), 6.11 (s, 1H), 6.78 (s, 1H), 7.08-7.17 (m, 3H), 7.19-7.25 (m, 2H), 7.31-7.40 (m, 3H), 7.87 (d, 8.7 Hz, 1H), 8.01 (d, 8.7 Hz, 2H).
MS (API-ES, pos) m/z=640, 642 [M+H]$^+$ Example 137

2-[6-Chloro-3-(4-methoxybenzenesulfonyl)-2-oxo-2,3-dihydrobenzimidazol-1-yl]-N-[3-(4-methylpiperazin-1-yl)propyl]-2-phenyl-acetamide was prepared in an analogous manner to that described in Example 132.
$^1$H-NMR (methanol-d4): 1.78-1.90 (m, 2H), 2.78-3.48 (m, 12H), 2.83 (s, 3H), 3.90 (s, 3H), 6.12 (s, 1H), 6.78 (s, 1H), 7.08-7.17 (m, 3H), 7.19-7.25 (m, 2H), 7.31-7.40 (m, 3H), 7.87 (d, 8.7 Hz, 1H), 8.01 (d, 8.7 Hz, 2H).
MS (API-ES, pos) m/z=612, 614 [M+H]$^+$ Example 138

3-{2-[3-(4-Benzylpiperazin-1-yl)-azetidin-1-yl]-2-oxo-1-phenylethyl}-5-chloro-1-(4-methoxybenzene-sulfonyl)-1,3-dihydrobenzimidazol-2-one 450 mg (1.36 mmol) of tert-butyl 3-(4-benzylpiperazin-1-yl)azetidine-1-carboxylate (XXIe) were dissolved in dichloromethane (8 ml) and, while stirring at room temperature, trifluoroacetic acid (8 ml) was added. The reaction solution was stirred for 2 h and then the solvent and excess trifluoroacetic acid were removed in vacuo. The residue was taken up again in toluene, concentrated in vacuo and then dried in vacuo. 286 mg (1.49 mmol) of EDCl were added to a solution of 642 mg (1.36 mmol) of 6-chloro-3-(4-methoxybenzenesulfonyl)-2-oxo-2,3-dihydrobenzimidazol-1-yl]phenylacetic acid (XIIIa), 276 mg (2.03 mmol) of HOBt, the residue obtained above, and 2.13 ml (12.2 mmol) of ethyldiisopropylamine in 50 ml of dichloromethane while cooling in ice.
The reaction solution was slowly warmed and stirred at room temperature for 16 h. Half-saturated aqueous sodium bicarbonate solution was added, and the aqueous phase was extracted with ethyl acetate (4×50 ml). The combined organic phases were washed with sat. NaHCO3 solution, dried over magnesium sulfate and concentrated under reduced pressure. The residue was purified by chromatography on silica gel (mobile phase gradient 1-5% methanol in dichloromethane). Yield: 500 g (54%) of colorless oil
MS (API-ES, pos) m/z=686, 688 [M+H]$^+$ Example 139

3-{2-[3-(4-Benzylpiperazin-1-yl)piperidin-1-yl]-2-oxo-1-phenylethyl}-5-chloro-1-(4-methoxybenzene-sulfonyl)-1,3-dihydrobenzimidazol-2-one was prepared in an analogous manner to that described in Example 138 from compounds XIIIa and XXIc.
$^1$H-NMR (methanol-d4): 1.25-4.32 (m, 22H), 6.34-6.63 (m, 2H), 7.07-7.54 (m, 13H), 7.82-7.91 (m, 1H), 7.97-8.08 (m, 2H).
MS (API-ES, pos) m/z=357, 358 [M+H/2]$^+$ Example 140

3-{2-[(S)-3-(4-Benzylpiperazin-1-yl)pyrrolidin-1-yl]-2-oxo-1-phenylethyl}-5-chloro-1-(4-methoxy-benzenesulfonyl)-1,3-dihydrobenzimidazol-2-one was prepared in an analogous manner to that described in Example 138 from compounds XIIIa and XXIb.
$^1$H-NMR (methanol-d4): 1.75-1.99 (m, 1H), 2.07-2.21 (m, 1H), 2.25-3.88 (m, 13H), 3.89 (s, 3H), 4.25-4.34 (m, 2H), 6.34-6.45 (m, 1H), 6.52-6.61 (m, 1H), 7.06-7.25 (m, 5H), 7.34-7.44 (m, 3H), 7.45-7.54 (m, 5H), 7.83-7.88 (m, 1H), 7.97-8.05 (m, 2H).
MS (API-ES, pos) m/z=700, 702 [M+H]$^+$ Example 141

3-{2-[3-(4-Benzylpiperazin-1-yl)-pyrrolidin-1-yl]-2-oxo-1-phenylethyl}-5-chloro-1-(4-methoxybenzene-sulfonyl)-1,3-dihydrobenzimidazol-2-one was prepared in an analogous manner to that described in Example 138 from compounds XIIIa and XXId.
$^1$H-NMR (methanol-d4): 1.76-1.98 (m, 1H), 2.08-2.21 (m, 1H), 2.28-3.87 (m, 13H), 3.89 (s, 3H), 4.25-4.33 (m, 2H), 6.35-6.45 (m, 1H), 6.52-6.60 (m, 1H), 7.07-7.14 (m, 3H), 7.15-7.24 (m, 2H), 7.34-7.43 (m, 3H), 7.46-7.53 (m, 5H), 7.83-7.88 (m, 1H), 7.98-8.05 (m, 2H).
MS (API-ES, pos) m/z=700, 702 [M+H]$^+$

Example 142

3-{2-[(R)-3-(4-Benzylpiperazin-1-yl)-pyrrolidin-1-yl]-2-oxo-1-phenylethyl}-5-chloro-1-(4-methoxy-benzenesulfonyl)-1,3-dihydrobenzimidazol-2-on was prepared in an analogous manner to that described in Example 138 from compounds XIIIa and XXIa.

$^1$H-NMR (methanol-d4): 1.76-1.98 (m, 1H), 2.08-2.21 (m, 1H), 2.28-3.87 (m, 13H), 3.89 (s, 3H), 4.25-4.33 (m, 2H), 6.35-6.45 (m, 1H), 6.52-6.60 (m, 1H), 7.07-7.14 (m, 3H), 7.15-7.24 (m, 2H), 7.34-7.43 (m, 3H), 7.46-7.53 (m, 5H), 7.83-7.88 (m, 1H), 7.98-8.05 (m, 2H).

MS (API-ES, pos) m/z=700, 702 [M+H]$^+$

Example 143

3-{2-[(S)-3-(4-Benzylpiperazin-1-yl)-pyrrolidin-1-yl]-2-oxo-1-phenylethyl}-1-(4-methoxybenzene-sulfonyl)-2-oxo-2,3-dihydro-1H-benzimidazole-5-carbonitrile A mixture of [6-cyano-3-(4-methoxy-benzenesulfonyl)-2-oxo-2,3-dihydrobenzoimidazol-1-yl]-phenyl-acetic acid XIIIc (200 mg, 0.43 mmol), 1-hydroxybenzotriazole (88 mg, 0.65 mmol) and PS-carbodiimide resin (Argonaut; 1.18 mmol/g; 439 mg, 0.52 mmol) in CH$_2$Cl$_2$ (5 mL) was agitated for 10 min at room temperature. Then, 1-benzyl-4-(S)-pyrrolidin-3-yl-piperazine (166 mg, 0.47 mmol) was added and the reaction mixture was agitated at room temperature overnight. To this mixture MP-carbonate resin (Argonaut; 2.69 mmol/g; 481 mg, 1.29 mmol) was added and the reaction mixture was agitated for another 2 hours, filtered and concentrated in vacuo. The residue was purified by flash chromatography on silica gel using 5% MeOH in CH$_2$Cl$_2$ as eluent to afford 3-{2-[(S)-3-(4-benzyl-piperazin-1-yl)-pyrrolidin-1-yl]-2-oxo-1-phenyl-ethyl}-1-(4-methoxy-benzenesulfonyl)-2-oxo-2,3-dihydro-1H-benzoimidazole-5-carbonitrile (135 mg, 45%) as a white solid.

$^1$H-NMR (methanol-d4): 1.77-2.01 (m, 1H), 2.08-2.22 (m, 1H), 2.34-3.95 (m, 13H), 3.89 (s, 3H), 3.91 (s, 3H), 4.25-4.33 (m, 2H), 6.40-6.51 (m, 1H), 6.74-6.83 (m, 1H), 7.09-7.16 (m, 2H), 7.21-7.32 (m, 2H), 7.46-7.53 (m, 9H), 8.02-8.08 (m, 3H).

MS (API-ES, pos) m/z=691 [M+H]$^+$

Example 144

3-{2-[(R)-3-(4-Benzylpiperazin-1-yl)-pyrrolidin-1-yl]-2-oxo-1-phenylethyl}-1-(4-methoxybenzene-sulfonyl)-2-oxo-2,3-dihydro-1H-benzimidazole-5-carbonitrile was prepared in an analogous manner to that described in Example 138 from compounds XIIIc and XXIa.

$^1$H-NMR (methanol-d4): 1.77-2.01 (m, 1H), 2.08-2.22 (m, 1H), 2.34-3.95 (m, 13H), 3.89 (s, 3H), 3.91 (s, 3H), 4.25-4.33 (m, 2H), 6.40-6.51 (m, 1H), 6.74-6.83 (m, 1H), 7.09-7.16 (m, 2H), 7.21-7.32 (m, 2H), 7.46-7.53 (m, 9H), 8.02-8.08 (m, 3H).

MS (API-ES, pos) m/z=691 [M+H]$^+$

Example 145

5-Chloro-1-(4-methoxybenzenesulfonyl)-3-[2-oxo-1-phenyl-2-((R)-3-piperazin-1-yl-pyrrolidin-1-yl)-ethyl]-1,3-dihydrobenzimidazol-2-one 118 mg (0.82 mmol) of 1-chloroethyl chloroformate were added to a solution of 550 mg (0.79 mmol) of 3-{2-[(R)-3-(4-benzylpiperazin-1-yl)-pyrrolidin-1-yl]-2-oxo-1-phenylethyl}-5-chloro-1-(4-methoxybenzenesulfonyl)-1,3-dihydrobenzimidazol-2-one (Example 142) in 5 ml dry dichloromethane while stirring at 0° C. The reaction mixture was subsequently stirred at 0° C. for 1 h and then at room temperature overnight. The solvent was removed in vacuo, and the residue was dissolved in 20 ml of methanol. The methanolic solution was stirred at 60° C. for 1 h and then concentrated under reduced pressure. The residue was dissolved in dichloromethane, mixed with 3 eq. of MP-carbonate (Argonaut, 1.69 mmol/g) and stirred at room temperature for 2 h. The solid phase reagent was filtered off and washed with dichloromethane. The filtrate was concentrated under reduced pressure and dried in vacuo. The residue was purified by chromatography on silica gel (mobile phase gradient 4-7% 1N ammoniacal methanol in dichloromethane) or by HPLC as described above. Yield: 231 mg (48%) of colorless solid $^1$H-NMR (methanol-d4): 1.77-1.98 (m, 1H), 2.08-2.22 (m, 1H), 2.52-2.82 (m, 4H), 2.93-3.92 (m, 9H), 3.90 (s, 3H), 6.35-6.47 (m, 1H), 6.52-6.61 (m, 1H), 7.07-7.14 (m, 3H), 7.14-7.26 (m, 2H), 7.35-7.46 (m, 3H), 7.82-7.88 (m, 1H), 7.96-8.04 (m, 2H).

MS (API-ES, pos) m/z=610, 612 [M+H]$^+$

Example 146

5-Chloro-1-(4-methoxybenzenesulfonyl)-3-[2-oxo-1-phenyl-2-(3-piperazin-1-ylpyrrolidin-1-yl)-ethyl]-1,3-dihydrobenzimidazol-2-one was prepared in an analogous manner to that described in example 145 from example 141.

$^1$H-NMR (methanol-d4): 1.77-1.98 (m, 1H), 2.08-2.22 (m, 1H), 2.52-2.82 (m, 4H), 2.93-3.92 (m, 9H), 3.90 (s, 3H), 6.35-6.47 (m, 1H), 6.52-6.61 (m, 1H), 7.07-7.14 (m, 3H), 7.14-7.26 (m, 2H), 7.35-7.46 (m, 3H), 7.82-7.88 (m, 1H), 7.96-8.04 (m, 2H).

MS (API-ES, pos) m/z=610, 612 [M+H]$^+$

Example 147

5-Chloro-1-(4-methoxybenzenesulfonyl)-3-[2-oxo-1-phenyl-2-(3-piperazin-1-ylpiperidin-1-yl)ethyl]-1,3-dihydrobenzimidazol-2-one was prepared in an analogous manner to that described in example 145 from example 139.

$^1$H-NMR (DMSO-d$_6$): 0.88-2.98 (m, 14H), 3.35-4.38 (m, 3H), 3.87 (s, 3H), 6.41-8.02 (m, 13H).

MS (API-ES, pos) m/z=624, 626 [M+H]$^+$

Example 148

5-Chloro-1-(4-methoxybenzenesulfonyl)-3-[2-oxo-1-phenyl-2-(3-piperazin-1-ylazetidin-1-yl)ethyl]-1,3-dihydrobenzimidazol-2-one was prepared in an analogous manner to that described in example 145 from example 138.

$^1$H-NMR (methanol-d4): 2.50-2.65 (m, 4H), 3.18-3.26 (m, 4H), 3.74-4.21 (m, 5H), 3.90 (s, 3H), 6.25 (s, 1H), 6.70 (s, 1H), 7.08-7.15 (m, 3H), 7.17-7.24 (m, 2H), 7.35-7.42 (m, 3H), 7.87 (d, 8.7 Hz, 1H), 7.98-8.05 (m, 2H).

MS (API-ES, pos) m/z=596, 598 [M+H]$^+$

Example 149

5-Chloro-1-(4-methoxybenzenesulfonyl)-3-[2-oxo-1-phenyl-2-((S)-3-piperazin-1-ylpyrrolidin-1-yl)ethyl]-1,3-dihydrobenzimidazol-2-one was prepared in an analogous manner to that described in example 145 from example 140.
$^1$H-NMR (methanol-d4): 1.77-1.98 (m, 1H), 2.08-2.22 (m, 1H), 2.52-2.82 (m, 4H), 2.93-3.92 (m, 9H), 3.90 (s, 3H), 6.36-6.48 (m, 1H), 6.53-6.62 (m, 1H), 7.07-7.25 (m, 5H), 7.35-7.46 (m, 3H), 7.82-7.88 (m, 1H), 7.97-8.04 (m, 2H).
MS (API-ES, pos) m/z=610, 612 [M+H]$^+$

Example 150

1-(4-Methoxybenzenesulfonyl)-2-oxo-3-[2-oxo-1-phenyl-2-((S)-3-piperazin-1-ylpyrrolidin-1-yl)ethyl]-2,3-dihydro-1H-benzimidazole-5-carbonitrile To a chilled solution of 3-{2-[(S)-3-(4-benzyl-piperazin-1-yl)-pyrrolidin-1-yl]-2-oxo-1-phenyl-ethyl}-1-(4-methoxy-benzenesulfonyl)-2-oxo-2,3-dihydro-1H-benzoimidazole-5-carbonitrile (135 mg, 0.19 mmol) in CH$_2$Cl$_2$ (3 mL) 1-chloroethyl chloroformate (0.03 mL, 0.23 mmol) was added. The reaction mixture was stirred at 0° C. for 1 hour, at room temperature for 2 hours, concentrated in vacuo and dissolved in MeOH (6 mL). Then, the reaction mixture was stirred at 60° C. for 1 hour and concentrated in vacuo. The residue was purified by preparative RP-HPLC (eluent: gradient from 10% to 80% acetonitrile in water, 0.1 trifluoroacetic acid as modulator) to afford 1-(4-methoxy-benzenesulfonyl)-2-oxo-3-[2-oxo-1-phenyl-2-((S)-3-piperazin-1-yl-pyrrolidin-1-yl)-ethyl]-2,3-dihydro-1H-benzoimidazole-5-carbonitrile; compound with trifluoroacetic acid (66 mg, 58%) as a white solid.
$^1$H-NMR (400 MHz, DMSO-d$_6$): δ 1.70 (m, 1H), 2.06 (m, 1H), 2.59-2.77 (m, 3H), 2.93-3.84 (m, 10H), 3.88 (s, 3H), 6.35-6.43 (m, 1H), 6.90-7.05 (m, 1H), 7.20 (d, 8.8 Hz, 2H), 7.21-7.27 (m, 2H), 7.39 (m, 3H), 7.62 (m, 1H), 7.95-8.02 (m, 3H).
MS (API-ES, pos) m/z=601 [M+H]$^+$

Example 151

1-(4-Methoxybenzenesulfonyl)-2-oxo-3-[2-oxo-1-phenyl-2-((R)-3-piperazin-1-ylpyrrolidin-1-yl)ethyl]-2,3-dihydro-1H-benzimidazole-5-carbonitrile was prepared in an analogous manner to that described in example 145 from example 144.
$^1$H-NMR (methanol-d4): 1.78-1.99 (m, 1H), 2.10-2.23 (m, 1H), 2.53-2.83 (m, 4H), 2.95-3.57 (m, 8H), 3.71-3.98 (m, 1H), 3.90 (s, 3H), 6.42-6.52 (m, 1H), 6.76-6.85 (m, 1H), 7.09-7.16 (m, 2H), 7.22-7.32 (m, 2H), 7.38-7.51 (m, 4H), 8.02-8.08 (m, 3H).
MS (API-ES, pos) m/z=601 [M+H]$^+$

Example 152

5-Chloro-3-{2-[(S)-3-(4-ethylpiperazin-1-yl)pyrrolidin-1-yl]-2-oxo-1-phenylethyl}-1-(4-methoxybenzenesulfonyl)-1,3-dihydrobenzimidazol-2-one A solution of 99.0 mg (0.16 mmol) of 5-chloro-1-(4-methoxybenzenesulfonyl)-3-[2-oxo-1-phenyl-2-((S)-3-piperazin-1-yl-pyrrolidin-1-yl)ethyl]-1,3-dihydrobenzimidazol-2-one (example 149) in 4 ml of THF was mixed with 7.15 mg (0.16 mmol) of acetaldehyde and 160 mg of MP-triacetoxyborohydride resin (Argonaut, 2.55 mmol/g, 0.41 mmol) and shaken at room temperature overnight. The solid phase reagent was filtered off and washed with dichloromethane. The filtrate was concentrated under reduced pressure. The residue was purified by preparative RP-HPLC (mobile phase: gradient from 10% to 80% acetonitrile in water, 0.1% trifluoroacetic acid as modulator). Yield: 38.6 mg (38%) of colorless solid
$^1$H-NMR (methanol-d4): 1.27-1.39 (m, 3H), 1.75-1.98 (m, 1H), 2.07-2.22 (m, 1H), 2.25-3.88 (m, 15H), 3.90 (s, 3H), 6.36-6.47 (m, 1H), 6.53-6.61 (m, 1H), 7.06-7.14 (m, 3H), 7.15-7.25 (m, 2H), 7.34-7.45 (m, 3H), 7.82-7.88 (m, 1H), 7.98-8.06 (m, 2H).
MS (API-ES, pos) m/z=638, 640 [M+H]$^+$

Example 153

5-Chloro-1-(4-methoxybenzenesulfonyl)-3-{2-[(S)-3-(4-methylpiperazin-1-yl)pyrrolidin-1-yl]-2-oxo-1-phenylethyl}-1,3-dihydrobenzimidazol-2-one was prepared in an analogous manner to that described in example 152 from example 149.
$^1$H-NMR (methanol-d4): 1.76-1.99 (m, 1H), 2.07-2.22 (m, 1H), 2.23-2.82 (m, 2H), 2.83-3.91 (m, 14H), 3.90 (s, 3H), 6.36-6.47 (m, 1H), 6.53-6.62 (m, 1H), 7.07-7.15 (m, 3H), 7.15-7.26 (m, 2H), 7.35-7.44 (m, 3H), 7.82-7.89 (m, 1H), 7.98-8.05 (m, 2H).
MS (API-ES, pos) m/z=624, 626 [M+H]$^+$

Example 154

5-Chloro-1-(4-methoxybenzenesulfonyl)-3-{2-oxo-1-phenyl-2-[3-(4-propylpiperazin-1-yl)azetidin-1-yl]ethyl}-1,3-dihydrobenzimidazol-2-one was prepared in an analogous manner to that described in example 152 from example 148.
$^1$H-NMR (methanol-d4): 0.98-1.05 (m, 3H), 1.69-1.82 (m, 2H), 2.19-2.36 (m, 2H), 2.85-3.14 (m, 6H), 3.46-3.61 (m, 2H), 3.74-4.22 (m, 5H), 3.90 (s, 3H), 6.25 (s, 1H), 6.69 (s, 1H), 7.08-7.15 (m, 3H), 7.17-7.24 (m, 2H), 7.34-7.42 (m, 3H), 7.87 (d, 8.7 Hz, 1H), 7.98-8.05 (m, 2H).
MS (API-ES, pos) m/z=638, 640 [M+H]$^+$

Example 155

5-Chloro-1-(4-methoxybenzenesulfonyl)-3-{2-oxo-1-phenyl-2-[3-(4-propylpiperazin-1-yl)piperidin-1-yl]ethyl}-1,3-dihydrobenzimidazol-2-one was prepared in an analogous manner to that described in example 152 from example 147.
$^1$H-NMR (methanol-d4): 0.97-1.07 (m, 3H), 1.25-4.30 (m, 21H), 3.88-3.92 (m, 3H), 6.34-6.65 (m, 2H), 7.07-7.48 (m, 8H), 7.82-7.91 (m, 1H), 7.97-8.06 (m, 2H).
MS (API-ES, pos) m/z=666, 668 [M+H]$^+$

Example 156

5-Chloro-1-(4-methoxybenzenesulfonyl)-3-{2-[3-(4-methylpiperazin-1-yl)piperidin-1-yl]-2-oxo-1-phenylethyl}-1,3-dihydrobenzimidazol-2-one was prepared in an analogous manner to that described in example 152 from example 147.
$^1$H-NMR (methanol-d4): 1.25-4.51 (m, 20H), 3.87-3.93 (m, 3H), 6.32-6.64 (m, 2H), 7.07-7.48 (m, 8H), 7.82-7.91 (m, 1H), 7.97-8.06 (m, 2H).
MS (API-ES, pos) m/z=638, 640 [M+H]$^+$

Example 157

5-Chloro-1-(4-methoxybenzenesulfonyl)-3-{2-oxo-1-phenyl-2-[(R)-3-(4-propylpiperazin-1-yl)pyrrolidin-1-yl]ethyl}-1,3-dihydrobenzimidazol-2-one was prepared in an analogous manner to that described in example 152 from example 145.
$^1$H-NMR (methanol-d4): 0.97-1.06 (m, 3H), 1.68-1.99 (m, 3H), 2.08-2.21 (m, 1H), 1.66-3.86 (m, 15H), 3.90 (s, 3H), 6.35-6.48 (m, 1H), 6.53-6.62 (m, 1H), 7.07-7.15 (m, 3H), 7.15-7.26 (m, 2H), 7.35-7.44 (m, 3H), 7.83-7.89 (m, 1H), 7.98-8.05 (m, 2H).
MS (API-ES, pos) m/z=652, 654 [M+H]$^+$

Example 158

5-Chloro-1-(4-methoxybenzenesulfonyl)-3-{2-oxo-1-phenyl-2-[(S)-3-(4-propylpiperazin-1-yl)pyrrolidin-1-yl]ethyl}-1,3-dihydrobenzimidazol-2-one was prepared in an analogous manner to that described in example 152 from example 149.
$^1$H-NMR (DMSO-d$_6$): 0.77-0.87 (m, 3H), 1.32-1.45 (m, 2H), 1.49-1.69 (m, 1H), 1.86-2.83 (m, 12H), 2.96-3.12 (m, 1H), 3.16-3.74 (m, 3H), 3.87 (s, 3H), 6.27-6.42 (m, 1H), 6.64-6.75 (m, 1H), 7.12-7.24 (m, 5H), 7.32-7.43 (m, 3H), 7.71-7.84 (m, 1H), 7.94-8.02 (m, 2H).
MS (API-ES, pos) m/z=652, 654 [M+H]$^+$

Example 159

5-Chloro-1-(4-methoxybenzenesulfonyl)-3-{2-[(R)-3-(4-methylpiperazin-1-yl)pyrrolidin-1-yl]-2-oxo-1-phenylethyl}-1,3-dihydrobenzimidazol-2-one was prepared in an analogous manner to that described in example 152 from example 145.
$^1$H-NMR (methanol-d4): 1.76-1.99 (m, 1H), 2.07-2.22 (m, 1H), 2.23-2.76 (m, 2H), 2.84-3.91 (m, 14H), 3.90 (s, 3H), 6.36-6.47 (m, 1H), 6.53-6.62 (m, 1H), 7.07-7.15 (m, 3H), 7.15-7.26 (m, 2H), 7.35-7.44 (m, 3H), 7.82-7.89 (m, 1H), 7.98-8.05 (m, 2H).
MS (API-ES, pos) m/z=624, 626 [M+H]$^+$

Example 160

1-(4-Methoxybenzenesulfonyl)-3-{2-[(S)-3-(4-methylpiperazin-1-yl)-pyrrolidin-1-yl]-2-oxo-1-phenylethyl}-2-oxo-2,3-dihydro-1H-benzimidazole-5-carbonitrile was prepared in an analogous manner to that described in example 152 from example 150.
$^1$H-NMR (methanol-d4): 1.77-2.00 (m, 1H), 2.08-2.22 (m, 1H), 2.24-2.75 (m, 2H), 2.84-3.95 (m, 14H), 3.91 (s, 3H), 6.42-6.51 (m, 1H), 6.76-6.85 (m, 1H), 7.10-7.16 (m, 2H), 7.22-7.31 (m, 2H), 7.39-7.50 (m, 4H), 8.02-8.09 (m, 3H).
MS (API-ES, pos) m/z=615 [M+H]$^+$

Example 161

1-(4-Methoxybenzenesulfonyl)-2-oxo-3-{2-oxo-1-phenyl-2-[(S)-3-(4-propylpiperazin-1-yl)pyrrolidin-1-yl]ethyl}-2,3-dihydro-1H-benzimidazole-5-carbonitrile was prepared in an analogous manner to that described in example 152 from example 150.
$^1$H-NMR (methanol-d4): 0.96-1.05 (m, 3H), 1.67-2.00 (m, 3H), 2.10-2.22 (m, 1H), 2.28-3.94 (m, 15H), 3.91 (s, 3H), 6.42-6.51 (m, 1H), 6.76-6.85 (m, 1H), 7.10-7.17 (m, 2H), 7.22-7.33 (m, 2H), 7.38-7.51 (m, 4H), 8.02-8.09 (m, 3H).
MS (API-ES, pos) m/z=643 [M+H]$^+$

Example 162

1-(4-Methoxybenzenesulfonyl)-3-{2-[(R)-3-(4-methylpiperazin-1-yl)-pyrrolidin-1-yl]-2-oxo-1-phenylethyl}-2-oxo-2,3-dihydro-1H-benzimidazole-5-carbonitrile was prepared in an analogous manner to that described in example 152 from example 151.
$^1$H-NMR (methanol-d4): 1.77-2.00 (m, 1H), 2.08-2.22 (m, 1H), 2.24-2.75 (m, 2H), 2.84-3.95 (m, 14H), 3.91 (s, 3H), 6.42-6.51 (m, 1H), 6.76-6.85 (m, 1H), 7.10-7.16 (m, 2H), 7.22-7.31 (m, 2H), 7.39-7.50 (m, 4H), 8.02-8.09 (m, 3H).
MS (API-ES, pos) m/z=615 [M+H]$^+$

Example 163

1-(4-Methoxybenzenesulfonyl)-2-oxo-3-{2-oxo-1-phenyl-2-[(R)-3-(4-propylpiperazin-1-yl)pyrrolidin-1-yl]ethyl}-2,3-dihydro-1H-benzimidazole-5-carbonitrile was prepared in an analogous manner to that described in example 152 from example 151.
$^1$H-NMR (methanol-d4): 0.96-1.05 (m, 3H), 1.67-2.00 (m, 3H), 2.10-2.22 (m, 1H), 2.28-3.94 (m, 15H), 3.91 (s, 3H), 6.42-6.51 (m, 1H), 6.76-6.85 (m, 1H), 7.10-7.17 (m, 2H), 7.22-7.33 (m, 2H), 7.38-7.51 (m, 4H), 8.02-8.09 (m, 3H).
MS (API-ES, pos) m/z=643 [M+H]$^+$

Example 164

3-[2-(3-Aminoazetidin-1-yl)-2-oxo-1-phenylethyl]-5-chloro-1-(4-methoxybenzenesulfonyl)-1,3-dihydrobenzimidazol-2-one 89.0 mg (0.19 mmol) of 6-chloro-3-(4-methoxybenzenesulfonyl)-2-oxo-2,3-dihydrobenzimidazol-1-yl]phenylacetic acid (XIIIa), 30.7 mg (0.23 mmol) of HOBt and 166 mg (0.22 mmol) of solid phase-bound PS-carbodiimide (Argonaut, 1.3 mmol/g) were dissolved in 5 ml of dry dichloromethane in a screw-cap tube and shaken mechanically at room temperature for 10 min. 35.7.0 mg (0.21 mmol) of tert-butyl 3-aminoazetidine-1-carboxylate were added, and the mixture was then shaken mechanically overnight. Three equivalents of solid phase-bound MP-carbonate were then added to the reaction mixture, and shaking was continued for 2 h. The solid phase-bound reagents were filtered off and washed with dichloromethane. The filtrate was concentrated in vacuo, and the residue was dissolved in 3 ml of dichloromethane, mixed with 3 ml of trifluoroacetic acid and stirred at room temperature for 2 h. The solvent and excess trifluoroacetic acid were removed in vacuo, and the residue was taken up again in toluene and concentrated in vacuo. The residue was dissolved in dichloromethane, mixed with 3 eq. of MP-carbonate (Argonaut, 1.69 mmol/g) and stirred at room temperature for 2 h. The solid phase reagent was filtered off and washed with dichloromethane. The filtrate was concentrated under reduced pressure and dried in vacuo. The residue was purified by chromatography on silica gel (mobile phase gradient 2-4% 1N ammoniacal methanol in dichloromethane). Yield: 15 mg (15%) of colorless solid ¹H-NMR (methanol-d4): 3.54-4.34 (m, 5H), 3.90 (s, 3H), 6.23 (s, 1H), 6.73 (s, 1H), 7.08-7.16 (m, 3H), 7.18-7.26 (m, 2H), 7.32-7.42 (m, 3H), 7.87 (d, J=8.7 Hz, 1H), 8.01 (d, J=7.8 Hz, 2H).

MS (API-ES, pos) m/z=527, 529 [M+H]⁺

Example 165

5-Chloro-1-(4-methoxybenzenesulfonyl)-3-[2-oxo-1-phenyl-2-(4-piperidin-3-ylpiperazin-1-yl)ethyl]-1,3-dihydrobenzimidazol-2-one was prepared in an analogous manner to that described in example 164 using tert-butyl 3-piperazin-1-ylpiperidine-1-carboxylate. Purification was achieved by HPLC as described above.

¹H-NMR (methanol-d4): 1.62-1.77 (m, 2H), 1.90-2.06 (m, 2H), 2.51-2.86 (m, 5H), 2.92-3.14 (m, 2H), 3.22-3.40 (m, 2H), 3.47-3.58 (m, 1H), 3.61-3.70 (m, 1H), 3.77-3.85 (m, 1H), 3.90 (s, 3H), 6.54 (s, 1H), 6.60 (s, 1H), 7.08-7.14 (m, 3H), 7.19-7.25 (m, 2H), 7.37-7.44 (m, 3H), 7.86 (d, 8.7 Hz, 1H), 8.02 (d, 8.7 Hz, 2H).

MS (API-ES, pos) m/z=624, 626 [M+H]⁺

Example 166

3-[2-(3-Aminopyrrolidin-1-yl)-2-oxo-1-phenyl-ethyl]-5-chloro-1-(4-methoxybenzenesulfonyl)-1,3-dihydrobenzimidazol-2-one was prepared in an analogous manner to that described in example 164.

¹H-NMR (DMSO-d₆): 1.46-1.61 (m, 1H), 1.78-1.96 (m, 3H), 2.68-3.62 (m, 3H), 3.87 (s, 3H), 6.26-6.34 (m, 1H), 6.64-6.70 (m, 1H), 7.14-7.24 (m, 5H), 7.32-7.40 (m, 3H), 7.81 (d, 8.7 Hz, 1H), 7.95-8.02 (m, 2H).

MS (API-ES, pos) m/z=541, 543 [M+H]⁺

Example 167

3-[2-(3-Aminopiperidin-1-yl)-2-oxo-1-phenylethyl]-5-chloro-1-(4-methoxybenzenesulfonyl)-1,3-dihydrobenzimidazol-2-one was prepared in an analogous manner to that described in example 164. Purification was achieved by HPLC as described above.

¹H-NMR (methanol-d4): 1.31-2.22 (m, 4H), 2.73-2.98 (m, 1H), 3.07-4.78 (m, 4H), 3.90 (s, 3H), 6.34-6.62 (m, 2H), 7.06-7.15 (m, 3H), 7.16-7.28 (m, 2H), 7.36-7.48 (m, 3H), 7.83-7.90 (m, 1H), 7.98-8.06 (m, 2H).

MS (API-ES, pos) m/z=555, 557 [M+H]⁺

Example 168

3-[2-((S)-3-Aminopyrrolidin-1-yl)-2-oxo-1-phenyl-ethyl]-5-chloro-1-(4-methoxybenzenesulfonyl)-1,3-dihydrobenzimidazol-2-one was prepared in an analogous manner to that described in example 164.

¹H-NMR (methanol-d4): 1.94-2.16 (m, 1H), 2.31-2.44 (m, 1H), 3.18-3.99 (m, 5H), 3.90 (s, 3H), 6.37-6.47 (m, 1H), 6.52-6.64 (m, 1H), 7.07-7.16 (m, 3H), 7.18-7.28 (m, 2H), 7.36-7.47 (m, 3H), 7.87 (d, 8.7 Hz, 1H), 8.02 (d, 8.3 Hz, 2H).

MS (API-ES, pos) m/z=541, 543 [M+H]⁺

Example 169

3-[2-((R)-3-Aminopyrrolidin-1-yl)-2-oxo-1-phenyl-ethyl]-5-chloro-1-(4-methoxybenzenesulfonyl)-1,3-dihydrobenzimidazol-2-one was prepared in an analogous manner to that described in example 164.

¹H-NMR (methanol-d4): 1.95-2.17 (m, 1H), 2.31-2.44 (m, 1H), 3.40-3.84 (m, 3H), 3.88-3.98 (m, 2H), 3.90 (s, 3H), 6.37-6.47 (m, 1H), 6.53-6.64 (m, 1H), 7.08-7.15 (m, 3H), 7.19-7.28 (m, 2H), 7.36-7.46 (m, 3H), 7.83-7.89 (m, 1H), 7.98-8.05 (m, 2H).

MS (API-ES, pos) m/z=541, 543 [M+H]⁺

Example 170

3-[2-(3-Aminopiperidin-1-yl)-2-oxo-1-phenylethyl]-1-(4-methoxybenzenesulfonyl)-2-oxo-2,3-dihydro-1H-benzimidazole-5-carbonitrile was prepared in an analogous manner to that described in example 164.

¹H-NMR (methanol-d4): 1.33-2.24 (m, 4H), 2.73-2.97 (m, 1H), 3.06-4.78 (m, 4H), 3.91 (s, 3H), 6.62-6.83 (m, 2H), 7.11-7.16 (m, 2H), 7.22-7.35 (m, 2H), 7.40-7.51 (m, 4H), 8.03-8.09 (m, 3H).

MS (API-ES, pos) m/z=546 [M+H]⁺

Example 171

3-[2-((S)-3-Aminopyrrolidin-1-yl)-2-oxo-1-phenyl-ethyl]-1-(4-methoxybenzenesulfonyl)-2-oxo-2,3-dihydro-1H-benzimidazole-5-carbonitrile was prepared in an analogous manner to that described in example 164.

¹H-NMR (methanol-d4): 1.96-2.16 (m, 1H), 2.31-2.45 (m, 1H), 3.16-4.00 (m, 5H), 3.91 (s, 3H), 6.43-6.52 (m, 1H), 6.78-6.87 (m, 1H), 7.09-7.16 (m, 2H), 7.25-7.34 (m, 2H), 7.39-7.52 (m, 4H), 8.02-8.09 (m, 3H).

MS (API-ES, pos) m/z=532 [M+H]⁺

Example 172

3-[2-((R)-3-Aminopyrrolidin-1-yl)-2-oxo-1-phenyl-ethyl]-1-(4-methoxybenzenesulfonyl)-2-oxo-2,3-dihydro-1H-benzimidazole-5-carbonitrile was prepared in an analogous manner to that described in example 164.

¹H-NMR (methanol-d4): 1.96-2.16 (m, 1H), 2.31-2.45 (m, 1H), 3.16-4.00 (m, 5H), 3.91 (s, 3H), 6.43-6.52 (m, 1H), 6.78-6.87 (m, 1H), 7.09-7.16 (m, 2H), 7.25-7.34 (m, 2H), 7.39-7.52 (m, 4H), 8.02-8.09 (m, 3H).

MS (API-ES, pos) m/z=532 [M+H]⁺

Example 173

2-[6-Chloro-3-(4-methoxybenzenesulfonyl)-2-oxo-2,3-dihydrobenzimidazol-1-yl]-2-phenyl-N—(S)-pyrrolidin-3-ylacetamide was prepared in an analogous manner to that described in example 164.

¹H-NMR (methanol-d4): 1.99-2.11 (m, 2H), 2.29-2.42 (m, 2H), 3.19-3.63 (m, 4H), 3.89 (s, 3H), 4.40-4.51 (m, 1H), 6.16 (s, 1H), 6.72-6.78 (m, 1H), 7.07-7.24 (m, 5H), 7.31-7.40 (m, 3H), 7.87 (d, 8.7 Hz, 1H), 8.01 (d, 8.7 Hz, 2H).

MS (API-ES, pos) m/z=541, 543 [M+H]⁺

Example 174

2-[6-Chloro-3-(4-methoxybenzenesulfonyl)-2-oxo-2,3-dihydrobenzimidazol-1-yl]-2-phenyl-N—(R)-pyrrolidin-3-ylacetamide was prepared in an analogous manner to that described in example 164.

$^1$H-NMR (methanol-d4): 1.99-2.11 (m, 2H), 2.29-2.42 (m, 2H), 3.19-3.63 (m, 4H), 3.89 (s, 3H), 4.40-4.51 (m, 1H), 6.16 (s, 1H), 6.72-6.78 (m, 1H), 7.07-7.24 (m, 5H), 7.31-7.40 (m, 3H), 7.87 (d, 8.7 Hz, 1H), 8.01 (d, 8.7 Hz, 2H).

MS (API-ES, pos) m/z=541, 543 [M+H]$^+$

Example 175

5-Chloro-1-(4-methoxybenzenesulfonyl)-3-{2-oxo-1-phenyl-2-[3-(piperidin-4-ylamino)pyrrolidin-1-yl]ethyl}-1,3-dihydrobenzimidazol-2-one A solution of 88.0 mg (0.16 mmol) of 3-[2-(3-aminopyrrolidin-1-yl)-2-oxo-1-phenylethyl]-5-chloro-1-(4-methoxybenzenesulfonyl)-1,3-dihydrobenzimidazol-2-one (example 166) in 5 ml of THF was mixed with 34.0 mg (0.17 mmol) of 1-tertbutoxycarbonyl-4-piperidone and 162 mg of MP-triacetoxyborohydride resin (Argonaut, 2.55 mmol/g, 0.41 mmol) and shaken at room temperature overnight. The solid phase reagent was filtered off and washed with dichloromethane. The filtrate was concentrated in vacuo, and the residue was dissolved in 3 ml of dichloromethane, mixed with 3 ml of trifluoroacetic acid and stirred at room temperature for 2 h. The solvent and excess trifluoroacetic acid were removed in vacuo, and the residue was taken up again in toluene and concentrated in vacuo. The residue was dissolved in dichloromethane, mixed with 3 eq. of MP-carbonate (Argonaut, 1.69 mmol/g) and stirred at room temperature for 2 h. The solid phase reagent was filtered off and washed with dichloromethane. The filtrate was concentrated under reduced pressure and dried in vacuo. The residue was purified by preparative RP-HPLC (mobile phase: gradient from 10% to 80% acetonitrile in water, 0.1% trifluoroacetic acid as modulator). Yield: 73.0 mg (72%) of colorless solid $^1$H-NMR (methanol-d4): 1.68-2.49 (m, 6H), 2.98-3.16 (m, 2H), 3.39-3.75 (m, 5H), 3.76-3.88 (m, 1H), 3.90 (s, 3H), 4.00-4.14 (m, 2H), 6.38-6.48 (m, 1H), 6.52-6.62 (m, 1H), 7.07-7.15 (m, 3H), 7.18-7.27 (m, 2H), 7.35-7.46 (m, 3H), 7.82-7.89 (m, 1H), 7.96-8.06 (m, 2H).

MS (API-ES, pos) m/z=624, 626 [M+H]$^+$

Example 176

5-Chloro-1-(4-methoxybenzenesulfonyl)-3-{2-oxo-1-phenyl-2-[(R)-3-(piperidin-4-ylamino)pyrrolidin-1-yl]ethyl}-1,3-dihydrobenzimidazol-2-one was prepared in an analogous manner to that described in example 175 from example 169.

$^1$H-NMR (methanol-d4): 1.78-2.51 (m, 6H), 3.02-3.17 (m, 2H), 3.46-3.74 (m, 5H), 3.77-3.92 (m, 1H), 3.90 (s, 1H), 4.01-4.16 (m, 2H), 6.39-6.49 (m, 1H), 6.53-6.62 (m, 1H), 7.08-7.16 (m, 3H), 7.18-7.27 (m, 2H), 7.36-7.45 (m, 3H), 7.87 (d, 8.7 Hz, 1H), 7.98-8.04 (m, 2H).

MS (API-ES, pos) m/z=624, 626 [M+H]$^+$

Example 177

5-Chloro-1-(4-methoxybenzenesulfonyl)-3-{2-oxo-1-phenyl-2-[(S)-3-(piperidin-4-ylamino)pyrrolidin-1-yl]ethyl}-1,3-dihydrobenzimidazol-2-one was prepared in an analogous manner to that described in example 174 from example 168.

$^1$H-NMR (methanol-d4): 1.78-2.51 (m, 6H), 3.02-3.17 (m, 2H), 3.46-3.74 (m, 5H), 3.77-3.92 (m, 1H), 3.90 (s, 1H), 4.01-4.16 (m, 2H), 6.39-6.49 (m, 1H), 6.53-6.62 (m, 1H), 7.08-7.16 (m, 3H), 7.18-7.27 (m, 2H), 7.36-7.45 (m, 3H), 7.87 (d, 8.7 Hz, 1H), 7.98-8.04 (m, 2H).

MS (API-ES, pos) m/z=624, 626 [M+H]$^+$

The following compounds can be prepared in an analogous manner using the synthesis steps described in synthesis scheme 1 and 2 and using the appropriately substituted starting compounds:

Example 178

1-(4-Methoxybenzenesulfonyl)-2-oxo-3-{2-oxo-1-phenyl-2-[(R)-3-(piperidin-4-ylamino)pyrrolidin-1-yl]ethyl}-2,3-dihydro-1H-benzimidazole-5-carbonitrile

Example 179

1-(4-Methoxybenzenesulfonyl)-2-oxo-3-{2-oxo-1-phenyl-2-[(S)-3-(piperidin-4-ylamino)pyrrolidin-1-yl]ethyl}-2,3-dihydro-1H-benzimidazole-5-carbonitrile To a solution of 4-(1-{2-[6-cyano-3-(4-methoxy-benzenesulfonyl)-2-oxo-2,3-dihydrobenzoimidazol-1-yl]-2-phenyl-acetyl}-piperidin-4-ylamino]-piperidine-1-carboxylic acid tert-butyl ester (100 mg, 0.14 mmol) in CH$_2$Cl$_2$ (2 mL) trifluoroacetic acid (2 mL) was added. The reaction mixture was stirred at room temperature for 2 hours, concentrated in vacuo and co-evaporated the solvent with toluene (3×). The residue was purified by preparative RP-HPLC (eluent: gradient from 10% to 80% acetonitrile in water, 0.1% trifluoroacetic acid as modulator) to afford 1-(4-methoxybenzenesulfonyl)-2-oxo-3-{2-oxo-1-phenyl-2-[4-(piperidin-4-ylamino)-piperidin-1-yl]-ethyl}-2,3-dihydro-1H-benzoimidazole-5-carbonitrile; compound with trifluoroacetic acid (70 mg, 67%) as a white solid.

$^1$H-NMR (400 MHz, DMSO-d$_6$): δ 1.05-1.67 (m, 4H), 1.76-1.96 (m, 1H), 2.14 (m, 3H), 2.67-3.12 (m, 5H), 3.37-3.79 (m, 5H), 3.88 (s, 3H), 4.51 (m, 1H), 6.62-6-98 (m, 2H), 7.20 (d, 8.8 Hz, 2H), 7.24 (m, 1H), 7.36 (m, 1H), 7.41 (m, 3H), 7.62 (d, 8.5 Hz, 1H), 7.97 (dd, 8.5 Hz, 3.3 Hz, 1H), 8.01 (dm, 8.9 Hz, 2H).

MS (API-ES, pos) m/z=615

Example 180

5-Chloro-3-{2-[(R)-3-(4-ethylpiperazin-1-yl)pyrrolidin-1-yl]-2-oxo-1-phenylethyl}-1-(4-methoxybenzenesulfonyl)-1,3-dihydrobenzimidazol-2-one

Example 181

1-(4-Methoxybenzenesulfonyl)-3-{2-[(R)-3-(4-ethylpiperazin-1-yl)-pyrrolidin-1-yl]-2-oxo-1-phenylethyl}-2-oxo-2,3-dihydro-1H-benzimidazole-5-carbonitrile

Example 182

1-(4-Methoxybenzenesulfonyl)-3-{2-[(S)-3-(4-ethylpiperazin-1-yl)-pyrrolidin-1-yl]-2-oxo-1-phenylethyl}-2-oxo-2,3-dihydro-1H-benzimidazole-5-carbonitrile

Example 183

5-Chloro-3-{2-[(R)-3-(4-(2-propyl)piperazin-1-yl)pyrrolidin-1-yl]-2-oxo-1-phenylethyl}-1-(4-methoxybenzenesulfonyl)-1,3-dihydrobenzimidazol-2-one (R-ethyl)

Example 184

5-Chloro-3-{2-[(S)-3-(4-(2-propyl)piperazin-1-yl)pyrrolidin-1-yl]-2-oxo-1-phenylethyl}-1-(4-methoxybenzenesulfonyl)-1,3-dihydrobenzimidazol-2-one

Example 185

3-[2-((S)-3-Aminopiperidin-1-yl)-2-oxo-1-phenylethyl]-5-chloro-1-(4-methoxybenzenesulfonyl)-1,3-dihydrobenzimidazol-2-one

Example 186

3-[2-((R)-3-Aminopiperidin-1-yl)-2-oxo-1-phenylethyl]-5-chloro-1-(4-methoxybenzenesulfonyl)-1,3-dihydrobenzimidazol-2-one

Example 187

3-[2-((R)-3-Aminopiperidin-1-yl)-2-oxo-1-phenylethyl]-1-(4-methoxybenzenesulfonyl)-2-oxo-2,3-dihydro-1H-benzimidazole-5-carbonitrile

Example 188

3-[2-((S)-3-Aminopiperidin-1-yl)-2-oxo-1-phenylethyl]-1-(4-methoxybenzenesulfonyl)-2-oxo-2,3-dihydro-1H-benzimidazole-5-carbonitrile

Example 189

3-{2-[(S)-3-(4-Isopropylpiperazin-1-yl)pyrrolidin-1-yl]-2-oxo-1-phenylethyl}-1-(4-methoxybenzenesulfonyl)-2-oxo-2,3-dihydro-1H-benzimidazole-5-carbonitrile $^1$H-NMR (400 MHz, DMSO-$d_6$): δ 0.97 (br s, 6H), 1.63 (m, 1H), 1.99 (m, 1H), 2.20-2.79 (m, 10H), 2.94-3.43 (m, 3H), 3.54-3.74 (m, 1H), 3.87 (s, 3H), 6.33-6.42 (m, 1H), 6.99-7.08 (m, 1H), 7.19 (d, 8.7 Hz, 2H), 7.20-7.28 (m, 2H), 7.38 (m, 3H), 7.60-7.64 (m, 1H), 7.95-8.03 (m, 3H).
MS (API-ES, pos) m/z=643.30 [M+H]$^+$.

Example 190

3-{2-[(R)-3-(4-Isopropylpiperazin-1-yl)pyrrolidin-1-yl]-2-oxo-1-phenylethyl}-1-(4-methoxybenzenesulfonyl)-2-oxo-2,3-dihydro-1H-benzimidazole-5-carbonitrile

Example 191

1-(4-Methoxybenzenesulfonyl)-2-oxo-3-{2-oxo-1-phenyl-2-[(S)-3-(4-propylpiperazin-1-yl)piperidin-1-yl]ethyl}-2,3-dihydro-1H-benzimidazole-5-carbonitrile $^1$H-NMR (500 MHz, DMSO-$d_6$): δ 0.87 (s, 3H) [+0.91 (s, 3H) other diastereomer], 1.01-1.86 (m, 7H), 2.37-2.64 (m, 2H), 2.81-3.11 (m, 9H), 3.40-3.70 (m, 2H), 3.88 (s, 3H), 4.14-4.32 (m, 1H), 6.56-6.63 (m, 1H), 6.90-7.07 (m, 1H), 7.18-7.21 (m, 2H), 7.24-7.31 (m, 1H), 7.32-7.43 (m, 4H), 7.62 (m, 1H), 7.95-8.04 (m, 3H).
MS (API-ES, pos) m/z=657.80 [M+H]$^+$.

Example 192

1-(4-Methoxybenzenesulfonyl)-2-oxo-3-{2-oxo-1-phenyl-2-[(R)-3-(4-propylpiperazin-1-yl)piperidin-1-yl]ethyl}-2,3-dihydro-1H-benzimidazole-5-carbonitrile

Example 193

1-(4-Methoxybenzenesulfonyl)-3-{2-[(S)-3-(4-methylpiperazin-1-yl)piperidin-1-yl]-2-oxo-1-phenylethyl}-2-oxo-2,3-dihydro-1H-benzimidazole-5-carbonitrile $^1$H-NMR (400 MHz, DMSO-$d_6$): δ 0.84-1.78 (m, 7H), 2.20-2.97 (m, 11H), 3.87 (s, 3H), 3.38 (m, 1H), 4.29 (m, 1H), 6.52-6.61 (m, 1H), 6.86-7.13 (m, 1H), 7.20 (d, 8.7 Hz, 2H), 7.32-7.42 (m, 5H), 7.62 (m, 1H), 7.94-8.02 (m, 3H).
MS (API-ES, pos) m/z=629.20 [M+H]$^+$

Example 194

1-(4-Methoxybenzenesulfonyl)-3-{2-[(R)-3-(4-methylpiperazin-1-yl)piperidin-1-yl]-2-oxo-1-phenylethyl}-2-oxo-2,3-dihydro-1H-benzimidazole-5-carbonitrile

Example 195

1-(4-Methoxybenzenesulfonyl)-2-oxo-3-[2-oxo-1-phenyl-2-((S)-3-piperazin-1-ylpiperidin-1-yl)ethyl]-2,3-dihydro-1H-benzimidazole-5-carbonitrile

Example 196

1-(4-Methoxybenzenesulfonyl)-2-oxo-3-[2-oxo-1-phenyl-2-((R)-3-piperazin-1-ylpiperidin-1-yl)ethyl]-2,3-dihydro-1H-benzimidazole-5-carbonitrile

Example 197

3-{2-[(S)-3-(Azetidin-3-ylamino)piperidin-1-yl]-2-oxo-1-phenylethyl}-1-(4-methoxybenzenesulfonyl)-2-oxo-2,3-dihydro-1H-benzimidazole-5-carbonitrile

Example 198

3-{2-[(R)-3-(Azetidin-3-ylamino)piperidin-1-yl]-2-oxo-1-phenylethyl}-1-(4-methoxybenzenesulfonyl)-2-oxo-2,3-dihydro-1H-benzimidazole-5-carbonitrile

Example 199

1-(2,4-Dimethoxybenzenesulfonyl)-2-oxo-3-{2-oxo-1-phenyl-2-[(S)-3-(4-propylpiperazin-1-yl)pyrrolidin-1-yl]ethyl}-2,3-dihydro-1H-benzimidazole-5-carbonitrile To a solution of 2-oxo-3-{2-oxo-1-phenyl-2-[(S)-3-(4-propyl-piperazin-1-yl)-pyrrolidin-1-yl]-ethyl}-2,3-dihydro-1H-benzoimidazole-5-carbonitrile (32 mg, 0.07 mmol), triethylamine (0.02 mL, 0.13 mmol) and DMAP (catalytic amount) in CH$_2$Cl$_2$ (2 mL) 2,4-dimethoxybenzenesulfonyl chloride (17 mg, 0.077 mmol) was added. The reaction mixture was stirred at room temperature for 24 hours, diluted with water and extracted the aqueous phase with $CH_2Cl_2$ (3×). The combined organic phase was washed with saturated $NaHCO_3$ aqueous solution, dried over $Na_2SO_4$, filtered and concentrated in vacuo. The residue was purified by flash chromatography in silica gel using 4% methanol in $CH_2Cl_2$ as eluent to afford 1-(2,4-dimethoxybenzenesulfonyl)-2-oxo-3-{2-oxo-1-phenyl-2-[(S)-3-(4-propyl-piperazin-1-yl)-pyrrolidin-1-yl]ethyl}-2,3-dihydro-1H-benzoimidazole-5-carbonitrile (29 mg, 66%) as a white solid.

$^1$H-NMR (400 MHz, $CDCl_3$): δ 0.88-0.94 (m, 3H), 1.28 (m, 2H), 1.84 (m, 1H), 2.14 (m, 1H), 2.25-2.59 (m, 9H), 2.79-3.12 (m, 2H), 3.23-3.58 (m, 2H), 3.48 (s, 3H), 3.73-3.99 (m, 2H), 3.89 (s, 3H), 6.36-6.44 (m, 2H), 6.65 (d, 8.9 Hz, 1H), 7.00-7.10 (m, 1H), 7.22-7.26 (m, 2H), 7.34-7.39 (m, 4H), 7.94 (d, 8.5 Hz, 1H), 8.14 (d, 8.9 Hz, 1H).

MS (API-ES, pos) m/z=673

The following compounds were prepared in an analogous manner using the appropriately substituted starting compounds:

Example 200

2-oxo-3-{2-oxo-1-phenyl-2-[(S)-3-(4-propylpiperazin-1-yl)pyrrolidin-1-yl]-ethyl}-1-(quinoline-8-sulfonyl)-2,3-dihydro-1H-benzimidazole-5-carbonitrile $^1$H-NMR (400 MHz, DMSO-$d_6$): δ 0.79-0.86 (m, 3H), 1.34-1.43 (m, 2H), 1.49-1.62 (m, 1H), 1.87-2.02 (m, 1H), 2.12-2.45 (m, 10H), 2.62-2.78 (m, 1H), 2.93-3.72 (m, 4H), 6.18-6.28 (m, 1H), 6.87-6.97 (m, 2H), 7.02-7.12 (m, 1H), 7.24-7.35 (m, 3H), 7.60-7.72 (m, 2H), 7.90 (m, 1H), 8.07 (m, 1H), 8.38 (m, 1H), 8.47 (m, 1H), 8.57 (m, 1H), 8.68 (dd, 7.3 Hz, 3.0 Hz, 1H).

MS (API-ES, pos) m/z=664.15 [M+H]$^+$.

Example 201

2-oxo-3-{2-oxo-1-phenyl-2-[(S)-3-(4-propylpiperazin-1-yl)pyrrolidin-1-yl]-ethyl}-1-(thiophene-2-sulfonyl)-2,3-dihydro-1H-benzimidazole-5-carbonitrile $^1$H-NMR (400 MHz, DMSO-$d_6$): δ 0.84 (m, 3H), 1.41 (m, 2H), 1.59-1.72 (m, 1H), 2.00 (m, 1H), 2.14-2.79 (m, 10H), 2.72 (m, 1H), 2.96-3.78 (m, 4H), 6.36-6.46 (m, 1H), 7.02-7.13 (m, 1H), 7.25-7.31 (m, 3H), 7.39 (m, 3H), 7.63 (m, 1H), 7.91 (dd, 8.4 Hz, 4.9 Hz, 1H), 8.06 (m, 1H), 8.23 (dm, 4.9 Hz, 1H).

MS (API-ES, pos) m/z=619

Example 202

1-Benzenesulfonyl-2-oxo-3-{2-oxo-1-phenyl-2-[(S)-3-(4-propylpiperazin-1-yl)-pyrrolidin-1-yl]ethyl}-2,3-dihydro-1H-benzimidazole-5-carbonitrile $^1$H-NMR (500 MHz, DMSO-$d_6$): δ 0.84 (m, 3H), 1.39 (m, 2H), 1.65 (m, 1H), 1.99 (m, 1H), 2.16-2.44 (m, 10H), 2.72 (m, 1H), 2.94-3.75 (m, 4H), 6.33-6.43 (m, 1H), 6.99-7.10 (m, 1H), 7.22-7.28 (m, 2H), 7.39 (m, 3H), 7.63 (m, 1H), 7.68-7.71 (m, 2H), 7.84 (m, 1H), 7.98 (m, 1H), 8.08 (m, 2H).

MS (API-ES, pos) m/z=613

Example 203

2-oxo-3-{2-oxo-1-phenyl-2-[(S)-3-(4-propylpiperazin-1-yl)pyrrolidin-1-yl]-ethyl}-1-(thiophene-3-sulfonyl)-2,3-dihydro-1H-benzimidazole-5-carbonitrile MS (API-ES, pos) m/z=619
$^1$H-NMR (400 MHz, DMSO-$d_6$): δ 0.84 (m, 3H), 1.40 (m, 2H), 1.67 (m, 1H), 2.00 (m, 1H), 2.18-2.46 (m, 10H), 2.71 (m, 1H), 2.96-3.77 (m, 4H), 6.35-6.45 (m, 1H), 6.99-7.11 (m, 1H), 7.25-7.31 (m, 2H), 7.40 (m, 3H), 7.50-7.53 (m, 1H), 7.62 (m, 1H), 7.85 (m, 1H), 7.92 (dd, 8.4 Hz, 4.3 Hz, 1H), 8.75 (br s, 1H).

Example 204

1-(5-Methyl pyridine-2-sulfonyl)-2-oxo-3-{2-oxo-1-phenyl-2-[(S)-3-(4-propylpiperazin-1-yl)pyrrolidin-1-yl]ethyl}-2,3-dihydro-1H-benzimidazole-5-carbonitrile $^1$H-NMR (400 MHz, DMSO-$d_6$): δ 0.85 (m, 3H), 1.43 (m, 2H), 1.67 (m, 1H), 2.00 (m, 2H), 2.19-2.41 (m, 7H), 2.42 (s, 3H), 2.74 (m, 2H), 2.96-3.13 (m, 1H), 3.24-3.42 (m, 2H), 3.49-3.78 (m, 2H), 6.33-6.42 (m, 1H), 7.09-7.16 (m, 1H), 7.22-7.27 (m, 2H), 7.39-7.42 (m, 3H), 7.62 (m, 1H), 7.90 (br d, 8.4 Hz, 1H), 8.03 (br d, 7.9 Hz, 1H), 8.19 (dd, 8.0 Hz, 3.9 Hz, 1H), 8.53 (m, 1H).

MS (API-ES, pos) m/z=628

Example 205

1-(2-Methoxybenzenesulfonyl)-2-oxo-3-{2-oxo-1-phenyl-2-[(S)-3-(4-propylpiperazin-1-yl)pyrrolidin-1-yl]ethyl}-2,3-dihydro-1H-benzimidazole-5-carbonitrile To a solution of 2-oxo-3-{2-oxo-1-phenyl-2-[(S)-3-(4-propyl-piperazin-1-yl)-pyrrolidin-1-yl]-ethyl}-2,3-dihydro-1H-benzoimidazole-5-carbonitrile (70 mg, 0.15 mmol), DMAP (catalytic amount) and 2-methoxybenzenesulfonyl chloride (37 mg, 0.18 mmol) in $CH_2Cl_2$ (3 mL) SilicaBond-diethylamine resin (Silicycle; 1.04 mmol/g; 570 mg, 0.59 mmol) was added. The reaction mixture was agitated at room temperature for 24 hours, filtered and concentrated in vacuo. The residue was purified by flash chromatography on silica gel using 4% methanol in $CH_2Cl_2$ as eluent to afford 1-(2-methoxy-benzenesulfonyl)-2-oxo-3-{2-oxo-1-phenyl-2-[(S)-3-(4-propyl-piperazin-1-yl)-pyrrolidin-1-yl]ethyl}-2,3-dihydro-1H-benzoimidazole-5-carbonitrile (55 mg, 57%) as a white solid.

$^1$H-NMR (400 MHz, DMSO-$d_6$): δ 0.85 (m, 3H), 1.38 (m, 2H), 1.66 (m, 2H), 1.99 (m, 1H), 2.13-2.33 (m, 8H), 2.62-2.79 (m, 2H), 2.94-3.30 (m, 2H), 3.39 (s, 3H), 3.51-3.77 (m, 2H), 6.31-6.41 (m, 1H), 7.07-7.13 (m, 1H), 7.20-7.26 (m, 4H), 7.38-7.41 (m, 3H), 7.62 (m, 1H), 7.74-7.77 (m, 1H), 7.84 (m, 1H), 8.02 (br d, 7.7 Hz, 1H).

MS (API-ES, pos) m/z=643

Example 206

1-(4-Methoxybenzenesulfonyl)-3-{2-[4-(1-methylpiperidin-4-ylamino)piperidin-1-yl]-2-oxo-1-phenyl-ethyl}-2-oxo-2,3-dihydro-1H-benzimidazole-5-carbonitrile $^1$H-NMR (400 MHz, DMSO-$d_6$): δ 0.76-1.29 (m, 6H), 1.42-1.59 (m, 1H), 1.67-1.85 (m, 5H), 2.10 (s, 3H), 2.39 (m, 1H), 2.64-2.70 (m, 2H), 2.83-3.00 (m, 2H), 3.43-3.56 (m, 1H), 3.87 (s, 3H), 4.17 (m, 1H), 6.55-6.60 (m, 1H), 6.88-6.95 (m, 1H), 7.18-7.23 (m, 3H), 7.31 (m, 1H), 7.37-7.41 (m, 3H), 7.61 (m, 1H), 7.96 (dd, 8.4 Hz, 4.0 Hz, 1H), 8.01 (dd, 8.8 Hz, 4.9 Hz, 2H).

MS (API-ES, pos) m/z=643

Example 207

1-(4-Methoxybenzenesulfonyl)-3-{2-[(S)-3-(1-methyl piperidin-4-ylamino)-pyrrolidin-1-yl]-2-oxo-1-phenylethyl}-2-oxo-2,3-dihydro-1H-benzimidazole-5-carbonitrile To a solution of 3-[2-((S)-3-amino-pyrrolidin-1-yl)-2-oxo-1-phenyl-ethyl]-1-(4-methoxybenzenesulfonyl)-2-oxo-2,3-dihydro-1H-benzoimidazole-5-carbonitrile (Example 171, 200 mg, 0.38 mmol) and 1-methyl-4-piperidone (0.087 mL, 0.75 mmol) in THF (5 mL) MP-(OAc)$_3$BH resin (Argonaut; 2.55 mmol/g; 369 mg, 0.94 mmol) was added. The reaction mixture was agitated at room temperature for 24 hours, then filtered and concentrated in vacuo. The residue was purified by flash chromatography on silica gel using 15% methanol in CH$_2$Cl$_2$ to afford 1-(4-methoxy-benzenesulfonyl)-3-{2-[(S)-3-(1-methyl-piperidin-4-ylamino)-pyrrolidin-1-yl]-2-oxo-1-phenyl-ethyl}-2-oxo-2,3-dihydro-1H-benzoimidazole-5-carbonitrile (167 mg, 71%) as a white solid.

$^1$H-NMR (400 MHz, DMSO-d$_6$): δ 1.08-1.23 (m, 2H), 1.59-1.93 (m, 5H), 2.08-2.12 (m, 3H), 2.25-2.75 (m, 4H), 2.95-3.62 (m, 5H), 3.87 (s, 3H), 6.35 (m, 1H), 7.00 (m, 1H), 7.19 (d, 8.9 Hz, 2H), 7.24-7.29 (m, 2H), 7.38 (m, 3H), 7.60-7.64 (m, 1H), 7.97 (dd, 8.4 Hz, 2.9 Hz, 1H), 8.01 (br d, 8.8 Hz, 2H).

MS (API-ES, pos) m/z=629

Example 208

3-{2-[(S)-3-(1-Isopropylpiperidin-4-ylamino)pyrrolidin-1-yl]-2-oxo-1-phenylethyl}-1-(4-methoxybenzenesulfonyl)-2-oxo-2,3-dihydro-1H-benzimidazole-5-carbonitrile $^1$H-NMR (400 MHz, DMSO-d$_6$): δ 0.91-0.95 (m, 6H), 1.04-1.24 (m, 2H), 1.55-1.77 (m, 4H), 1.88-2.08 (m, 3H), 2.27 (m, 1H), 2.64 (m, 3H), 2.92-3.62 (m, 4H), 3.87 (s, 3H), 6.35 (m, 1H), 6.94-7.07 (m, 1H), 7.19 (d, 8.9 Hz, 2H), 7.24-7.30 (m, 2H), 7.38 (m, 3H), 7.62 (m, 1H), 7.97 (dd, 8.5 Hz, 2.9 Hz, 1H), 8.01 (d, 8.9 Hz, 2H).

MS (API-ES, pos) m/z=657

Example 209

3-{2-[(S)-3-(1-Ethylpiperidin-4-ylamino)pyrrolidin-1-yl]-2-oxo-1-phenylethyl}-1-(4-methoxybenzenesulfonyl)-2-oxo-2,3-dihydro-1H-benzimidazole-5-carbonitrile $^1$H-NMR (400 MHz, DMSO-d$_6$): δ 0.93-0.99 (m, 3H), 1.07-1.24 (m, 3H), 1.51-1.96 (m, 7H), 2.22-2.34 (m, 3H), 2.70-2.77 (m, 2H), 2.93-3.61 (m, 3H), 3.87 (s, 3H), 6.35 (m, 1H), 6.94-7.06 (m, 1H), 7.19 (d, 8.9 Hz, 2H), 7.24-7.30 (m, 2H), 7.38 (m, 3H), 7.62 (m, 1H), 7.97 (dd, 8.5 Hz, 3.1 Hz, 1H), 8.01 (d, 8.9 Hz, 2H).

MS (API-ES, pos) m/z=643.25 [M+H]$^+$.

Example 210

1-(4-Methoxybenzenesulfonyl)-2-oxo-3-{2-oxo-1-phenyl-2-[(S)-3-(1-propylpiperidin-4-ylamino)pyrrolidin-1-yl]ethyl}-2,3-dihydro-1H-benzimidazole-5-carbonitrile $^1$H-NMR (400 MHz, DMSO-d$_6$): δ 0.80-0.85 (m, 3H), 1.07-1.24 (m, 3H), 1.40 (m, 2H), 1.51-1.97 (m, 7H), 2.12-2.36 (m, 3H), 2.72 (m, 2H), 2.92-3.62 (m, 3H), 3.87 (s, 3H), 6.34 (m, 1H), 6.94-7.06 (m, 1H), 7.19 (d, 8.8 Hz, 2H), 7.24-7.29 (m, 2H), 7.38 (m, 3H), 7.62 (m, 1H), 7.97 (dd, 8.5 Hz, 2.8 Hz, 1H), 8.01 (d, 8.8 Hz, 2H).

MS (API-ES, pos) m/z=657.25 [M+H]$^+$.

Example 211

1-(4-Methoxybenzenesulfonyl)-3-(2-{(S)-3-[methyl-(1-methylpiperidin-4-yl)-amino]pyrrolidin-1-yl}-2-oxo-1-phenylethyl)-2-oxo-2,3-dihydro-1H-benzimidazole-5-carbonitrile To a chilled solution of [6-cyano-3-(4-methoxy-benzenesulfonyl)-2-oxo-2,3-dihydrobenzoimidazol-1-yl]-phenyl-acetic acid XIIIc (100 mg, 0.22 mmol), Methyl-(1-methylpiperidin-4-yl)-(S)-pyrrolidin-3-yl-amine (51 mg, 0.26 mmol, 180 mg as TFA salt), 1-hydroxybenzotriazole (44 mg, 0.32 mmol) and N,N-diisopropylethylamine (0.33 mL, 1.94 mmol) in CH$_2$Cl$_2$ (10 mL) EDC (46 mg, 0.24 mmol) was added. The reaction mixture was allowed to warm up to room temperature while stirring overnight. Then, the reaction mixture was diluted with water and extracted with CH$_2$Cl$_2$ (3×). The combined organic phase was washed with saturated NaHCO$_3$ aqueous solution, brine, dried over Na$_2$SO$_4$, filtered and concentrated in vacuo. The residue was purified by preparative RP-HPLC (eluent: gradient from 10% to 80% acetonitrile in water, 0.1% trifluoroacetic as modulator) to afford 1-(4-methoxybenzenesulfonyl)-3-(2-[(S)-3-[methyl-(1-methyl-piperidin-4-yl)-amino]-pyrrolidin-1-yl}-2-oxo-1-phenyl-ethyl)-2-oxo-2,3-dihydro-1H-benzoimidazole-5-carbonitrile; compound with trifluoroacetic acid (17.3 mg, 10%) as a white solid.

$^1$H-NMR (500 MHz, DMSO-d$_6$): δ 1.96-2.40 (m, 6H), 2.61-2.77 (m, 6H), 2.95-3.13 (m, 4H), 3.36-4.14 (m, 6H), 3.86 (s, 3H), 6.38-6.45 (m, 1H), 6.81-7.04 (m, 1H), 7.17-7.28 (m, 4H), 7.37 (m, 3H), 7.60 (m, 1H), 7.95-8.02 (m, 3H).

MS (API-ES, pos) m/z=643.25 [M+H]$^+$.

Example 212

3-{2-[(S)-3-(Azetidin-3-ylamino)pyrrolidin-1-yl]-2-oxo-1-phenylethyl}-1-(4-methoxybenzenesulfonyl)-2-oxo-2,3-dihydro-1H-benzimidazole-5-carbonitrile

Example 213

1-(4-Methoxybenzenesulfonyl)-3-{2-[(S)-3-(1-methylazetidin-3-ylamino)-pyrrolidin-1-yl]-2-oxo-1-phenylethyl}-2-oxo-2,3-dihydro-1H-benzimidazole-5-carbonitrile

Example 214

1-(4-Methoxybenzenesulfonyl)-3-(2-{(S)-3-[methyl-(1-methylazetidin-3-yl)-amino]pyrrolidin-1-yl}-2-oxo-1-phenylethyl)-2-oxo-2,3-dihydro-1H-benzimidazole-5-carbonitrile

Example 215

1-(4-Cyano-benzenesulfonyl)-2-oxo-3-{2-oxo-1-phenyl-2-[(S)-3-(4-propylpiperazin-1-yl)-pyrrolidin-1-yl]ethyl}-2,3-dihydro-1H-benzoimidazole-5-carbonitrile $^1$H-NMR (400 MHz, CDCl$_3$): δ 0.88-0.94 (m, 3H), 1.28 (m, 2H), 1.84 (m, 1H), 2.15 (m, 1H), 2.28-2.59 (m, 9H), 2.78-3.03 (m, 2H), 3.24-3.59 (m, 2H), 3.73-3.97 (m, 2H), 6.36-6.42 (m, 1H), 6.99-7.04 (m, 1H), 7.22-7.26 (m, 2H), 7.36-7.42 (m, 4H), 7.89 (dm, 8.5 Hz, 2H), 7.95 (d, 8.5 Hz, 1H), 8.26 (d, 8.2 Hz, 2H).
MS (API-ES, pos) m/z=638.35 [M+H]$^+$.

Example 216

((S)-1-{2-[6-Cyano-3-(4-methoxy-benzenesulfonyl)-2-oxo-2,3-dihydrobenzoimidazol-1-yl]-2-phenyl-acetyl}-pyrrolidin-3-yl)-carbamic acid tert-butyl ester $^1$H-NMR (500 MHz, DMSO-d$_6$): δ 1.39 (d, 7.4 Hz, 9H), 1.74 (m, 1H), 1.96 (m, 1H), 2.82-3.41 (m, 2H), 3.48-3.67 (m, 2H), 3.87 (s, 3H), 3.90-4.01 (m, 1H), 6.33-6.38 (m, 1H), 7.03-7.16 (m, 1H), 7.19 (d, 8.9 Hz, 2H), 7.24-7.28 (m, 2H), 7.38 (m, 3H), 7.62 (d, 8.7 Hz, 1H), 7.97 (dm, 8.5 Hz, 1H), 8.00-8.03 (m, 2H).
MS (API-ES, pos) m/z=654.20 [M−H+Na]$^+$.

Example 217

3-{2-[(S)-3-(4-Benzyl-piperazin-1-ylmethyl)-pyrrolidin-1-yl]-2-oxo-1-phenylethyl}-1-[4-(2-fluoro-ethoxy)-benzenesulfonyl]-2-oxo-2,3-dihydro-1H-benzoimidazole-5-carbonitrile MS (API-ES, pos) m/z=723.80 [M+H]$^+$.

Example 218

3-{2-[(S)-3-(4-Benzyl-piperazin-1-ylmethyl)-pyrrolidin-1-yl]-2-oxo-1-phenylethyl}-1-[4-(2,2-difluoro-ethoxy)-benzenesulfonyl]-2-oxo-2,3-dihydro-1H-benzoimidazole-5-carbonitrile MS (API-ES, pos) m/z=741.80 [M+H]$^+$.

Example 219

3-[2-((S)-3-{[(2-Benzylamino-ethyl)-ethyl-amino]-methyl}-pyrrolidin-1-yl)-2-oxo-1-phenyl-ethyl]-2-oxo-1-[4-(2,2,2-trifluoro-ethoxy)-benzenesulfonyl]-2,3-dihydro-1H-benzoimidazole-5-carbonitrile MS (API-ES, pos) m/z=759.80 [M+H]$^+$.

The following compounds were prepared by analogy to Example 143

Example 220

3-{2-[(R)-3-(4-Benzyl-piperazin-1-ylmethyl)-pyrrolidin-1-yl]-2-oxo-1-phenylethyl}-1-(4-methoxy-benzenesulfonyl)-2-oxo-2,3-dihydro-1H-benzoimidazole-5-carbonitrile; compound with trifluoroacetic acid $^1$H-NMR (500 MHz, DMSO-d$_6$): δ 1.58 (m, 1H), 1.98 (m, 1H), 3.87 (s, 3H) [+3.88 (s, 3H) other diastereomer], 2.65-4.09 (m, 17H), 6.33-6.39 (m, 1H), 6.90-7.02 (m, 1H), 7.18-7.21 (m, 2H), 7.23-7.28 (m, 2H), 7.38-7.44 (m, 8H), 7.60-7.64 (m, 1H), 7.96-7.99 (m, 1H), 8.00-8.03 (m, 2H).
MS (API-ES, pos) m/z=705.30 [M+H]$^+$.

Example 221

3-{2-[(S)-3-(4-Benzyl-piperazin-1-ylmethyl)-pyrrolidin-1-yl]-2-oxo-1-phenylethyl}-1-(4-methoxy-benzenesulfonyl)-2-oxo-2,3-dihydro-1H-benzoimidazole-5-carbonitrile; compound with trifluoroacetic acid $^1$H-NMR (500 MHz, DMSO-d$_6$): δ 1.57 (m, 1H), 1.97 (m, 1H), 2.65-4.09 (m, 17H), 3.86 (s, 3H), 6.33-6.39 (m, 1H), 6.88-7.00 (m, 1H), 7.18-7.21 (m, 2H), 7.23-7.28 (m, 2H), 7.39-7.43 (m, 8H), 7.61-7.65 (m, 1H), 7.96-7.99 (m, 1H), 8.01-8.03 (m, 2H).
MS (API-ES, pos) m/z=705.80 [M+H]$^+$.

Example 222

3-{2-[(S)-3-(4-Benzyl-piperazin-1-yl)-piperidin-1-yl]-2-oxo-1-phenyl-ethyl}-1-(4-methoxy-benzenesulfonyl)-2-oxo-2,3-dihydro-1H-benzoimidazole-5-carbonitrile MS (API-ES, pos) m/z=715.15 [M+H]$^+$.

Example 223

((S)-1-{2-[6-Cyano-3-(4-methoxy-benzenesulfonyl)-2-oxo-2,3-dihydrobenzoimidazol-1-yl]-2-phenyl-acetyl}-piperidin-3-yl)-carbamic acid tert-butyl ester MS (API-ES, pos) m/z=668.10 [M−H+Na]$^+$.

Example 224

((R)-1-{2-[6-Cyano-3-(4-methoxy-benzenesulfonyl)-2-oxo-2,3-dihydrobenzoimidazol-1-yl]-2-phenyl-acetyl}-piperidin-3-yl)-carbamic acid tert-butyl ester MS (API-ES, pos) m/z=668.20 [M−H+Na]$^+$.

Example 225

(1-{2-[6-Cyano-3-(4-methoxy-benzenesulfonyl)-2-oxo-2,3-dihydrobenzoimidazol-1-yl]-2-phenyl-acetyl}-piperidin-4-yl)-carbamic acid tert-butyl ester $^1$H-NMR (400 MHz, CDCl$_3$): δ 1.44 (s, 9H) [+1.46 (s, 9H) other diastereomer], 1.81-1.94 (m, 2H), 2.03 (m, 1H), 2.84-3.21 (m, 2H), 3.55-3.71 (m, 2H), 3.90 (s, 3H) [+3.91 (s, 3H) other diastereomer], 4.42-4.54 (m, 2H), 6.59 (s, 1H), 6.90-7.04 (m, 3H), 7.18 (m, 1H), 7.29 (m, 1H), 7.33-7.41 (m, 4H), 7.98 (m, 8.5 Hz, 1H), 8.07 (dd, 8.9 Hz, 4.3 Hz, 2H).
MS (API-ES, pos) m/z=668.30 [M−H+Na]$^+$.

The following compounds were prepared by analogy to Example 150

Example 226

1-(4-Methoxy-benzenesulfonyl)-2-oxo-3-[2-oxo-1-phenyl-2-((R)-3-piperazin-1-ylmethyl-pyrrolidin-1-yl)-ethyl]-2,3-dihydro-1H-benzoimidazole-5-carbonitrile $^1$H-NMR (500 MHz, DMSO-d$_6$): δ 1.61 (m, 1H), 2.03 (m, 1H), 2.56 (m, 1H), 2.83 (m, 1H), 2.96-3.44 (m, 12H), 3.57-

3.82 (m, 1H), 3.89 (s, 3H), 6.37-6.42 (m, 1H), 6.94-7.06 (m, 1H), 7.22 (d, 9.0 Hz, 2H), 7.26-7.31 (m, 2H), 7.42 (m, 3H), 7.64 (m, 1H), 7.98-8.01 (m, 1H), 8.03-8.05 (m, 2H).
MS (API-ES, pos) m/z=615.10 [M+H]$^+$.

Example 227

1-[4-(2-Fluoro-ethoxy)-benzenesulfonyl]-2-oxo-3-[2-oxo-1-phenyl-2-((S)-3-piperazin-1-yl-pyrrolidin-1-yl)-ethyl]-2,3-dihydro-1H-benzoimidazole-5-carbonitrile
MS (API-ES, pos) m/z=633.70 [M+H]$^+$.

Example 228

1-[4-(2,2-Difluoro-ethoxy)-benzenesulfonyl]-2-oxo-3-[2-oxo-1-phenyl-2-((S)-3-piperazin-1-yl-pyrrolidin-1-yl)-ethyl]-2,3-dihydro-1H-benzoimidazole-5-carbonitrile
MS (API-ES, pos) m/z=651.70 [M+H]$^+$.

Example 229

2-Oxo-3-[2-oxo-1-phenyl-2-((S)-3-piperazin-1-yl-pyrrolidin-1-yl)-ethyl]-1-[4-(2,2,2-trifluoro-ethoxy)-benzenesulfonyl]-2,3-dihydro-1H-benzoimidazole-5-carbonitrile MS (API-ES, pos) m/z=669.20 [M+H]$^+$.

Example 230

1-(4-Methoxy-benzenesulfonyl)-2-oxo-3-[2-oxo-1-phenyl-2-((S)-3-piperazin-1-yl)-piperidin-1-yl)-ethyl]-2,3-dihydro-1H-benzoimidazole-5-carbonitrile; compound with trifluoroacetic acid $^1$H-NMR (400 MHz, DMSO-d$_6$): δ 1.50 (m, 2H), 1.79 (m, 2H), 2.16-2.33 (m, 2H), 2.81 (m, 2H), 2.91 (m, 2H), 3.10 (m, 3H), 3.88 (s, 3H), 3.40-4.35 (m, 4H), 6.54-6.61 (m, 1H), 6.85-7.07 (m, 1H), 7.20 (d, 9.0 Hz, 2H), 7.32 (m, 1H), 7.41 (m, 4H), 7.62 (m, 1H), 7.94-8.03 (m, 3H).
MS (API-ES, pos) m/z=615.25 [M+H]$^+$.

The compounds of Examples 231 to 238 as well as compounds of examples 189, 191 and 193 were synthesized following the general method for reductive amination with MP-(OAc)$_3$BH resin General method for reductive amination with MP-(OAc)$_3$BH resin To a solution of the amine (1 eq.) and paraformaldehyde (2.0 eq.) or acetaldehyde (1.1 eq) or propionaldehyde (1.2 eq.) or acetone (2.0 eq.) in THF (3 mL) MP-(OAc)$_3$BH resin (Argonaut; 2.55 mmol/g; 2.5 eq.) was. The reaction mixture was agitated at room temperature for 24-96 hours. Then, the solution was filtered and concentrated in vacuo. The residue was purified by flash chromatography on silica gel (eluent: gradient from 3% to 6% MeOH in CH$_2$Cl$_2$) or by preparative RP-HPLC (eluent: gradient from 10% to 80% acetonitrile in water, 0.1% trifluoroacetic acid as modulator).

Example 231

3-{2-[(S)-3-(4-Ethyl-piperazin-1-yl)-piperidin-1-yl]-2-oxo-1-phenyl-ethyl}-1-(4-methoxy-benzenesulfonyl)-2-oxo-2,3-dihydro-1H-benzoimidazole-5-carbonitrile; compound with trifluoroacetic acid $^1$H-NMR (500 MHz, DMSO-d$_6$): δ 0.92 (s, 3H) [+1.01 (s, 3H) other diastereomer], 1.24-1.43 (m, 3H), 1.64-1.78 (m, 3H), 1.92 (m, 1H), 2.10-2.60 (m, 7H), 2.70-2.83 (m, 1H), 2.97-3.40 (m, 2H), 3.50-3.69 (m, 1H), 3.87 (s, 3H) [+3.88 (s, 3H) other diastereomer], 4.23-4.35 (m, 1H), 6.49-6.60 (m, 1H), 6.82-6.99 (m, 1H), 7.17-7.27 (m, 3H), 7.31-7.45 (m, 4H), 7.60 (ddd, 8.4 Hz, 4.6 Hz, 1.4 Hz, 1H), 7.94-8.04 (m, 3H).
MS (API-ES, pos) m/z=643.20 [M+H]$^+$.

Example 232

1-[4-(2-Fluoro-ethoxy)-benzenesulfonyl]-2-oxo-3-{2-oxo-1-phenyl-2-[(S)-3-(4-propyl-piperazin-1-yl)-pyrrolidin-1-yl]-ethyl}-2,3-dihydro-1H-benzoimidazole-5-carbonitrile $^1$H-NMR (400 MHz, DMSO-d$_6$): δ 0.81-0.86 (m, 3H), 1.41 (m, 2H), 1.66 (m, 1H), 1.98 (m, 1H), 2.10-2.45 (m, 9H), 2.64-2.79 (m, 2H), 2.93-3.45 (m, 2H), 3.54-3.74 (m, 2H), 4.38 (dm, 29.7 Hz, 2H), 4.76 (dm, 47.6 Hz, 2H), 6.32-6.42 (m, 1H), 6.98-7.08 (m, 1H), 7.21-7.29 (m, 4H), 7.38 (m, 3H), 7.60-7.64 (m, 1H), 7.95-8.04 (m, 3H).
MS (API-ES, pos) m/z=675.20 [M+H]$^+$.

Example 233

1-[4-(2,2-Difluoro-ethoxy)-benzenesulfonyl]-2-oxo-3-{2-oxo-1-phenyl-2-[(S)-3-(4-propyl-piperazin-1-yl)-pyrrolidin-1-yl]-ethyl}-2,3-dihydro-1H-benzoimidazole-5-carbonitrile $^1$H-NMR (400 MHz, DMSO-d$_6$): δ 0.81-0.86 (m, 3H), 1.41 (m, 2H), 1.66 (m, 1H), 1.93-2.04 (m, 2H), 2.16-2.45 (m, 7H), 2.67-2.80 (m, 2H), 2.94-3.13 (m, 1H), 3.18-3.39 (m, 2H), 3.43-3.75 (m, 2H), 4.48 (td, 14.5 Hz, 2.7 Hz, 2H), 6.27-6.55 (m, 2H), 6.98-7.08 (m, 1H), 7.22-7.29 (m, 4H), 7.38 (m, 3H), 7.60-7.64 (m, 1H), 7.97 (dd, 8.5 Hz, 3.7 Hz, 1H), 8.02-8.06 (m, 2H).
MS (API-ES, pos) m/z=693.80 [M+H]$^+$.

Example 234

2-oxo-3-{2-oxo-1-phenyl-2-[(S)-3-(4-propyl-piperazin-1-yl)-pyrrolidin-1-yl]-ethyl}1-[4-(2,2,2-trifluoro-ethoxy)-benzenesulfonyl]-2,3-dihydro-1H-benzoimidazole-5-carbonitrile $^1$H-NMR (400 MHz, DMSO-d$_6$): δ 0.81-0.86 (m, 3H), 1.41 (m, 2H), 1.66 (m, 1H), 1.99 (m, 2H), 2.13-2.44 (m, 7H), 2.66-2.80 (m, 2H), 2.92-3.13 (m, 1H), 3.19-3.36 (m, 2H), 3.37-3.75 (m, 2H), 4.94 (q, 8.6 Hz, 2H), 6.33-6.42 (m, 1H), 6.98-7.08 (m, 1H), 7.23-7.29 (m, 2H), 7.33 (d, 8.9 Hz, 2H), 7.38 (m, 3H), 7.61-7.64 (m, 1H), 7.97 (dd, 8.5 Hz, 3.7 Hz, 1H), 8.05-8.09 (m, 2H).
MS (API-ES, pos) m/z=711.80 [M+H]$^+$.

Example 235

1-(4-Methoxy-benzenesulfonyl)-2-oxo-3-{2-oxo-1-phenyl-2-[(R)-3-(4-propylpiperazin-1-ylmethyl)-pyrrolidin-1-yl]-ethyl}-2,3-dihydro-1H-benzoimidazole-5-carbonitrile; compound with trifluoroacetic acid $^1$H-NMR (500 MHz, DMSO-d$_6$): δ 0.88-0.92 (m, 3H), 1.52-1.69 (m, 3H), 1.96-2.00 (m, 1H), 2.44-3.78 (m, 17H), 3.87 (s, 3H), 6.36-6.41 (m, 1H), 6.94-7.05 (m, 1H), 7.22 (dd, 9.0 Hz, 1.9 Hz, 2H), 7.24-7.28 (m, 2H), 7.39 (m, 3H), 7.60-7.64 (m, 1H), 7.98 (ddd, 8.4 Hz, 3.6 Hz, 2.1 Hz, 1H), 8.01-8.03 (m, 2H).

MS (API-ES, pos) m/z=657.20 [M+H]$^+$.

Example 236

1-(4-Methoxy-benzenesulfonyl)-3-{2-[(R)-3-(4-methyl-piperazin-1-ylmethyl)-pyrrolidin-1-yl]-2-oxo-1-phenyl-ethyl}-2-oxo-2,3-dihydro-1H-benzoimidazole-5-carbonitrile; compound with trifluoroacetic acid $^1$H-NMR (500 MHz, DMSO-d$_6$): δ 1.60 (m, 1H), 2.00 (m, 1H), 2.81 (s, 3H), 2.47-3.81 (m, 15H), 3.87 (s, 3H), 6.35-6.40 (m, 1H), 6.92-7.04 (m, 1H), 7.19 (dd, 9.0 Hz, 2.2 Hz, 2H), 7.24-7.28 (m, 2H), 7.39 (m, 3H), 7.59-7.63 (m, 1H), 7.96-7.99 (m, 1H), 8.02 (dd, 9.0 Hz, 3.3 Hz, 2H).

MS (API-ES, pos) m/z=629.20 [M+H]$^+$.

Example 237

3-{2-[(R)-3-(4-Ethyl-piperazin-1-ylmethyl)-pyrrolidin-1-yl]-2-oxo-1-phenyl-ethyl}-1-(4-methoxy-benzenesulfonyl)-2-oxo-2,3-dihydro-1H-benzoimidazole-5-carbonitrile; compound with trifluoroacetic acid $^1$H-NMR (500 MHz, DMSO-d$_6$): δ 1.19-1.24 (m, 3H), 1.59 (m, 1H), 1.99 (m, 1H), 2.45-3.80 (m, 17H), 3.87 (s, 3H), 6.34-6.40 (m, 1H), 6.93-7.04 (m, 1H), 7.20 (d, 8.8 Hz, 2H), 7.24-7.29 (m, 2H), 7.40 (m, 3H), 7.59-7.64 (m, 1H), 7.96-7.99 (m, 1H), 8.02 (dd, 8.8 Hz, 3.2 Hz, 2H).

MS (API-ES, pos) m/z=643.25 [M+H]$^+$.

Example 238

3-{2-[(R)-3-(4-Isopropyl-piperazin-1-ylmethyl)-pyrrolidin-1-yl]-2-oxo-1-phenylethyl}-1-(4-methoxy-benzenesulfonyl)-2-oxo-2,3-dihydro-1H-benzoimidazole-5-carbonitrile; compound with trifluoroacetic acid $^1$H-NMR (500 MHz, DMSO-d$_6$): δ 1.23-1.27 (m, 6H), 1.60 (m, 1H), 1.99 (m, 1H), 2.49-3.79 (m, 16H), 3.87 (s, 3H), 6.35-6.40 (m, 1H), 6.93-7.04 (m, 1H), 7.20 (dd, 9.0 Hz, 2.1 Hz, 2H), 7.24-7.29 (m, 2H), 7.37-7.41 (m, 3H), 7.59-7.64 (m, 1H), 7.96-7.99 (m, 1H), 8.02 (dd, 9.0 Hz, 3.4 Hz, 2H).

MS (API-ES, pos) m/z=657.30 [M+H]$^+$.

Example 239

3-[2-(4-Amino-piperidin-1-yl)-2-oxo-1-phenyl-ethyl]-1-(4-methoxybenzenesulfonyl)-2-oxo-2,3-dihydro-1H-benzoimidazole-5-carbonitrile A solution of (1-{2-[6-cyano-3-(4-methoxy-benzenesulfonyl)-2-oxo-2,3-dihydrobenzoimidazol-1-yl]-2-phenyl-acetyl}piperidin-4-yl)-carbamic acid tert-butyl ester (254 mg, 0.39 mmol) in CH$_2$Cl$_2$ (5 mL) was treated with trifluoroacetic acid (5 mL). The reaction mixture was stirred at room temperature for 2 hours, concentrated in vacuo and co-evaporated the solvent with toluene (3×). The residue was dissolved in CH$_2$Cl$_2$ (30 mL) and treated with solid K$_2$CO$_3$. The reaction mixture was stirred at room temperature for 1 hour, filtered and concentrated in vacuo to afford 3-[2-(4-amino-piperidin-1-yl)-2-oxo-1-phenyl-ethyl]-1-(4-methoxy-benzenesulfonyl)-2-oxo-2,3-dihydro-1H-benzoimidazole-5-carbonitrile (179 mg, 83%) as a white solid.

$^1$H-NMR (400 MHz, CDCl$_3$): δ 1.28-2.05 (m, 4H), 2.84-3.17 (m, 3H), 3.62 (m, 1H), 3.90 (s, 3H) [+3.91 (s, 3H) other diastereomer], 4.50 (m, 1H), 6.61 (m, 1H), 6.94-7.04 (m, 3H), 7.20-7.29 (m, 2H), 7.33-7.42 (m, 4H), 7.97 (d, 8.5 Hz, 1H), 8.07 (dd, 8.9 Hz, 3.2 Hz, 2H).

MS (API-ES, pos) m/z=546.25 [M+H]$^+$.

The following compounds as well as the compound of Example 170 were prepared by analogy to Example 239

Example 240

3-[2-((S)-3-Amino-piperidin-1-yl)-2-oxo-1-phenyl-ethyl]-1-(4-methoxybenzenesulfonyl)-2-oxo-2,3-dihydro-1H-benzoimidazole-5-carbonitrile $^1$H-NMR (400 MHz, DMSO-d$_6$): δ 0.94-1.76 (m, 4H), 2.42 (m, 1H), 2.56-2.67 (m, 1H), 2.75-3.08 (m, 1H), 3.36-3.50 (m, 1H), 3.88 (s, 3H), 4.06-4.25 (m, 1H), 6.54-6.60 (m, 1H), 6.83-6.98 (m, 1H), 7.20 (d, 9.0 Hz, 2H), 7.19-7.24 (m, 1H), 7.30 (m, 1H), 7.39 (m, 3H), 7.59-7.64 (m, 1H), 7.94-8.03 (m, 3H).

MS (API-ES, pos) m/z=546.15 [M+H]$^+$.

Example 241

3-[2-((R)-3-Amino-piperidin-1-yl)-2-oxo-1-phenyl-ethyl]-1-(4-methoxybenzenesulfonyl)-2-oxo-2,3-dihydro-1H-benzoimidazole-5-carbonitrile $^1$H-NMR (400 MHz, DMSO-d$_6$): δ 0.94-1.78 (m, 4H), 2.30-2.45 (m, 1H), 2.56-2.67 (m, 1H), 2.75-3.08 (m, 1H), 3.26-3.50 (m, 1H), 3.88 (s, 3H), 4.06-4.25 (m, 1H), 6.54-6.60 (m, 1H), 6.83-6.98 (m, 1H), 7.20 (d, 8.9 Hz, 2H), 7.21-7.33 (m, 2H), 7.36-7.39 (m, 3H), 7.59-7.64 (m, 1H), 7.94-7.98 (m, 1H), 7.99-8.03 (m, 2H).

MS (API-ES, pos) m/z=546.15 [M+H]$^+$.

The following compounds as well as the compound of Example 206 and 208 to 210 were prepared by analogy to Example 207

Example 242

3-(2-{(S)-3-[(1H-Imidazol-4-ylmethyl)-amino]-pyrrolidin-1-yl}-2-oxo-1-phenylethyl)-1-(4-methoxy-benzenesulfonyl)-2-oxo-2,3-dihydro-1H-benzoimidazole-5-carbonitrile; compound with trifluoroacetic acid $^1$H-NMR (500 MHz, DMSO-d$_6$): δ 2.01-2.15 (m, 1H), 2.26 (m, 1H), 3.08-4.31 (m, 7H), 3.87 (s, 3H), 6.39-6.43 (m, 1H), 7.05 (m, 1H), 7.19 (d, 8.6 Hz, 2H), 7.24-7.28 (m, 2H), 7.38 (m, 3H), 7.66 (m, 2H), 7.96-8.03 (m, 3H), 8.85 (m, 1H).

MS (API-ES, pos) m/z=612.15 [M+H]$^+$.

Example 243

4-((S)-1-{2-[6-Cyano-3-(4-methoxy-benzenesulfonyl)-2-oxo-2,3-dihydrobenzoimidazol-1-yl]-2-phenyl-acetyl}-pyrrolidin-3-ylamino)-piperidine-1-carboxylic acid tert-butyl ester $^1$H-NMR (400 MHz, DMSO-d$_6$): δ 0.95-1.09 (m, 2H), 1.39 (s, 9H), 1.54-1.75 (m, 4H), 1.93 (m, 1H), 2.75 (m, 2H), 3.00-3.34 (m, 3H), 3.46 (m, 1H), 3.62 (m, 1H), 3.78 (m, 2H), 3.87 (s, 3H), 6.35 (m, 1H), 6.93-7.04 (m, 1H), 7.19 (d, 8.7 Hz, 2H), 7.23-7.29 (m, 2H), 7.38 (m, 3H), 7.60-7.63 (m, 1H), 7.97 (dd, 8.5 Hz, 2.7 Hz, 1H), 8.01 (d, 8.9 Hz, 2H).

MS (API-ES, pos) m/z=715.15 [M+H]⁺.

Example 244

3-{2-[(S)-3-(1-tert-Butyl-piperidin-4-ylamino)-pyrrolidin-1-yl]-2-oxo-1-phenylethyl}-1-(4-methoxy-benzenesulfonyl)-2-oxo-2,3-dihydro-1H-benzoimidazole-5-carbonitrile ¹H-NMR (400 MHz, DMSO-d₆): δ 1.18-1.21 (m, 9H), 1.36 (m, 1H), 1.66 (m, 1H), 1.78-2.00 (m, 3H), 2.35-2.77 (m, 2H), 3.04-3.69 (m, 9H), 3.90 (s, 3H), 6.38-6.40 (m, 1H), 6.94-7.04 (m, 1H), 7.22 (d, 8.8 Hz, 2H), 7.26-7.33 (m, 2H), 7.42 (m, 3H), 7.65 (m, 1H), 8.00 (dm, 8.4 Hz, 1H), 8.04 (d, 8.8 Hz, 2H).

MS (API-ES, pos) m/z=671.20 [M+H]⁺.

Example 245

3-(2-{(S)-3-[1-(2-Fluoro-ethyl)-piperidin-4-ylamino]-pyrrolidin-1-yl}-2-oxo-1-phenyl-ethyl)-1-(4-methoxy-benzenesulfonyl)-2-oxo-2,3-dihydro-1H-benzoimidazole-5-carbonitrile ¹H-NMR (400 MHz, DMSO-d₆): δ 1.09-1.26 (m, 3H), 1.56-1.78 (m, 4H), 1.88-2.13 (m, 4H), 2.33-2.59 (m, 2H), 2.78 (m, 2H), 2.97-3.65 (m, 3H), 3.87 (s, 3H), 4.48 (dm, 47.6 Hz, 2H), 6.34 (m, 1H), 6.94-7.05 (m, 1H), 7.20 (d, 8.9 Hz, 2H), 7.22-7.29 (m, 2H), 7.38 (m, 3H), 7.62 (m, 1H), 7.97 (dd, 8.3 Hz, 3.2 Hz, 1H), 8.01 (d, 8.8 Hz, 2H).

MS (API-ES, pos) m/z=661.20 [M+H]⁺.

Example 246

1-(4-Methoxy-benzenesulfonyl)-3-{2-[(S)-3-(1-methyl-piperidin-4-ylamino)-piperidin-1-yl]-2-oxo-1-phenyl-ethyl}-2-oxo-2,3-dihydro-1H-benzoimidazole-5-carbonitrile ¹H-NMR (400 MHz, DMSO-d₆): δ 0.80-1.48 (m, 5H), 1.62-2.33 (m, 8H), 2.54-2.67 (m, 3H), 2.77-2.98 (m, 2H), 3.25-3.37 (m, 1H), 3.49-3.63 (m, 1H), 3.87 (s, 3H), 3.97-4.28 (m, 1H), 6.52-6.59 (m, 1H), 6.89-7.05 (m, 1H), 7.19 (d, 8.2 Hz, 2H), 7.18-7.20 (m, 1H), 7.32-7.41 (m, 4H), 7.58-7.66 (m, 1H), 7.93-8.03 (m, 3H).

MS (API-ES, pos) m/z=643.20 [M+H]⁺.

Example 247

3-{2-[(S)-3-(1-Isopropyl-piperidin-4-ylamino)-piperidin-1-yl]-2-oxo-1-phenylethyl}-1-(4-methoxy-benzenesulfonyl)-2-oxo-2,3-dihydro-1H-benzoimidazole-5-carbonitrile ¹H-NMR (500 MHz, DMSO-d₆): δ 0.91-0.95 (m, 6H), 0.84 (m, 1H), 1.09-1.46 (m, 5H), 1.59-1.89 (m, 4H), 2.13 (m, 2H), 2.44-2.75 (m, 4H), 2.94 (m, 1H), 3.46-3.62 (m, 1H), 3.87 (s, 3H), 3.91-4.30 (m, 1H), 6.51-6.60 (m, 1H), 6.87-7.10 (m, 1H), 7.18-7.21 (m, 3H), 7.32-7.41 (m, 4H), 7.59-7.69 (m, 1H), 7.93-8.04 (m, 3H).

MS (API-ES, pos) m/z=671.20 [M+H]⁺.

Example 248

1-(4-Methoxy-benzenesulfonyl)-3-{2-[(R)-3-(1-methyl-piperidin-4-ylamino)-piperidin-1-yl]-2-oxo-1-phenyl-ethyl}-2-oxo-2,3-dihydro-1H-benzoimidazole-5-carbonitrile ¹H-NMR (500 MHz, DMSO-d₆): δ 0.81-1.48 (m, 5H), 1.66-2.32 (m, 8H), 2.54-2.67 (m, 3H), 2.80-2.98 (m, 2H), 3.25-3.37 (m, 1H), 3.50-3.62 (m, 1H), 3.87 (s, 3H), 3.98-4.27 (m, 1H), 6.51-6.60 (m, 1H), 6.89-7.05 (m, 1H), 7.19 (d, 8.7 Hz, 2H), 7.18-7.20 (m, 1H), 7.32-7.41 (m, 4H), 7.58-7.66 (m, 1H), 7.93-8.03 (m, 3H).

MS (API-ES, pos) m/z=643.80 [M+H]⁺.

Example 249

3-{2-[(R)-3-(1-Isopropyl-piperidin-4-ylamino)-piperidin-1-yl]-2-oxo-1-phenylethyl}-1-(4-methoxy-benzenesulfonyl)-2-oxo-2,3-dihydro-1H-benzoimidazole-5-carbonitrile ¹H-NMR (500 MHz, DMSO-d₆): δ 0.98-1.02 (m, 6H), 0.82 (m, 1H), 1.10-1.50 (m, 5H), 1.61-1.98 (m, 4H), 2.12 (m, 2H), 2.35-2.69 (m, 4H), 2.92 (m, 1H), 3.21-3.64 (m, 1H), 3.87 (s, 3H), 3.96-4.29 (m, 1H), 6.52-6.61 (m, 1H), 6.88-7.07 (m, 1H), 7.18-7.21 (m, 3H), 7.32-7.42 (m, 4H), 7.59-7.68 (m, 1H), 7.94-8.04 (m, 3H).

MS (API-ES, pos) m/z=671.80 [M+H]⁺.

Example 250

4-(1-{2-[6-Cyano-3-(4-methoxy-benzenesulfonyl)-2-oxo-2,3-dihydrobenzoimidazol-1-yl]-2-phenyl-acetyl}-piperidin-4-ylamino]-piperidine-1-carboxylic acid tert-butyl ester MS (API-ES, pos) m/z=729.25 [M+H]⁺.

Example 251

1-(4-Methoxy-benzenesulfonyl)-2-oxo-3-{2-oxo-1-phenyl-2-[4-(piperidin-4-ylamino)-piperidin-1-yl]-ethyl}-2,3-dihydro-1H-benzoimidazole-5-carbonitrile; compound with trifluoroacetic acid To a solution of 4-(1-{2-[6-cyano-3-(4-methoxy-benzenesulfonyl)-2-oxo-2,3-dihydrobenzoimidazol-1-yl]-2-phenyl-acetyl}-piperidin-4-ylamino]-piperidine-1-carboxylic acid tert-butyl ester (100 mg, 0.14 mmol) in CH₂Cl₂ (2 mL) was added trifluoroacetic acid (2 mL). The reaction mixture was stirred at room temperature for 2 hours, concentrated in vacuo and co-evaporated the solvent with toluene (3×). The residue was purified by preparative RP-HPLC (eluent: gradient from 10% to 80% acetonitrile in water, 0.1% trifluoroacetic acid as modulator) to afford 1-(4-methoxybenzenesulfonyl)-2-oxo-3-{2-oxo-1-phenyl-2-[4-(piperidin-4-ylamino)-piperidin-1-yl]ethyl}-2,3-dihydro-1H-benzoimidazole-5-carbonitrile; compound with trifluoroacetic acid (70 mg, 67%) as a white solid.

¹H-NMR (400 MHz, DMSO-d₆): δ 1.05-1.67 (m, 4H), 1.76-1.96 (m, 1H), 2.14 (m, 3H), 2.67-3.12 (m, 5H), 3.37-3.79 (m, 5H), 3.88 (s, 3H), 4.51 (m, 1H), 6.62-6.98 (m, 2H), 7.20 (d, 8.8 Hz, 2H), 7.24 (m, 1H), 7.36 (m, 1H), 7.41 (m, 3H), 7.62 (d, 8.5 Hz, 1H), 7.97 (dd, 8.5 Hz, 3.3 Hz, 1H), 8.01 (dm, 8.9 Hz, 2H).
MS (API-ES, pos) m/z=629.25 [M+H]+.

Example 252

1-Methyl-piperidine-4-carboxylic acid ((S)-1-{2-[6-cyano-3-(4-methoxybenzenesulfonyl)-2-oxo-2,3-dihydro-benzoimidazol-1-yl]-2-phenyl-acetyl}-pyrrolidin-3-yl)-amide; compound with trifluoroacetic acid A mixture of 1-methylpiperidine-4-carboxylic acid hydrochloride (16 mg, 0.09 mmol), 1-hydroxybenzotriazole (15 mg, 0.11 mmol) and PS-carbodiimide resin (Argonaut; 1.25 mmol/g; 72 mg, 0.09 mmol) in $CH_2Cl_2$ (3 mL) was agitated for 10 min at room temperature. Then, 3-[2-((S)-3-amino-pyrrolidin-1-yl)-2-oxo-1-phenyl-ethyl]-1-(4-methoxy-benzenesulfonyl)-2-oxo-2,3-dihydro-1H-benzoimidazole-5-carbonitrile (40 mg, 0.08 mmol) was added and the reaction mixture was agitated at room temperature overnight. To this was then added MP-carbonate resin (Argonaut; 3.08 mmol/g; 73 mg, 0.23 mmol) and the reaction mixture was agitated for another 2 hours, filtered and concentrated in vacuo. The residue was purified by preparative RP-HPLC (eluent: gradient from 10% to 80% acetonitrile in water, 0.1% trifluoroacetic acid as modulator) to afford 1-methyl-piperidine-4-carboxylic acid ((S)-1-{2-[6-cyano-3-(4-methoxy-benzenesulfonyl)-2-oxo-2,3-dihydro-benzoimidazol-1-yl]-2-phenyl-acetyl}-pyrrolidin-3-yl)-amide; compound with trifluoroacetic acid (13 mg, 21%) as a white solid.
$^1$H-NMR (500 MHz, DMSO-$d_6$): δ 1.61-2.04 (m, 5H), 2.15-2.33 (m, 1H), 2.77 (m, 3H), 2.90 (m, 2H), 3.11 (m, 1H), 3.27 (m, 1H), 3.42-3.98 (m, 6H), 3.87 (s, 3H), 6.32-6.42 (m, 1H), 6.97-7.10 (m, 1H), 7.20 (dd, 9.1 Hz, 2.4 Hz, 2H), 7.22-7.30 (m, 2H), 7.39 (m, 3H), 7.61-7.65 (m, 1H), 7.97 (dd, 8.5 Hz, 4.7 Hz, 1H), 7.99-8.03 (m, 2H).
MS (API-ES, pos) m/z=657.20 [M+H]+.
The following compounds were prepared by analogy to Example 211

Example 253

1-(4-Methoxy-benzenesulfonyl)-2-oxo-3-{2-oxo-1-phenyl-2-[(S)-3-(pyridine-4-ylamino)-pyrrolidin-1-yl]-ethyl}-2,3-dihydro-1H-benzoimidazole-5-carbonitrile; compound with trifluoroacetic acid $^1$H-NMR (500 MHz, DMSO-$d_6$): δ 1.94 (m, 1H), 2.25 (m, 1H), 2.96-3.93 (m, 5H), 3.86 (s, 3H), 6.36-6.44 (m, 1H), 6.81-7.08 (m, 3H), 7.17-7.21 (m, 2H), 7.23-7.31 (m, 3H), 7.38-7.40 (m, 2H), 7.62 (m, 1H), 7.94-8.03 (m, 3H), 8.20 (m, 2H).
MS (API-ES, pos) m/z=609.15 [M+H]+.

Example 254

1-(4-Methoxy-benzenesulfonyl)-3-{2-[(S)-3-(2-methyl-pyridine-4-ylamino)-pyrrolidin-1-yl]-2-oxo-1-phenyl-ethyl}-2-oxo-2,3-dihydro-1H-benzoimidazole-5-carbonitrile; compound with trifluoroacetic acid $^1$H-NMR (500 MHz, DMSO-$d_6$): δ 1.93 (m, 1H), 2.24 (m, 1H), 2.40-2.53 (m, 5H), 3.43-3.54 (m, 2H), 3.86 (s, 3H), 4.25 (br s, 1H), 6.34-6.43 (m, 1H), 6.61-6.89 (m, 2H), 7.02-7.08 (m, 1H), 7.17-7.21 (m, 2H), 7.22-7.30 (m, 3H), 7.39 (m, 2H), 7.62 (m, 1H), 7.94-8.03 (m, 4H).
MS (API-ES, pos) m/z=623.20 [M+H]+.

Example 255

1-(4-Methoxy-benzenesulfonyl)-3-(2-{(R)-3-[(1-methyl-piperidin-4-ylamino)-methyl]-pyrrolidin-1-yl}-2-oxo-1-phenyl-ethyl)-2-oxo-2,3-dihydro-1H-benzoimidazole-5-carbonitrile; compound with trifluoroacetic acid $^1$H-NMR (400 MHz, DMSO-$d_6$): δ 1.65-1.76 (m, 3H), 2.03 (m, 1H), 2.21 (m, 2H), 2.77 (m, 4H), 3.17-3.39 (m, 4H), 3.51-3.80 (m, 7H), 3.88 (s, 3H), 6.33-6.40 (m, 1H), 6.88-7.01 (m, 1H), 7.20 (dd, 9.1 Hz, 2.6 Hz, 2H), 7.25-7.27 (m, 2H), 7.40 (m, 3H), 7.63 (tm, 8.0 Hz, 1H), 7.98 (dd, 9.0 Hz, 3.8 Hz, 1H), 8.02 (dd, 9.0 Hz, 3.8 Hz, 2H).
MS (API-ES, pos) m/z=643.25 [M+H]+.

Example 256

1-(4-Methoxy-benzenesulfonyl)-3-[2-((R)-3-{[methyl-(1-methyl-piperidin-4-yl)-amino]-methyl}-pyrrolidin-1-yl)-2-oxo-1-phenyl-ethyl]-2-oxo-2,3-dihydro-1H-benzoimidazole-5-carbonitrile; compound with trifluoroacetic acid $^1$H-NMR (400 MHz, DMSO-$d_6$): δ 1.64 (m, 1H), 1.86 (m, 2H), 2.06-2.23 (m, 3H), 2.66-2.84 (m, 7H), 2.99 (m, 1H), 3.10-3.48 (m, 4H), 3.56-3.84 (m, 6H), 3.88 (s, 3H), 6.34-6.42 (m, 1H), 6.92-7.02 (m, 1H), 7.20 (dd, 9.0 Hz, 2.6 Hz, 2H), 7.24-7.29 (m, 2H), 7.39-7.41 (m, 3H), 7.61-7.65 (m, 1H), 7.98 (dd, 8.6 Hz, 4.2 Hz, 1H), 8.00-8.03 (m, 2H).
MS (API-ES, pos) m/z=657.30 [M+H]+.

Example 257

3-(1-tert-Butoxycarbonyl-propyl)-5-cyano-2-oxo-2,3-dihydro-benzoimidazole-1-carboxylic acid tert-butyl ester To a chilled solution of 5-cyano-2-oxo-2,3-dihydro-benzoimidazole-1-carboxylic acid tert-butyl ester (50 mg, 0.19 mmol) in dry DMF (1 mL) NaH (60% dispersion mineral oil, 8 mg, 0.20 mmol) was added under $N_2$ atmosphere. The reaction was stirred at room temperature for 15 min. Then, a solution of tert-butyl-2-bromobutyrate (0.054 mL, 0.29 mmol) in DMF (2 mL) was added at 0° C. The reaction mixture was stirred at room temperature for 3 hours, diluted with ethyl acetate, washed with water, with a saturated $NH_4Cl$ aqueous solution, brine, dried over $Na_2SO_4$, filtered and concentrated in vacuo. The residue was purified by flash chromatography in silica gel using 15% ethyl acetate in n-heptane as eluent to afford 3-(1-tert-butoxycarbonylpropyl)-5-cyano-2-oxo-2,3-dihydro-benzoimidazole-1-carboxylic acid tert-butyl ester (55 mg, 72%) as a white solid.
$^1$H-NMR (400 MHz, DMSO-$d_6$): δ 0.82-0.88 (m, 3H), 1.37 (s, 9H), 1.61 (s, 9H), 2.12-2.23 (m, 2H), 4.98 (dd, 9.6 Hz, 6.2 Hz, 1H), 7.62 (dd, 8.4 Hz, 1.2 Hz, 1H), 7.77 (d, 1.2 Hz, 1H), 7.87 (d, 8.4 Hz, 1H).
MS (API-ES, pos) m/z=424.10 [M−H+Na]+.

Example 258

2-(6-Cyano-2-oxo-2,3-dihydro-benzoimidazol-1-yl)-butyric acid tert-butyl ester

To a stirred solution of 3-(1-tert-butoxycarbonyl-propyl)-5-cyano-2-oxo-2,3-dihydrobenzoimidazole-1-carboxylic acid tert-butyl ester (55 mg, 0.14 mmol) in $CH_2Cl_2$ (5 mL) trifluoroacetic acid (0.10 mL) was added. The reaction mixture was stirred at room temperature for 4 hours, concentrated in vacuo and co-evaporated the solvent with toluene (3×). The residue was purified by flash chromatography in silica gel using 40% ethyl acetate in n-heptane as eluent to afford 2-(6-cyano-2-oxo-2,3-dihydro-benzoimidazol-1-yl)-butyric acid tert-butyl ester (28 mg, 68%) as a white solid.

MS (API-ES, pos) m/z=324.10 [M−H+Na]$^+$.

Example 259

2-[6-Cyano-3-(4-methoxy-benzenesulfonyl)-2-oxo-2,3-dihydro-benzoimidazol-1-yl]-butyric acid tert-butyl ester To a solution of 2-(6-cyano-2-oxo-2,3-dihydro-benzoimidazol-1-yl)-butyric acid tert-butyl ester (28 mg, 0.09 mmol), triethylamine (0.03 mL, 0.19 mmol) and DMAP (catalytic amount) in $CH_2Cl_2$ (3 mL) 4-methoxybenzenesulfonyl chloride (21 mg, 0.10 mmol) was added. The reaction mixture was stirred at room temperature for 3 hours, diluted with water and extracted the aqueous phase with $CH_2Cl_2$ (3×). The combined organic phase was washed with brine, dried over $Na_2SO_4$, filtered and concentrated in vacuo. The residue was purified by flash chromatography in silica gel using 15% ethyl acetate in n-heptane as eluent to afford 2-[6-cyano-3-(4-methoxybenzenesulfonyl)-2-oxo-2,3-dihydro-benzoimidazol-1-yl]-butyric acid tert-butyl ester (38 mg, 87%) as a white solid.

MS (API-ES, pos) m/z=494.10 [M−H+Na]$^+$.

Example 260

2-[6-Cyano-3-(4-methoxy-benzenesulfonyl)-2-oxo-2,3-dihydro-benzoimidazol-1-yl]-butyric acid A stirred solution of 2-[6-cyano-3-(4-methoxy-benzenesulfonyl)-2-oxo-2,3-dihydrobenzoimidazol-1-yl]-butyric acid tert-butyl ester (34 mg, 0.07 mmol) in $CH_2Cl_2$ (1 mL) was treated with trifluoroacetic acid (1 mL). The reaction mixture was stirred at room temperature for 3 hours, concentrated in vacuo and co-evaporated the solvent with toluene (3×) to afford 2-[6-cyano-3-(4-methoxy-benzenesulfonyl)-2-oxo-2,3-dihydrobenzoimidazol-1-yl]-butyric acid (29 mg, 99%) as a white solid.

MS (API-ES, pos) m/z=416.05 [M+H]$^+$.

Example 262

3-{1-[(S)-3-(4-Benzyl-piperazin-1-yl)-pyrrolidine-1-carbonyl]-propyl}-1-(4-methoxy-benzenesulfonyl)-2-oxo-2,3-dihydro-1H-benzoimidazole-5-carbonitrile To a chilled solution of 2-[6-cyano-3-(4-methoxy-benzenesulfonyl)-2-oxo-2,3-dihydrobenzoimidazol-1-yl]-butyric acid (30 mg, 0.07 mmol), 1-benzyl-4-(S)-pyrrolidin-3-ylpiperazine (21 mg, 0.09 mmol, 71 mg as TFA salt), 1-hydroxybenzotriazole (15 mg, 0.11 mmol) and N,N-diisopropylethylamine (0.11 mL, 0.65 mmol) in $CH_2Cl_2$ (4 mL) EDC (15 mg, 0.08 mmol) was added. The reaction mixture was allowed to warm up to room temperature while stirring for 48 hours. Then, the reaction mixture was diluted with water and extracted with $CH_2Cl_2$ (3×). The combined organic phases were washed with saturated $NaHCO_3$ aqueous solution, brine, dried over $Na_2SO_4$, filtered and concentrated in vacuo. The residue was purified by preparative RP-HPLC (eluent: gradient from 10% to 80% acetonitrile in water, 0.1% trifluoroacetic as modulator) to afford 3-{1-[(S)-3-(4-benzyl-piperazin-1-yl)-pyrrolidine-1-carbonyl]-propyl}-1-(4-methoxy-benzenesulfonyl)-2-oxo-2,3-dihydro-1H-benzoimidazole-5-carbonitrile (19 mg, 43%) as a white solid.

$^1$H-NMR (500 MHz, DMSO-d$_6$): δ 0.58 (br q, 7.3 Hz, 3H), 1.57-2.11 (m, 4H), 2.62-3.30 (m, 11H), 3.41-3.71 (m, 2H), 3.84 (s, 3H), 4.22 (m, 2H), 4.97-5.05 (m, 1H), 7.14-7.17 (m, 2H), 7.42-7.50 (m, 5H), 7.65-7-78 (m, 2H), 7.93-8.01 (m, 3H).

MS (API-ES, pos) m/z=643.20 [M+H]$^+$.

The compounds of the invention represent antagonists of the so-called receptors of the vasopressin/oxytocin family. Such compounds can be investigated in suitable assays which establish the affinity to a receptor, with the affinity constant Ki representing a measure of the potency of the compounds and a smaller value representing a larger potency. The compounds of the invention were tested in the following receptor binding assay for their affinity for the V1b receptor. The compounds of the invention have also affinity for the V1a receptor.

Vasopressin V1b Receptor Binding Assay:

Substances:

The test substances were dissolved in a concentration of $10^{-2}$ M in DMSO and further diluted to $5 \times 10^{-4}$ M to $5 \times 10^{-9}$ M in DMSO. This series of DMSO predilutions was diluted 1:10 with assay buffer. The substance concentration was again diluted 1:5 in the assay mixture (2% DMSO in the mixture).

Membrane Preparation:

CHO-K1 cells with stably expressed human vasopressin V1b receptor (clone 3H2) were harvested and homogenized in 50 mM Tris-HCl and in the presence of protease inhibitors (Roche complete Mini #1836170) with a Polytron homogenizer at a medium setting for 2×10 seconds and subsequently centrifuged at 40 000×g for 1 h. The membrane pellet was again homogenized and centrifuged as described and then taken up in 50 mM Tris-HCl, pH 7.4, homogenized and stored in aliquots frozen in liquid nitrogen at −190° C.

Binding Assay:

The binding assay was carried out by a method based on that of Tahara et al. (Tahara A et al., Brit. J. Pharmacol. 125, 1463-1470 (1998)). The incubation buffer was: 50 mM Tris, 10 mM $MgCl_2$, 0.1% BSA, pH 7.4. In the assay mixture (250 μl), membranes (50 μg/ml protein in incubation buffer) from CHO-K1 cells with stably expressed human V1b receptors (cell line hV1b_3H2_CHO) were incubated with 1.5 nM $^3$H-AVP (8-Arg-vasopressin, PerkinElmer #18479) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 uM AVP (Bachem #H1780). All determinations were carried out as triplicate determinations. After incubation (60 minutes at room temperature), the free radioligand was removed by vacuum filtration (Skatron cell harvester 7000) through Wathman GF/B glass fiber filter mats, and the filters were transferred into scintillation vials. The liquid scintillation measurement took place in a Tricarb model 2000 or 2200CA instrument (Packard). Conversion of the measured cpm into dpm was carried out with the aid of a standard quench series.

Evaluation:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant hV2 receptors is 0.4 nM and was used to determine the Ki value.

The above assay was used to measure the affinities of the compounds of the invention for the human vasopressin V1b receptor and to determine the affinity constants (Ki). The V1b receptor affinity of selected compounds is detailed in table I below (+++ means<100 nM, ++ means 100-500 nM and + means 500-10 000 nM).

TABLE 1

| | |
|---|---|
| (+++): | 4, 17, 20, 28, 52, 53, 57, 58, 74, 76, 78, 79, 80, 91, 106, 107, 118, 139, 140, 141, 143, 145, 146, 147, 149, 150, 151, 152, 153, 155, 156, 157, 158, 159, 160, 161, 167, 175, 176, 177, 179, 189, 191, 193, 195, 199, 203, 206, 207, 208, 209, 210, 211, 220, 221, 226, 231, 233, 235, 236, 237, 238, 242, 244, 245, 247, 249, 253, 255, 256. |
| (++): | 1, 2, 5, 6, 18, 19, 21, 22, 24, 25, 27, 31, 33, 38, 44, 45, 46, 47, 54, 56, 55, 63, 64, 65, 68, 73, 75, 77, 81, 92, 93, 96, 102, 110, 115, 117, 119, 124, 126, 129, 131, 132, 133m, 135, 136, 137, 142, 148, 154, 162, 163, 166, 168, 201, 202, 204, 215, 232, 234, 240, 246, 248, 252, 254. |
| (+): | 3, 7, 8, 9, 10, 11, 12, 13, 14, 15, 16, 23, 26, 29, 30, 32, 34, 35, 36, 37, 39, 40, 41, 42, 43, 48, 49, 50, 51, 54, 59, 60, 61, 62, 66, 67, 69, 70, 71, 72, 82, 83, 84, 85, 86, 87, 88, 89, 90, 94, 95, 97, 98, 99, 100, 101, 103, 104, 105, 108, 111, 112, 113, 114, 116, 120, 121, 122, 125, 127, 130, 144, 164, 165, 169, 170, 171, 172, 173, 174, 200, 205, 216, 239, 241, 243. |

In addition, the following assays can be used to determine the affinities for further vasopressin receptors or their subtypes such as, for example, V1a and V2, and the oxytocin (OT) receptor. The quotients, obtainable therein, of the corresponding Ki values, i.e. "Ki(V1a)/Ki(V1b)", "Ki(V2)/Ki(V1b)" and/or "Ki(OT)Ki(V1b)", can serve as a measure of a possible selectivity of the compounds of the invention in relation to a particular vasopressin or oxytocin receptor.

Vasopressin V1a Receptor Binding Assay:
Substances:
The test substances were dissolved in a concentration of $10^{-2}$ M in DMSO. These DMSO solutions were further diluted in incubation buffer (50 mM Tris, 10 mM $MgCl_2$, 0.1% BSA, pH 7.4).

Membrane Preparation:
CHO-K1 cells with stably expressed human vasopressin V1a receptor (clone 5) were harvested and homogenized in 50 mM Tris-HCl and in the presence of protease inhibitors (Roche complete Mini #1836170) with a Polytron homogenizer at a medium setting for 2×10 seconds and subsequently centrifuged at 40 000×g for 1 h. The membrane pellet was again homogenized and centrifuged as described and then taken up in 50 mM Tris-HCl, pH 7.4, homogenized and stored in aliquots frozen in liquid nitrogen at −190° C.

Binding Assay:
The binding assay was carried out by a method based on that of Tahara et al. (Tahara A et al., Brit. J. Pharmacol. 125, 1463-1470 (1998)).

The incubation buffer was: 50 mM Tris, 10 mM $MgCl_2$, 0.1% BSA, pH 7.4.

In the assay mixture (250 μl), membranes (20 μg/ml protein in incubation buffer) from CHO-K1 cells with stably expressed human V1a receptors (cell line hV1a_5_CHO) were incubated with 0.04 nM $^{125}$I-AVP (8-Arg-vasopressin, NEX 128) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 μM AVP (Bachem #H1780). Triplicate determinations were carried out.

After incubation (60 minutes at room temperature), the free radioligand was removed by vacuum filtration (Skatron cell harvester 7000) through Wathman GF/B glass fiber filter mats, and the filters were transferred into scintillation vials.

The liquid scintillation measurement took place in a Tricarb model 2000 or 2200CA instrument (Packard). Conversion of the measured cpm into dpm was carried out with the aid of a standard quench series.

Evaluation:
The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^{125}$I-AVP for the recombinant hV1a receptors was determined in saturation experiments. A Kd of 1.33 nM was used to determine the Ki value.

Vasopressin V2 Receptor Binding Assay:
Substances:
The test substances were dissolved in a concentration of $10^{-2}$ M in DMSO. This DMSO solution was further diluted in incubation buffer (50 mM Tris, 10 mM $MgCl_2$, 0.1% BSA, pH 7.4).

Membrane Preparation:
CHO-K1 cells with stably expressed human vasopressin V2 receptor (clone 23) were harvested and homogenized in 50 mM Tris-HCl and in the presence of protease inhibitors (Roche complete Mini #1836170) with a Polytron homogenizer at a medium setting for 2×10 seconds and subsequently centrifuged at 40 000×g for 1 h. The membrane pellet was again homogenized and centrifuged as described and then taken up in 50 mM Tris-HCl, pH 7.4, homogenized and stored in aliquots frozen in liquid nitrogen at −190° C.

Binding Assay:
The binding assay was carried out by a method based on that of Tahara et al. (Tahara A et al., Brit. J. Pharmacol. 125, 1463-1470 (1998)).

The incubation buffer was: 50 mM Tris, 10 mM $MgCl_2$, 0.1% BSA, pH 7.4.

In the assay mixture (250 μl), membranes (50 μg/ml protein in incubation buffer) from CHO-K1 cells with stably expressed human V2 receptors (cell line hV2_23_CHO) were incubated with 1-2 nM $^3$H-AVP (8-Arg-vasopressin, PerkinElmer #18479) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 μM AVP (Bachem #H1780). Triplicate determinations were carried out.

After incubation (60 minutes at room temperature), the free radioligand was removed by vacuum filtration (Skatron cell harvester 7000) through Wathman GF/B glass fiber filter mats, and the filters were transferred into scintillation vials.

The liquid scintillation measurement took place in a Tricarb model 2000 or 2200CA instrument (Packard). Conversion of the measured cpm into dpm was carried out with the aid of a standard quench series.

Evaluation:
The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant hV2 receptors is 2.4 nM and was used to determine the Ki value.

Oxytocin Receptor Binding Assay
Substances:
The substances were dissolved in a concentration of $10^{-2}$ M in DMSO and diluted with incubation buffer (50 mM Tris, 10 mM $MgCl_2$, 0.1% BSA, pH 7.4).

Cell Preparation:

Confluent HEK-293 cells with transiently expressing recombinant human oxytocin receptors were centrifuged at 750×g and at room temperature for 5 minutes. The residue was taken up in ice-cold lysis buffer (50 mM Tris-HCl, 10% glycerol, pH 7.4 and Roche Complete Protease Inhibitor) and subjected to an osmotic shock at 4° C. for 20 minutes. The lyzed cells were then centrifuged at 750×g and at 4° C. for 20 minutes, the residue was taken up in incubation buffer, and aliquots of $10^7$ cells/ml were prepared. The aliquots were frozen at −80° C. until used.

Binding Assay:

On the day of the experiment, the cells were thawed, diluted with incubation buffer and homogenized using a Multipette Combitip (Eppendorf, Hamburg). The reaction mixture of 0.250 ml was composed of 2 to $5 \times 10^4$ recombinant cells, 3-4 nM $^3$H-oxytocin (Perkin Elmer, NET 858) in the presence of test substance (inhibition plot) or only incubation buffer (total binding). The nonspecific binding was determined with $10^{-6}$ M oxytocin (Bachem AG, H2510). Determinations in triplicate were set up. Bound and free radioligand were separated by filtration under vacuum with Whatman GF/B glass fiber filters using a Skatron cell harvester 7000. The bound radioactivity was determined by liquid scintillation measurement in a Tricarb beta counter, model 2000 or 2200CA (Packard).

Evaluation:

The binding parameters were calculated by nonlinear regression analysis (SAS), in analogy to the LIGAND program of Munson and Rodbard (Analytical Biochem 1980; 107: 220-239). The Kd of $^3$H-oxytocin for the recombinant hOT receptors is 7.6 nM and was used to determine the Ki value.

The metabolic stability of the compounds of the invention was determined in the following assay.

Determination of the Microsomal Half-Life:

The test substances are incubated in a concentration of 0.5 µM as follows: 0.5 µM test substance is preincubated together with liver microsomes of various species (0.25 mg of protein/ml) in 0.05M potassium phosphate buffer pH 7.4 in microtiter plates at 37° C. for 5 min. The reaction is started by adding NADPH (1 mg/ml). Aliquots are taken after 0, 5, 10, 15, 20 and 30 min, and the reaction is stopped with the same volume of acetonitrile and cooled down. The samples are frozen until analyzed. The half-life of the compound can be calculated, assuming first order kinetics, from the decrease in the concentration of the compound with time.

The invention claimed is:

1. A method for the treatment of a vasopressin-dependent disease selected from the group consisting of anxiety disorders, depressive disorders, and hyponatremia, the method comprising administering to a subject in need thereof a compound of the general formula (I),

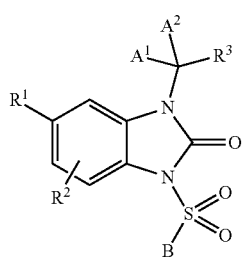

(I)

in which $A^1$ is hydrogen, in each case optionally substituted $C_1$-$C_6$-alkyl, $C_1$-$C_6$-alkenyl, $C_2$-$C_6$-alkynyl, $C_3$-$C_6$-cycloalkyl, $C_3$-$C_6$-cycloalkenyl or $C_1$-$C_4$-alkylene-phenyl, or an aromatic, heteroaromatic, partly aromatic or partly heteroaromatic mono- or bicyclic ring having 1, 2, 3, 4, 5, 6, 7, 8, 9 or 10 carbon atoms as ring members, which may besides additionally comprise 0, 1, 2, 3 or 4 identical or different heteroatoms independently of one another selected from the group consisting of nitrogen, oxygen and sulfur as ring members, and which may be substituted by one, two or three radicals $R_A^{11}$, $R_A^{12}$ and/or $R_A^{13}$ which are selected independently of one another and independently of their respective occurrence from the group consisting of hydrogen, bromine, chlorine, iodine, fluorine, CN, $CF_3$, $OCF_3$, $OCHF_2$, OH, COOH, CO—$NH_2$, $NH_2$, NH—CO—NH, or in each case optionally substituted $C_1$-$C_6$-alkyl, O—$C_1$-$C_6$-alkyl, $C_1$-$C_6$-alkenyl, $C_1$-$C_6$-alkynyl, $C_3$-$C_6$-cycloalkyl, O—$C_3$-$C_6$-cycloalkyl, $C_3$-$C_6$-cycloalkenyl, $C_1$-$C_4$-alkylene-aryl, NH—($C_1$-$C_6$-alkyl), N($C_1$-$C_6$-alkyl)-$C_1$-$C_4$—NH—$C_1$-$C_4$-alkylene-NH—($C_1$-$C_6$-alkyl), $C_1$-$C_4$-alkylene-N($C_1$-$C_6$-alkyl)-$C_1$-$C_4$-alkylene-OH, $C_1$-$C_4$alkylene-O—$C_1$-$C_6$-alkyl, CO—$C_1$-$C_6$-alkyl, CO—O—$C_1$-$C_6$-alkyl, CO—NH($C_1$-$C_6$-alkyl), $C_1$-$C_6$-alkyl)-NH—CO—$C_1$-$C_6$-alkyl, NH—CO—N($C_1$-$C_6$-alkyl)$_2$, and N($C_1$-$C_6$-alkyl)-CO—$C_1$-$C_6$-alkyl;

$A^2$ is hydrogen or in each case optionally substituted $C_1$-$C_6$-alkyl, $C_1$-$C_6$-alkenyl, $C_1$-$C_6$-alkynyl or $C_3$-$C_6$-cycloalkyl, or where the radicals $A^1$ and $A^2$ may form together with the carbon atom to which they are bonded an in each case optionally substituted 3- to 7-membered carbocyclic ring (spiro linkage) which may additionally comprise a heteroatom as ring member selected from the group consisting of 0, S and $NR_A^{14}$ in which $R_A^{14}$ is a radical selected from the group consisting of hydrogen and in each case optionally substituted $C_1$-$C_6$-alkyl, aryl and $C_1$-$C_4$-alkylene-aryl, and where the ring formed in this way may be substituted by one, two or three radicals $R_A^{11}$, $R_A^{12}$ and/or $R_A^{13}$ which may independently of one another and independently of their respective occurrence assume the aforementioned meanings;

B is an aromatic, heteroaromatic, partly aromatic or partly heteroaromatic mono- or bicyclic ring having 1, 2, 3, 4, 5, 6, 7, 8, 9 or 10 C atoms as ring members, which may additionally comprise 0, 1, 2, 3 or 4 identical or different heteroatoms independently of one another selected from the group consisting of nitrogen, oxygen and sulfur as ring members, and which may be substituted by one, two or three radicals $R_B^1$, $R_B^2$ and/or $R_B^3$, where $R_B^1$, $R_B^2$ and $R_B^3$ are selected independently of one another and independently of their respective occurrence from the group consisting of hydrogen, chlorine, bromine, fluorine, CN, $CF_3$, $OCF_3$, $OCHF_2$, $OCH_2F$, $OCH_2CF_3$, $OCH_2$—$CHF_2$, OH, and in each case optionally substituted O—$C_1$-$C_4$-alkyl, $C_1$-$C_4$-alkyl, $C_2$-$C_4$-alkenyl and $C_2$-$C_4$-alkynyl;

$R^1$ is selected from the group consisting of hydrogen, bromine, chlorine, fluorine, iodine, CN, $CF_3$, $OCF_3$, $OCHF_2$, O—$C_1$-$C_4$-alkyl, $C_1$-$C_4$-alkyl, $C_1$-$C_4$-alkenyl, $C_2$-$C_4$-alkynyl, NH($C_1$-$C_4$-alkyl), N($C_1$-$C_4$-alkyl)($C_1$-$C_4$-alkyl), $NO_2$, NHCHO, NHCO($C_1$-$C_4$-alkyl) and $NHCONH_2$;

R² is selected from the group consisting of hydrogen, and in each case optionally substituted $C_1$-$C_4$-alkyl, O—$C_1$-$C_4$-alkyl, chlorine, fluorine, difluoromethyl ($CHF_2$) and trifluoromethyl;

R³ is a radical (X)—(Y), where
X is CO, $SO_2$ or (C═NH),
Y is selected from the group consisting of OH, $NH_2$, $NH(C_1$-$C_4$-alkyl), $N(C_1$-$C_4$-alkyl)($C_1$-$C_4$-alkyl), $NH(C_2$-$C_4$-alkylene-OH), $N(C_1$-$C_4$-alkyl)($C_2$-$C_4$-alkylene-OH), $NH(C_2$-$C_4$-alkylene-O—$C_1$-$C_4$-alkyl), $N(C_1$-$C_4$-alkyl)($C_2$-$C_4$-alkylene-O—$C_1$-$C_4$-alkyl), $NH(C_3$-$C_7$-cycloalkyl), $N(C_1$-$C_4$-alkyl)($C_1$-$C_7$-cyclo-alkyl), $NH(C_1$-$C_4$-haloalkyl), $N(C_1$-$C_4$-alkyl)($C_1$-$C_4$-haloalkyl), $N(R^5)(C_1$-$C_4$-alkylene)-$R_Y^3$, and radical $R_Y^1$;

$R_Y^1$ is selected independently of its respective occurrence from the group consisting of the respective individual radicals mentioned below

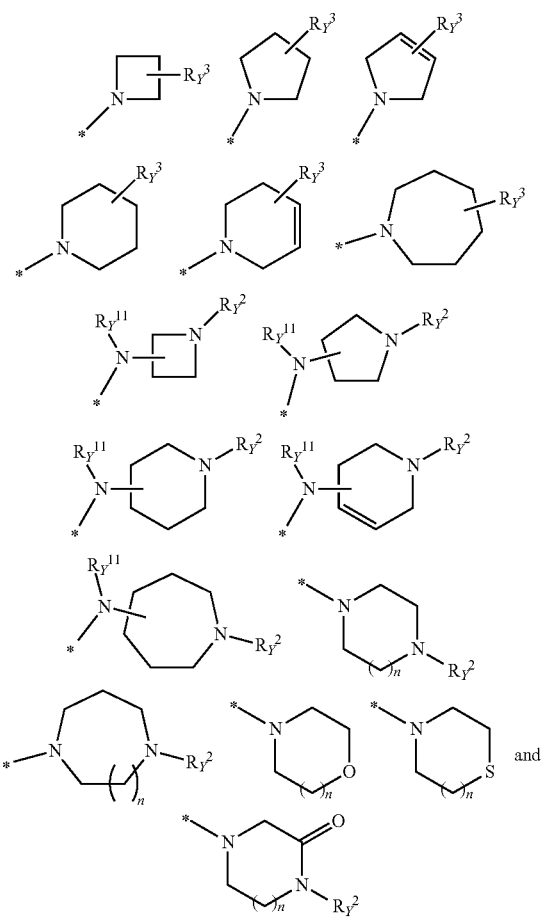

n = 1, 2 where n is independently of its occurrence the integer 1 or 2,
where the aforementioned radicals may independently of one another each have one or two substituents $R_Y^{12}$ and/or $R_Y^{13}$ which are selected independently of one another and independently of their respective occurrence from the group consisting of hydrogen, fluorine, OH, in each case optionally substituted O—$C_1$-$C_4$-alkyl, phenyl and $C_1$-$C_4$-alkyl;

$R_Y^{11}$ is a radical selected from the group consisting of hydrogen, in each case optionally substituted $C_1$-$C_6$-alkyl, $C_2$-$C_6$-alkenyl and $C_2$-$C_6$-alkynyl;

$R_Y^2$ is a radical selected from the group consisting of hydrogen, in each case optionally substituted $C_1$-$C_6$-alkyl, $C_2$-$C_6$-alkenyl, $C_2$-$C_6$-alkynyl, phenyl, $C_1$-$C_4$-alkylene-phenyl, $C_1$-$C_4$-haloalkyl, $C_3$-$C_7$-cycloalkyl, pyridine, pyrimidine, pyrazine, pyridazine, furan, thiophene, pyrrole, oxazole, isoxazole, thiazole, imidazole, pyrazole, 1,2,4-oxadiazole, 1,2,5-oxadiazole, 1,3,4-oxadiazole, thiadiazole, triazole, 1,3,5-triazine, tetrazole, ($C_2$-$C_4$-alkylene)-$R_Y^3$ and ring radical $R_Y^{22}$, where $R_Y^{22}$ is selected independently of its respective occurrence from the group consisting of the respective individual radicals

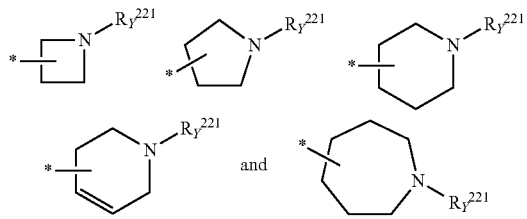

where the aforementioned radicals may independently of one another in each case have one or two substituents $R_Y^{222a}$ and/or $R_Y^{223a}$ which are selected independently of one another and independently of their respective occurrence from the group consisting of hydrogen, fluorine, OH and in each case optionally substituted O—$C_1$-$C_4$-alkyl, phenyl and $C_1$-$C_4$-alkyl;

$R_Y^{221}$ is a radical selected from the group consisting of hydrogen, and in each case optionally substituted $C_1$-$C_6$-alkyl, $C_2$-$C_6$-alkenyl, $C_2$-$C_6$-alkynyl and $C_1$-$C_4$-alkylene-phenyl, in particular hydrogen, and in each case optionally substituted $C_1$-$C_6$-alkyl, $C_2$-$C_6$-alkenyl and $C_1$-$C_6$-alkynyl;

$R_Y^3$ is a radical selected from the group consisting of hydrogen, $NH_2$, $N(R_Y^{3a})R_Y^{3b}$, $NH(C_2$-$C_4$-alkylene)-$R_Y^8$, $N(R_Y^7)(C_2$-$C_4$-alkylene)-$R_Y^8$, $N(R_Y^7)R_Y^9$, $N(R_Y^7)CH_2R_Y^9$, a radical $R_Y^{33}$, a radical $CH_2R_Y^{33}$ and an aromatic radical, selected from phenyl, pyridine, pyrimidine, pyrazine, pyridazine, furan, thiophene, pyrrole, oxazole, isoxazole, thiazole, isothiazole, imidazole, pyrazole, 1,2,4-oxadiazole, 1,2,5-oxadiazole, 1,3,4-oxadiazole, thiadiazole, triazole, 1,3,5-triazine and tetrazole, the aromatic radical being substituted or carrying 1 or 2 substitutens $R_Y^{331}$ and/or $R_Y^{332}$, where $R_Y^{33}$ is independently of its respective occurrence a radical selected from the group consisting of the respective individual radicals

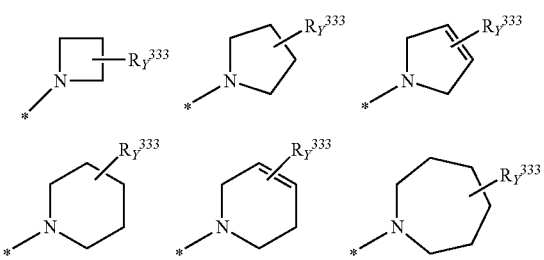

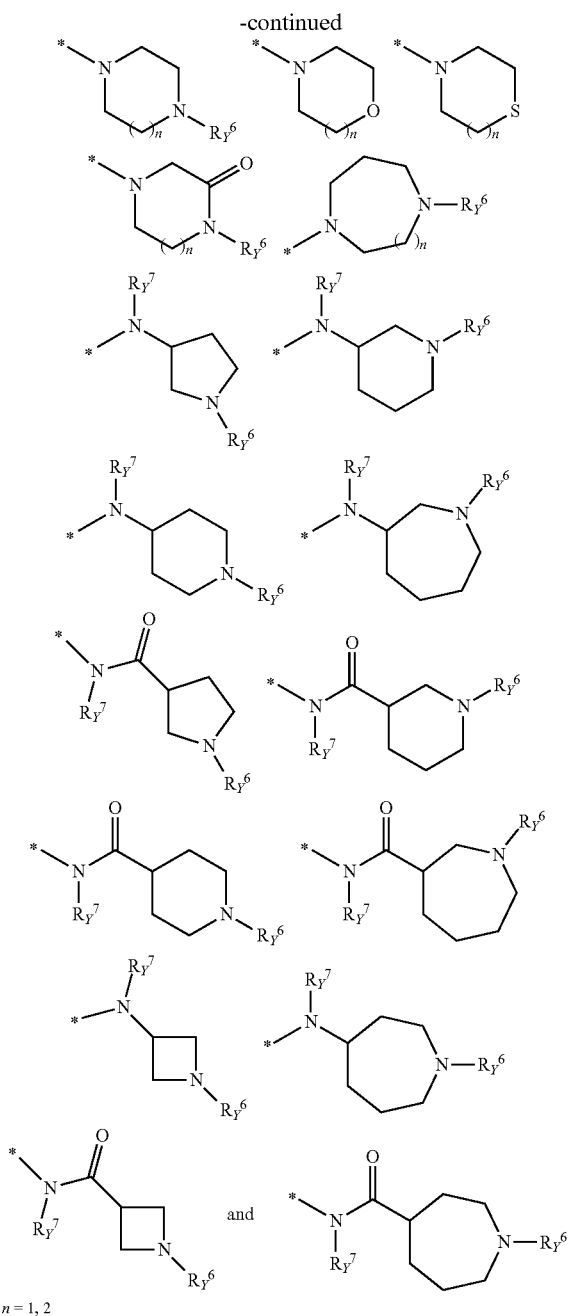

where n is independently of its occurrence the integer 1 or 2, where the aforementioned radicals $R^{33}$ may independently of one another in each case have one or two substituents $R_Y^{331}$ and/or $R_Y^{332}$;

$R_Y^{331}$, $R_Y^{332}$ are selected independently of one another and independently of their respective occurrence from the group consisting of hydrogen, fluorine, OH, and in each case optionally substituted O—$C_1$-$C_4$-alkyl, phenyl and $C_1$-$C_4$-alkyl;

$R_Y^{333}$ is a radical selected from the group consisting of hydrogen and in each case optionally substituted $C_1$-$C_6$-alkyl, $C_2$-$C_6$-alkenyl, $C_2$-$C_6$-alkynyl, phenyl and $C_1$-$C_4$-alkylene-phenyl;

$R_Y^{3a}$ is a radical selected from the group consisting of hydrogen, and in each case optionally substituted $C_1$-$C_6$-alkyl, $C_3$-$C_7$-cycloalkyl, $C_2$-$C_6$-alkenyl, $C_2$-$C_6$-alkynyl, phenyl and $C_1$-$C_4$-alkylene-phenyl;

$R_Y^{3b}$ is a radical selected from the group consisting of in each case optionally substituted $C_1$-$C_6$-alkyl and $C_1$-$C_4$-alkylene-phenyl;

$R_Y^5$ is a radical selected from the group consisting of hydrogen and in each case optionally substituted $C_1$-$C_4$-alkyl;

$R_Y^6$ is a radical selected from the group consisting of hydrogen and in each case optionally substituted $C_1$-$C_6$-alkyl, $C_2$-$C_6$-alkenyl, $C_2$-$C_6$-alkynyl, phenyl and $C_1$-$C_4$-alkylene-phenyl;

$R_Y^7$ is a radical selected from the group consisting of hydrogen and in each case optionally substituted $C_1$-$C_6$-alkyl, $C_2$-$C_6$-alkenyl, $C_2$-$C_6$-alkynyl, phenyl and $C_1$-$C_4$-alkylene-phenyl;

$R_Y^8$ is a radical selected from the group consisting of OH, $NH_2$, and in each case optionally substituted $NH(C_1$-$C_4$-alkyl), $N(C_1$-$C_4$-alkyl)($C_1$-$C_4$alkyl), $NH(C_2$-$C_4$-alkylene-OH), $N(C_1$-$C_4$-alkyl)($C_2$-$C_4$-alkylene-OH), $NH(C_2$-$C_4$-alkylene-O—$C_1$-$C_4$-alkyl), $N(C_1$-$C_4$-alkyl) ($C_2$-$C_4$alkylene-O—$C_1$-$C_4$-alkyl), $NH(C_3$-$C_7$-cycloalkyl), $N(C_1$-$C_4$-alkyl)($C_3$-$C_7$-cycloalkyl), $NH(C_1$-$C_4$haloalkyl), $N(C_1$-$C_4$-alkyl)($C_1$-$C_4$-haloalkyl), O—$C_1$-$C_4$-alkyl, and the ring radical $R_Y^{81}$, where $R_Y^{81}$ is a radical independently of its respective occurrence selected from the group consisting of the respective individual radicals

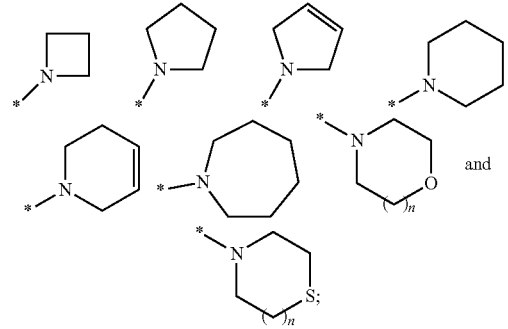

$n = 1, 2$ $R_Y^9$ is a 5- or 6-membered heteroaromatic radical having 2, 3, 4 or 5 carbon atom as ring members and 1, 2 or 3 heteroatoms, selected from O, S and N, wherein the 5- or 6-membered heteroaromatic radical may be unsubstituted or may have one or two substituents $R_Y^{331}$ and/or $R_Y^{332}$;

the tautomeric, enantiomeric and/or diastereomeric forms thereof, and the physiologically tolerated salts of the aforementioned compound or compounds;

with the proviso that $R^1 \neq H$ (is not hydrogen) when $A^1 = A^2 =$ hydrogen;

and with the proviso that $R^1$ is halogen, cyano, or in each case optionally substituted $C_1$-$C_6$-alkoxy or $C_1$-$C_6$-alkyl when $A^1 = A^2 =$ hydrogen.

2. The method of claim 1, wherein the compound of the formula (I) has a binding affinity Ki for the vasopressin V1b receptor subtype of less than about 100 nM.

3. The method of claim 1, wherein the compound of the formula (I) has a binding affinity Ki for the vasopressin V1b receptor subtype of between about 10 nM and about 100 nM.

4. The method of claim 1, wherein the compound of the formula (I) has a binding affinity Ki for the vasopressin V1b receptor subtype of less than or equal to about 10 nM.

5. The method of claim 1, wherein the method comprises administering an effective amount of a compound of formula (I), or of a physiologically tolerated salt thereof, to a subject that is a mammal.

6. A method for the treatment of a vasopressin-dependent disease selected from the group consisting of hypertension, pulmonary hypertension, heart failure, myocardial infarction, coronary spasm, unstable angina, PTCA (percutaneous transluminal coronary angioplasty), ischemias of the heart, disorders of the renal system, renal vasospasm, necrosis of the renal cortex, hypokalemia, Schwartz-Bartter syndrome, disorders of the gastrointestinal tract, gastric vasospasm, hepatocirrhosis, gastric and intestinal ulcers, emesis, emesis occurring during chemotherapy, travel sickness, diabetes insipidus, nocturnal enuresis, and incontinence, or for delaying micturition, the method comprising administering to a subject in need thereof a compound of the general formula (I),

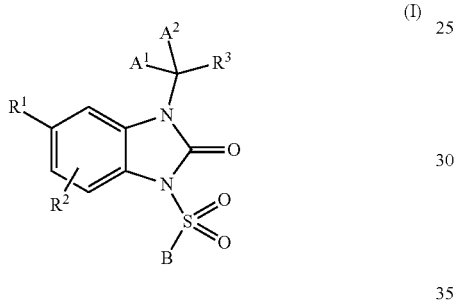

in which

A$^1$ is hydrogen, in each case optionally substituted C$_1$-C$_6$-alkyl, C$_2$-C$_6$-alkenyl, C$_2$-C$_6$-alkynyl, C$_3$-C$_6$-cycloalkyl, C$_3$-C$_6$-cycloalkenyl or C$_1$-C$_4$-alkylene-phenyl, or an aromatic, heteroaromatic, partly aromatic or partly heteroaromatic mono- or bicyclic ring having 1, 2, 3, 4, 5, 6, 7, 8, 9 or 10 carbon atoms as ring members, which may besides additionally comprise 0, 1, 2, 3 or 4 identical or different heteroatoms independently of one another selected from the group consisting of nitrogen, oxygen and sulfur as ring members, and which may be substituted by one, two or three radicals R$_A$$^{11}$, R$_A$$^{12}$ and/or R$_A$$^{13}$ which are selected independently of one another and independently of their respective occurrence from the group consisting of hydrogen, bromine, chlorine, iodine, fluorine, CN, CF$_3$, OCF$_3$, OCHF$_2$OH, COOH, CO—NH$_2$, NH$_2$, NH—CO—NH$_2$ or in each case optionally substituted C$_1$-C$_6$-alkyl, O—C$_1$-C$_6$-alkyl, C$_2$-C$_6$-alkenyl, C$_2$-C$_6$-alkynyl, C$_3$-C$_6$-cycloalkyl, O—C$_3$-C$_6$-cycloalkyl, C$_3$-C$_6$-cycloalkenyl, C$_1$-C$_4$-alkylene-aryl, NH—(C$_1$-C$_6$-alkyl), N(C$_1$-C$_6$-alkyl)-C$_1$-C$_4$—NH$_2$, C$_1$-C$_4$-alkylene-NH—(C$_1$-C$_6$-alkyl), C$_1$-C$_4$-alkylene-N(C$_1$-C$_6$-alkyl)-C$_1$-C$_4$-alkylene-OH, C$_1$-C$_4$alkylene-O—C$_1$-C$_6$-alkyl, CO—C$_1$-C$_6$-alkyl, CO—O—C$_1$-C$_6$-alkyl, CO—NH(C$_1$-C$_6$-alkyl), CO—N(C$_1$-C$_6$-alkyl)$_2$, NH—CO—C$_1$-C$_6$-alkyl, NH—CO—N(C$_1$-C$_6$-alkyl)$_2$, and N(C$_1$-C$_6$-alkyl)-CO—C$_1$-C$_6$-alkyl;

A$^2$ is hydrogen or in each case optionally substituted C$_1$-C$_6$-alkyl, C$_1$-C$_6$-alkenyl, C$_1$-C$_6$-alkynyl or C$_3$-C$_6$-cycloalkyl, or where the radicals A$^1$ and A$^2$ may form together with the carbon atom to which they are bonded an in each case optionally substituted 3- to 7-membered carbocyclic ring (spiro linkage) which may additionally comprise a heteroatom as ring member selected from the group consisting of O, S and NR$_A$$^{14}$ in which R$_A$$^{14}$ is a radical selected from the group consisting of hydrogen and in each case optionally substituted C$_1$-C$_6$-alkyl, aryl and C$_1$-C$_4$-alkylene-aryl, and where the ring formed in this way may be substituted by one, two or three radicals R$_A$$^{11}$, R$_A$$^{12}$ and/or R$_A$$^{13}$ which may independently of one another and independently of their respective occurrence assume the aforementioned meanings;

B is an aromatic, heteroaromatic, partly aromatic or partly heteroaromatic mono- or bicyclic ring having 1, 2, 3, 4, 5, 6, 7, 8, 9 or 10 C atoms as ring members, which may additionally comprise 0, 1, 2, 3 or 4 identical or different heteroatoms independently of one another selected from the group consisting of nitrogen, oxygen and sulfur as ring members, and which may be substituted by one, two or three radicals R$_B$$^1$, R$_B$$^2$ and/or R$_B$$^3$, where R$_B$$^1$, R$_B$$^2$ and R$_B$$^3$ are selected independently of one another and independently of their respective occurrence from the group consisting of hydrogen, chlorine, bromine, fluorine, CN, CF$_3$, OCF$_3$, OCHF$_2$, OCH$_2$F, OCH$_2$CF$_3$, OCH$_2$—CHF$_2$, OH, and in each case optionally substituted O—C$_1$-C$_4$-alkyl, C$_1$-C$_4$-alkyl, C$_2$-C$_4$-alkenyl and C$_2$-C$_4$-alkynyl;

R$^1$ is selected from the group consisting of hydrogen, bromine, chlorine, fluorine, iodine, CN, CF$_3$, OCF$_3$, OCHF$_2$, O—C$_1$-C$_4$-alkyl, C$_1$-C$_4$-alkyl, C$_1$-C$_4$-alkenyl, C$_2$-C$_4$-alkynyl, NH(C$_1$-C$_4$-alkyl), N(C$_1$-C$_4$-alkyl)(C$_1$-C$_4$-alkyl), NO$_2$, NHCHO, NHCO(C$_1$-C$_4$-alkyl) and NHCONH$_2$;

R$^2$ is selected from the group consisting of hydrogen, and in each case optionally substituted C$_1$-C$_4$-alkyl, O—C$_1$-C$_4$-alkyl, chlorine, fluorine, difluoromethyl (CHF$_2$) and trifluoromethyl;

R$^3$ is a radical (X)—(Y), where

X is CO, SO$_2$ or (C=NH),

Y is selected from the group consisting of OH, NH$_2$, NH(C$_1$-C$_4$-alkyl), N(C$_1$-C$_4$-alkyl)(C$_1$-C$_4$-alkyl), NH(C$_2$-C$_4$-alkylene-OH), N(C$_1$-C$_4$-alkyl)(C$_2$-C$_4$-alkylene-OH), NH(C$_2$-C$_4$-alkylene-O—C$_1$-C$_4$-alkyl), N(C$_1$-C$_4$-alkyl)(C$_2$-C$_4$-alkylene-O—C$_1$-C$_4$-alkyl), NH(C$_3$-C$_7$-cycloalkyl), N(C$_1$-C$_4$-alkyl)(C$_1$-C$_7$-cyclo-alkyl), NH(C$_1$-C$_4$-haloalkyl), N(C$_1$-C$_4$-alkyl)(C$_1$-C$_4$-haloalkyl), N(R$_Y$$^5$)(C$_1$-C$_4$-alkylene)-R$_Y$$^3$, and radical R$_Y$$^1$;

R$_Y$$^1$ is selected independently of its respective occurrence from the group consisting of the respective individual radicals mentioned below

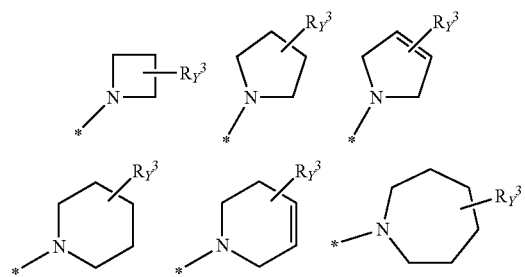

-continued

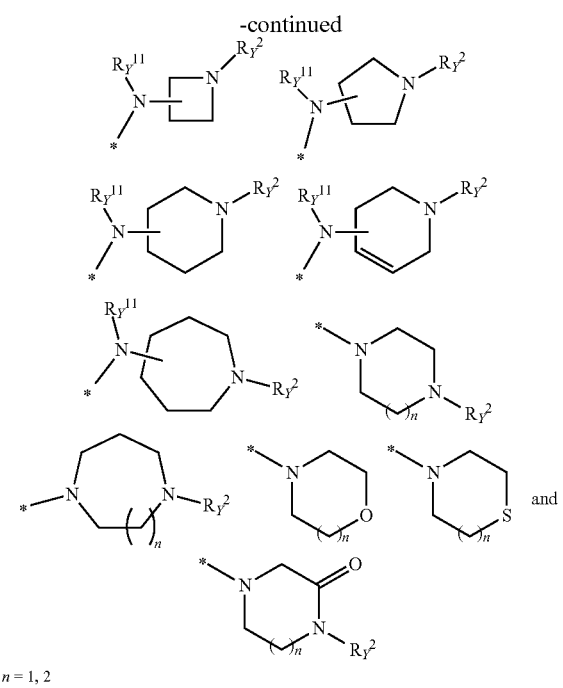

n = 1, 2 where n is independently of its occurrence the integer 1 or 2, where the aforementioned radicals may independently of one another each have one or two substituents $R_Y^{12}$ and/or $R_Y^{13}$ which are selected independently of one another and independently of their respective occurrence from the group consisting of hydrogen, fluorine, OH, in each case optionally substituted O—$C_1$-$C_4$-alkyl, phenyl and $C_1$-$C_4$-alkyl;

$R_Y^{11}$ is a radical selected from the group consisting of hydrogen, in each case optionally substituted $C_1$-$C_6$-alkyl, $C_2$-$C_6$-alkenyl and $C_2$-$C_6$-alkynyl;

$R_Y^2$ is a radical selected from the group consisting of hydrogen, in each case optionally substituted $C_1$-$C_6$-alkyl, $C_2$-$C_6$-alkenyl, $C_2$-$C_6$-alkynyl, phenyl, $C_1$-$C_4$-alkylene-phenyl, $C_1$-$C_4$-haloalkyl, $C_3$-$C_7$-cycloalkyl, pyridine, pyrimidine, pyrazine, pyridazine, furan, thiophene, pyrrole, oxazole, isoxazole, thiazole, imidazole, pyrazole, 1,2,4-oxadiazole, 1,2,5-oxadiazole, 1,3,4-oxadiazole, thiadiazole, triazole, 1,3,5-triazine, tetrazole, ($C_2$-$C_4$-alkylene)-$R_Y^3$ and ring radical $R_Y^{22}$, where $R_Y^{22}$ is selected independently of its respective occurrence from the group consisting of the respective individual radicals

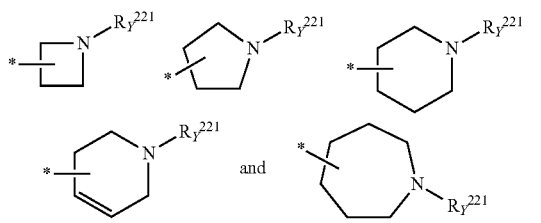

where the aforementioned radicals may independently of one another in each case have one or two substituents $R_Y^{222a}$ and/or $R_Y^{223a}$ which are selected independently of one another and independently of their respective occurrence from the group consisting of hydrogen, fluorine, OH and in each case optionally substituted O—$C_1$-$C_4$-alkyl, phenyl and $C_1$-$C_4$-alkyl;

$R_Y^{221}$ is a radical selected from the group consisting of hydrogen, and in each case optionally substituted $C_1$-$C_6$-alkyl, $C_2$-$C_6$-alkenyl, $C_2$-$C_6$-alkynyl and $C_1$-$C_4$-alkylene-phenyl, in particular hydrogen, and in each case optionally substituted $C_1$-$C_6$-alkyl, $C_2$-$C_6$-alkenyl and $C_2$-$C_6$-alkynyl;

$R_Y^3$ is a radical selected from the group consisting of hydrogen, $NH_2$, $N(R_Y^{3a})R_Y^{3b}$, $NH(C_2$-$C_4$-alkylene)-$R_Y^8$, $N(R_Y^7)(C_2$-$C_4$-alkylene)-$R_Y^8$, $N(R_Y^7)R_Y^9$, $N(R_Y^7)CH_2R_Y^9$, a radical $R_Y^{33}$, a radical $CH_2R_Y^{33}$ and an aromatic radical, selected from phenyl, pyridine, pyrimidine, pyrazine, pyridazine, furan, thiophene, pyrrole, oxazole, isoxazole, thiazole, isothiazole, imidazole, pyrazole, 1,2,4-oxadiazole, 1,2,5-oxadiazole, 1,3,4-oxadiazole, thiadiazole, triazole, 1,3,5-triazine and tetrazole, the aromatic radical being substituted or carrying 1 or 2 substitutens $R_Y^{331}$ and/or $R_Y^{332}$, where $R_Y^{33}$ is independently of its respective occurrence a radical selected from the group consisting of the respective individual radicals

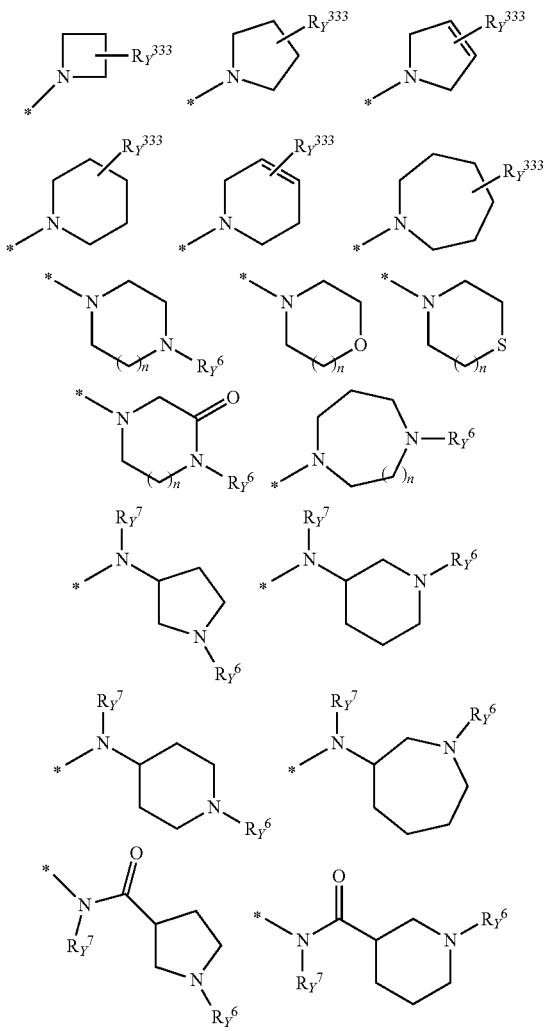

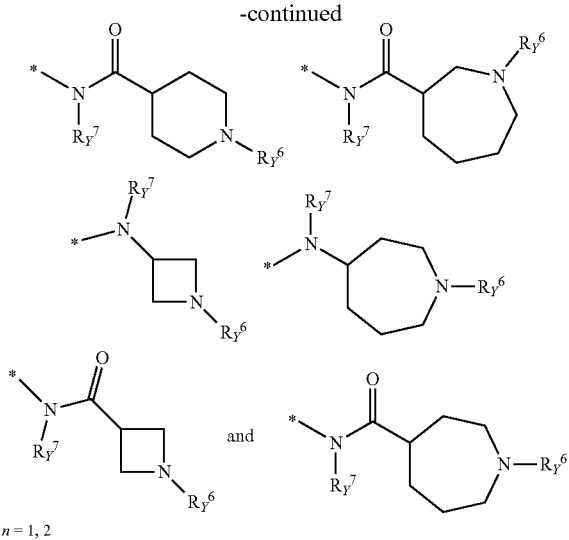

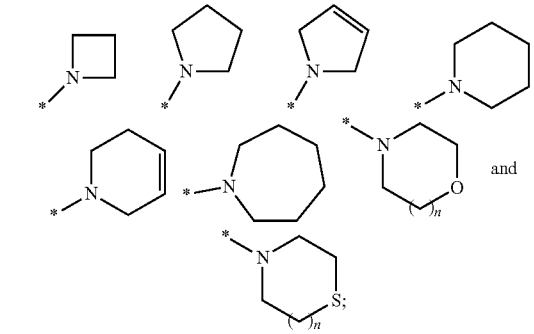

$n = 1, 2$ where n is independently of its occurrence the integer 1 or 2, where the aforementioned radicals $R^{33}$ may independently of one another in each case have one or two substituents $R_Y^{331}$ and/or $R_Y^{332}$;

$R_Y^{331}$, $R_Y^{332}$ are selected independently of one another and independently of their respective occurrence from the group consisting of hydrogen, fluorine, OH, and in each case optionally substituted O—$C_1$-$C_4$-alkyl, phenyl and $C_1$-$C_4$-alkyl;

$R_Y^{333}$ is a radical selected from the group consisting of hydrogen and in each case optionally substituted $C_1$-$C_6$-alkyl, $C_2$-$C_6$-alkenyl, $C_2$-$C_6$-alkynyl, phenyl and $C_1$-$C_4$-alkylene-phenyl;

$R_Y^{3a}$ is a radical selected from the group consisting of hydrogen, and in each case optionally substituted $C_1$-$C_6$-alkyl, $C_3$-$C_7$-cycloalkyl, $C_2$-$C_6$-alkenyl, $C_2$-$C_6$-alkynyl, phenyl and $C_1$-$C_4$-alkylene-phenyl;

$R_Y^{3b}$ is a radical selected from the group consisting of in each case optionally substituted $C_1$-$C_6$-alkyl and $C_1$-$C_4$-alkylene-phenyl;

$R_Y^5$ is a radical selected from the group consisting of hydrogen and in each case optionally substituted $C_1$-$C_4$-alkyl;

$R_Y^A$ is a radical selected from the group consisting of hydrogen and in each case optionally substituted $C_1$-$C_6$-alkyl, $C_2$-$C_6$-alkenyl, $C_2$-$C_6$-alkynyl, phenyl and $C_1$-$C_4$-alkylene-phenyl;

$R_Y^7$ is a radical selected from the group consisting of hydrogen and in each case optionally substituted $C_1$-$C_6$-alkyl, $C_2$-$C_6$-alkenyl, $C_2$-$C_6$-alkynyl, phenyl and $C_1$-$C_4$-alkylene-phenyl;

$R_Y^8$ is a radical selected from the group consisting of OH, $NH_2$, and in each case optionally substituted NH($C_1$-$C_4$-alkyl), N($C_1$-$C_4$-alkyl) ($C_1$-$C_4$-alkyl), NH($C_2$-$C_4$-alkylene-OH), N($C_1$-$C_4$-alkyl)($C_2$-$C_4$-alkylene-OH), NH($C_2$-$C_4$-alkylene-O—$C_1$-$C_4$alkyl), N($C_1$-$C_4$-alkyl)($C_2$-$C_4$-alkylene-O—$C_1$-$C_4$-alkyl), NH($C_3$-$C_7$-cycloalkyl), N($C_1$-$C_4$-alkyl)($C_3$-$C_7$-cycloalkyl), NH($C_1$-$C_4$haloalkyl), N($C_1$-$C_4$-alkyl)($C_1$-$C_4$-haloalkyl), O—$C_1$-$C_4$-alkyl, and the ring radical $R_Y^{81}$, where $R_Y^{81}$ is a radical independently of its respective occurrence selected from the group consisting of the respective individual radicals $R_Y^9$ is a 5- or 6-membered heteroaromatic radical having 2, 3, 4 or 5 carbon atom as ring members and 1, 2 or 3 heteroatoms, selected from the group consisting of O, S and N, wherein the 5- or 6-membered heteroaromatic radical may be unsubstituted or may have one or two substituents $R_Y^{331}$ and/or $R_Y^{332}$;

the tautomeric, enantiomeric and/or diastereomeric forms thereof, and the physiologically tolerated salts of the aforementioned compound or compounds;

with the proviso that $R^1$—H (is not hydrogen) when $A^1$=$A^2$=hydrogen;

and with the proviso that $R^1$ is halogen, cyano, or in each case optionally substituted $C_1$-$C_6$-alkoxy or $C_1$-$C_6$-alkyl when $A^1$=$A^2$=hydrogen.

7. The method of claim 6, wherein the compound of the formula (I) has a binding affinity Ki for the vasopressin V1b receptor subtype of less than about 100 nM.

8. The method of claim 6, wherein the compound of the formula (I) has a binding affinity Ki for the vasopressin V1b receptor subtype of between about 10 nM and about 100 nM.

9. The method of claim 6, wherein the compound of the formula (I) has a binding affinity Ki for the vasopressin V1b receptor subtype of less than or equal to about 10 nM.

10. The method of claim 6, wherein the method comprises administering an effective amount of a compound of formula (I), or of a physiologically tolerated salt thereof, to a subject that is a mammal.

11. A method for the treatment of a vasopressin-dependent disease selected from the group consisting of memory impairments, Alzheimer's disease, psychoses, psychotic disorders, Cushing's syndrome, sleep disorders, schizophrenia, vasomotor symptoms, and thermoregulatory dysfunctions, the method comprising administering to a subject in need thereof a compound of the general formula (I),

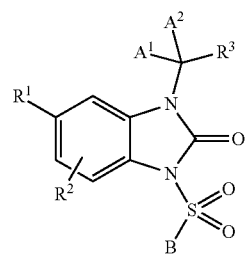

(I)

in which

A$^1$ is hydrogen, in each case optionally substituted C$_1$-C$_6$-alkyl, C$_1$-C$_6$-alkenyl, C$_1$-C$_6$-alkynyl, C$_3$-C$_6$-cycloalkyl, C$_3$-C$_6$-cycloalkenyl or C$_1$-C$_4$-alkylene-phenyl, or
an aromatic, heteroaromatic, partly aromatic or partly heteroaromatic mono- or bicyclic ring having 1, 2, 3, 4, 5, 6, 7, 8, 9 or 10 carbon atoms as ring members, which may besides additionally comprise 0, 1, 2, 3 or 4 identical or different heteroatoms independently of one another selected from the group consisting of nitrogen, oxygen and sulfur as ring members, and which may be substituted by one, two or three radicals R$_A^{11}$, R$_A^{12}$ and/or R$_A^{13}$ which are selected independently of one another and independently of their respective occurrence from the group consisting of hydrogen, bromine, chlorine, iodine, fluorine, CN, CF$_3$, OCF$_3$, OCHF$_2$, OH, COOH, CO—NH$_2$, NH$_2$, NH—CO—NH, or in each case optionally substituted C$_1$-C$_6$-alkyl, O—C$_1$-C$_6$-alkyl, C$_1$-C$_6$-alkenyl, C$_1$-C$_6$-alkynyl, C$_3$-C$_6$-cycloalkyl, O—C$_3$-C$_6$-cycloalkyl, C$_3$-C$_6$-cycloalkenyl, C$_1$-C$_4$-alkylene-aryl, NH—(C$_1$-C$_6$-alkyl), N(C$_1$-C$_6$-alkyl)-C$_1$-C$_4$—NH$_2$, C$_1$-C$_4$-alkylene-NH—(C$_1$-C$_6$-alkyl), C$_1$-C$_4$-alkylene-N(C$_1$-C$_6$-alkyl)$_2$, C$_1$-C$_4$alkylene-O— C$_1$-C$_6$-alkyl, CO—C$_1$-C$_6$-alkyl, CO—O—C$_1$-C$_6$-alkyl, CO—NH(C$_1$-C$_6$-alkyl), CO—N(C$_1$-C$_6$-alkyl)-NH—CO—C$_1$-C$_6$-alkyl, NH—CO—N(C$_1$-C$_6$-alkyl)$_2$, N(C$_1$-C$_6$-alkyl)-CO—C$_1$-C$_6$-alkyl;

A$^2$ is hydrogen or in each case optionally substituted C$_1$-C$_6$-alkyl, C$_1$-C$_6$-alkenyl, C$_1$-C$_6$-alkynyl or C$_3$-C$_6$-cycloalkyl,
or where the radicals A$^1$ and A$^2$ may form together with the carbon atom to which they are bonded an in each case optionally substituted 3- to 7-membered carbocyclic ring (spiro linkage) which may additionally comprise a heteroatom as ring member selected from the group consisting of O, S and NR$_A^{14}$ in which R$_A^{14}$ is a radical selected from the group consisting of hydrogen and in each case optionally substituted C$_1$-C$_6$-alkyl, aryl and C$_1$-C$_4$-alkylene-aryl, and where the ring formed in this way may be substituted by one, two or three radicals R$_A^{11}$, R$_A^{12}$ and/or R$_A^{13}$ which may independently of one another and independently of their respective occurrence assume the aforementioned meanings;

B is an aromatic, heteroaromatic, partly aromatic or partly heteroaromatic mono- or bicyclic ring having 1, 2, 3, 4, 5, 6, 7, 8, 9 or 10 C atoms as ring members, which may additionally comprise 0, 1, 2, 3 or 4 identical or different heteroatoms independently of one another selected from the group consisting of nitrogen, oxygen and sulfur as ring members, and which may be substituted by one, two or three radicals R$_B^1$, R$_B^2$ and/or R$_B^3$, where R$_B^1$, R$_B^2$ and R$_B^3$ are selected independently of one another and independently of their respective occurrence from the group consisting of hydrogen, chlorine, bromine, fluorine, CN, CF$_3$, OCF$_3$, OCHF$_2$, OCH$_2$F, OCH$_2$CF$_3$, OCH$_2$—CHF$_2$, OH, and in each case optionally substituted O—C$_1$-C$_4$-alkyl, C$_1$-C$_4$-alkyl, C$_2$-C$_4$-alkenyl and C$_2$-C$_4$-alkynyl;

R$^1$ is selected from the group consisting of hydrogen, bromine, chlorine, fluorine, iodine, CN, CF$_3$, OCF$_3$, OCHF$_2$, and in each case O—C$_1$-C$_4$-alkyl, C$_1$-C$_4$-alkyl, C$_1$-C$_4$-alkenyl and C$_2$-C$_4$-alkynyl; NH(C$_1$-C$_4$-alkyl), N(C$_1$-C$_4$-alkyl)(C$_1$-C$_4$-alkyl), NO$_2$, NHCHO, NHCO(C$_1$-C$_4$-alkyl) or NHCONH$_2$;

R$^2$ is selected from the group consisting of hydrogen, and in each case optionally substituted C$_1$-C$_4$-alkyl, O—C$_1$-C$_4$-alkyl, chlorine, fluorine, difluoromethyl (CHF$_2$) and trifluoromethyl;

R$^3$ is a radical (X)—(Y), where
X is CO, SO$_2$ or (C═NH),
Y is selected from the group consisting of
OH, NH$_2$, NH(C$_1$-C$_4$-alkyl), N(C$_1$-C$_4$-alkyl)(C$_1$-C$_4$-alkyl), NH(C$_2$-C$_4$-alkylene-OH), N(C$_1$-C$_1$-alkyl)(C$_2$-C$_4$-alkylene-OH), NH(C$_2$-C$_4$-alkylene-O—C$_1$-C$_4$-alkyl), N(C$_1$-C$_4$-alkyl)(C$_2$-C$_4$-alkylene-O—C$_1$-C$_4$-alkyl), NH(C$_1$-C$_7$-cycloalkyl), N(C$_1$-C$_1$-alkyl)(C$_1$-C$_7$-cyclo-alkyl), NH(C$_1$-C$_4$-haloalkyl), N(C$_1$-C$_4$-alkyl)(C$_1$-C$_1$-haloalkyl), N(R$_Y^5$)(C$_1$-C$_4$-alkylene)-R$_Y^3$, and radical R$_Y^1$;

R$_Y^1$ is selected independently of its respective occurrence from the group consisting of the respective individual radicals mentioned below

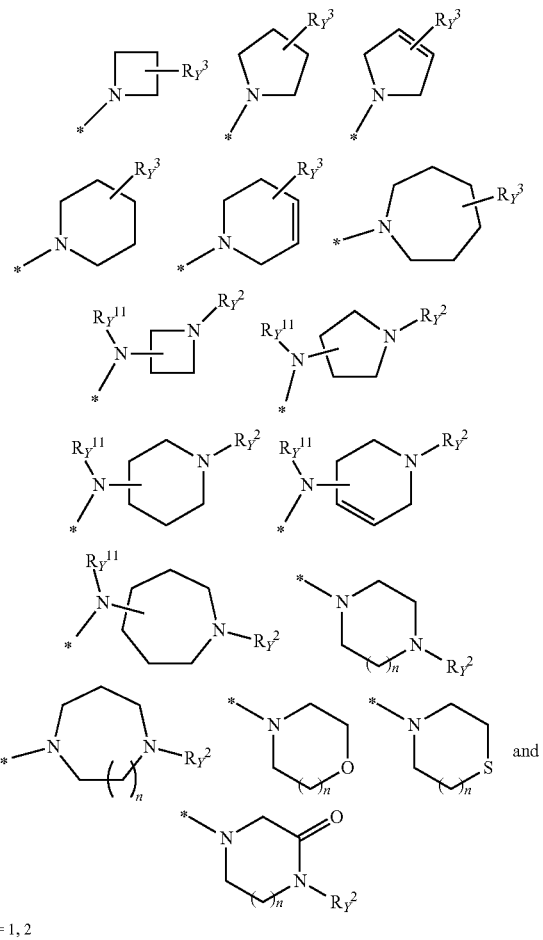

$n = 1, 2$ where n is independently of its occurrence the integer 1 or 2,
where the aforementioned radicals may independently of one another each have one or two substituents R$_Y^{12}$ and/or R$_Y^{13}$ which are selected independently of one another and independently of their respective occurrence from the group consisting of hydrogen, fluorine, OH, in each case optionally substituted O—C$_1$-C$_4$-alkyl, phenyl and C$_1$-C$_4$-alkyl;

$R_Y^{11}$ is a radical selected from the group consisting of hydrogen, in each case optionally substituted $C_1$-$C_6$-alkyl, $C_2$-$C_6$-alkenyl and $C_2$-$C_6$-alkynyl;

$R_Y^2$ is a radical selected from the group consisting of hydrogen, in each case optionally substituted $C_1$-$C_6$-alkyl, $C_2$-$C_6$-alkenyl, $C_2$-$C_6$-alkynyl, phenyl, $C_1$-$C_4$alkylene-phenyl, $C_1$-$C_4$-haloalkyl, $C_3$-$C_7$-cycloalkyl, pyridine, pyrimidine, pyrazine, pyridazine, furan, thiophene, pyrrole, oxazole, isoxazole, thiazole, imidazole, pyrazole, 1,2,4-oxadiazole, 1,2,5-oxadiazole, 1,3,4-oxadiazole, thiadiazole, triazole, 1,3,5-triazine, tetrazole, ($C_2$-$C_4$-alkylene)-$R_Y^3$ and ring radical $R_Y^{22}$, where $R_Y^{22}$ is selected independently of its respective occurrence from the group consisting of the respective individual radicals

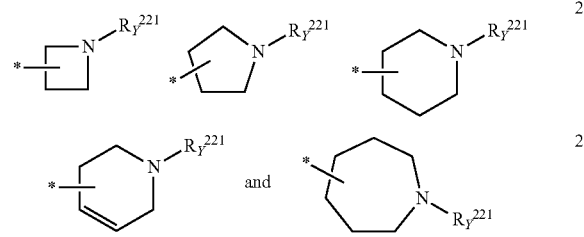

where the aforementioned radicals may independently of one another in each case have one or two substituents $R_Y^{222a}$ and/or $R_Y^{223a}$ which are selected independently of one another and independently of their respective occurrence from the group consisting of hydrogen, fluorine, OH and in each case optionally substituted O—$C_1$-$C_4$-alkyl, phenyl and $C_1$-$C_4$-alkyl;

$R_Y^{221}$ is a radical selected from the group consisting of hydrogen, and in each case optionally substituted $C_1$-$C_6$-alkyl, $C_2$-$C_6$-alkenyl, $C_2$-$C_6$-alkynyl and $C_1$-$C_4$-alkylene-phenyl, in particular hydrogen, and in each case optionally substituted $C_1$-$C_6$-alkyl, $C_2$-$C_6$-alkenyl and $C_2$-$C_6$-alkynyl;

$R_Y^3$ is a radical selected from the group consisting of hydrogen, $NH_2$, $N(R_Y^{3a})R_Y^{3b}$, $NH(C_2$-$C_4$-alkylene)-$R_Y^8$, $N(R_Y^7)(C_2$-$C_4$-alkylene)-$R_Y^8$, $N(R_Y^7)R_Y^9$, $N(R_Y^7)CH_2R_Y^9$, a radical $R_Y^{33}$, a radical $CH_2R_Y^{33}$ and an aromatic radical, selected from phenyl, pyridine, pyrimidine, pyrazine, pyridazine, furan, thiophene, pyrrole, oxazole, isoxazole, thiazole, isothiazole, imidazole, pyrazole, 1,2,4-oxadiazole, 1,2,5-oxadiazole, 1,3,4-oxadiazole, thiadiazole, triazole, 1,3,5-triazine and tetrazole, the aromatic radical being substituted or carrying 1 or 2 substitutens $R_Y^{331}$ and/or $R_Y^{332}$, where $R_Y^{33}$ is independently of its respective occurrence a radical selected from the group consisting of the respective individual radicals

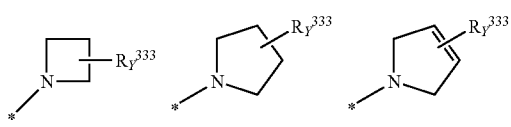

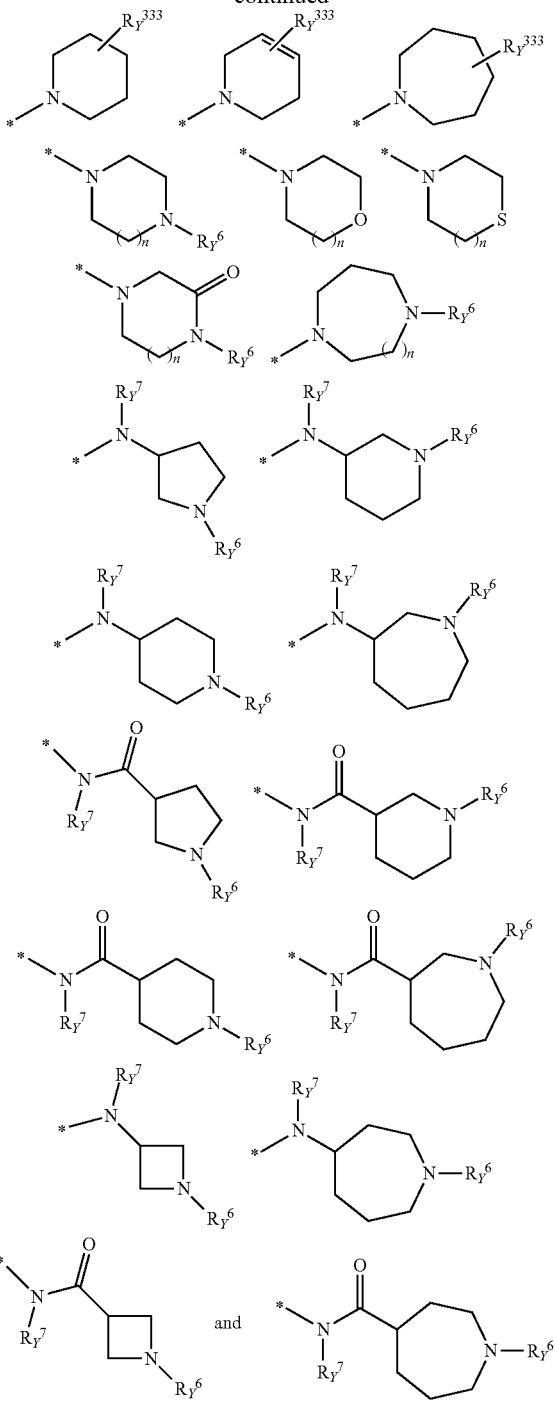

$n = 1, 2$ where n is independently of its occurrence the integer 1 or 2, where the aforementioned radicals $R^{33}$ may independently of one another in each case have one or two substituents $R_Y^{331}$ and/or $R_Y^{332}$;

$R_Y^{331}$, $R_Y^{332}$ are selected independently of one another and independently of their respective occurrence from the group consisting of hydrogen, fluorine, OH, and in each case optionally substituted O—$C_1$-$C_4$-alkyl, phenyl and $C_1$-$C_4$-alkyl;

$R_Y^{333}$ is a radical selected from the group consisting of hydrogen and in each case optionally substituted $C_1$-$C_6$-alkyl, $C_2$-$C_6$-alkenyl, $C_2$-$C_6$-alkynyl, phenyl and $C_1$-$C_4$-alkylene-phenyl;

$R_Y^{3a}$ is a radical selected from the group consisting of hydrogen, and in each case optionally substituted $C_1$-$C_6$-alkyl, $C_3$-$C_7$-cycloalkyl, $C_2$-$C_6$-alkenyl, $C_2$-$C_6$-alkynyl, phenyl and $C_1$-$C_4$-alkylene-phenyl;

$R_Y^{3b}$ is a radical selected from the group consisting of in each case optionally substituted $C_1$-$C_6$-alkyl and $C_1$-$C_4$-alkylene-phenyl;

$R_Y^{5}$ is a radical selected from the group consisting of hydrogen and in each case optionally substituted $C_1$-$C_4$-alkyl;

$R_Y^{A}$ is a radical selected from the group consisting of hydrogen and in each case optionally substituted $C_1$-$C_6$-alkyl, $C_2$-$C_6$-alkenyl, $C_2$-$C_6$-alkynyl, phenyl and $C_1$-$C_4$-alkylene-phenyl;

$R_Y^{7}$ is a radical selected from the group consisting of hydrogen and in each case optionally substituted $C_1$-$C_6$-alkyl, $C_2$-$C_6$-alkenyl, $C_2$-$C_6$-alkynyl, phenyl and $C_1$-$C_4$-alkylene-phenyl;

$R_Y^{8}$ is a radical selected from the group consisting of OH, $NH_2$, and in each case optionally substituted $NH(C_1$-$C_4$-alkyl), $N(C_1$-$C_4$-alkyl)($C_1$-$C_4$alkyl), $NH(C_2$-$C_4$-alkylene-OH), $N(C_1$-$C_4$-alkyl)($C_2$-$C_4$-alkylene-OH), $NH(C_2$-$C_4$-alkylene-O—$C_1$-$C_4$-alkyl), $N(C_1$-$C_4$-alkyl)($C_2$-$C_4$-alkylene-O—$C_1$-$C_4$-alkyl), $NH(C_3$-$C_7$-cycloalkyl), $N(C_1$-$C_4$-alkyl)($C_3$-$C_7$-cycloalkyl), $NH(C_1$-$C_4$haloalkyl), $N(C_1$-$C_4$-alkyl)($C_1$-$C_4$-haloalkyl), O—$C_1$-$C_4$-alkyl, and the ring radical $R_Y^{81}$, where $R_Y^{81}$ is a radical independently of its respective occurrence selected from the group consisting of the respective individual radicals

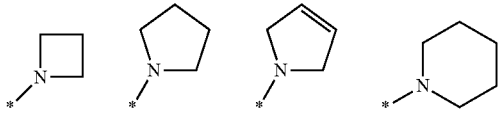

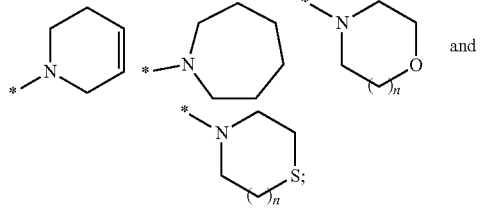

$n = 1, 2$ $R_Y^{9}$ is a 5- or 6-membered heteroaromatic radical having 2, 3, 4 or 5 carbon atom as ring members and 1, 2 or 3 heteroatoms, selected from 0, S and N, wherein the 5- or 6-membered heteroaromatic radical may be unsubstituted or may have one or two substituents $R_Y^{331}$ and/or $R_Y^{332}$;

the tautomeric, enantiomeric and/or diastereomeric forms thereof, and the physiologically tolerated salts of the aforementioned compound or compounds;

with the proviso that $R^1$—H (is not hydrogen) when $A^1=A^2$=hydrogen;

and with the proviso that $R^1$ is halogen, cyano, or in each case optionally substituted $C_1$-$C_6$-alkoxy or $C_1$-$C_6$-alkyl when $A^1=A^2$=hydrogen.

12. The method of claim 11, wherein the compound of the formula (I) has a binding affinity Ki for the vasopressin V1b receptor subtype of less than about 100 nM.

13. The method of claim 11, wherein the compound of the formula (I) has a binding affinity Ki for the vasopressin V1b receptor subtype of between about 10 nM and about 100 nM.

14. The method of claim 11, wherein the compound of the formula (I) has a binding affinity Ki for the vasopressin V1b receptor subtype of less than or equal to about 10 nM.

15. The method of claim 11, wherein the method comprises administering an effective amount of a compound of formula (I), or of a physiologically tolerated salt thereof, to a subject that is a mammal.

* * * * *